1754542B2

United States Patent
Connor

(10) Patent No.: US 11,754,542 B2
(45) Date of Patent: Sep. 12, 2023

(54) SYSTEM FOR NUTRITIONAL MONITORING AND MANAGEMENT

(71) Applicant: Robert A. Connor, St. Paul, MN (US)

(72) Inventor: Robert A. Connor, St. Paul, MN (US)

(73) Assignee: Medibotics LLC, St. Paul, MN (US)

(*) Notice: Subject to any disclaimer, the term of this patent is extended or adjusted under 35 U.S.C. 154(b) by 417 days.

(21) Appl. No.: 16/737,052

(22) Filed: Jan. 8, 2020

(65) Prior Publication Data

US 2020/0152312 A1 May 14, 2020

Related U.S. Application Data

(63) Continuation-in-part of application No. 16/568,580, filed on Sep. 12, 2019, and a continuation-in-part of application No. 15/963,061, filed on Apr. 25, 2018, now Pat. No. 10,772,559, said application No. 16/568,580 is a continuation-in-part of application No. 15/963,061, filed on Apr. 25, 2018, now Pat. No. 10,772,559, and a continuation-in-part of application No. 15/725,330, filed on Oct. 5, 2017, now Pat. No. 10,607,507, application No. 16/737,052 is a continuation-in-part of application No. 15/725,330, filed on Oct. 5, 2017, now Pat. No. 10,607,507, and (Continued)

(51) Int. Cl.
| | |
|---|---|
| *G01N 33/02* | (2006.01) |
| *G06F 3/01* | (2006.01) |
| *G06F 1/16* | (2006.01) |
| *A61B 5/00* | (2006.01) |
| *G06V 40/20* | (2022.01) |
| *G06V 20/68* | (2022.01) |
| *G16H 20/60* | (2018.01) |
| *G09B 19/00* | (2006.01) |
| *G06V 20/20* | (2022.01) |
| *G06V 10/24* | (2022.01) |

(52) U.S. Cl.
CPC ............ *G01N 33/02* (2013.01); *A61B 5/681* (2013.01); *G06F 1/163* (2013.01); *G06F 3/015* (2013.01); *G06V 10/245* (2022.01); *G06V 20/20* (2022.01); *G06V 40/20* (2022.01); *G09B 19/0092* (2013.01); *G16H 20/60* (2018.01); *G06V 20/68* (2022.01)

(58) Field of Classification Search
CPC ...... G16H 20/60; A61B 5/681; A61B 5/0077; A61B 5/6898; G01N 33/02; G06F 1/163; G06F 3/011; G09B 19/0092; G06V 20/68
See application file for complete search history.

(56) References Cited

U.S. PATENT DOCUMENTS 6,157,024 A * 12/2000 Chapdelaine .......... G01V 13/00
250/221
9,146,147 B1 9/2015 Bakhsh
(Continued)

*Primary Examiner* — Jacqueline Cheng
*Assistant Examiner* — Tho Q Tran

(57) ABSTRACT

This invention is a system for nutritional monitoring and management which includes a camera, a spectroscopic sensor, a fiducial component, a wearable biometric sensor, a smart utensil or dish, a passive feedback mechanism which provides a person with information concerning food item types and/or quantities, and an active stimulus mechanism which modifies the person's food-related physiological processes. This system can help a person to improve their dietary habits and health.

1 Claim, 1 Drawing Sheet

Related U.S. Application Data a continuation-in-part of application No. 15/431,769, filed on Feb. 14, 2017, now abandoned, said application No. 15/725,330 is a continuation-in-part of application No. 15/431,769, filed on Feb. 14, 2017, now abandoned, said application No. 16/568,580 is a continuation-in-part of application No. 15/431,769, filed on Feb. 14, 2017, now abandoned, and a continuation-in-part of application No. 15/418,620, filed on Jan. 27, 2017, now abandoned, said application No. 15/431,769 is a continuation-in-part of application No. 15/294,746, filed on Oct. 16, 2016, now Pat. No. 10,627,861, said application No. 16/568,580 is a continuation-in-part of application No. 15/294,746, filed on Oct. 16, 2016, now Pat. No. 10,627,861, application No. 16/737,052 is a continuation-in-part of application No. 15/294,746, filed on Oct. 16, 2016, now Pat. No. 10,627,861, said application No. 15/431,769 is a continuation-in-part of application No. 15/206,215, filed on Jul. 8, 2016, now abandoned, and a continuation-in-part of application No. 14/992,073, filed on Jan. 11, 2016, now abandoned, said application No. 15/206,215 is a continuation-in-part of application No. 14/951,475, filed on Nov. 24, 2015, now Pat. No. 10,314,492, said application No. 15/418,620 is a continuation-in-part of application No. 14/951,475, filed on Nov. 24, 2015, now Pat. No. 10,314,492, said application No. 15/294,746 is a continuation-in-part of application No. 14/951,475, filed on Nov. 24, 2015, now Pat. No. 10,314,492, said application No. 15/294,746 is a continuation-in-part of application No. 14/951,475, filed on Nov. 24, 2015, now Pat. No. 10,314,492, said application No. 15/206,215 is a continuation-in-part of application No. 14/948,308, filed on Nov. 21, 2015, now abandoned, said application No. 15/963,061 is a continuation-in-part of application No. 14/550,953, filed on Nov. 22, 2014, now abandoned, said application No. 14/948,308 is a continuation-in-part of application No. 14/449,387, filed on Aug. 1, 2014, now abandoned, said application No. 15/431,769 is a continuation-in-part of application No. 14/330,649, filed on Jul. 14, 2014, now abandoned, said application No. 14/948,308 is a continuation-in-part of application No. 14/132,292, filed on Dec. 18, 2013, now Pat. No. 9,442,100, said application No. 14/951,475 is a continuation-in-part of application No. 14/071,112, filed on Nov. 4, 2013, now abandoned, and a continuation-in-part of application No. 13/901,131, filed on May 23, 2013, now Pat. No. 9,536,449, said application No. 14/948,308 is a continuation-in-part of application No. 13/901,099, filed on May 23, 2013, now Pat. No. 9,254,099, said application No. 14/330,649 is a continuation-in-part of application No. 13/523,739, filed on Jun. 14, 2012, now Pat. No. 9,042,596.

(60) Provisional application No. 62/930,013, filed on Nov. 4, 2019, provisional application No. 62/857,942, filed on Jun. 6, 2019, provisional application No. 62/814,713, filed on Mar. 6, 2019, provisional application No. 62/814,692, filed on Mar. 6, 2019, provisional application No. 62/800,478, filed on Feb. 2, 2019, provisional application No. 62/549,587, filed on Aug. 24, 2017, provisional application No. 62/439,147, filed on Dec. 26, 2016, provisional application No. 62/349,277, filed on Jun. 13, 2016, provisional application No. 62/311,462, filed on Mar. 22, 2016, provisional application No. 62/297,827, filed on Feb. 20, 2016, provisional application No. 62/245,311, filed on Oct. 23, 2015.

(56) References Cited

U.S. PATENT DOCUMENTS

| | | | |
|---|---|---|---|
| 9,198,621 B2 | 12/2015 | Fernstrom et al. | |
| 9,349,297 B1 | 5/2016 | Ortiz et al. | |
| 9,364,106 B1 | 6/2016 | Ortiz | |
| 10,006,896 B2 | 6/2018 | Fernstrom et al. | |
| 10,058,283 B2 | 8/2018 | Zerick et al. | |
| 10,102,342 B1 | 10/2018 | Vleugels et al. | |
| 10,143,420 B2 | 12/2018 | Contant | |
| 10,249,214 B1 | 4/2019 | Novotny et al. | |
| 10,359,381 B2 | 7/2019 | Lewis et al. | |
| 10,373,716 B2 | 8/2019 | Vleugels et al. | |
| 10,423,045 B2 | 9/2019 | Roberts et al. | |
| 10,499,833 B2 | 12/2019 | Li et al. | |
| 2003/0208113 A1* | 11/2003 | Mault | G16H 40/63 600/316 |
| 2009/0012433 A1 | 1/2009 | Fernstrom et al. | |
| 2011/0318717 A1* | 12/2011 | Adamowicz | G16H 20/60 434/127 |
| 2012/0257024 A1* | 10/2012 | Inaba | G02B 7/102 348/E13.074 |
| 2013/0267794 A1 | 10/2013 | Fernstrom et al. | |
| 2014/0107493 A1* | 4/2014 | Yuen | A61B 5/0022 600/479 |
| 2014/0255882 A1 | 9/2014 | Hadad et al. | |
| 2015/0088546 A1* | 3/2015 | Balram | G16H 10/60 705/3 |
| 2015/0109610 A1* | 4/2015 | Gunji | G01N 30/74 356/72 |
| 2015/0294450 A1 | 10/2015 | Eyring | |
| 2015/0302160 A1 | 10/2015 | Muthukumar et al. | |
| 2015/0325142 A1 | 11/2015 | Ghalavand | |
| 2016/0091419 A1 | 3/2016 | Watson et al. | |
| 2016/0103910 A1 | 4/2016 | Kim et al. | |
| 2016/0140869 A1 | 5/2016 | Kuwahara et al. | |
| 2016/0148535 A1 | 5/2016 | Ashby | |
| 2016/0148536 A1 | 5/2016 | Ashby | |
| 2016/0163037 A1 | 6/2016 | Dehais et al. | |
| 2016/0299061 A1 | 10/2016 | Goldring et al. | |
| 2016/0313241 A1 | 11/2016 | Ochi et al. | |
| 2017/0061821 A1 | 3/2017 | Choi et al. | |
| 2017/0156634 A1 | 6/2017 | Li et al. | |
| 2017/0160131 A1 | 6/2017 | Goldring et al. | |
| 2017/0193854 A1 | 7/2017 | Yuan et al. | |
| 2017/0220772 A1 | 8/2017 | Vleugels et al. | |
| 2017/0249445 A1 | 8/2017 | Devries et al. | |
| 2017/0292908 A1 | 10/2017 | Wilk et al. | |
| 2018/0005545 A1 | 1/2018 | Pathak et al. | |
| 2018/0085003 A1 | 3/2018 | Goldring et al. | |
| 2018/0120155 A1 | 5/2018 | Rosen et al. | |
| 2018/0136042 A1 | 5/2018 | Goldring et al. | |
| 2018/0143073 A1 | 5/2018 | Goldring et al. | |
| 2018/0180478 A1 | 6/2018 | Goldring et al. | |
| 2018/0252580 A2 | 9/2018 | Goldring et al. | |
| 2018/0300458 A1 | 10/2018 | Vleugels et al. | |
| 2018/0348187 A1 | 12/2018 | Fernstrom et al. | |
| 2019/0033130 A1 | 1/2019 | Goldring et al. | |
| 2019/0033132 A1 | 1/2019 | Goldring et al. | |
| 2019/0041265 A1 | 2/2019 | Rosen et al. | |
| 2019/0167190 A1 | 6/2019 | Choi et al. | |
| 2019/0213416 A1 | 7/2019 | Cho et al. | |
| 2019/0236465 A1 | 8/2019 | Vleugels | |
| 2019/0244541 A1 | 8/2019 | Hadad et al. | |
| 2019/0244704 A1 | 8/2019 | Kim et al. | |
| 2019/0290172 A1 | 9/2019 | Hadad et al. | |
| 2019/0295440 A1 | 9/2019 | Hadad | |
| 2019/0333634 A1 | 10/2019 | Vleugels et al. | |

* cited by examiner

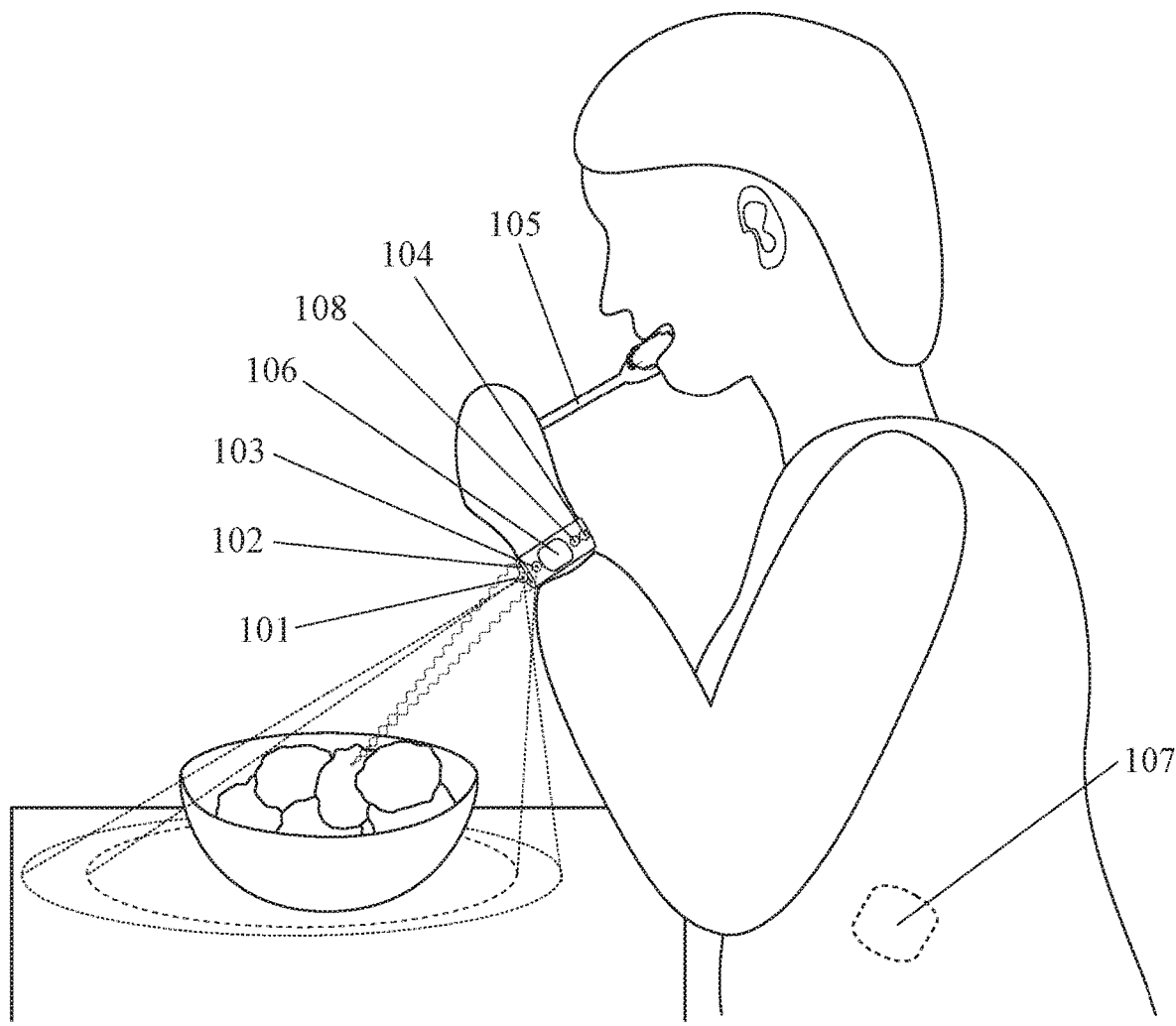

SYSTEM FOR NUTRITIONAL MONITORING AND MANAGEMENT

CROSS-REFERENCE TO RELATED APPLICATIONS

This application claims the priority benefit of U.S. provisional patent application 62/930,013 filed on 2019 Nov. 4. This application is a continuation in part of U.S. patent application Ser. No. 16/568,580 filed on 2019 Sep. 12. This application claims the priority benefit of U.S. provisional patent application 62/857,942 filed on 2019 Jul. 6. This application claims the priority benefit of U.S. provisional patent application 62/814,713 filed on 2019 Mar. 6. This application claims the priority benefit of U.S. provisional patent application 62/814,692 filed on 2019 Mar. 6. This application claims the priority benefit of U.S. provisional patent application 62/800,478 filed on 2019 Feb. 2. This application is a continuation in part of U.S. patent application Ser. No. 15/963,061 filed on 2018 Apr. 25. This application is a continuation in part of U.S. patent application Ser. No. 15/725,330 filed on 2017 Oct. 5. This application is a continuation in part of U.S. patent application Ser. No. 15/431,769 filed on 2017 Feb. 14. This application is a continuation in part of U.S. patent application Ser. No. 15/294,746 filed on 2016 Oct. 16.

U.S. patent application Ser. No. 16/568,580 claimed the priority benefit of U.S. provisional patent application 62/857,942 filed on 2019 Jul. 6. U.S. patent application Ser. No. 16/568,580 claimed the priority benefit of U.S. provisional patent application 62/814,713 filed on 2019 Mar. 6. U.S. patent application Ser. No. 16/568,580 claimed the priority benefit of U.S. provisional patent application 62/814,692 filed on 2019 Mar. 6. U.S. patent application Ser. No. 16/568,580 was a continuation in part of U.S. patent application Ser. No. 15/963,061 filed on 2018 Apr. 25. U.S. patent application Ser. No. 16/568,580 was a continuation in part of U.S. patent application Ser. No. 15/725,330 filed on 2017 Oct. 5. U.S. patent application Ser. No. 16/568,580 was a continuation in part of U.S. patent application Ser. No. 15/431,769 filed on 2017 Feb. 14. U.S. patent application Ser. No. 16/568,580 was a continuation in part of U.S. patent application Ser. No. 15/418,620 filed on 2017 Jan. 27. U.S. patent application Ser. No. 16/568,580 was a continuation in part of U.S. patent application Ser. No. 15/294,746 filed on 2016 Oct. 16.

U.S. patent application Ser. No. 15/963,061 was a continuation in part of U.S. patent application Ser. No. 14/550,953 filed on 2014 Nov. 22. U.S. patent application Ser. No. 15/725,330 claimed the priority benefit of U.S. provisional patent application 62/549,587 filed on 2017 Aug. 24. U.S. patent application Ser. No. 15/725,330 was a continuation in part of U.S. patent application Ser. No. 15/431,769 filed on 2017 Feb. 14. U.S. patent application Ser. No. 15/725,330 claimed the priority benefit of U.S. provisional patent application 62/439,147 filed on 2016 Dec. 26. U.S. patent application Ser. No. 15/725,330 was a continuation in part of U.S. patent application Ser. No. 14/951,475 filed on 2015 Nov. 24 which issued as U.S. Pat. No. 10,314,492 on 2019 Jul. 11.

U.S. patent application Ser. No. 15/431,769 claimed the priority benefit of U.S. provisional patent application 62/439,147 filed on 2016 Dec. 26. U.S. patent application Ser. No. 15/431,769 was a continuation in part of U.S. patent application Ser. No. 15/294,746 filed on 2016 Oct. 16. U.S. patent application Ser. No. 15/431,769 was a continuation in part of U.S. patent application Ser. No. 15/206,215 filed on 2016 Jul. 8. U.S. patent application Ser. No. 15/431,769 claimed the priority benefit of U.S. provisional patent application 62/349,277 filed on 2016 Jun. 13. U.S. patent application Ser. No. 15/431,769 claimed the priority benefit of U.S. provisional patent application 62/311,462 filed on 2016 Mar. 22. U.S. patent application Ser. No. 15/431,769 was a continuation in part of U.S. patent application Ser. No. 14/992,073 filed on 2016 Jan. 11. U.S. patent application Ser. No. 15/431,769 was a continuation in part of U.S. patent application Ser. No. 14/330,649 filed on 2014 Jul. 14.

U.S. patent application Ser. No. 15/418,620 claimed the priority benefit of U.S. provisional patent application 62/297,827 filed on 2016 Feb. 20. U.S. patent application Ser. No. 15/418,620 was a continuation in part of U.S. patent application Ser. No. 14/951,475 filed on 2015 Nov. 24 which issued as U.S. Pat. No. 10,314,492 on 2019 Jun. 11. U.S. patent application Ser. No. 15/294,746 claimed the priority benefit of U.S. provisional patent application 62/349,277 filed on 2016 Jun. 13. U.S. patent application Ser. No. 15/294,746 was a continuation in part of U.S. patent application Ser. No. 14/951,475 filed on 2015 Nov. 24 which issued as U.S. Pat. No. 10,314,492 on 2019 Jun. 11. U.S. patent application Ser. No. 15/294,746 claimed the priority benefit of U.S. provisional patent application 62/245,311 filed on 2015 Oct. 23. U.S. patent application Ser. No. 15/206,215 claimed the priority benefit of U.S. provisional patent application 62/349,277 filed on 2016 Jun. 13. U.S. patent application Ser. No. 15/206,215 was a continuation in part of U.S. patent application Ser. No. 14/951,475 filed on 2015 Nov. 24 which issued as U.S. Pat. No. 10,314,492 on 2019 Jun. 11. U.S. patent application Ser. No. 15/206,215 was a continuation in part of U.S. patent application Ser. No. 14/948,308 filed on 2015 Nov. 21. U.S. patent application Ser. No. 14/951,475 was a continuation in part of U.S. patent application Ser. No. 14/071,112 filed on 2013 Nov. 4. U.S. patent application Ser. No. 14/951,475 was a continuation in part of U.S. patent application Ser. No. 13/901,131 filed on 2013 May 23 which issued as U.S. Pat. No. 9,536,449 on 2017 Jan. 3. U.S. patent application Ser. No. 14/948,308 was a continuation in part of U.S. patent application Ser. No. 14/449,387 filed on 2014 Aug. 1. U.S. patent application Ser. No. 14/948,308 was a continuation in part of U.S. patent application Ser. No. 14/132,292 filed on 2013 Dec. 18 which issued as U.S. Pat. No. 9,442,100 on 2016 Sep. 13. U.S. patent application Ser. No. 14/330,649 was a continuation in part of U.S. patent application Ser. No. 13/523,739 filed on 2012 Jun. 14 which issued as U.S. Pat. No. 9,042,596 on 2015 May 26.

The entire contents of these applications are incorporated herein by reference.

FEDERALLY SPONSORED RESEARCH

Not Applicable

SEQUENCE LISTING OR PROGRAM

Not Applicable

BACKGROUND—FIELD OF INVENTION

This invention relates to systems for nutritional management.

INTRODUCTION

Many health problems are caused by poor nutrition. Many people consume too much unhealthy food or not enough healthy food. Although there are complex behavioral reasons for poor dietary habits, better nutritional monitoring and awareness concerning the types and quantities of food consumed can help a person to improve their dietary habits and health. Information concerning the types and quantities of food consumed can be part of a system that provides constructive feedback and/or incentives to help a person improve their nutritional intake. A person can try to track the types and quantities of food consumed without technical assistance. Their unassisted estimates of the types and quantities of consumed food can be translated into types and quantities of nutrients consumed. However, such unassisted tracking can be subjective. Also, such unassisted tracking can be particularly challenging for non-standardized food items such as food prepared in an ad hoc manner at restaurants or in homes. It would be useful to have a relatively-unobtrusive system which can help a person to accurately track the types and quantities of food which they consume. Such a system can also provide passive feedback and/or active stimuli to improve the person's dietary habits and health. That is the purpose of this invention.

REVIEW OF THE RELEVANT ART

Fernstrom et al. of the University of Pittsburgh are early innovators in the development of wearable devices with cameras to monitor eating. U.S. patent application publications 20090012433 (Fernstrom et al., Jan. 8, 2009, "Method, Apparatus and System for Food Intake and Physical Activity Assessment"), 20130267794 (Fernstrom et al., Oct. 10, 2013, "Method, Apparatus and System for Food Intake and Physical Activity Assessment"), and 20180348187 (Fernstrom et al., Dec. 6, 2018, "Method, Apparatus and System for Food Intake and Physical Activity Assessment"), as well as U.S. Pat. No. 9,198,621 (Fernstrom et al., Dec. 1, 2015, "Method, Apparatus and System for Food Intake and Physical Activity Assessment") and U.S. Pat. No. 10,006,896 (Fernstrom et al., Jun. 26, 2018, "Method, Apparatus and System for Food Intake and Physical Activity Assessment"), disclose wearable buttons and necklaces for monitoring eating with cameras.

Goldring et al. of Consumer Physics and Verifood are pioneers in the development of compact spectroscopy sensors (including the SCiO) to measure food. U.S. patent application publication 20180252580 (Goldring et al., Sep. 6, 2018, "Low-Cost Spectrometry System for End-User Food Analysis") discloses a compact spectrometer that can be used in mobile devices such as smart phones. U.S. patent application publication 20190041265 (Rosen et al., Feb. 7, 2019, "Spatially Variable Filter Systems and Methods") discloses a compact spectrometer system with a spatially variable filter. U.S. patent application publications 20170292908 (Wilk et al., Oct. 12, 2017, "Spectrometry System Applications") and 20180143073 (Goldring et al., May 24, 2018, "Spectrometry System Applications") disclose a spectrometer system to determine spectra of an object. U.S. patent application publication 20190033132 (Goldring et al., Jan. 31, 2019, "Spectrometry System with Decreased Light Path") discloses a spectrometer with a plurality of isolated optical channels. U.S. patent application publication 20180136042 (Goldring et al., May 17, 2018, "Spectrometry System with Visible Aiming Beam") discloses a handheld spectrometer with a visible aiming beam. U.S. patent application publications 20160299061 (Goldring et al., Oct. 13, 2016, "Spectrometry Systems, Methods, and Applications"), 20170160131 (Goldring et al., Jun. 8, 2017, "Spectrometry Systems, Methods, and Applications"), 20180085003 (Goldring et al., Mar. 29, 2018, "Spectrometry Systems, Methods, and Applications"), 20180120155 (Rosen et al., May 3, 2018, "Spectrometry Systems, Methods, and Applications"), and 20180180478 (Goldring et al., Jun. 28, 2018, "Spectrometry Systems, Methods, and Applications") disclose a handheld spectrometer to measure the spectra of objects. U.S. patent application publication 20190033130 (Goldring et al., Jan. 31, 2019, "Spectrometry Systems, Methods, and Applications") discloses a hand held spectrometer with wavelength multiplexing.

Vleugels et al. of Savor Labs and Klue have done innovative work using gesture recognition to monitor eating. U.S. patent application publication 20190236465 (Vleugels, Aug. 1, 2019, "Activation of Ancillary Sensor Systems Based on Triggers from a Wearable Gesture Sensing Device") discloses an eating monitor with gesture recognition. U.S. patent application publication 20190333634 (Vleugels et al., Oct. 31, 2019, "Method and Apparatus for Tracking of Food Intake and Other Behaviors and Providing Relevant Feedback"), 20170220772 (Vleugels et al., Aug. 3, 2017, "Method and Apparatus for Tracking of Food Intake and Other Behaviors and Providing Relevant Feedback"), and 20180300458 (Vleugels et al., Oct. 18, 2018, "Method and Apparatus for Tracking of Food Intake and Other Behaviors and Providing Relevant Feedback"), as well as U.S. Pat. No. 10,102,342 (Vleugels et al., Oct. 16, 2018, "Method and Apparatus for Tracking of Food Intake and Other Behaviors and Providing Relevant Feedback") and U.S. Pat. No. 10,373,716 (Vleugels et al., Aug. 6, 2019, "Method and Apparatus for Tracking of Food Intake and Other Behaviors and Providing Relevant Feedback"), disclose a method for detecting, identifying, analyzing, quantifying, tracking, processing and/or influencing food consumption.

Hadad et al. of Nutrino Health have developed an extensive database and analytic methods concerning different types of foods and their effects on health. U.S. patent application publication 20190295440 (Hadad, Sep. 26, 2019, "Systems and Methods for Food Analysis, Personalized Recommendations and Health Management") discloses a method for developing a food ontology. U.S. patent application publications 20190244541 (Hadad et al., Aug. 8, 2019, "Systems and Methods for Generating Personalized Nutritional Recommendations"), 20140255882 (Hadad et al., Sep. 11, 2014, "Interactive Engine to Provide Personal Recommendations for Nutrition, to Help the General Public to Live a Balanced Healthier Lifestyle"), and 20190290172 (Hadad et al., Sep. 26, 2019, "Systems and Methods for Food Analysis, Personalized Recommendations, and Health Management") disclose methods to provide nutrition recommendations based on a person's preferences, habits, medical and activity.

Samsung is also working toward diet monitoring devices. For example, U.S. patent application publication 20190244704 (Kim et al., Aug. 8, 2019, "Dietary Habit Management Apparatus and Method") discloses a dietary habit management apparatus using biometric measurements. U.S. patent application publication 20190213416 (Cho et al., Jul. 11, 2019, "Electronic Device and Method for Processing Information Associated with Food") discloses a food tracking device with a camera. U.S. patent application publication 20190167190 (Choi et al., Jun. 6, 2019, "Healthcare Apparatus and Operating Method Thereof") discloses a dietary monitoring device which emits light of different wavelengths.

U.S. patent application publication 20180005545 (Pathak et al., Jan. 4, 2018, "Assessment of Nutrition Intake Using a Handheld Tool") discloses a smart food utensil for measuring food mass. U.S. patent application publication 20160091419 (Watson et al., Mar. 31, 2016, "Analyzing and Correlating Spectra, Identifying Samples and Their Ingredients, and Displaying Related Personalized Information") discloses a spectral analysis method for food analysis. U.S. patent application publication 20150302160 (Muthukumar et al., Oct. 22, 2015, "Method and Apparatus for Monitoring Diet and Activity") discloses a method and device for analyzing food with a camera and a spectroscopic sensor.

U.S. patent application publication 20170156634 (Li et al., Jun. 8, 2017, "Wearable Device and Method for Monitoring Eating") and U.S. Pat. No. 10,499,833 (Li et al., Dec. 10, 2019, "Wearable Device and Method for Monitoring Eating") disclose a wearable device with an acceleration sensor to monitor eating. U.S. patent application publication 20170193854 (Yuan et al., 2016 Jan. 5, "Smart Wearable Device and Health Monitoring Method") discloses a wearable device with a camera to monitor eating. U.S. patent application publication 20160103910 (Kim et al., Apr. 14, 2016, "System and Method for Food Categorization") discloses a food categorization engine.

U.S. Pat. No. 9,349,297 (Ortiz et al., May 24, 2016, "System and Method for Nutrition Analysis Using Food Image Recognition") discloses a system and method for determining the nutritional value of a food item. U.S. Pat. No. 9,364,106 (Ortiz, Jun. 14, 2016, "Apparatus and Method for Identifying, Measuring and Analyzing Food Nutritional Values and Consumer Eating Behaviors") discloses a food container for determining the nutritional value of a food item. U.S. patent application publication 20160148535 (Ashby, May 26, 2016, "Tracking Nutritional Information about Consumed Food") discloses an eating monitor which monitors swallowing and/or chewing. U.S. patent application publication 20160148536 (Ashby, May 26, 2016, "Tracking Nutritional Information about Consumed Food with a Wearable Device") discloses an eating monitor with a camera.

U.S. Pat. No. 10,058,283 (Zerick et al., 2016 Apr. 6, "Determining Food Identities with Intra-Oral Spectrometer Devices") discloses an intra-oral device for food analysis. U.S. Pat. No. 9,146,147 (Bakhsh, Sep. 29, 2015, "Dynamic Nutrition Tracking Utensils") discloses nutritional intake tracking with a smart utensil. U.S. Pat. No. 10,423,045 (Roberts et al., Sep. 24, 2019, "Electro-Optical Diffractive Waveplate Beam Shaping System") discloses optical beam shaping systems with a diffractive waveplate diffuser. U.S. patent application publication 20170249445 (Devries et al., Aug. 31, 2017, "Portable Devices and Methods for Measuring Nutritional Intake") discloses a nutritional intake monitoring system with biosensors. U.S. patent application publication 20170061821 (Choi et al., Mar. 2, 2017, "Systems and Methods for Performing a Food Tracking Service for Tracking Consumption of Food Items") discloses a food tracking service.

U.S. Pat. No. 10,143,420 (Contant, Dec. 4, 2018, "Eating Utensil to Monitor and Regulate Dietary Intake") discloses a dietary intake regulating device that also monitors physical activity. U.S. patent application publication 20160163037 (Dehais et al., Jun. 9, 2016, "Estimation of Food Volume and Carbs") discloses an image-based food identification system including a projected light pattern. U.S. patent application publication 20160140869 (Kuwahara et al., May 19, 2016, "Food Intake Controlling Devices and Methods") discloses image-based technologies for controlling food intake. U.S. patent application publication 20150325142 (Ghalavand, Nov. 12, 2015, "Calorie Balance System") discloses a calorie balance system with smart utensils and/or food scales. U.S. Pat. No. 10,249,214 (Novotny et al., Apr. 2, 2019, "Personal Wellness Monitoring System") discloses a personal nutrition, health, wellness and fitness monitor which analyzes food images.

U.S. patent application publication 20160313241 (Ochi et al., Nov. 27, 2016, "Calorie Measurement Device") disclose, Mar. 17, 2016, "Food Intake Monitor") discloses a jaw motion sensor to measure food intake. U.S. patent application publication 20150294450 (Eyring, Oct. 15, 2015, "Systems and Methods for Measuring Calorie Intake") discloses an image-based system for measuring caloric input. U.S. Pat. No. 10,359,381 (Lewis et al., Jul. 23, 2019, "Methods and Systems for Determining an Internal Property of a Food Product") discloses a system and method for measuring an internal property of a food item.

SUMMARY OF THE INVENTION

This invention is a system and/or method for nutritional monitoring and management. This system for nutritional monitoring and management can include: a camera which records food images which are analyzed to identify food item types and estimate food item quantities; a spectroscopic sensor which scans food items to measure their nutritional and/or chemical composition; a fiducial component which is used to calibrate food images; a wearable biometric sensor which collects data to detect eating, help to identify food types, and/or help to estimate food quantities; a smart utensil or dish which collects data to help identify food types, help estimate food quantities, and/or measure eating speed; a passive feedback mechanism which provides a person with information concerning food item types and/or quantities; an active stimulus mechanism which modifies the person's food-related physiological processes; and a data processor. Simplified versions of this system, without all of these components, can be adequate for some nutritional monitoring and management applications and are also within the scope of this invention. The system for nutritional monitoring and management disclosed herein can provide passive feedback and/or active stimuli to help a person to improve their dietary habits and health.

INTRODUCTION TO THE FIGURES

FIG. 1 shows a system for nutritional monitoring and management which includes a camera, a spectroscopic sensor, a fiducial component, a biometric sensor, a smart utensil, a passive feedback mechanism, an active stimulus mechanism, and a data processor.

DETAILED DESCRIPTION OF THE FIGURES

FIG. 1 shows an example of a system for nutritional monitoring and management comprising: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a fiducial component which displays objects in images of food items which help to calibrate the distance, size, shape, color, and/or brightness of the food items; wherein the fiducial component is selected from the group consisting of: an object with (markings of) known size, shape, and/or colors which is placed near the food items; a light emitter (e.g. low-power laser) which projects a light pattern with known size, shape, and/or colors on or near the food items; and a mobile device with a screen which is placed near the food items and displays an image on the screen with known size, shape, and/or colors; (d) a wearable biometric sensor which collects biometric data concerning a person whose nutritional intake is being monitored, wherein the biometric sensor is selected from the group consisting of: motion sensor (e.g. accelerometer, gyroscope, and/or compass), electromagnetic energy sensor (e.g. impedance sensor, EMG sensor, EKG sensor), spectroscopic sensor (e.g. spectrometer) and/or photoplethysmographic sensor, sound sensor (e.g. microphone, chew sensor, swallow sensor), and chemical sensor (e.g. sweat sensor, saliva sensor); wherein data from the biometric sensor is used for one or more functions selected from the group consisting of: recognizing when the person is eating in order to automatically activate the system to take an action (e.g. recording images or monitoring sounds) to help identify food item types and/or estimate food item quantities; recognizing when the person is eating in order to automatically prompt the person to take an action (e.g. recording images or entering food descriptions) to help identify food item types and/or estimate food item quantities; and identifying relationships between consumption of selected food item types and/or food item quantities by the person and subsequent changes in the person's biometric parameters (e.g. glucose level, blood pressure, lactic acid level, or oxygen level); and wherein the biometric sensor is part of a device selected from the group consisting of: smart watch or other wrist-worn device, smart finger ring, smart armband, smart eyewear, smart earwear, smart necklace or pendant, smart button, smart belt, smart garment, adhesive sensor patch, mobile EEG device, and continuous glucose monitor; (e) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; (f) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); (g) an active stimulus mechanism which automatically responds to food consumption by the person, wherein the active stimulus mechanism automatically modifies a person's physiological processes (e.g. by delivering a therapeutic agent, such as insulin, into the person's body; by delivering a therapeutic pattern of electromagnetic energy to a selected portion of the person's body, such as the vagus nerve; or by delivering a taste-modifying substance into a person's mouth); and (h) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

Specifically, FIG. 1 shows a system for nutritional monitoring and management comprising: (a) camera 101; (b) spectroscopic sensor 102; (c) fiducial component 103; (d) wearable biometric sensor 104; (e) smart utensil 105; (f) passive feedback mechanism 106; (g) active stimulus mechanism 107; and (h) data processor 108. In the example shown in FIG. 1, camera 101 is worn on a person's wrist and records images of food items, spectroscopic sensor 102 is worn on the person's wrist and scans nearby food; fiducial component 103 is a light projector worn on the person's wrist and projects a laser pattern on or near food to help calibrate the distance, size, shape, color, and/or brightness of the food; wearable biometric sensor 104 is a motion sensor worn on the person's wrist which tracks arm, wrist, and/or hand motion; smart utensil 105 is a smart spoon held by the person which measures the weight of each spoonful of food; passive feedback mechanism 106 is a display screen which is worn on the person's wrist and provides visual information concerning the person's food consumption; active stimulus mechanism 107 delivers insulin to the person's body based on food consumption; and data processor 108 processes data from the camera, spectroscopic sensor, and/or biometric sensor. We now discuss example variations on systems for nutritional monitoring and management. The example variations which follow and also the example variations which are disclosed in priority-linked applications can be applied where relevant to the system which is shown in FIG. 1. Also, simplified versions of this system without all of the system components shown in FIG. 1 can be adequate for some nutritional monitoring and management applications and are also within the scope of this invention.

In an example, a system for nutritional monitoring and management can include a general purpose handheld device (such as a smart phone or electronic tablet). In an example, a system can incorporate information from a camera, a touch screen, a microphone, and/or a motion sensor on a general purpose handheld device. In an example, a system can include a software application for nutritional monitoring and management which runs on a general purpose handheld device (such as a smart phone or electronic tablet).

In an example, a system for nutritional monitoring and management can include a handheld camera. In an example, a system can include a handheld electronic tablet. In an example, a system can include a handheld food imaging device. In an example, a system can include a handheld food probe. In an example, a system can include a handheld food scanner. In an example, a system can include a handheld invasive food probe. In an example, a system can include a handheld non-invasive spectroscopic food scanner. In an example, a system can include a handheld removable accessory for a cell phone. In an example, a system can include a handheld removable attachment for a conventional food utensil. In an example, a system can include a removable component of a smart watch or wrist band. In an example, a system can include a smart phone component. In an example, a system can include a smart phone, cell phone, and/or mobile phone. In an example, a system can include a smart utensil.

In an example, a system for nutritional monitoring and management can include a specialized handheld device, such as a specialized handheld device with a camera, spectroscopic sensor, and motion sensor. In an example, a system can include a specialized handheld device with a spectroscopic sensor, a camera, and a laser beam projector. In an example, a laser can form a light pattern near food which serves as a fiducial marker for analyzing food size and/or color. In an example, a system can include a specialized handheld device with a spectroscopic sensor, a camera, and a food interior probe. In an example, a handheld spectroscopic sensor can be placed in juxtaposition with a food item for spectroscopic analysis of the food item. In an example, a handheld spectroscopic sensor can be placed over different locations on a meal to perform spectroscopic analyses of different food items in the meal and/or different locations within a non-homogenous food item.

In an example, a system for nutritional monitoring and management can include a smart food utensil (e.g. smart spoon, fork, or chop sticks) or beverage holder (e.g. smart cup, glass, or mug). In an example, a smart food utensil or beverage holder can have a camera which takes pictures of nearby food and/or food being transported by the utensil or beverage holder. In an example, a smart food utensil or beverage holder can have a spectroscopic sensor which scans nearby food and/or food being transported by the utensil or beverage holder to measure the reflection or absorption spectrum of the food and thereby identify the molecular composition of the food. In an example, a spoon can have a transparent cup (distal concave) portion which contains a spectroscopic sensor. In an example, data on the molecular composition of food in this cup portion can be collected by the spectroscopic sensor.

In an example, a system for nutritional monitoring and management can include a smart spoon with a scale which tracks the individual weights (and cumulative weight) of mouthfuls of food carried and/or consumed during an eating event. In an example, a smart spoon can approximate the weights of mouthfuls of food carried by the spoon by measuring the effect of those mouthfuls on the motion of the spoon as a whole or the relative motion of one part of the spoon relative to another. In an example, a smart spoon can include a motion sensor and/or inertial sensor. In an example, a smart spoon can include one or more accelerometers in different, motion-variable locations along the length of the spoon. In an example, a smart spoon can include a spring and/or strain gauge between the food-carrying scoop of the spoon and the handle of the spoon. In an example, food weight can estimated by measuring distension of the spring and/or strain gauge as food is brought up to a person's mouth.

In an example, a system for nutritional monitoring and management can include a food utensil rest that functions as a bite counter and/or food scale. In an example, it can track the number of times that a utensil is put down or weigh each bite or mouthful. In an example, a food scale can be incorporated into a smart utensil which tracks the cumulative weight of cumulative mouthfuls of food during an eating event. In an example, a smart utensil can approximate the weight of mouthfuls of food by measuring the effect of food carried by the utensil on an accelerometer or other inertial sensor. In an example, a smart utensil can incorporate a spring between the food-carrying portion and the handheld portion of a utensil and food weight can be estimated by measuring distension of the spring as food is brought up to a person's mouth.

In an example, a system for nutritional monitoring and management can include a smart food utensil with a motion sensor to detect when a person is eating. A food utensil with a motion sensor can be less prone to false alarms than a motion sensor worn on a person's wrist, hand, arm, or finger because the utensil is only used when the person eats food. Since the utensil is only used for food consumption, analysis of complex motion and differentiation of food consumption actions vs. other hand gestures is less important with a utensil than it is with a device that is worn on the person's body. In an example, a smart utensil can estimate the amount of food consumed by the number of hand-to-mouth motions (combined with information concerning how much food is conveyed by the utensil with each movement). In an example, a smart utensil can encourage a person to eat slower. The idea is that if the person eats more slowly, then they will tend to not overeat past the point of internal identification of satiety.

In an example, a system for nutritional monitoring and management can include a smart utensil (e.g. smart spoon or smart fork) which uses a motion sensor to estimate the weight of the distal (food-carrying) end of the utensil at a first point in time (such as during an upswing motion as the utensil carries a mouthful of food up to the person's mouth) and also at a second point in time (such as during a downswing motion as the person lowers the utensil from their mouth). In an example, a smart utensil can estimate the weight of food actually consumed by calculating the difference in food weights between the first and second points in time. In an example, a system can track cumulative food consumption by tracking the cumulative weights of multiple mouthfuls of (different types of) food during an eating event or during a defined period of time (such as a day or week). In an example, a smart utensil can use an inertial sensor, accelerometer, or strain gauge to estimate the weight of the distal (food-carrying) end of the utensil at a first time (during an upswing motion as the utensil carries a mouthful of food up to the person's mouth), can use this sensor to estimate the weight of the food-carrying end of the utensil at a second time (during a downswing motion as the person lowers the utensil from their mouth), and can estimate the weight of the mouthful of food by calculating the difference in weight between the first and second times.

In an example, a system for nutritional monitoring and management can include a smart utensil which identifies types and quantities of consumed foods, ingredients, or nutrients by being in optical communication with food. In an example, a smart utensil can identify food item types and quantities by recording images of food. In an example, a smart utensil can record images of food that is within a reachable distance of a person. In an example, a smart utensil can record images of food on a plate. In an example, a smart utensil can record images of a portion of food as that food is conveyed to a person's mouth via the utensil.

In an example, a system for nutritional monitoring and management can include a smart utensil (e.g. smart fork, smart spoon, or smart chop sticks). In an example, a smart utensil can identifies food type, nutritional composition, and/or molecular composition by optically analyzing food. In an example, a system can include a smart utensil with a spectroscopic sensor which identifies food type, nutritional composition, and/or molecular composition by spectroscopic analysis. In an example, a smart utensil can identify the type, nutritional composition, and/or molecular composition of a food item by projecting light beams toward the food item and then receiving those light beams after they have been reflected by (or passed through) the food item. In an example, the effects of interaction with food on the spectral distribution of light beams can provide information on food type and/or nutritional composition. In an example, a smart utensil can spectroscopically analyze food as that food is being brought up to a person's mouth using the utensil. In an example, a smart utensil can spectroscopically analyze a nearby food item before a portion of the food item is brought onto the utensil. In an example, a smart utensil can spectroscopically analyze a nearby food item while the food item is still on a plate or in a bowl.

In an example, a system for nutritional monitoring and management can include a smart utensil (e.g. smart fork, smart spoon, or smart chop sticks) which measures the weight of a piece and/or portion of food which is carried by the utensil. In an example, a smart utensil can have a moveable portion such as a flexible joint or bend sensor between the distal (food carrying) end of the utensil and the handle of the utensil. In an example, the weight and/or momentum of a piece of food being carried by the distal end of a utensil can cause this moveable portion to bend or flex. In an example, bending or flexing of this moveable portion can be measured by a force sensor, strain sensor, bend sensor, goniometer, or pressure sensor in order to estimate the weight of a piece or portion of food being carried by the utensil. In an example, a smart fork can estimate the weight of solid food on the tines of the fork using a force sensor, strain sensor, bend sensor, or pressure sensor. In an example, a smart spoon can estimate the weight of a liquid in the concavity of the spoon using a force sensor, strain sensor, bend sensor, or pressure sensor.

In an example, a system for nutritional monitoring and management can include a smart utensil (e.g. smart fork, smart spoon, or smart chop sticks) with two motion sensors, a first motion sensor in the distal (e.g. food carrying) end of the utensil and a second motion sensor in the handle of the utensil, wherein the first and second motion sensors are separated by a moveable portion such as a flexible joint. In an example, differences in motion patterns between the first and second motion sensors can be analyzed in order to estimate the weight of a piece of food carried by the utensil. In an example, the greater the weight of a piece or portion of food being carried by the distal end of a smart utensil, the greater the bending and/or flexing of a joint between the distal end of the utensil and the proximal handle of the utensil. In an example, the faster a piece or portion of food is conveyed up to a person's mouth, the greater the bending and/or flexing of a joint between the distal end of the utensil and the proximal handle of the utensil.

In an example, a system for nutritional monitoring and management can include a smart utensil (e.g. smart fork, smart spoon, or smart chop sticks) which performs a function selected from the group consisting of: communicating information concerning food type and/or quantity to other system components; detecting use of the utensil for eating; estimating the nutritional and/or molecular composition of food via spectroscopic analysis; identifying a type of food via image analysis; identifying a type of food via spectroscopic analysis; influencing and/or changing the amount of food consumed by a person via visual, audio, or haptic stimuli; influencing and/or changing the speed of a person's food consumption via visual, audio, or haptic stimuli; measuring the amount of food consumed via a bend sensor, force sensor, or pressure sensor; measuring the amount of food consumed via a motion sensor; measuring the amount of food consumed via image analysis; measuring the speed, rate, or pace of food consumption via a bend sensor, force sensor, or pressure sensor; measuring the speed, rate, or pace of food consumption via a motion sensor; measuring the speed, rate, or pace of food consumption via image analysis; providing a user with feedback concerning the speed, rate, or pace of food consumption via light, sound, or vibration; signaling the amount of food consumed to a user via light, sound, or vibration; and signaling the speed, rate, or pace of food consumption to a user via light signals, sound signals, or haptic signals.

In an example, a system for nutritional monitoring and management can include a smart utensil (e.g. smart fork, smart spoon, or smart chop sticks) with a camera which records images of nearby food (e.g. food within a person's reach). In an example, a system can include a smart utensil with a camera which records images of a piece or portion of food being carried to a person's mouth by the utensil. In an example, a smart utensil can have a nutritional, molecular, and/or chemical composition sensor. In an example, a smart utensil can have a spectroscopic sensor which emits light beams toward food and receives these light beams after they have been reflected by (or passed through) food. In this manner, a spectroscopic sensor can scan nearby food and/or food being carried to a person's mouth by a utensil in order to estimate the nutritional composition of the food. In an example, a system can include a smart spoon with a spectroscopic sensor which scans food being carried in the concavity of the spoon. In an example, a system can include a smart fork with a spectroscopic sensor which scans food being carried on the tines of the fork.

In an example, a system for nutritional monitoring and management can include a smart utensil (e.g. a smart fork, smart spoon, or smart chop sticks). In an example, a smart utensil can have a motion sensor (e.g. an accelerometer and/or gyroscope) that tracks how many times and/or how quickly a person brings the utensil up to their mouth. In an example, analysis of the roll, pitch, and yaw of smart utensil motion can be analyzed to help identify the types and quantities of food items consumed by a person. In an example, the speed, acceleration, or distance of smart utensil motion can be analyzed to help identify the types and quantities of food items consumed by a person.

In an example, a system for nutritional monitoring and management can include both a smart utensil (e.g. smart fork, smart spoon, or smart chop sticks) and a wearable device (e.g. smart watch, smart ring, or augmented reality eyewear). In an example, a wearable component of such a system can continually monitor whether a person is eating, but the smart utensil component of the system may only be triggered (e.g. activated) when a person starts eating. In an example, a system can prompt a person to use a smart utensil when the system detects that a person has started to eat but is not using the smart utensil. In an example, a system can monitor the proximity of a smart utensil to a wrist-worn device. In an example, a system can compare the motion of a smart utensil to the motion of a wrist-worn device. In an example, this comparison can determine whether the smart utensil is being used when a person eats. In an example, differences in motion between the motion of a smart utensil and the motion of a wearable device (such as a smart watch or finger ring) can be analyzed to help identify types and quantities of food being consumed.

In an example, a smart food utensil or beverage holder can have a motion sensor (e.g. accelerometer and/or gyroscope) which measures the number of times and/or the frequency with which a person brings the utensil or beverage holder up to their mouth. The number and frequency with which a utensil or beverage holder is brought up to a person's mouth can help to estimate the amount of food that a person actually consumes. In an example, details concerning the movement and acceleration of the utensil or beverage holder can help to identify the weight and type of food, as well as the quantity of food, actually consumed by a person. In an example, specific sequential patterns of roll, pitch, and yaw can be associated with specific types and/or weights of food. In an example, a smart food utensil can include a force, bend, and/or strain sensor. In an example, a force, bend, and/or strain sensor can be on a moveable joint between a food holding portion of a smart utensil and the handle of the utensil. In an example, such a force, bend, and/or strain sensor can measure the force and/or inertia of food relative to the utensil handle, thereby helping to measure food weight.

In an example, a system for nutritional monitoring and management can include a food probe with actuators which move a spectroscopic sensor up and down a longitudinal axis of the probe, thereby scanning different depths of the interior of a food item. In an example, a food probe can have a spectroscopic sensor which slides within the probe in a longitudinal manner, scanning different depths of the interior of a food item. In an example, a food probe can have moving mirrors or lenses which change the location, distance, and/or depth from which the food probe spectroscopically scans the interior of food. In an example, a food probe can have a spectroscopic sensor which rotates within the probe, thereby scanning different radial sections of the interior of a food item. In an example, a food probe can have a spectroscopic sensor which rotates around a longitudinal axis of the food probe, thereby scanning different radial sections of the interior of a food item.

In an example, a system for nutritional monitoring and management can include a food probe which is inserted into the interior of a food item. In an example, a system can include a handheld food probe. In an example, a food probe can have a spectroscopic sensor which takes spectroscopic scans of the interior of a food item. This is particularly useful for food which is not homogenous, such as food with different interior layers or structures. In an example, a food probe can have a longitudinal protrusion (like a fork tine) which is inserted into the interior of a food item. In an example, a food probe can have a transparent exterior surface and a spectroscopic sensor located inside this transparent exterior surface. For example, a food probe can be light a transparent fork tine with a spectroscopic sensor inside the tine. In an example, a food probe can be a removable component of a wearable device. In an example, a food probe can be removed from a wearable device, inserted into the interior of food, cleaned off, and then inserted back into the wearable device.

In an example, a system for nutritional monitoring and management can include a handheld food probe which is inserted into food to analyze the molecular composition of the food interior. In an example, this food probe can measure impedance inside a food item. In an example, this food probe can perform spectroscopic analysis of the interior of a food item. In an example, this food probe can use sound (e.g. low frequency or high frequency) to scan the interior of a food item. In an example, a food probe can scan different layers or depths of the interior of a food item using spectroscopic analysis, ultrasound scanning, and/or electromagnetic impedance analysis. In an example, a spectroscopic sensor inside a food probe can rotate within the food probe and/or move in a proximal-to-distal manner within the food probe to scan different areas of the interior of a food item.

In an example, a system for nutritional monitoring and management can include a wearable device. In an example, a system can include smart eyewear (such as smart eyeglasses, augmented reality eyeglasses, goggles, a smart visor, or a smart contact lens). In an example, smart eyewear can have a camera. In an example, smart eyewear can have two stereoscopic cameras for 3D imaging. In an example, smart eyewear can have augmented reality (AR) functionality. In an example, smart eyewear with AR functionality can serve as a computer-to-human interface, displaying information about food in a person's field of view. In an example, smart eyewear with AR functionality can serve as a human-to-computer interface, enabling a person to input user information about food in the person's field of view. In an example, a person can input user information about food via voice (e.g. speech recognition), gesture (e.g. gesture recognition), touch (e.g. touch screen), text (e.g. via a keypad), or thought (e.g. via a mobile EEG sensor device).

In an example, a system for nutritional monitoring and management can include a wrist-worn device (e.g. smart watch, smart watch band, wrist band, fitness band, smart bracelet, smart sleeve, or smart cuff) with a camera for recording images of nearby food items, wherein the camera is located on the anterior/palmar/lower side or a lateral/narrow side of a person's wrist. In an example, a system can include a wrist-worn device (e.g. smart watch, smart watch band, wrist band, fitness band, smart bracelet, smart sleeve, or smart cuff) with a spectroscopic sensor for scanning nearby food items, wherein the spectroscopic sensor is located on the anterior/palmar/lower side or a lateral/narrow side of a person's wrist. In an example, a system can include a watch band with two cameras facing in different directions, wherein the two cameras collectively record images of interaction between a person's hand and nearby food; and interaction between the person's mouth and food.

In an example, a system for nutritional monitoring and management can include a device which is worn on a person's wrist and/or arm (such as a smart watch, smart watch band, smart wrist band, fitness band, smart glove, or smart bracelet). In an example, a system can include a watch that is not so smart, but has potential and should be given a chance. In an example, a wearable device on a person's wrist and/or arm can include a motion sensor which detects when a person is eating based on a series of distinctive upward/downward, pausing, and roll/tilt motions. In an example, a wearable device on a person's wrist and/or arm can include a camera which takes pictures of food at different and/or selected times during upward/downward and roll/tilt motions when a person is eating. In an example, a wearable device on a person's wrist and/or arm can include (a circumferential array of) one or more biometric sensors which measure biometric parameters associated with food consumption. In an example, a wearable device on a person's wrist and/or arm can include (a circumferential array of) one or more spectroscopic sensors which measure biometric parameters associated with food consumption. In an example, a wearable device on a person's wrist and/or arm can include (a circumferential array of) one or more electromagnetic energy sensors which measure biometric parameters associated with food consumption.

In an example, a system for nutritional monitoring and management can include a finger-worn device (e.g. finger ring) with a camera for recording images of nearby food items. In an example, a system can include a finger-worn device (e.g. finger ring) with a spectroscopic sensor for scanning nearby food items. In an example, a system can include a finger ring with two cameras facing in different directions, wherein the two cameras collectively record images of interaction between a person's hand and nearby food; and interaction between the person's mouth and food.

In an example, a system for nutritional monitoring and management can include a device (such as a smart finger ring or finger nail attachment) which is worn on a person's finger. In an example, a finger ring can include a motion sensor which detects when a person is eating based on a series of distinctive upward/downward and roll/tilt motions. In an example, a finger ring can include a camera which takes pictures of food at different and/or selected times during upward/downward and roll/tilt motions. In an example, a finger ring can include (a circumferential array of) one or more biometric sensors which measure biometric parameters associated with food consumption. In an example, a finger ring can include (a circumferential array of) one or more spectroscopic sensors which measure biometric parameters associated with food consumption. In an example, a finger ring can include (a circumferential array of) one or more electromagnetic energy sensors which measure biometric parameters associated with food consumption.

In an example, a system for nutritional monitoring and management can include a device (e.g. earware or "hearable") which is worn in (or on) a person's ear. In an example, this device can include a smart ear ring. In an example, a smart ear ring can include a camera, a pulse oximeter, and/or a glucose sensor. In an example, this device can include an ear bud. In an example, a smart ear-worn device can encircle at least two-thirds of the perimeter of a person's outer ear. In an example, a smart ear-worn device can encircle at least two-thirds of the perimeter of a person's outer ear and have an extension (e.g. arm or prong) which extends from the perimeter of the ear onto a portion of a person's temple and/or forehead. In an example, this extension can include an electromagnetic energy sensor (such as an EEG sensor) whose data is also used by the system to: detect food consumption by a person; and/or evaluate the types and quantities of food consumed by the person.

In an example, a system for nutritional monitoring and management can include a device which is worn on (or around) a person's neck. In an example, a system can include a smart necklace and/or pendant with a camera which records images of food in front of a person and/or food near the person's mouth. In an example, a smart necklace and/or pendant can monitor movement of a person's hand up to their mouth as part of nutritional intake tracing. In an example, a system can include a smart collar, scarf, or tie which is worn around a person's neck. In an example, a smart collar, scarf, or tie can have a microphone which monitors sounds associated with eating such as chewing, swallowing, and teeth grinding sounds. In an example, a smart collar, scarf, or tie can have an electromagnetic energy sensor (such as an EMG sensor) which monitors muscle movements associated with eating. In an example, a smart collar, scarf, or tie can have a camera which records images of food in front of a person.

In an example, a system for nutritional monitoring and management can include a handheld device which is selected from the group consisting of: handheld camera; handheld electronic tablet; handheld food imaging device; handheld food probe; handheld food scanner; handheld invasive food probe; handheld non-invasive spectroscopic food scanner; handheld removable accessory for a cell phone; handheld removable attachment for a conventional food utensil; removable component of a smart watch or wrist band; smart phone component; smart phone, cell phone, and/or mobile phone; and smart utensil. In an example, a system can include a wearable device which is selected from the group consisting of: arm band, augmented reality (AR) eyewear, smart belt, bluetooth device, bracelet, brooch, smart button, collar, cuff link, dog tags, ear bud or insert, ear plug, ear ring, ear-mounted bluetooth device, smart eyeglasses, finger ring, fitness band, headband, hearing aid, intra-oral device, mobile EEG device, smart necklace, pendant, smart pants, smart shirt, smart sleeve or cuff, wearable mouth microphone, watch phone, wrist band, and wrist watch. In an example, a system can include both a wearable device component and a handheld device component.

In an example, a system for nutritional monitoring and management can include one or more wearable devices selected from the group consisting of: an adhesive sensor patch or strip which is worn directly on a person's skin; an article of smart clothing (such as clothing with embedded or integrated biometric sensors); a face-worn device other than eyewear (such as a nose ring); a head-worn circumferential device (such as a head band, hat, or cap); a head-worn half-circumferential device (such as headphones); a leg-worn device (such as an ankle band, garter, or sock); a smart pin-type button; a sweat sensor; and a torso-worn device (such as a smart belt or chest strap).

In an example, a system for nutritional monitoring and management can include an implanted device. In an example, such a system can include a pacemaker or implanted neurological sensor. In an example, such a system can include an intra-oral device, such as a smart dental fixture, retainer, device attached to palate, tongue ring, or device attached below tongue. In an example, such a system can include an implanted drug delivery device. In an example, such a system can include an implanted neurostimulation device. In an example, an implanted device can have an electromagnetic energy sensor. In an example, an implanted device can have a spectroscopic sensor.

In an example, a system for nutritional monitoring and management can include a camera which records images (e.g. takes pictures) of food. In an example, a system can include a camera which records images of food at different times (e.g. at different times during a meal). In an example, a system can include a camera which moves to record multiple still images of food from different angles and/or distances (e.g. from different locations above a meal). In an example, a camera can record videos (e.g. moving pictures) of food. In an example, recorded food images can be automatically analyzed to identify food item types and estimate food item quantities. In an example, a system can include a food-imaging camera on a handheld device. In an example, a system can include a food-imaging camera on a wearable device. In an example, a system can include a food-imaging camera on a wrist-worn device (such as a smart watch and/or smart watch band). In an example, a camera can be located on the side of a person's wrist, where the main housing of a conventional wrist watch is generally located. In an example, a camera can be located on the opposite side of a person's wrist, opposite where the main housing of a conventional wrist watch is generally located.

In an example, a system for nutritional monitoring and management can comprise a plurality of cameras which simultaneously record images of food items from different locations, angles, and/or distances. In an example, images of food items from different angles and/or distances can be integrated to create a 3D (three-dimensional, volumetric) model of the food items which is useful for identification of food item types and estimating food item quantities. In an example, a system can include a device with two cameras (e.g. stereoscopic cameras) which simultaneously record images of food items from different locations to create stereoscopic images of food items. In an example, smart eyewear can have two cameras, one on the right side of the eyewear and one on the left side of the eyewear. In an example, a smart watch can have two cameras on different sides of the watch housing or on different sides of the watch band. In an example, a system can comprise one camera which faces away from a person (e.g. toward nearby food on a table) and one camera which faces toward the person (e.g. toward the person's face and mouth).

In an example, a system for nutritional monitoring and management can have two (or more) cameras which are worn on the narrow sides of a person's wrist (between the posterior and anterior surfaces of the wrist) such that the moving field of vision of a first camera automatically encompasses the person's mouth (as the person moves their arm when they eat) and the moving field of vision of a second camera automatically encompasses nearby food items (as the person moves their arm when they eat). This design is comparable to a wrist-watch that has been rotated 90 degrees around a person's wrist, with a first camera located where the watch face would normally be and a second camera located on the opposite side of the wrist. In an example, a system can have two (or more) cameras which record images of food at different times, from different directions, and/or with different focal lengths.

In an example, a system for nutritional monitoring and management can have two cameras for recording images of food. In an example, these two cameras can point in generally the same direction. In an example, these two cameras can be stereoscopic. In an example, these two cameras can point in different (e.g. opposite) directions. In an example, fields of vision from two cameras can collectively and automatically encompass both nearby food items and a person's mouth as the person eats. In an example, fields of vision from two wrist-worn cameras can encompass both nearby food items and a person's mouth as the person moves their arm (and wrist) while eating. In an example, a system can have two cameras which are both on the same wearable device. Alternatively, a system can have two cameras which are worn on two different wearable devices. In an example, a system can include a first camera which is worn on a first body member (e.g. wrist, hand, lower arm, or finger) wherein the field of vision from the first camera automatically encompasses the person's mouth as the person eats and a second camera is worn on a second body member (e.g. neck, head, torso, or upper arm) wherein the field of vision from the second camera automatically encompasses nearby food items as the person eats. In an example, a system can include a first camera in a wearable device and a second camera in a non-wearable (e.g. handheld) device.

In an example, a system for nutritional monitoring and management can include a wide-angle camera. A wide-angle camera can automatically record images of a person's mouth, nearby food items, or both as the person moves their arm (and hand) while eating. In an example, a wide-angle camera can be worn on the anterior surface of a person's wrist (or upper arm) in a manner similar to a conventional watch or bracelet that has been rotated approximately 180 degrees. In an example, a camera can be worn on a person's finger in a manner similar to a finger ring, such that the camera automatically records images of the person's mouth, nearby food items, or both as the person moves their arm and hand while eating.

In an example, a system for nutritional monitoring and management can include two (or more) cameras on two (or more) different locations, respectively, around the circumference of a person's wrist. In an example, a system can comprise two cameras which are located on opposite sides of a person's wrist. In an example, these two cameras can be directed radially outward from the person's wrist. In an example, having cameras mounted on opposite sides of a person's wrist can increase the probability of encompassing both a person's mouth and nearby food items as the person moves their arm (and hand) to get a food item and then moves the food item up to their mouth. In an example, two cameras in different locations can generally track different things. For example, a first camera can generally track a person's hand and fingers (including interaction between the person's hand and nearby food) while a second camera can generally track the person's mouth (including interaction between the person's mouth and handheld or utensil-carried food). Tracking both types of interactions can provide more accurate estimates of actual food consumption by the person than tracking either interaction alone.

In an example, a system for nutritional monitoring and management can have two cameras (on one or more wearable devices) which move when a person eats. In an example, a system can include a wearable device with a first camera which records images along an imaging vector which generally points toward a person's mouth (when the person eats) and a second camera which records images along an imaging vector which generally points toward nearby food items (when the person eats). In an example, a system can comprise a first camera that is worn on a person's wrist, hand, arm, or finger (such that the field of vision from this camera automatically encompasses the person's mouth as the person eats) and a second camera that is worn on the person's neck, head, or torso (such that the field of vision from this camera automatically encompasses nearby food items as the person eats).

In an example, a system for nutritional monitoring and management can include two separate devices, each of which has at least one camera, wherein the separate devices simultaneously record images of nearby food items from different locations, angles, and/or distances. In an example, a system can include smart eyewear with a camera to record images of food items from a first perspective and a smart watch with a camera to record images of food items from a second perspective. In an example, a system can include smart eyewear with a camera to record images of food items from a first perspective and a smart phone with a camera to record images of food items from a second perspective. In an example, a system can include smart earware with a camera to record images of food items from a first perspective and a smart watch with a camera to record images of food items from a second perspective.

In an example, a system for nutritional monitoring and management can include a camera which automatically scans in selected directions or tracks selected objects in order to detect eating behavior and/or food items. In an example, a camera can track the location of a person's hand and/or mouth in order to detect eating behavior and/or foot items. In an example, a camera can continuously track the a person's hand and/or mouth. In an example, a camera can only be activated to track a person's hand and/or mouth when some less intrusive sensor (e.g. a motion sensor) indicates that the person is eating. In an example, a camera can track a person's hand scan near the person's hand to detect food items. In an example, a camera can track a person's hand scan near the person's hand to detect interaction between the person's hand and food items. In an example, a camera can track a person's mouth and scan near the person's mouth to detect food items. In an example, a camera can track a person's mouth and scan near the person's mouth to detect interaction between the person's mouth and food items.

In an example, a system for nutritional monitoring and management can include a camera which scans nearby space for a person's hand in order to detect and identify food items. In an example, a system can include a camera with a focal direction which points away from a person's body in order to capture interaction between the person's hand and food. In an example, a system can include a camera which records images along an imaging vector which points toward a person's mouth and/or face when the person eats. In an example, a system can use face recognition methods to adjust the direction and/or focal length of a camera in order to stay focused on a person's mouth and/or face. Face recognition methods and/or gesture recognition methods can be used to detect and measure hand-to-mouth proximity and interaction.

In an example, a system for nutritional monitoring and management can include a camera whose focal direction and/or depth is moved automatically to track a person's hand, a person's mouth, and/or nearby food items (which have been detected near a person's hand and/or mouth). In an example, the focal direction and/or depth of a camera can be changed independently of movement of a body member to which a camera is attached. In an example, a camera on a wearable device can be moved automatically to maintain a line of sight to a person's hand, person's mouth, or nearby food item despite movement of a body member to which the camera is attached. In an example, a camera lens can be moved automatically so that the camera tracks a person's hand, the person's mouth, and/or a food item. In an example, a reflective member (e.g. mirror) can be moved so that a camera tracks a person's hand, the person's mouth, and/or a food item. In an example, a system can use face recognition to track the location of a person's mouth and automatically move a camera lens and/or mirror so that the person's mouth remains in the camera's field of view. In an example, a system can use pattern recognition to track the location of nearby food and automatically move a camera lens and/or mirror so that the nearby food remains in the camera's field of view. In an example, a system can include a camera which scans nearby space in a spiral, radial, or back-and-forth pattern in order to track a person's hand, the person's mouth, and/or nearby food items. In an example, this scanning and/or tracking activity may be done only eating activity is detected by a less-intrusive sensor modality (such as a wearable motion sensor).

In an example, a system for nutritional monitoring and management can integrate video or sequential still images from a single moving camera (which is moves relative to food items) in order to create a 3D and/or volumetric model of the food items for analyzing food item types and/or quantities. In an example, a single moving camera can sequentially record images of food items from different angles and/or distances. In an example, a system can automatically move a camera relative to food items in order to capture sequential images of the food items from different angles and/or distances. In an example, a system can include a wrist-worn device (such as a "Willpower Watch") with multiple cameras which is worn on a person's arm. In an example, such a wrist-worn device can record sequential images from different locations as a person moves their arm while eating, thereby sequentially recording images of nearby food from different angles and distances as the arm moves. In an example, a first camera in such a wrist-worn device can tend to capture images of a food source (e.g. on a plate on a table) while a second camera in the device can tend to capture images of a person's mouth eating the food. A combination of images of both a food item and a person's mouth eating the food item can better determine types and quantities of food consumed than either images of a food item alone or images of the person's mouth alone.

In an example, a system for nutritional monitoring and management can prompt a person and/or guide the person concerning how to move a camera (in a selected pattern) relative to food items in order to capture images of the food items from different angles and/or distances. In an example, a system can prompt and/or guide a person how to move a mobile device (such as a smart phone) in a selected pattern relative to food items in order to record images of the food items from selected different angles and/or distances to create a 3D (three-dimensional) model of the food items. In an example, a system can prompt and/or guide a person how to move a smart watch in a selected pattern relative to food items in order to record images of the food items from different angles and/or distances. In an example, a system can prompt and/or guide a person to continue moving a device relative to food items until a sufficient variety of food images from different angles and/or distances has been collected to determine food item types and quantities with a desired level of accuracy.

In an example, a system for nutritional monitoring and management can prompt and/or guide a person how to move a device with a camera in a selected pattern relative to nearby food items. In an example, this prompting and/or guidance can be visual (e.g. through augmented reality or via a light beam projected from a device). In an example, this prompting and/or guidance can be auditory (e.g. through verbal commands or sequential changes in sounds associated with sequential movement of a device). In an example, this prompting and/or guidance can be haptic (e.g. through a sequence of vibrations indicating a sequence of movement directions). In an example, a person can be prompted and/or guided to move a device with a camera in a selected pattern relative to nearby food items, wherein this selected pattern is selected from the group consisting of: movement in circles around (or above) the food items; movement in a spiral around (or above) the food items; movement back and forth (e.g. in a zigzag or sinusoidal manner) over the food items; movement toward and away from the food items; and movement along an arcuate light path which is displayed virtually in augmented reality in the person's field of view.

In an example, a system for nutritional monitoring and management can estimate the distance from a handheld or wearable device to a food item using: an infrared light emitter and receiver, a visible light projector and image analysis, a spectroscopic sensor, a radio wave emitter and receiver, or a sound (e.g. ultrasonic) energy emitter and receiver. In an example, the distance from a handheld or wearable device to a food item can be estimated via the timing and/or angle of light reflected by the food item. In an example, the distance from a handheld or wearable device to a food item can be estimated via the timing and/or angle of radio waves reflected by the food item. In an example, the distance from a handheld or wearable device to a food item can be estimated by analyzing the shape and size of a light pattern projected onto (or near) the food item.

In an example, a mobile device can project one or more visible beams of (coherent) light toward food. In an example, a mobile device can have one or more lasers which project one or more visible beams of light toward food. In an example, beams of light projected from a device can form a pattern on (or near) a food item which helps to calibrate food images and determine food item distance, angle, size, shape, orientation, and/or quantity. In an example, a mobile device can project an oscillating (or otherwise moving) beam of light on (or near) food items, wherein the size, shape, and/or orientation of a (geometric) figure formed by this oscillating (or otherwise moving) beam of light helps to calibrate food images and determine food distance, angle, size, shape, orientation, and/or quantity. In an example, a (geometric) figure projected onto (or near) food items can be selected from the group consisting of: line, cross, triangle, circle, square, rectangle, sine wave, spiral, checkerboard, dot array, hexagonal mesh, and matrix. In an example, a mobile device can further comprise an infrared distance finder to estimate the distance from the mobile device to food items. In an example, a mobile device can further comprise a radio wave distance finder to estimate the distance from the mobile device to food items.

In an example, a system for nutritional monitoring and management can include an ambient light sensor. In an example, if there is insufficient ambient light to record a good picture of nearby food, then the system can activate a light (e.g. flash) toward food to illuminate the food so that a good picture of the food can be recorded. In an example, a system can determine whether a camera is directed toward nearby food so that the food is within the field of view of the camera. If the nearby food is not within the field of view of the camera, then a person can be notified and/or guided by the system concerning how to move the camera and/or the food so that the food is brought within the field of view of the camera. In an example, a system can determine whether a nearby food is in focus by a camera. If the food is not in focus, then a person can be notified and/or guided by the system concerning how to move the camera and/or the food so that the food is brought into focus. In an example, a device can project a light beam and/or pattern toward nearby food to help a person to move a camera and/or to move the food so that the food is brought within the field of view of the camera and brought within focus by the camera.

In an example, a system for nutritional monitoring and management can include a wearable device with one or more cameras. In an example, this wearable device with one or more cameras can be selected from the group consisting of: augmented reality (AR) eyewear, bracelet, brooch, button, collar, contact lens, cuff link, dog tag, ear ring, ear-mounted bluetooth device, eyeglasses, finger ring, fitness band, headband, mobile EEG device, necklace, pendant, shirt, sleeve or cuff, visor, watch phone, wrist band, and wrist watch.

In an example, a system for nutritional monitoring and management can include one (or more) cameras which are worn on one (or more) locations on a person from which the one (or more) cameras have a line of sight to the person's mouth and a line of sight to a nearby food item. In an example, these one (or more) cameras can simultaneously or sequentially record images along at least two different vectors, one of which points toward a person's mouth and one of which points toward a food item. In an example, a system can comprise multiple cameras that are worn on a person's wrist, hand, arm, or finger, wherein some cameras point toward the person's mouth (when the person eats) and some cameras point toward nearby food items (when the person eats). In an example, a system can comprise one (or more) cameras that record images of interaction (e.g. biting, chewing, or swallowing) between a person's mouth and food. In an example, a system can comprise one (or more) cameras which collectively and automatically record images of a person's mouth when the person eats and record images of nearby food items when the person eats. In an example, these images can be automatically analyzed to estimate types and quantities of food consumed by the person.

In an example, a commonly-available object (e.g. a coin, dollar bill, credit card, die, paper clip, or ruler) of known size (and color) can be placed near food to serve as a fiducial marker in a food image for calibration of food size (and color) in image analysis. In an example, a (second) mobile device (such as a second smart phone) displaying an image of known size and colors can be placed near food to serve as a fiducial marker in the image for calibration of food size (and color) in image analysis. In an example, technical details of the display hardware of a particular type and/or brand of mobile device can also be considered in the calibration of food images. In an example, a mobile or wearable device can project one or more (coherent) light beams toward food and the resulting light beam pattern can serve as a fiducial marker in the image for calibration of food size (and color) in image analysis. In an example, one or more projected light beams can form a projected geometric shape on (or near) food. In an example, the size, shape, and/or orientation of this projected geometric shape on (or near) food can be used to help determine (e.g. calibrate) the distance, size, shape, orientation, and volume of the food.

In an example, a system for nutritional monitoring and management can include a light projector which light beams toward food. In an example, the light beams can be coherent. In an example, the light projector can be a laser. In an example, projected beams of light can form a geometric pattern on (or near) food items. In an example, a projected pattern of light can serve as a fiducial marker to estimate and/or calibrate food item distance, food item size, food item orientation, and/or food item color. In an example, a projected pattern of light can be selected from the group consisting of: a single line; a plurality of parallel lines; two intersecting lines; a grid of intersecting lines; a checkerboard pattern; a square; a hexagon; a circle; an array of concentric circles; and a (different type of) conic section.

In an example, a system for nutritional monitoring and management can include a light projector which projects a pattern of light onto food (or a surface within 12 inches of the food). In an example, the light pattern can serve as fiducial marker to calibrate and/or determine the size and/or quantity of the food. In an example, this light pattern can serve as fiducial marker to calibrate and/or determine the color of the food. In an example, a light projector can include one or more LEDs. In an example, a light projector can include one or more lasers. In an example, a light projector can project a pattern of coherent light onto food. In an example, a system can comprise a laser which projects coherent light beams onto nearby food (or on a surface near the food), wherein these light beams comprise a fiducial marker which helps to calibrate and/or measure the food scale, size, shape, volume, quantity, and/or color. In an example, a light projector can emit ultraviolet light or infrared light. In an example, a light projector can project collimated light. In an example, a projected light pattern can be used to link different locations on a food image with the results of spectroscopic scans at those different locations.

In an example, a system can project a circular pattern or ring of light onto food and/or a surface near food. In an example, a circle or ring of light can be a circle or ring of points (or dots) of light. In an example, a circle or ring of light can be a continuous circle or ring of light, such as is produced when a projecting member is rotated. In an example, a circle or ring of light can be a continuous circle or ring of light, such as is produced by a rotating micromirror onto which a beam of light is directed. In an example, the angle of the food or the surface on which the food is resting can be estimated by the degree of distortion of the circle or ring. If the food is imaged from directly above the food (or surface), then the projected light pattern is a circle, but if the food is imaged from an angle then it will be an ellipse. The angle of imaging can be determined by the compression of the observed ellipse. In an example, the light pattern projector can project a convex light pattern onto food or surfaces near the food.

In an example, a system can project a linear pattern of light onto food and/or a surface near food. In an example, a light pattern projector can project a polygonal light pattern onto food and/or a surface near food. In an example, a light pattern projector can project an array of three points of light onto food or a surface near the food. In an example, a light pattern projector can project a triangular light pattern onto food or a surface near food. In an example, a light pattern projector can project a matrix or grid of light onto food or a surface near food. In an example, a light pattern projector can project a matrix or grid of points (or dots) of light onto food or a surface near food. In an example, a light pattern projector can project an orthogonal light grid onto food. In an example, a light pattern projector can project a two-dimensional array of points of light onto or near food.

In an example, a light pattern which is projected from a projector can be moved across the surface of food by one or more moving micro-mirrors and/or lenses. In an example, an array of moving micromirrors or lenses can move a beam of light across food (or a surface near food) in order to create a pattern or configuration of light. In an example, an array of moving micromirrors or lenses can move a beam of light across food (or a surface near food) in order to create a line of light on the food. In an example, an array of moving micromirrors or lenses can move a beam of light across food (or a surface near food) in order to create a ring or other arcuate configuration of light on the food. In an example, an array of moving micromirrors or lenses can move a beam of light across food (or a surface near food) in order to create a grid or matrix of light on the food.

In an example, a system for nutritional monitoring and management can identify types of food items and/or their nutritional composition via spectroscopy. In an example, types of food, ingredients, and/or nutrients can be identified by the spectral patterns of light which has been reflected from (absorbed by) food at different wavelengths. In an example, an optical sensor can emit and/or detect white light, infrared light, or ultraviolet light. In an example, a system can include a spectroscopic sensor which is selected from the group consisting of: ambient light spectroscopic sensor, backscattering spectrometry sensor, coherent light spectroscopic sensor, infrared spectroscopic sensor, ion mobility spectroscopic sensor, mass spectrometry sensor, near-infrared spectroscopic sensor, Raman spectroscopic sensor, spectral measurement sensor, spectrometry sensor, spectrophotometer, ultraviolet spectroscopic sensor, visible light spectroscopic sensor, and white light spectroscopic sensor.

In an example, a system for nutritional monitoring and management can include a spectroscopic sensor (or, using the noun form as a modifier, a "spectroscopy sensor"). In an example, a spectroscopic sensor can collect data to identify a food item type by projecting light beams toward the food item and receiving those light beams after they have interacted with (e.g. passed through or been reflected by) the food item. In an example, changes in the spectral distribution of the light beams caused by interaction with a food item can be analyzed in order to identify food item type. In an example, a spectroscopic sensor can collect data concerning the nutritional composition and/or molecular composition of a food item by projecting light beams toward the food item and receiving those light beams after they have interacted with (e.g. passed through or been reflected by) the food item. In an example, changes in the spectral distribution of the light beams caused by interaction with a food item can be analyzed in order to estimate the nutritional and/or molecular composition of the food item.

In an example, a system for nutritional monitoring and management can include a wearable device with a spectroscopic sensor which collects data concerning a person's biometric parameters by projecting light beams toward the person's body and receiving those light beams after they have interacted with (e.g. passed through or been reflected by) body tissue. In example, changes in the spectral distribution of the light beams caused by interaction with body tissue can be analyzed in order to estimate biometric parameters. In an example, a wearable device can have a spectroscopic sensor which collects data concerning the molecular composition of body tissue by projecting light beams toward a person's body and receiving those light beams after they have interacted with (e.g. passed through or been reflected by) body tissue. In example, changes in the spectral distribution of the light beams caused by interaction with body tissue can be analyzed in order to estimate the molecular composition of the body tissue.

In an example, a system for nutritional monitoring and management can have a light receiver which collects data concerning light reflected from food items at two different times, wherein a light emitter which directs light beams toward food items is turned on at a first point in time but is turned off at a second point in time. In an example, during the first point in time, the light receiver receives a combination of light from the light emitter and ambient light which has been reflected by (or passed through) the food items. However, during the second point in time, the light receiver only receives ambient light which has been reflected by (or passed through) the food items. In an example, analyzing differences in light received by the receiver at these two different points in time can help to control for the effects of variation in ambient light on spectroscopic analysis of food. In an example, analyzing light reflected by (or passed through) the food items at these two different times can control for the effects of variation in ambient light on spectroscopic analysis of food. In an example, analyzing light received by the light receiver at these two different times can isolate interaction between food items and light beams from the light emitter vs. interaction between food items and ambient light.

In an example, a system for nutritional monitoring and management can have a light receiver which collects data concerning light reflected from body tissue at two different times, wherein a light emitter which directs light beams toward body tissue is turned on at a first point in time but is turned off at a second point in time. In an example, during the first point in time, the light receiver receives a combination of light from the light emitter and ambient light which has been reflected by (or passed through) the body tissue. However, during the second point in time, the light receiver only receives ambient light which has been reflected by (or passed through) the body tissue. In an example, analyzing differences in light received by the receiver at these two different points in time can help to control for the effects of variation in ambient light on spectroscopic analysis of biometric parameters. In an example, analyzing light reflected by (or passed through) the body tissue at these two different times can control for the effects of variation in ambient light on spectroscopic analysis of biometric parameters. In an example, analyzing light received by the light receiver at these two different times can isolate interaction between body tissue and light beams from the light emitter vs. interaction between body tissue and ambient light.

In an example, a system for nutritional monitoring and management can have a wearable or handheld device with an spectroscopic sensor which has a light receiver, but no light emitter. In an example, a light receiver can receive ambient light after that ambient light has been reflected from a food item. In an example, a system can have a first light receiver which receives ambient light directly from an environmental source and a second light receiver which receives ambient light after that light has been reflected from a food item. In an example, differences between the spectra of light received by the first and second light receivers can be analyzed to determine food item type, nutritional composition, and/or molecular composition. In an example, a system can reflect, redirect, and/or focus ambient light toward food instead of using a light emitter. In an example, a system can have a mirror or lens which is adjusted in order to reflect or direct sunlight (or other ambient light) toward food. In an example, reflection of ambient light from the food can be analyzed in order to identify food type and/or estimate food composition.

In an example, a system for nutritional monitoring and management can have an optical sensor. In an example, an optical sensor can measure ambient light level. In an example, an optical sensor can be a chromatographic sensor, spectrographic sensor, analytical chromatographic sensor, liquid chromatographic sensor, gas chromatographic sensor, optoelectronic sensor, photochemical sensor, and photocell. In an example, an optical sensor can collect data concerning modulation of light wave parameters by the interaction of that light with food. In an example, an optical sensor can detect modulation of light reflected from, or absorbed by, a receptor when the receptor is exposed to food. In an example, an optical sensor can collect data concerning wavelength spectra of light reflected from, or absorbed by, food. In an example, an optical sensor can emit and/or detect white light, infrared light, or ultraviolet light. In an example, an optical sensor can detect ambient light before and after interaction of the ambient light with food. In an example, changes in ambient light before vs. after interaction with food can be analyzed to identify food type and/or nutritional composition.

In an example, a system for nutritional monitoring and management can include a spectroscopic sensor which collects data to identify types of foods, ingredients, nutrients, and/or chemicals by being in optical communication with food items without actually touching the food items. In an example, light beams with different wavelengths can be reflected off (or absorbed by) food items and the results can be analyzed using spectral analysis. Selected types of foods, ingredients, nutrients, and/or chemicals can be identified by the spectral distributions of light which are reflected from, or absorbed by, food items at different wavelengths. In an example, reflection of light from the surface of the food items changes the spectrum of light, wherein these changes are measured by a spectroscopic sensor in order to estimate the nutritional and/or chemical composition of the food. In an example, the passing light through food items changes the spectrum of light, wherein these changes are measured by a spectroscopic sensor in order to estimate the nutritional and/or chemical composition of the food items.

In an example, a system for nutritional monitoring and management can include a wearable device with an spectroscopic sensor which has a light receiver, but no light emitter. In an example, a light receiver can receive ambient light after that ambient light has been reflected from body tissue. In an example, a system can have a first light receiver which receives ambient light directly from an environmental source and a second light receiver which receives ambient light after that light has been reflected from body tissue. In an example, differences between the spectra of light received by the first and second light receivers can be analyzed to determine biometric parameters. In an example, a system can reflect, redirect, and/or focus ambient light toward body tissue instead of using a light emitter. In an example, a system can have a mirror or lens which is adjusted in order to reflect or direct sunlight (or other ambient light) toward body tissue. In an example, reflection of ambient light from the body tissue can be analyzed in order to measure biometric parameters.

In an example, a system for nutritional monitoring and management can include a wearable or handheld device with one or more spectroscopic sensors which collect data concerning the effects of interaction between light energy and food. In an example, a spectroscopic sensor can collects data concerning changes in the spectrum of light energy caused by reflection from (or passage through) food items. In an example, a spectroscopic sensor can collect data concerning light reflection spectra, absorption spectra, or emission spectra. In an example, a spectroscopic sensor can collect data which is used to analyze the chemical composition of food by measuring the degree of reflection or absorption of light by food at different light wavelengths.

In an example, a system for nutritional monitoring and management can comprise one or more spectroscopic sensors which analyze light which has been passed through and/or reflected by food items. In an example, a spectroscopic sensor can comprise a light emitter and a light receiver, wherein the light receiver receives light which has passed through and/or been reflected by a food item. In an example, changes in the spectrum of light caused by interaction with food (e.g. by transmission through or reflection by food) can be analyzed to estimate the nutritional and/or molecular composition of the food. In an example, transmission and/or reflection spectra of different food items can be analyzed to identify these food items and/or to estimate their compositions. In an example, modification of spectral distributions of light by food items can be compared to spectral distributions in a database of such spectral distributions to help identify food and the composition of ingredients/nutrients therein. In an example, a spectroscopic sensor can be selected from the group consisting of: atomic absorption spectrometer, diffusion spectroscopic sensor, emission spectroscopic sensor, fluorescence spectroscopic sensor, gas chromatography sensor, infrared absorption spectrometer, infrared reflectance spectrometer, mass spectrometer, mass spectrometry sensor, near-infrared spectroscopic sensor, photodiode array spectrophotometer, Raman spectroscopy sensor, spectrometer, spectrophotometer, and ultra-violet reflectance spectrometer.

In an example, a spectroscopic sensor can have one or more light emitters selected from the group consisting of: Light Emitting Diode (LED), laser, and tunable laser. In an example, a spectroscopic sensor can comprise a plurality of light emitters which emit light beams of different colors and/or different wavelengths. In an example, a spectroscopic sensor can comprise a plurality of light emitters which emit light at different times. In an example, a spectroscopic sensor can comprise a plurality of light emitters which emit light from different locations on a device. In example, a system can comprise a wearable device with a circumferential array (e.g. a ring) of spectroscopic sensors around the circumference of a person's wrist, arm, or finger. In an example, one or more light emitters can emit light in a wavelength range selected from the group consisting of: far infrared, infrared, near infrared, ultraviolet, and visible. In an example, a spectroscopic sensor can use ambient light which has passed through and/or been reflected by a food item. In an example, spectroscopic readings can be taken when a light emitter is on and when the light emitter is off in order to isolate the effects of ambient light and more precisely measure the spectroscopic effects of interaction between light from a light emitter and food items. In an example, one or more light receivers can be selected from the group consisting of: charge coupled device (CCD), complementary metal oxide semiconductor (CMOS), detector array, photo transistor, photodetector, photodiode, and photosensor array.

In an example, a spectroscopic sensor can comprise components selected from the group consisting of: aperture; beam splitter; coaxial light emitter and light receiver; diffraction grating; lens (e.g. spherical, aspheric, biconvex, Fresnel lens, Carlavian lens, microlens array, plano-convex); light emitter; light receiver; mirror (e.g. Digital Micromirror Device, parabolic reflector, Quasi Fresnel Reflector, mirror array); opaque light shield; optical fiber; and optical filter (e.g. Fabry-Perot, tunable, acousto-optic, liquid crystal, cascaded, interference).

In an example, a system for nutritional monitoring and management can comprise: a camera that records images of nearby food; an optical sensor (e.g. a spectroscopic sensor) which collects data concerning light that is reflected from (or passed through) this food; an attachment mechanism (e.g. a wrist band); and a data processing unit which analyzes images. In an example, a system can comprise: a camera which records images of food items, wherein these food images are automatically analyzed to identify food item types and quantities; an optical sensor which collects data concerning light that has been reflected by (or transmitted through) the food items, wherein this data is automatically analyzed to identify the types of food, the types of ingredients in the food, and/or the types of nutrients in the food; one or more attachment mechanisms which hold the camera and the spectroscopic sensor in close proximity to a person's body; a data processing unit which analyzes images; and a computer-to-human interface which provides feedback to the person concerning the person's nutritional intake.

In an example, a system for nutritional monitoring and management can include a spectroscopic sensor with a light emitter which emits near infrared light. In an example, a spectroscopic sensor can include a light emitter which emits infrared light. In an example, a spectroscopic sensor can include a light emitter which emits ultraviolet light. In an example, a spectroscopic sensor can include a light emitter which emits light with a wavelength in the range of 400 to 700 nanometers. In an example, emitted light can have a wavelength in the range of 300 to 1200 nanometers. In an example, a spectroscopic sensor can include a light energy receiver which is particularly receptive to near-infrared, infrared, or ultraviolet light. In an example, a system can comprise one or more spectroscopic sensors selected from the group consisting of: near-infrared spectroscopic sensor; infrared spectroscopic sensor; white light spectroscopic sensor; and ultraviolet spectroscopic sensor. In an example, one or more light emitters can be selected from the group consisting of: white LED, blue LED, red LED, infrared LED, and green LED.

In an example, a system for nutritional monitoring and management can comprise: a finger ring, wherein this finger ring has an interior surface which faces toward the surface of a person's finger, wherein this finger ring has a central proximal-to-distal axis which is defined as the straight line which most closely fits a proximal-to-distal series of centroids of cross-sections of the interior surface, and wherein proximal is defined as being closer to the person's elbow and distal is defined as being further from the person's elbow; a light projector which projects a beam of light along a proximal-to-distal vector toward a food item, wherein this vector, or a virtual extension of this vector, is either parallel to the central proximal-to-distal axis or intersects a line which is parallel to the central proximal-to-distal axis forming a distally-opening angle whose absolute value is less than 45 degrees; and a spectroscopic sensor which collects data concerning the spectrum of light which has been reflected from, or has passed through, the food item, and wherein data from the spectroscopic sensor is used to analyze the composition of this food.

In an example, a system for nutritional monitoring and management can comprise: a handheld food probe with a spectroscopic sensor which collects data concerning light which has been reflected from (or passed through) a food item, wherein this data is used to analyze the nutritional and/or chemical composition of the food item; a camera which records images of the food item; and a light projector which projects a light pattern near (or on) the food, wherein the projected light pattern serves as a fiducial market to estimate and/or calibrate the size and/or color of the food.

In an example, a system for nutritional monitoring and management can have a spectroscopic sensor with an array of light emitters and an array of light receivers. In an example, a spectroscopic sensor can include one light emitter and two light receivers. In an example, a spectroscopic sensor can include two light emitters and one light receiver. In an example, a spectroscopic sensor can include a plurality of light emitters at different locations. In an example, a spectroscopic sensor can have a two-dimensional arcuate array with at least one light emitter and at least one light receiver. In an example, a spectroscopic sensor can have a three-dimensional array of light emitters and receivers. In an example, a spectroscopic sensor can have a plurality of light emitters and receivers in a three-dimensional matrix or grid. In an example, a spectroscopic sensor can have a plurality of light emitters which emit light at different angles.

In an example, a system for nutritional monitoring and management can include a spectroscopic sensor having a circular or annular array with at least one light emitter and at least one light receiver. In an example, a spectroscopic sensor can have a ring of light emitters and receivers. In an example, a spectroscopic sensor can have a plurality of light emitters in a ring or circle around a light receiver. In an example, a spectroscopic sensor can have at least one light emitter and at least one light receiver in a concentric configuration. In an example, a spectroscopic sensor can have a plurality of light emitters in a polygonal configuration around a light receiver. In an example, a spectroscopic sensor can have a polygonal array with at least one light emitter and at least one light receiver.

In an example, a system for nutritional monitoring and management can include a handheld device with a spectroscopic sensor which located at the distal end of the handheld device. In an example, the proximal end of the handheld device can be held by a person's hand and the distal end can be pointed toward a food item in order to take a spectroscopic scan of the food item. In an example, a spectroscopic sensor comprising a light emitter and a light receiver can be located at the distal end of a handheld device. In an example, a light emitter can emit a beam of light toward food from the distal end of a handheld device. In an example, a central vector of this emitted beam of light can be substantially parallel to the proximal-to-distal axis of the handheld device.

In an example, a system for nutritional monitoring and management can include a spectroscopic sensor with an optical filter. In an example, a spectroscopic sensor can include a two-dimensional array of optical filters. In an example, a spectroscopic sensor can have one or more optical filters selected from the group consisting of: optical absorption filter; acousto-optic filter; Bragg filter; cascaded filter; dielectric thin-film filter; Fabry-Perot filter; hybrid filter; and optical interference filter. In an example, a system can include a spectroscopic sensor with an optical diffuser. In an example, a spectroscopic sensor can include a two-dimensional lens array. In an example, a spectroscopic sensor can include a three-dimensional lens array. In an example, a spectroscopic sensor can have a moving mirror. In an example, a spectroscopic sensor can have a moving micromirror array.

In an example, a system for nutritional monitoring and management can comprise one or more actuators which change the focal direction and/or distance of a spectroscopic sensor. In an example, a system can comprise one or more actuators which move the focal direction and/or distance of a spectroscopic sensor back and forth across the surface of nearby food. In an example, a system can comprise one or more actuators which move the focal direction and/or distance of a spectroscopic sensor in an arcuate pattern over the surface of nearby food. In an example, a system can include a visible light beam which is moved in tandem with (e.g. aligned with) the focal direction of a spectroscopic sensor so that the location on a meal or a food item which is targeted for spectroscopic scanning at a given time can be identified in a food image. In this manner, information concerning food item type and/or quantity from food image analysis at a particular location (on a meal or food item) at a given time can be linked with information concerning foot item type and/or composition from spectroscopic analysis of that particular location at a given time.

In an example, a system for nutritional monitoring and management can have a spectroscopic sensor with a plurality of light emitters which emit light in different wavelength ranges. In an example, a spectroscopic sensor can have a plurality of light emitters which emit light at different frequencies and/or wavelengths. In an example, a system can have a plurality of spectroscopic sensors which sequentially emit light at different frequencies. In an example, a system can have a plurality of spectroscopic sensors which simultaneously emit light at different frequencies. In an example, the operation of a spectroscopic sensor can include frequency-based modulation.

In an example, a system for nutritional monitoring and management can include a spectroscopic sensor which emits light at different frequencies at different times. In an example, a system can comprise a spectroscopic sensor which emits a sequence of light beams at different frequencies. In an example, a light emitter can emit light with scanning variation in frequencies and/or wavelength. In an example, a light emitter can emit light in a sweeping series of frequencies. In an example, a light emitter sensor can emit light in a sequentially-varying range of frequencies. In an example, a light emitter can emit light with a frequency which changes over time. In an example, a light emitter can emit light in a sweeping series of wavelengths. In an example, a light emitter can emit light in a sequentially-varying range of wavelengths. In an example, a light emitter can emit light with a wavelength which changes over time.

In an example, a system for nutritional monitoring and management can include a spectroscopic sensor with a plurality of light emitters which emit light at different times. In an example, a spectroscopic sensor can have an array of light emitters which emit light pulses at different times. In an example, a spectroscopic sensor can have a linear array of light emitters which emit light pulses at different times. In an example, a spectroscopic sensor can have an annular array of light emitters which emit light pulses at different times. In an example, a spectroscopic sensor can have a plurality of light emitters which are selectively and sequentially activated. In an example, a plurality of light emitters can be selectively and sequentially activated via time-based multiplexing. In an example, a spectroscopic sensor can operate with time-based multiplexing.

In an example, a system for nutritional monitoring and management can have a spectroscopic sensor with a moveable cover or lid. In an example, the moveable cover or lid can open when the sensor is a first distance from food and close when the sensor is a second distance from food. In an example, a cover or lid for a spectroscopic sensor can open when the sensor is close enough to food to record an accurate spectroscopic scan, but can close if the spectroscopic sensor is so close to the food that it could actually touch the food. This can help to ensure sufficient closeness to food to get an accurate spectroscopic scan, but avoid smearing food on the surface of the sensor. In an example, a distance range during which a cover or lid automatically opens can be close enough that a high proportion of light entering the sensor has been reflected from the surface of nearby food, but not so close that food actually touches the sensor. In an example, a cover or lid can be automatically opened and the sensor can be activated to emit and receive beams of light at a distance from food which is greater than X and less than Y. In an example, X can be between 1 and 200 microns, while Y can be between 5 and 500 microns. In an example, X can be between 1/10th of an inch and 1 inch, while Y can be between 1/4 of an inch and 3 inches. In an example, a cover or lid on a spectroscopic sensor can close automatically when it gets too close to food. This can prevent the sensor from being smeared with food.

In an example, a system for nutritional monitoring and management can suggest a plurality of locations for spectroscopic analysis of a food item and/or food items in a meal. In an example, a system can guide a person concerning where the person should take a plurality of spectroscopic scans of a food item and/or food items in a meal. In an example, the number and/or breadth of locations suggested by a system for spectroscopic scans of food items can depend on the homogeneity and/or variability of food items and/or a meal. In an example, a larger number and/or broader area of spectroscopic scans can be suggested by a system for food items and/or meals which are less homogeneous and/or have greater apparent compositional variability. In an example, a smaller number and/or narrower area of spectroscopic scans can be suggested by a system for food items and/or meals which are more homogeneous and/or have less apparent compositional variability.

In an example, a system for nutritional monitoring and management can analyze food images from a camera to evaluate the apparent uniformity or homogeneity of food items. In an example, food images from a camera can be analyzed to automatically direct locations on the food where a person should direct spectroscopic scans of the food. In an example, food images from a camera can be analyzed to direct a light projector to shine on food. In an example, a system can guide a person concerning where to take spectroscopic scans of the food (e.g. based on inter-portion and intra-portion food variability). In an example, food images from a camera can be analyzed to suggest locations on the food where a person should take spectroscopic scans of the food.

In an example, a system for nutritional monitoring and management can suggest different numbers or locations of spectroscopic scans of food items, depending on intra-portion food homogeneity and/or inter-portion food homogeneity. In an example, the number or locations suggested by a system for spectroscopic scans of food items can depend on intra-portion food variation and/or inter-portion food variation. Analysis of food uniformity or homogeneity can include inter-portion variation (e.g. differences in food type between different portions of food in a meal) and intra-portion variation (e.g. differences in ingredients between different parts in a portion of one type of food). In an example, analysis of inter-portion and intra-portion food variability can inform the number and locations of suggested spectroscopic scans for a meal. In an example, a larger number of spectroscopic scans and/or scans over a wider range of locations can be suggested for meals with greater inter-portion and/or intra-portion variability. In an example, a smaller number of spectroscopic scans and/or scans over a narrower range of locations can be suggested for meals with greater inter-portion and/or intra-portion variability.

In an example, a system for nutritional monitoring and management can include a light projector which projects a light beam which is moved to (sequentially) highlight different portions (types) of food in a meal or on a dish, which can then be linked to sequential spectroscopic analysis of the chemical composition of those different portions (types) of food. In an example, food images from a camera can be analyzed to suggest different locations in a meal where a person should take spectroscopic scans. In an example, food images from a camera can be analyzed to direct a light projector so as to guide a user where to take spectroscopic scans of the food (e.g. based on inter-portion and intra-portion food variability).

In an example, a system for nutritional monitoring and management can analyze the degree of uniformity and/or homogeneity of food items and use the results to suggest a number and/or selected set of locations for spectroscopic scans of the food items. When a food item (or meal) is less-uniform or less-homogenous, then a larger number and wider range of spectroscopic scans can be required for identification and quantification of foods, ingredients, and/or nutrients. When a food item (or meal) is more-uniform or more-homogenous, then a smaller number and narrower range of spectroscopic scans can be required for identification and quantification of foods, ingredients, and/or nutrients. In an example, a system can show a person where spectroscopic scans should be made by sequentially projecting a light pattern onto different locations on food (like a three-dimensional cursor). In an example, the results of spectroscopic scans at selected locations can be linked to pattern analysis of food images for assessing inter-portion and intra-portion variation in the molecular composition of food.

In an example, a system for nutritional monitoring and management can further comprise one or more wearable or implanted devices which collect biometric information concerning a person whose nutritional intake is being monitored and managed. In an example, a wearable device which is part of the system can be selected from group consisting of: smart watch (e.g. smart watch housing or band), wrist-worn fitness band or bracelet, arm band, smart eyewear (e.g. smart eyeglasses, AR eyewear, EEG eyewear), smart earware (e.g. ear buds, ear pod), smart clothing, smart adhesive patch, continuous glucose monitor, head band and/or mobile EEG band, sweat sensor, and intra-oral device (e.g. dental implant, retainer, upper palate attachment, tongue piercing). In an example, an implanted device which is part of the system can be selected from the group consisting of: cardiac rhythm device (e.g. pacemaker), implanted neurostimulator, implanted drug delivery device, and smart stent.

In an example, a system for nutritional monitoring and management can monitor and respond to changes in a person's body glucose level and/or body oxygen level. In an example, a system can monitor and respond to changes in a person's blood pressure and/or heart rate. In an example, a system can monitor and respond to changes in photoplethysmographic (PPG) data and/or ballistocardiographic (BCG) data. In an example, a system can monitor and respond to changes in a person's body temperature and/or respiration rate. In an example, a system can include a biometric sensor which measures one or more biometric parameters selected from the group consisting of blood pressure, body glucose level, body temperature, heart rate, lactic acid level, and body oxygen level. In an example, a system can be in electromagnetic communication with a biometric sensor device which measures one or more of these biometric parameters.

In an example, system with a spectroscopic sensor and a wearable device which measures heart rate, rhythm, and/or rate variability can together comprise an integrated system for food identification and quantification. In an example, when a wearable device detects changes in a person's heart rate, rhythm, and/or rate variation which indicates that the person is eating, then the system can prompt the person to scan food using a spectroscopic sensor. In an example, a mobile device with a camera and a wearable device which measures heart rate, rhythm, and/or rate variability can together comprise a system for food identification and quantification. In an example, when a wearable device detects changes in a person's heart rate, rhythm, and/or rate variation which indicates that the person is eating, then the system can prompt the person to take pictures of the food using the camera.

In an example, a system for nutritional monitoring and management can monitor and respond to changes in a person's electrocardiographic (ECG) data, electromyographic (EMG) data, and/or electroencephalographic (EEG) data. In an example, a system can monitor and respond to changes in a person's body pH level and/or lactic acid level. In an example, a system can monitor and respond to changes in a person's body chemistry. In an example, a system can monitor and respond to changes in a person's galvanic skin response. In an example, a system can track and respond to a person's eye movements.

In an example, changes in one or more (of the above discussed) biometric parameters can trigger actions by the system. In an example, changes in one or more (of the above discussed) biometric parameters which indicate that a person is probably eating can trigger actions by the system. In an example, actions triggered by the system in response to a person eating can be selected from the group consisting of: automatically recording images to record images of nearby food items (which are being consumed); prompting a person to record images of nearby food items (which are being consumed); automatically increasing the level or types of sensor activity to more accurately collect information to determine types and quantities of nearby food items (which are being consumed); and prompting a person to provide additional user information (e.g. verbal descriptions) concerning nearby food items (which are being consumed).

In an example, a system for nutritional monitoring and management can analyze changes in one or more biometric parameters to identify relationships between the consumption of specific types and/or quantities of food by a person and subsequent health effects or health status concerning that person. In an example, a system can identify relationships between consumption of specific types and/or quantities of food by a person and subsequent changes in the person's blood glucose levels. In an example, a system can identify relationships between consumption of specific types and/or quantities of food by a person and subsequent changes in the person's self-reported wellness status and/or energy level. In an example, a system can identify food allergies, intolerances, or diseases related to consumption of specific types of food. In an example, relationships identified between consumption of specific types and/or quantities of food by a person and subsequent changes in the person's biometric parameters can be used by a system in personalized future recommendations that this person consume more of a first type of food and/or recommend that this person consume less (or none) of a second type of food.

In an example, a system for nutritional monitoring and management can investigate, identify, track, and respond to correlations between consumption of specific types and/or quantities of food by a person and subsequent biometric parameters and/or health effects concerning that person. In an example, a system can track correlations between consumption of (selected) foods and subsequent self-reported well-being of that person. In an example, a system can track correlations between consumption of (selected) foods and subsequent blood pressure levels of that person. In an example, a system can track correlations between consumption of (selected) foods and subsequent blood glucose levels of that person. In an example, a system can track correlations between consumption of (selected) foods and subsequent blood flow of that person. In an example, a system can track correlations between eating selected types of food and subsequent illness in order to identify food allergies, food intolerances, and/or diseases. In an example, causal associations between consumption of specific types of food and subsequent changes in one or more biometric parameters can be identified and used by the system to make food consumption recommendations. In an example, causal associations between consumption of specific types of food and subsequent changes in one or more of these biometric parameters can be identified and used to refine future measurements of food types and/or quantities by the system.

In an example, the effects of consumption of specific types of food on one or more biometric parameters can be analyzed. In an example, causal associations between consumption of specific types of food and subsequent changes in one or more of these biometric parameters can be identified and used to make food consumption recommendations. In an example, causal associations between consumption of specific types of food and subsequent changes in one or more biometric parameters can be identified for a specific person and used to refine future measurements of food types and/or quantities for that person.

In an example, a system for nutritional monitoring and management can include a lower-level eating-related sensor and a higher-level eating-related sensor. In an example, the lower-level eating-related sensor can be relatively accurate in detecting that a person is eating, be relatively non-intrusive with respect to privacy, and/or have relatively low power consumption, but not be very accurate in identifying specific food types and/or estimating food quantities. In an example, the higher-level eating-related sensor can be relatively accurate in identifying specific food types and/or estimating food quantities, but can be relatively non-intrusive with respect to privacy and/or have relatively high power consumption. In an example, a system can activate and/or trigger operation of the higher-level eating-related sensor when the lower-level eating-related sensor detects that a person is eating. In an example, a lower-level eating-related sensor can be selected from the group consisting of: wearable motion sensor; motion sensor which is part of a smart utensil; wearable microphone; wearable EMG sensor; wearable EEG sensor, and wearable camera. In an example, a higher-level eating-related sensor can be selected from the group consisting of: wearable camera; wearable spectroscopic sensor; handheld camera; and handheld spectroscopic sensor.

In an example, a system for nutritional monitoring and management can continuously monitor eating via a "level 1" sensor, but only activate a "level 2" sensor when eating is detected. In an example, a "level 1" sensor can be less intrusive with respect to a person's privacy, but also less accurate with respect to determining food item types and quantities. In an example, a "level 2" sensor can be more intrusive with respect to a person's privacy, but also more accurate with respect to determining food item types and quantities. In an example, a "level 1" sensor can be a motion sensor and a "level 2" sensor can be a camera. In an example, a "level 1" sensor can be a motion sensor and a "level 2" sensor can be a microphone. In an example, a "level 1" sensor can be a motion sensor and a "level 2" sensor can be an electromagnetic energy sensor.

In an example, a system for nutritional monitoring and management can include a camera which is aimed toward a person's hand, the person's mouth, or a food item in order to record an image of a food item which the person reaches for, grasps, and/or holds. In an example, a system can use gesture recognition to track a person's hand or use face recognition to track a person's mouth. In an example, the focal direction and/or imaging vector of a camera can be automatically adjusted so that the camera stays focused on a hand, mouth, or food item. In an example, if the line of sight from a camera to one of these objects is obscured, then the system can monitor the last known location of the object and/or extrapolate expected movement of the object to a new location in order regain a line of sight to the object.

In an example, a system for nutritional monitoring and management can include a wearable device with a camera, wherein the device is worn like a watch, worn like a necklace, worn on clothing (like a button), worn like a finger ring, or worn like an ear ring. In an example, the focal direction and/or distance of a camera can adjusted in real time to record images of food, but minimizing privacy-intruding images of people or other objects. In an example, a camera can be kept oriented toward a person's hand so that nearby people are generally not in focus in images. In an example, face recognition and/or pattern recognition can be used to automatically blur privacy-intruding portions of an image such as other people's faces. In an example, the focal range of a camera can be adjusted in real time to automatically blur privacy-intruding portions of an image such as other people's faces.

In an example, a system for nutritional monitoring and management can record food images in an intermittent, periodic, or random manner which does not requiring voluntary actions by the person associated with particular eating events other than the actions of eating. In an example, a system can record food images which one or more sensors indicate that a person is eating. In an example, these sensors can be motion sensors, sound sensors, and/or electromagnetic energy sensors.

In an example, a system for nutritional monitoring and management can include a camera which takes pictures of food and/or records images of food. In an example, a system can include a camera which automatically records images of food when the system detects that a person is probably eating. In an example, a system can include a camera which automatically records images of food when the system detects food nearby. In an example, a system can include two cameras which record stereoscopic images of food for three-dimensional analysis of the food. In an example, a system can include a barcode and/or QR code reader. In an example, a system can include optical character recognition capability. In an example, a system can include food-associated logo recognition capability.

In an example, a system for nutritional monitoring and management can analyze food items using spectroscopic analysis in a targeted manner, searching for one or more specific substances of interest. In an example, a person can be allergic to a specific type of food or a specific substance which may be in food. In an example, there may be reason to believe that food may have been adulterated with a specific substance. In an example, a system can focus in-depth spectroscopic analysis within a specific spectral range to more accurately search for a selected substance.

In an example, a system for nutritional monitoring and management can include a spectroscopic sensor which collects data which is used to determine food item types and/or quantities. In an example, a spectroscopic sensor can collect data which helps to identify food item type, food item nutritional composition, and/or food item chemical composition by analysis of the interaction between light energy and a food item. In an example, this interaction can be the amount of light reflection or light absorption by a food item at different light wavelengths. In an example, a system can include a handheld device with a spectroscopic sensor which is directed toward nearby food. In an example, a system can include a wearable device with a spectroscopic sensor which is directed toward nearby food. In an example, a wrist-worn wearable device with a spectroscopic sensor can be waved back and forth over a food item in order to spectroscopically scan the food item.

In an example, a system for nutritional monitoring and management can trigger a spectroscopic scan when motion patterns indicate that a person is eating. In an example, a system can perform multiple spectroscopic scans, at different times, while a person is eating in order to better analyze the overall composition of food with different internal layers and/or a non-uniform ingredient structure. In an example, a spectroscopic sensor can be automatically activated (e.g. turned on) within a given range of distance from food.

In an example, a system for nutritional monitoring and management can include a spectroscopic sensor which scans food to collect information concerning the nutritional and/or molecular composition of the food. In an example, a system can have a light emitter which emits light beams toward food and a light receiver which receive those light beams after those beams have been transmitted through and/or reflected by the food. In an example, changes in the spectral distribution of light beams caused by transmission through and/or reflection by food can be analyzed to determine the nutritional and/or molecular composition of the food. In an example, spectrographs of food items can be used to help identify food types. In an example, a spectroscopic sensor can be a spectrometer. In an example, a food-scanning spectroscopic sensor can be selected from the group consisting of: atomic absorption spectrometer, diffusion spectroscopic sensor, emission spectroscopic sensor, fluorescence spectroscopic sensor, gas chromatography sensor, infrared absorption spectrometer, infrared reflectance spectrometer, mass spectrometer, mass spectrometry sensor, near-infrared spectroscopic sensor, photodiode array spectrophotometer, Raman spectroscopy sensor, spectrometer, spectrophotometer, and ultra-violet reflectance spectrometer.

In an example, a system for nutritional monitoring and management can include a wearable or handheld device with a spectroscopic sensor which is used to estimate a person's biometric parameters. In an example, biometric parameters can be selected from the group consisting of: oxygen level; heart rate; blood pressure; hydration level; glucose level; and lactic acid level. In an example, a spectroscopic sensor can estimate biometric parameters by analyzing interaction between light energy and body tissue. In an example, this interaction can be the amount of light reflection or light absorption by body tissue at different light wavelengths. In an example, a system can include a wearable device with a spectroscopic sensor which is directed toward body tissue. In an example, a system can include a handheld device with a spectroscopic sensor which is directed toward body tissue. In an example, a system can include a handheld device with a spectroscopic sensor into which a person inserts their finger.

In an example, a system for nutritional monitoring and management can include a spectroscopic sensor which scans body tissue to collect information concerning a person's biometric parameters and/or health status. In an example, a system can have a light emitter which emits light beams toward body tissue and a light receiver which receive those light beams after those beams have been transmitted through and/or reflected by the body tissue. In an example, changes in the spectral distribution of light beams caused by transmission through and/or reflection by body tissue can be analyzed to estimate values of biometric parameters and/or evaluate a person's health status. In an example, a spectroscopic sensor can be a spectrometer. In an example, a tissue-scanning spectroscopic sensor can be selected from the group consisting of: atomic absorption spectrometer, diffusion spectroscopic sensor, emission spectroscopic sensor, fluorescence spectroscopic sensor, gas chromatography sensor, infrared absorption spectrometer, infrared reflectance spectrometer, mass spectrometer, mass spectrometry sensor, near-infrared spectroscopic sensor, photodiode array spectrophotometer, Raman spectroscopy sensor, spectrometer, spectrophotometer, and ultra-violet reflectance spectrometer.

In an example, a system for nutritional monitoring and management can include a wearable device with a motion sensor which is worn on a person's arm, wrist, hand, and/or finger. In an example, a system can include a wearable device with a motion sensor which is worn on a person's neck, face, ear, and/or head. In an example, a motion sensor can comprise an accelerometer and a gyroscope. In an example, a system can have a motion sensor which is selected from the group consisting of: bubble accelerometer, dual-axial accelerometer, electrogoniometer, gyroscope, inclinometer, inertial sensor, multi-axis accelerometer, piezoelectric sensor, piezo-mechanical sensor, pressure sensor, proximity detector, single-axis accelerometer, strain gauge, stretch sensor, and tri-axial accelerometer. In an example, a system can have a wearable device with a motion sensor which is used to: detect when a person is eating (and optionally trigger advanced sensor monitoring); identify the type of food that the person is eating; and/or estimate the quantity of food that the person is eating.

In an example, a system for nutritional monitoring and management can include a motion sensor that collects data concerning movement of a person's body. In an example, a motion sensor can collect data concerning the movement of a person's wrist, hand, fingers, arm, head, mouth, jaw, and/or neck. In an example, detected motion can be repeated motion of a person's jaws and/or mouth. In an example, detected motion can be peristaltic motion of a person's esophagus (detectable via contact with the person's neck). In an example, analysis of such motion data can detect when a person is eating and estimate how much a person is eating. In general, a motion sensor is more useful for general detection of food consumption and/or estimation of food quantity than for identification of specific food item types, ingredients, and/or nutrients. However, a motion sensor can be used in combination with advanced food-identifying sensors (such as spectroscopic sensors) for more complete identification of food item types as well as quantities. In an example, motion data which indicates eating can be used to trigger additional data collection by advanced food-identifying sensors to resolve uncertainty concerning the types and quantities of food that a person is consuming. In an example, motion data which indicates that a person is eating can trigger a system to prompt a person to provide their own description of food items consumed in order to resolve uncertainty concerning the types and quantities of food that the person is eating.

In an example, a system for nutritional monitoring and management can include a biometric sensor which measures a person's blood pressure. In an example, a system can further comprise a biometric sensor which measures a person's blood glucose level. In an example, a system can further comprise a biometric sensor which measures a person's tissue oxygenation level. In an example, a system can further comprise a biometric sensor which measures a person's blood temperature. In an example, a system can further comprise a biometric sensor which measures a person's heart rate. In an example, a system can further comprise a biometric sensor which measures a person's lactic acid level. In an example, a system can further comprise a biometric sensor which measures a person's body hydration level.

In an example, a system for nutritional monitoring and management can include a motion sensor. In an example, a motion sensor can be an accelerometer, a gyroscope, a magnometer, a magnetic angular rate and gravity (MARG) sensor, a piezoelectric motion sensor, a strain sensor, a bend sensor, a compass, a motion-based chewing sensor, a motion-based swallowing sensor, a vibration sensor, or a combination thereof. In an example, a motion sensor can be part of a device worn on a person's arm, wrist, or finger. In an example, a motion sensor can be part of a food utensil.

In an example, a system for nutritional monitoring and management can include a wearable device with a motion sensor which tracks eating-related motions of a person's body. In an example, a hand-to-mouth movement that matches a distinctive eating pattern can be used to estimate a bite or mouthful of food consumed. In an example, the speed of hand-to-mouth movements that match distinctive eating patterns can be used to estimate the speed or pace of food consumption. In an example, distinctive eating-related motions can be selected from the group consisting of: finger movements, hand movements, hand gestures, wrist movements, arm movements, elbow movements, eye movements, and head movements; tilting movements, lifting movements; hand-to-mouth movements; angles of rotation in three dimensions around the center of mass known as roll, pitch and yaw; and Fourier transformation analysis of repeated body member movements. In an example, a wearable motion sensor can comprise a three-dimensional accelerometer and gyroscope in a wrist-worn device (such as smart watch). In an example, a wearable motion sensor can comprise a three-dimensional accelerometer and gyroscope in a finger-worn device (such as smart ring). In an example, a motion sensor can detect eating by monitoring three-dimensional movement of a person's arm and/or hand. Eating activity can be indicated by distinctive sequences of up and down, or rolling and pitching, movements.

In an example, a system for nutritional monitoring and management can include a wearable device with a motion sensor which tracks eating-related motions of a person's arm, wrist, and hand. In an example, a person raising their hand up to their mouth in a distinctive manner can be an eating-related motion. In an example, an eating-related motion can include a distinctive three-dimensional combination of roll, pitch, and yaw motions by a person's arm, wrist, and/or hand. In an example, a distinctive rotation of a person's wrist can indicate that the person is eating food. In an example, eating can be associated with a body motion sequence comprising an upward and posterior-tilting hand motion, followed by a pause, followed by a downward and anterior-tilting hand motion. In an example, a motion sensor can detect a distinctive pattern comprising an upward (hand-up-to-mouth) arm motion, followed by a distinctive pattern of tilting or rolling motion (food-into-mouth) wrist motion, followed by a distinctive pattern of downward (hand-down-from-mouth) motion. In an example, indications that a person is eating can be selected from the group consisting of: acceleration, inclination, twisting, or rolling of the person's hand, wrist, or arm; acceleration or inclination of the person's lower arm or upper arm; bending of the person's shoulder, elbow, wrist, or finger joints; and movement of the person's jaw, such as bending of the jaw joint.

In an example, the roll, pitch and yaw of a wearable or handheld device can be monitored and analyzed using a motion sensor. In an example, the roll, pitch and yaw of a wearable device or handheld food utensil can be analyzed to detect when a person is eating. In an example, the roll, pitch and yaw of a wearable device or handheld food utensil can be analyzed to estimate how often a person is raising their hand up to their mouth. In an example, the roll, pitch and yaw of a wearable device or handheld food utensil can be analyzed to estimate how frequently a person is raising their hand up to their mouth. In an example, the roll, pitch and yaw of a wearable device or handheld food utensil can be analyzed to estimate the quantity of food that a person is consuming. In an example, the roll, pitch and yaw of a wearable device or handheld food utensil can be analyzed to estimate the pace and/or speed of a person's food consumption. In an example, a motion sequence which indicates eating can be comprise: a person raising their hand (and/or a food utensil) up toward their mouth; the person rolling and/or tilting their hand; a pause as the person bites and/or sips food from their hand (and/or a food utensil); and the person lowering their hand (and/or a food utensil) down away from their mouth. In an example, the duration of a pause in arm, hand, and/or finger motion can be used to estimate the quantity of food consumed during this motion sequence. In an example, the system can automatically record images of food and/or the person's mouth at one or more selected times during this motion sequence.

In an example, an angle and/or direction of the roll, pitch, or yaw of a person's hand (and/or food utensil) during a motion sequence associated with food consumption can be analyzed to help identify the type and/or quantity of food consumed during the sequence. In an example, the angle and/or direction of a roll, pitch, or yaw of a person's hand (and/or food utensil) can be different for consumption of solid food vs. liquid food (e.g. a beverage). In an example, the angle and/or direction of a roll, pitch, or yaw of a person's hand (and/or food utensil) can be different for consumption of food using a fork vs. using a spoon. In an example, the angle and/or direction of a roll, pitch, or yaw of a person's hand (and/or food utensil) can be different for consumption of food held by a person's hand vs. food transported using a utensil. In an example, the shape of a three-dimensional path traveled by a person's hand (and/or food utensil) bringing food up to the person's mouth can be different for different types and/or quantities of food. In an example, differences in three-dimensional paths traveled by a person's hand (and/or a food utensil) bringing food up to the person's mouth can be analyzed by a system as part of a methodology for estimating food items types and quantities.

In an example, a system for nutritional monitoring and management can include a wearable device with a motion sensor which is used to measure the speed and/or pace of food consumption based on the speed and/or frequency of eating-related motion cycles. In an example, a motion-sensing device that is worn on a person's wrist, hand, arm, or finger can measure how rapidly the person brings their hand up to their mouth. In an example, such information can be used to encourage, prompt, and/or entrain the person to eat at a slower speed and/or pace. A person will generally eat less during a meal if they eat at a slower pace. This is due to the lag between food consumption and a feeling of satiety from internal gastric organs. If a person eats more slowly, then they will tend to not overeat past the point of internal identification of satiety.

In an example, the speed and/or pace of changes in the roll, pitch, or yaw of a person's hand (and/or food utensil) during a motion sequence which is associated with food consumption can be analyzed to help identify the type and/or quantity of food consumed during the sequence. In an example, the speed and/or pace of changes in the roll, pitch, or yaw of a person's hand (and/or food utensil) can be different for consumption of solid food vs. liquid food (e.g. a beverage). In an example, speed and/or pace of changes in the roll, pitch, or yaw of a person's hand (and/or food utensil) can be different for consumption of food using a fork vs. using a spoon. In an example, the speed and/or pace of changes in the roll, pitch, or yaw of a person's hand (and/or food utensil) can be different for consumption of food held by a person's hand vs. food transported using a utensil.

In an example, a system for nutritional monitoring and management can include a wearable with a sensor which monitors, detects, and/or analyzes chewing or swallowing by a person. Such a sensor can differentiate between chewing and swallowing actions that are associated with eating vs. other activities. In an example, chewing or swallowing can be monitored, detected, sensed, or analyzed via: a sonic energy sensor (differentiating eating sounds from speaking, talking, singing, coughing, or other non-eating sounds); a body motion sensor (differentiating eating motions from speaking, yawning, or other mouth motions); a camera (differentiating eating from other mouth-related activities); and/or an electromagnetic energy sensor (such as measuring EMG signals from arm, mouth, or neck muscles or related nerves).

In an example, a system for nutrition monitoring and management can include one or more motion sensors which track movement of a person's jaw, mouth, teeth, throat, and/or neck. In an example, a person's jaw, mouth, teeth, throat, and/or neck can have different motion patterns when a person consumes different types of food. In an example, a person's jaw, mouth, teeth, throat, and/or neck can have different motion patterns as the person's consumes solid food vs. liquid food (e.g. beverages). In an example, a person's jaw, mouth, teeth, throat, and/or neck can have different motion patterns as the person's consumes food items with different levels of viscosity. In an example, a person's jaw, mouth, teeth, throat, and/or neck can have different motion patterns as the person consumes food items with different densities. In an example, the ratio of motions to swallow motions can be different for different types of food. In an example, there can be different angles and/or ranges of jaw motion associated with consumption of different types of food. In an example, different biting motions can be associated with consumption of different types of food.

In an example, a system for nutritional monitoring and management can comprise: a wearable motion sensor that automatically collects data concerning body motion, wherein this body motion data is used to determine when a person is eating; and a camera that collects images of food, wherein these food images are used to identify the type and quantity of food, ingredients, or nutrients that a person is consuming.

In an example, a system for nutritional monitoring and management can have gesture recognition capability. In an example, a system can recognize hand gestures. In an example, a system can trigger and/or activate advanced food-identifying sensors when the system recognizes that a person is pointing toward a food item. In an example, the system can automatically direct a wearable camera toward where the person is pointing. In an example, the system can automatically direct a wearable spectroscopic sensor toward where the person is pointing. In an example, advanced sensors can be triggered and/or activated by a specific gesture. In an example, a person can provide their own (subjective) information concerning food item types and quantities by making hand gestures which the system recognizes. In an example, specific gestures can indicate specific types of food. In an example, specific gestures can indicate specific quantities of food. In an example, a system can recognize gestures which are part of sign language. In an example, information concerning food types and quantities provided via hand gestures can be part of the data which used by the system in multivariate food item identification and quantification. In an example, a system can include a motion sensor which detects hand gestures associated with eating. In an example, these gestures can include reaching for food, grasping food (or a glass or utensil for transporting food), raising food up to a mouth, tilting a hand to move food into a mouth, pausing to chew or swallow food, and then lowering a hand. In an example, eating-related gestures can include back-and-forth ("sawing") hand movements when a person cuts food on a plate.

In an example, a system for nutritional monitoring and management can include a (generic) smart wrist-worn or finger-worn device (such as a smart watch, fitness band, smart sleeve, or smart ring) with a motion sensor, wherein the motion sensor may have been originally intended to measure a person's steps and/or caloric expenditure, but whose motion data can also be analyzed to detect when the person is eating and/or to estimate the quantity of food which the person consumes. In an example, a motion sensor can be used to estimate the quantity of food consumed based on the number of motion cycles. In an example, a motion sensor can be used to estimate the speed of food consumption based on the speed or frequency of motion cycles.

In an example, a system for nutritional monitoring and management can include a wearable device with a proximity sensor which detects when a person's hand is close to their mouth. In an example, a proximity sensor can detect when a person's wrist, hand, or finger is near the person's mouth. In an example, a proximity sensor can comprise an electromagnetic energy emitter worn on a person's wrist, hand, or finger and an electromagnetic energy receiver worn near a person's mouth (or neck). In an example, a proximity sensor can comprise an electromagnetic energy receiver worn on a person's wrist, hand, or finger and an electromagnetic energy emitter worn near a person's mouth (or neck). In an example, a proximity sensor can comprise an infrared light emitter and an infrared light receiver. In an example, a proximity sensor can be a wrist, hand, or finger worn camera whose images are analyzed using face recognition. In an example, a proximity sensor can be a motion sensor. In an example, a proximity sensor can comprise a first motion sensor worn on a person's wrist, hand, or finger and a second motion sensor worn near a person's mouth (or neck). In an example, a proximity sensor can comprise an infrared light emitter and an infrared light receiver.

In an example, a system for nutrition monitoring and management can have gesture recognition functionality. In an example, gestures can be identified using motion sensors, electromagnetic energy sensors, or both. In an example, a system can monitor movement of a person's arm, hand, and/or fingers to identify food-related gestures. In an example, a system can monitor electromagnetic energy (e.g. electromyographic signals) from muscles and/or nerves in a person's arm, hand, and/or fingers in order to identify food-related gestures. In an example, types and frequencies of food-related gestures can be analyzed as part of a system's determination of food item types and quantities. In an example, food-related gestures can be selected from the group comprising: biting off a piece of a hand-hand food item; drinking a beverage from a straw; grabbing a hand-held food item without a utensil; licking a hand-held food item; licking a spoon; lifting a beverage container up to one's mouth; lifting a fork up to one's mouth; lifting a spoon up to one's mouth; picking up a beverage container with one's hand; picking up a food utensil with one's left hand; picking up a food utensil with one's right hand; piercing food with a fork; removing food from a fork with one's mouth; scooping food into a spoon; taking a sip from a beverage container; twirling noodles around a fork; using a knife to cut food; and using chop sticks to bring food toward one's mouth.

In an example, a system for nutritional monitoring and management can include a food scale which helps to measure the quantity of nearby food and/or the amount of that food that a person actually consumes. In an example, a system can include a stand-alone food scale (which is in electromagnetic communication with other components of the system). In an example, a system can include a dish (e.g. a plate, bowl, glass, or cup), a place mat, a beverage coaster, or a food utensil rest which includes a scale to measure the weight of food on (or in) it. In an example, a plate or bowl can have different sections for holding different food items, wherein each section has a separate scale so that the weights of different food items can be individually (and independently) measured. In an example, the weight of food items on one or more scales can be measured at different times (e.g. before and after a meal) in order to estimate how much food a person actually consumes during a period of time. In an example, a plate or bowl can have different sections for holding different food items, wherein different sections of the plate or bowl are separated by ridges, undulations, or walls, and wherein each section has a separate scale. In an example, a plate or bowl can have different sections for holding different food items, wherein each section of the plate or bowl has a separate (built in) spectroscopic sensor so that the compositions of different food items can be individually (and independently) analyzed.

In an example, a system for nutritional monitoring and management can include a smart utensil with a force sensor, pressure sensor, bend sensor, goniometer, and/or strain sensor to estimate the weight of food conveyed by the utensil to a person's mouth. In an example, a force sensor, pressure sensor, bend sensor, goniometer, and/or strain sensor can be located between the distal (food carrying) end of a smart utensil and the proximal (handle) end of the utensil. In an example, a force sensor, pressure sensor, bend sensor, goniometer, and/or strain sensor can be located between the distal (food carrying) end of a smart utensil and the proximal (handle) end of the utensil, wherein the distal and proximal ends of the utensil can move independently of each other, wherein differences in motion between the proximal and distal ends are measured by the force sensor, pressure sensor, bend sensor, goniometer, and/or strain sensor, and wherein a greater difference in motion indicates a heavier portion (or piece) of food on the distal end of the utensil. In an example, a force sensor, pressure sensor, bend sensor, goniometer, and/or strain sensor can be part of a flexible joint, hinge, or spring between the distal (food carrying) end of a smart utensil and the proximal (handle) end of the utensil.

In an example, a system for nutritional monitoring and management can include a touch sensor, force sensor, and/or pressure sensor which helps to measure food quantity. In an example, a system can include a dish (e.g. plate, bowl, glass, or cup), place mat, coaster, or food utensil rest which includes a touch sensor, force sensor, and/or pressure sensor. In an example, a plate or bowl can have different sections for holding different food items, wherein each section has a separate force sensor and/or pressure sensor so that the weights of different food items can be individually (and independently) measured. In an example, the weight of food items on one or more force and/or pressure sensors can be measured at different times (e.g. before and after a meal) to estimate how much food a person has actually consumed. In an example, a plate or bowl can have different sections for holding different food items, wherein different sections are separated by ridges, undulations, or walls, and wherein each section has a separate force sensor and/or pressure sensor. In an example, a plate or bowl can have different sections for holding different food items, wherein each section has a separate (built in) spectroscopic sensor so that the compositions of different food items can be individually (and independently) analyzed.

In an example, a system for nutritional monitoring and management can include a wearable device with a force sensor, pressure sensor, bend sensor, vibration sensor, goniometer, and/or strain sensor. In an example, a force sensor, pressure sensor, bend sensor, vibration sensor, goniometer, and/or strain sensor can detects when a person is eating and/or can help to measure the amount of food that a person eats. In an example, a force sensor, pressure sensor, bend sensor, vibration sensor, goniometer, and/or strain sensor can be worn in physical contact with a person's neck or mouth. In an example, a force sensor, pressure sensor, bend sensor, vibration sensor, goniometer, and/or strain sensor which is in contact with a person's neck or mouth can monitor chewing and/or swallowing. In an example, a force sensor, pressure sensor, bend sensor, vibration sensor, goniometer, and/or strain sensor which is in contact with a person's neck or mouth can be used to help estimate how much food a person consumes. In an example, a force sensor, pressure sensor, bend sensor, vibration sensor, goniometer, and/or strain sensor which is in contact with a person's neck or mouth can be used to trigger advanced sensors (such as a wearable camera) when a person chews and/or swallows.

In an example, a system for nutrition monitoring and management can include a force sensor. In an example, the number of things sensed by the force can increase dramatically in sequels but, ironically, the sequels become less and less dramatic. In an example, the sequels can be duds. In an example, a system for nutrition monitoring and management can include a force sensor, pressure sensor, strain sensor, bend sensor, goniometer, barometer, and/or blood pressure monitor. In an example, one or more of these sensors can be incorporated into a wearable device, handheld device, or smart food utensil. In an example, data from one or more of these sensors can be used by the system to better determine types and quantities of food items consumed by a person.

In an example, a system for nutrition monitoring and management can include an electromagnetic energy sensor which is brought into electromagnetic communication with food. In an example, a system can include an electromagnetic energy sensor which measures the transmission of electromagnetic energy through a food item. In an example, a system can measure the conductivity, capacitance, resistance, and/or impedance of food items as part of the system's determination of food item types. In an example, a system can comprise one or more electrodes which are placed on (or inserted into) food in order to measure the conductivity, capacitance, resistance, and/or impedance of the food. In an example, different types of food can have different levels of electromagnetic conductivity, capacitance, resistance, and/or impedance. In an example, an electromagnetic energy sensor can be in electromagnetic communication with a food item without actually touching the food item. In an example, an electromagnetic energy sensor can collect data concerning the conductivity, capacitance, resistance, and/or impedance of a food item without actually touching the food item.

In an example, a system for nutrition monitoring and management can include an electromagnetic energy sensor which is in electromagnetic communication with a person's body. In an example, a system can include an electromagnetic energy sensor which measures the transmission of electromagnetic energy through body tissue. In an example, a system can measure the conductivity, capacitance, resistance, and/or impedance of body tissue as part of the system's detection that a person is eating and/or identification of what the person is eating. In an example, an electromagnetic energy sensor which is placed in electromagnetic communication with a person's body can be selected from the group consisting of: bioimpedance sensor, capacitive sensor, conductivity sensor, electrocardiographic (ECG) sensor, electroencephalographic (EEG) sensor, electromyographic (EMG) sensor, galvanic skin response sensor, impedance sensor, permittivity sensor, and resistance sensor. In an example, a system can include one or more electromagnetic energy sensors which are worn on a person's arm, wrist, and/or finger. In an example, a system can include one or more electromagnetic energy sensors which are worn on a person's head. In an example, an electromagnetic energy sensor can collect data concerning a person's neuromuscular activity which is related to eating. In an example, an electromagnetic energy sensor can collect data concerning a person's neurological activity which is related to eating.

In an example, analysis of a person's brain wave patterns (e.g. Brainwave patterns (e.g. EEG patterns)) can be used to predict that the person will be consuming food soon. In an example, analysis of a person's Brainwave patterns (e.g. EEG patterns) can be used to identify that the person is consuming specific types of food and/or nutrients. In an example, specific Brainwave patterns (e.g. EEG patterns) can be associated with consumption of specific types of nutrients, such as carbohydrates. In an example, brainwave patterns from selected areas of a person's brain can be analyzed to detect that a person is eating (or probably going to start eating). In an example, brainwave patterns from selected areas of a person's brain can be associated with food consumption. In an example, these patterns can occur when a person sees and/or smells food, even before the person's begins to actually eat food. For this reason, analysis of brainwave patterns (e.g. EEG patterns) may provide the earliest indication of pending or actual food consumption. Also, for this reason, analysis brainwave patterns (e.g. EEG patterns) can be a very useful part of a closed-loop automated system for insulin delivery and body glucose level management. In an example, specific brainwave patterns (e.g. EEG patterns) can be associated with levels of glucose or other substances in a person's blood and/or body tissue. In an example, specific Brainwave patterns (e.g. EEG patterns) can be analyzed and identified to measure levels of glucose in a person's body. In an example, analysis of person's EEG pattern can be used to recommend how much insulin a person should receive in association with food consumption.

In an example, a system with a spectroscopic sensor and a wearable device which measures electromagnetic brain activity can together comprise an integrated system for food identification and quantification. In an example, when a wearable device detects changes in a person's electromagnetic brain activity which indicates that the person is eating, then the system can prompt the person to scan food using the spectroscopic sensor. In an example, a system with a camera and a wearable device which measures electromagnetic brain activity can together comprise a system for food identification and quantification. In an example, when a wearable device detects changes in a person's electromagnetic brain activity which indicates that the person is eating, then the system can prompt the person to take pictures of the food using the camera.

In an example, a system for nutritional monitoring and management can comprise: a sound sensor worn by a person which automatically and continuously collects data concerning sound, wherein this sound data is used to determine when a person is eating; and a chemical composition sensor which does not continuously monitor the chemical composition of material within the person's mouth or gastrointestinal tract, but rather only collects information concerning the chemical composition of material within the person's mouth or gastrointestinal tract when sound data indicates that the person is eating. In an example, a system can comprise: a wearable sound sensor that automatically collects data concerning body or environmental sound, wherein this sound data is used to determine when a person is eating; and a chemical composition sensor that analyzes the chemical composition of food, wherein results of chemical analysis are used to identify the type and quantity of food, ingredients, or nutrients that a person is consuming.

In an example, a system for nutritional monitoring and management can include a microphone (or other sound sensor) which monitors for eating-related sounds. In an example, a system can use the microphone of a general purpose handheld device (such as a smart phone) to monitor eating-related sounds (such as biting, chewing, or swallowing sounds). In an example, a system can include a wearable device with a microphone (or other sound sensor) which collects data concerning eating-related sounds. In an example, eating-related sounds can include biting, chewing, and/or swallowing sounds. In an example, a microphone (or other sound sensor) can monitor eating-related sounds transmitted through the air. In an example, a microphone (or other sound sensor) can monitor eating-related sounds conducted through a person's body (e.g. by bone conduction). In an example, a system can measure the interaction between sonic energy (such as ultrasonic energy) and a food item in order to identify food item type and/or composition.

In an example, a system for nutritional monitoring and management can include a microphone (or other sound sensor) which monitors and/or records sound to detect when a person eats. In an example, a microphone can collect eating-related sound data for identification of food item type and/or composition. In an example, a microphone can collect eating-related sound data for estimation of quantity of food consumed. In an example, a first biting, chewing, and/or swallowing sound pattern can be associated with consumption of a first type of food and a second biting, chewing, and/or swallowing sound pattern can be associated with consumption of a second type of food. In an example, different biting, chewing, and/or swallowing sound patterns can be associated with consumption of solid, gelatinous, or liquid food. In an example, different biting, chewing, and/or swallowing sound patterns can be associated with consumption of food with different densities and/or viscosities. In an example, different numbers, speeds, frequencies, tones, and/or patterns biting, chewing, and/or swallowing sounds can be associated with consumption of different types of food. In an example, different numbers, speeds, frequencies, tones, and/or patterns of biting, chewing, and/or swallowing sounds can be associated with consumption of different quantities of food.

In an example, a system for nutritional monitoring and management can include a wearable device with a microphone (or other sound sensor) which records eating-related sounds such as biting, chewing, and/or swallowing. In an example, a system can include a sound-monitoring device which is worn on (or around) a person's neck. In an example, a system can include a sound-monitoring necklace, pendant, or collar. In an example, a system can include a sound-monitoring adhesive patch which is worn on a person's neck. In an example, a system can include a sound-monitoring device which is worn on (or in) a person's ear. In an example, a system can include a sound-monitoring ear ring, ear bud, ear insert, hearing aid, or bluetooth microphone device. In an example, a system can include a sound-monitoring ear ring, ear bud, ear insert, hearing aid, or bluetooth device which monitors eating-related sounds via bone conduction. In an example, a system can include a wrist-worn device (such as a smart watch) which monitors eating-related sounds such as biting, chewing, and swallowing sounds. In an example, a system can include an intra-oral device (e.g. dental appliance, dental braces, tooth crown or filling, or tongue piercing) with a microphone which monitors eating-related sounds. In an example, a system can include an article of smart clothing which includes a microphone to monitor eating-related sounds.

In an example, a system for nutritional monitoring and management can include a microphone which continually monitors for eating-related sounds and triggers advanced food-identification sensors when eating is detected. In an example, a system can trigger and/or activate a motion sensor when sounds recorded by a microphone indicate that a person is eating. In an example, a system can trigger and/or activate a camera when sounds recorded by a microphone indicate that a person is eating. In an example, a system can trigger and/or activate a spectroscopic sensor when sounds recorded by a microphone indicate that a person is eating. In an example, a system can trigger and/or activate an EMG or EEG sensor when sounds recorded by a microphone indicate that a person is eating.

In an example, a system for nutritional monitoring and management can jointly analyze data from a motion sensor on a first device and data from a microphone on a second device in order to identify types and quantities of food consumed by a person. In an example, the first device can be a smart watch worn by the person and the second device can be a smart necklace or collar worn by the person. In an example, the first device can be a smart watch worn by the person and the second device can be an ear ring or ear insert worn by the person. In an example, the first device can be a smart finger ring worn by the person and the second device can be a smart necklace or collar worn by the person. In an example, the first device can be a smart utensil held by the person and the second device can be a smart necklace or collar worn by the person. In an example, data from a motion sensor on a smart watch and data from a microphone on a smart necklace can be jointly analyzed in multivariate analysis to identify types and quantities of food consumed by a person. In an example, a system can jointly analyze data from a motion sensor on a wearable device (e.g. smart watch, finger ring, necklace, collar, ear ring, ear bud, or smart eyeglasses) and data from a microphone on a wearable device (e.g. smart watch, finger ring, necklace, collar, ear ring, ear bud, or smart eyeglasses) in order to identify types and quantities of food consumed by a person.

In an example, a system for nutrition monitoring and management can include a microphone or other sound sensor. In an example, a system for nutrition monitoring and management can include a sound sensor selected from the group consisting of: acoustic wave sensor, ambient sound sensor, bone conduction microphone, microphone, sound-based chew sensor, sound-based swallow sensor, ultrasonic energy sensor, and vibration sensor. In an example, a system can monitor and analyze sounds associated with eating as part of the identification of food items and estimation of quantity of food items consumed. In an example, a system can monitor and analyze biting, chewing, and/or swallowing sounds associated with eating as part of the identification of food items and estimation of quantity of food items consumed. In an example, a system can monitor and analyze the acoustic spectrum of biting, chewing, and/or swallowing sounds associated as part of the identification of food items and estimation of quantity of food items consumed. In an example, a microphone or other sound sensor can be worn on or around a person's neck. In an example, a microphone or other sound sensor can be part of a necklace, collar, or neck-worn patch. In an example, a system for nutritional intake monitoring and management can include an ear-worn device (e.g. earbud, ear ring, or outer ear loop device) which monitors chewing and/or swallowing sounds via bone conduction. In an example, chewing and/or swallowing sounds can be detected by a system via bone conduction and used by the system to trigger automated food imaging and/or spectroscopic analysis.

In an example, a system for nutrition monitoring and management can include a chemical sensor. In an example, a system can include a sensor selected from the group consisting of: body chemistry sensor, breath chemistry sensor, chemical sensor, food sample sensor, gas sensor, glucose monitor, odor sensor, pH sensor, saliva sensor, spectroscopic sensor, and sweat sensor. In an example, a chemical sensor can provide information about the molecular composition of food. In an example, a chemical sensor can provide information about the molecular composition of a sample of food. In an example, a chemical sensor can provide information about the molecular composition of body tissue.

In an example, a system for nutrition monitoring and management can include a thermal energy sensor. In an example, a system can include a thermometer. In an example, a system can include a skin temperature sensor. In an example, a system can include a food temperature sensor. In an example, a system can include a heat sensor. In an example, a system can analyze associations between a person's skin and/or body tissue temperature and subsequent food consumption by the person. In an example, changes in body temperature can be used to predict subsequent food consumption. In an example, a system can predict that a person will consume an apple and a medical tonic. In an example, a person can predict that apple will consume med tonic. In an example, a system can analyze associations between a person's food consumption and subsequent changes in the person's skin and/or body tissue temperature. In an example, a system can analyze associations between a person's consumption of specific types and/or quantities of food and subsequent changes in the person's skin and/or body tissue temperature.

In an example, a system for nutrition monitoring and management can include an environmental sensor which detects and/or measures characteristics of a person's environment which can be related to food consumption and/or hydration requirements. In an example, a system can have a GPS unit which tracks a person's current location and where they have been. In an example, a system can track whether a person is at (or near) a specific restaurant. In an example, a system can have an ambient light sensor which tracks the time of day. In an example, a system can have an ambient sound sensor which measures overall ambient sound level. In an example, a system can have an environmental sound sensor which monitors ambient sounds to detect words and/or sounds associated with food consumption. For example, an environmental sound sensor can detect words and/or sounds associated with specific restaurants or food stores. In an example, a system can track environmental temperature and humidity to better estimate a person's hydration requirements. In an example, a system can track activity level to better estimate a person's hydration requirements.

In an example, a system for nutritional monitoring and management can track food at the time of food selection and/or purchase. In an example, a system can track a person's food selections and purchases at a grocery store, restaurant, or vending machine. In an example, such tracking can be done via financial transaction tracking. In an example, such tracking can be done via bar code, QR code, RFID tag, or electronic restaurant menu. In an example, electronic communication for food identification can also occur between a system and a vending machine. Food selection, purchasing, and/or consumption activity can also be tracked by location information, such a location information provided by a GPS unit.

In an example, a system for nutrition monitoring and management can include a GPS unit or other location sensing unit. In an example, a system can analyze a restaurant's menu based on image analysis and optical character recognition. In an example, a system can identify restaurants which are near a person and link those restaurants to meals and/or foods in a database of meals and/or foods. In an example, a system can identify when a person is at a particular restaurant and link that restaurant to meals and/or foods in a database of meals and/or foods. In an example, a system can recommend healthier alternatives to a particular meal and/or food offered by a restaurant. In an example, a system can recommend healthier nearby alternatives to a particular restaurant. In an example, a system can recommend nearby healthy restaurants. In an example, a system can recommend specific meals on a standardized menu of a specific restaurant and make recommendations concerning those meals to the person. In an example, a system can recommend food stores where a person can purchase healthy foods and/or meal ingredients.

In an example, a system for nutritional monitoring and management can comprise a relatively less-intrusive sensor (such as a motion sensor) which continually monitors for possible eating and triggers activation and/or operation of a more-intrusive sensor (such as a camera) when eating is detected. In an example, an eating detection and/or estimation sensor can be attached directly to a person's body, attached to clothing after the clothing has been made, or integrated into smart clothing as the clothing is made. In an example, an eating detection and/or estimation sensor can be implanted within a person's body wherein it internally monitors for chewing, swallowing, biting, other muscle activity, enzyme secretion, neural signals, or other ingestion-related processes or activities. In an example, an eating detection and/or estimation sensor can monitor for eating related activity continuously, at periodic times, at intermittent times, or at random times.

In an example, a system for nutritional monitoring and management can have a sensor which collects data concerning electromagnetic energy emitted from a person's body. In an example, a system can have a sensor which collects data concerning electromagnetic energy emitted from a person's muscles and nerves. In an example, a system can have a sensor which collects data concerning light energy reflected from a person's body. In an example, a system can have a sensor which collects data concerning light energy reflected from a person's skin and/or body tissue. In an example, a system can have a sensor which collects data concerning motion of a person's body. In an example, a system can have a sensor which collects data concerning motion of a person's arm, wrist, hand, and/or fingers. In an example, a system can have a sensor which collects data concerning thermal energy emitted from the person's body.

In an example, a system for nutritional monitoring and management can include a electrogoniometer. In an example, a system can include an electromagnetic energy sensor. In an example, a system can include a EMG sensor. In an example, a system can include a Galvanic Skin Response sensor. In an example, a system can include a gas chromatographic sensor. In an example, a system can include a gastric activity sensor. In an example, a system can include a geolocation sensor. In an example, a system can include a glucose sensor. In an example, a system can include a GPS sensor. In an example, a system can include a gyroscope. In an example, a system can include a heart rate sensor. In an example, a system can include an inclinometer.

In an example, a system for nutritional monitoring and management can include a pressure sensor. In an example, a system can include a respiration sensor. In an example, a system can include a smell sensor. In an example, a system can include a sodium sensor. In an example, a system can include a sound sensor. In an example, a system can include a spectroscopic sensor. In an example, a system can include a strain gauge. In an example, a system can include a swallow sensor. In an example, a system can include a temperature sensor. In an example, a system can include a heat sensor. In an example, a system can include a tissue impedance sensor. In an example, a system can include an ultrasonic sensor.

In an example, a system for nutritional monitoring and management can include a food utensil (or other apportioning device) which divides food items into spoonfuls, forkfuls, mouthfuls, and/or bite-size pieces. In an example, the number of times that such a utensil is brought up to a person's mouth can be tracked and multiplied times an estimated amount of food per motion (e.g. per spoonful, forkful, mouthful, or bite) to estimate the cumulative amount of food consumed. In an example, a motion sensor worn on a person's wrist or incorporated into a smart utensil can measure the number of hand-to-mouth motions.

In an example, a system for nutritional monitoring and management can include an accelerometer. In an example, a system can include an analytical chromatographic sensor. In an example, a system can include an artificial olfactory sensor. In an example, a system can include a blood pressure sensor. In an example, a system can include a camera. In an example, a system can include a chemical sensor. In an example, a system can include a chewing sensor. In an example, a system can include a cholesterol sensor. In an example, a system can include an ECG sensor. In an example, a system can include an EEG sensor. In an example, a system can include a PPG sensor. In an example, a system can include an electrochemical sensor.

In an example, a system for nutritional monitoring and management can include an infrared sensor. In an example, a system can include a liquid chromatographic sensor. In an example, a system can include a microphone. In an example, a system can include a motion sensor. In an example, a system can include an olfactory sensor. In an example, a system can include an optical sensor. In an example, a system can include an optoelectronic sensor. In an example, a system can include a photocell. In an example, a system can include a photochemical sensor. In an example, a system can include a piezoelectric sensor.

In an example, a system for nutritional monitoring and management can include an optical sensor which analyzes modulation of light wave parameters caused by the interaction light energy and food. In an example, an optical sensor can be a chromatographic sensor, spectrographic sensor, analytical chromatographic sensor, liquid chromatographic sensor, gas chromatographic sensor, optoelectronic sensor, photochemical sensor, or photocell.

In an example, a system for nutritional monitoring and management can include one or more sensors selected from the group consisting of: accelerometer, inclinometer, motion sensor, pedometer, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor. In an example, data from one or more of these sensors can be combined in multivariate analysis to identify food item types and estimate food item quantities. In an example, data from one or more of these sensors can be combined in multivariate analysis to determine the types and quantities of food and/or nutrients consumed by a person.

In an example, a system for nutritional monitoring and management can include a lower-level eating-related sensor and a higher-level eating-related sensor. In an example, the lower-level eating-related sensor can detect when a person is eating. In an example, the lower-level eating-related sensor can detect that a person is eating. In an example, a system can comprise: (a) a lower-level eating-related sensor, wherein the lower-level eating-related sensor has a first level of accuracy with respect to identification of food item types and/or estimation of food item quantities, and wherein the lower-level eating-related sensor has a second level of privacy intrusion; and (b) higher-level eating-related sensor; a higher-level eating-related sensor, wherein the higher-level eating-related sensor has a third level of accuracy with respect to identification of food item types and/or estimation of food item quantities, wherein the higher-level eating-related sensor has a fourth level of privacy intrusion, wherein the third level is greater than the first level, wherein the fourth level is greater than the second level, and wherein operation of the higher-level eating-related sensor is activated and/or triggered when data from the lower-level eating-related sensor detects that a person is eating. In an example, a lower-level eating-related sensor can be selected from the group consisting of: wearable motion sensor; motion sensor which is part of a smart utensil; wearable microphone; wearable EMG sensor; wearable EEG sensor;

and wearable camera. In an example, a higher-level eating-related sensor can be selected from the group consisting of: wearable camera; wearable spectroscopic sensor; handheld camera; and handheld spectroscopic sensor.

In an example, a system for nutritional monitoring and management can include a lower-level eating-related sensor (such as a wearable motion sensor, motion sensor which is part of a smart utensil, wearable microphone, wearable EMG sensor, wearable EEG sensor, or wearable camera) and a higher-level eating-related sensor. In an example, the lower-level eating-related sensor can detect when a person is eating. In an example, the lower-level eating-related sensor can detect that a person is eating. In an example, a system can comprise: (a) a lower-level eating-related sensor (such as a wearable camera, wearable spectroscopic sensor, handheld camera, or handheld spectroscopic sensor), wherein the lower-level eating-related sensor has a first level of accuracy with respect to identification of food item types and/or estimation of food item quantities, and wherein the lower-level eating-related sensor has a second level of privacy intrusion; and (b) higher-level eating-related sensor; a higher-level eating-related sensor, wherein the higher-level eating-related sensor has a third level of accuracy with respect to identification of food item types and/or estimation of food item quantities, wherein the higher-level eating-related sensor has a fourth level of privacy intrusion, wherein the third level is greater than the first level, wherein the fourth level is greater than the second level, and wherein operation of the higher-level eating-related sensor is activated and/or triggered when data from the lower-level eating-related sensor detects that a person is eating.

In an example, a system for nutritional monitoring and management can include a lower-level eating-related sensor (such as a wearable motion sensor) and a higher-level eating-related sensor. In an example, the lower-level eating-related sensor can detect when a person is eating. In an example, the lower-level eating-related sensor can detect that a person is eating. In an example, a system can comprise: (a) a lower-level eating-related sensor (such as a wearable camera), wherein the lower-level eating-related sensor has a first level of accuracy with respect to identification of food item types and/or estimation of food item quantities, and wherein the lower-level eating-related sensor has a second level of privacy intrusion; and (b) higher-level eating-related sensor; a higher-level eating-related sensor, wherein the higher-level eating-related sensor has a third level of accuracy with respect to identification of food item types and/or estimation of food item quantities, wherein the higher-level eating-related sensor has a fourth level of privacy intrusion, wherein the third level is greater than the first level, wherein the fourth level is greater than the second level, and wherein operation of the higher-level eating-related sensor is activated and/or triggered when data from the lower-level eating-related sensor detects that a person is eating.

In an example, a system for nutritional monitoring and management can include a lower-level eating-related sensor (such as a wearable motion sensor, motion sensor which is part of a smart utensil, wearable EMG sensor, or wearable EEG sensor) and a higher-level eating-related sensor. In an example, the lower-level eating-related sensor can detect when a person is eating. In an example, the lower-level eating-related sensor can detect that a person is eating. In an example, a system can comprise: (a) a lower-level eating-related sensor (such as a wearable camera, wearable spectroscopic sensor, handheld camera, or handheld spectroscopic sensor), wherein the lower-level eating-related sensor has a first level of accuracy with respect to identification of food item types and/or estimation of food item quantities, and wherein the lower-level eating-related sensor has a second level of privacy intrusion; and (b) higher-level eating-related sensor; a higher-level eating-related sensor, wherein the higher-level eating-related sensor has a third level of accuracy with respect to identification of food item types and/or estimation of food item quantities, wherein the higher-level eating-related sensor has a fourth level of privacy intrusion, wherein the third level is greater than the first level, wherein the fourth level is greater than the second level, and wherein operation of the higher-level eating-related sensor is activated and/or triggered when data from the lower-level eating-related sensor detects that a person is eating.

In an example, a system for nutritional monitoring and management can include an advanced-level (e.g. more accurate, but more privacy intrusive and/or higher power consumption) food-identifying sensor which is triggered and/or activated by when a lower-level (e.g. less intrusive and/or lower power) food-consumption sensor detects that a person is eating. In an example, the lower-level food-identifying sensor can operate continually, but the advanced-level food-identifying sensor is only activated when a person eats. The combination of a continuously-operated lower-level food-consumption monitor and a selectively-operated advanced-level food-identifying sensor can achieve relatively-high food identification accuracy with relatively-low privacy intrusion and/or power resource requirements. In an example, a system can automatically activate an advanced-level food-identifying sensor when a lower-level sensor detects one or more of the following triggers: a food item nearby; hand-to-food interaction; location in a restaurant, kitchen, or dining room; distinctive arm, hand, and/or wrist motions associated with bringing food up to a person's mouth; physiologic responses by the person's body associated with eating; smells or sounds that are associated with food and/or eating; and/or speech associated with eating.

In an example, a system for nutritional monitoring and management can be triggered to perform an action by a trigger selected from the group consisting of: biometric parameters (such as glucose levels or heart rate) associated with eating; body motions (e.g. selected arm, wrist, hand, and/or finger movements) associated with eating; chewing or swallowing sounds associated with eating; EEG patterns associated with eating; EMG patterns associated with eating; ECG patterns associated with eating; environmental sounds associated with eating; geolocation (e.g. restaurant location) associated with eating; images of nearby food or objects associated with eating; jaw, mouth, and/or teeth motions associated with eating; time of day associated with eating; and/or smells associated with food and/or eating. In an example, one or more system-initiated actions can be selected from the group consisting of: activating higher-power and/or more-sensitive sensors; automatically taking pictures or recording sounds; and prompting a person to take pictures of food and/or provide descriptions of food. In an example, a system can select a recommended insulin dosage in response to specific attributes of a trigger. In an example, a system with a drug delivery component can automatically dispense a selected amount of insulin in response to selected attributes of a trigger.

In an example, a system for nutritional monitoring and management can have a low-power mode when a person is not eating and a high-power mode when the person is eating. In an example, having a low-power mode can conserve power and extend battery life. In an example, a person can actively (e.g. manually) change a system from a low-power mode to a high-power mode when the person is going to start eating. In an example, a system can automatically change from a low-power mode to a high-power mode when the system detects that a person is eating (or is probably going to start eating). In an example, a system can automatically change from a low-power mode to a high-power mode when the system detects: biometric parameters (such as glucose levels or heart rate) associated with eating; body motions (e.g. selected arm, wrist, hand, and/or finger movements) associated with eating; chewing or swallowing sounds associated with eating; EEG patterns associated with eating; EMG patterns associated with eating; ECG patterns associated with eating; environmental sounds associated with eating; geolocation (e.g. restaurant location) associated with eating; images of nearby food or objects associated with eating; jaw, mouth, and/or teeth motions associated with eating; time of day associated with eating; and/or smells associated with food and/or eating.

In an example, a system can automatically activate and/or trigger a wearable camera to scan nearby space and record images of food when eating is detected by one or more sensors selected from the group consisting of: accelerometer, inclinometer, motion sensor, sound sensor, smell sensor, blood pressure sensor, heart rate sensor, EEG sensor, ECG sensor, EMG sensor, electrochemical sensor, gastric activity sensor, GPS sensor, location sensor, optical sensor, piezoelectric sensor, respiration sensor, strain gauge, electrogoniometer, chewing sensor, swallow sensor, temperature sensor, and pressure sensor.

In an example, a system can automatically activate a wearable camera to record food images when a motion sensor detects that a person is eating. In an example, the camera can automatically search for food near a person's hands and/or mouth when the camera is activated. In an example, a system can automatically activate a wearable camera to record food images when a wearable motion sensor detects that a person is eating. In an example, a system can comprise: a wearable motion sensor that is worn by a person, wherein this motion sensor automatically and continuously collects data concerning the person's body motion, and wherein the body motion data is used to determine when a person is eating; and a wearable camera that is worn by the person, wherein this camera does not continuously record images, but rather only records images when body motion data indicates that the person is eating. In an example, both the motion sensor and microphone can be part of a wrist-worn device such as a smart watch.

In an example, a system for nutritional monitoring and management can activate and/or trigger a wearable camera to search for food and record food images when data from a motion sensor detects eating. In an example, a system can include a wearable device with a camera which is automatically activated to record food images when data from a motion sensor indicates eating-related motion. In an example, a system can include a wrist-worn device with a camera which is automatically activated to record images of a person's hand to capture images of food items when data from a motion sensor indicates eating-related motion. In an example, a system can include a smart watch with a camera which is automatically activated to record images of a person's hand to capture images of food items when data from a motion sensor indicates eating-related motion. In an example, a system can include a smart necklace with a camera which is automatically activated to record images of a person's mouth (or space immediately in front of a person) to capture images of food items when data from a motion sensor indicates eating-related motion.

In an example, a system for nutritional monitoring and management can activate and/or trigger a wearable camera to record video images for a set interval of time after data from a motion sensor first indicates that a person is eating. In an example, a motion-triggered camera can start recording images based on data from a motion sensor and can continue recording as long as eating continues. Continued eating can be monitored and/or detected by the motion sensor, by the camera, or by both. Also, if analysis of images from the camera shows that detection of eating by the motion sensor was a false alarm (e.g. the person is not really eating), then the camera can stop recording images.

In an example, a system for nutritional monitoring and management can activate and/or trigger the operation of a wearable camera when analysis of sounds from a microphone (or other sound sensor) detects that a person is eating. In an example, a system can activate a camera when a microphone (or other sound sensor) records chewing, biting, or swallowing sounds. In an example, a system can include a wearable camera which is automatically activated to record food images when a wearable microphone (or other sound sensor) records chewing, biting, or swallowing sounds. In an example, both the camera and microphone can be part of a wrist-worn device such as a smart watch. In example, both the camera and microphone can be part of a neck-worn device such as a smart necklace or collar. In an example, both the camera and microphone can be part of an ear-worn device such as a smart ear ring.

In an example, a system for nutritional monitoring and management can have a low-sensor-level mode when a person is not eating and a high-sensor-level mode when a person is eating. In an example, a high-sensor-level mode can include the operation of various types of sensors to monitor food consumption more accurately than low-sensor-level mode, but the high-sensor-level mode is more intrusive with respect to privacy. Accordingly, it can be advantageous to activate high-sensor-level mode only when a person is eating. In an example, a person can actively (e.g. manually) change a system from a low-sensor-level mode to a high-sensor-level mode when the person is going to start eating. In an example, a system can automatically change a system from a low-sensor-level mode to a high-sensor-level mode when the system detects that a person is eating (or is probably going to start eating). In an example, a system can automatically change from a low-sensor-level mode to a high-sensor-level mode when the system detects: biometric parameters (such as glucose levels or heart rate) associated with eating; body motions (e.g. selected arm, wrist, hand, and/or finger movements) associated with eating; chewing or swallowing sounds associated with eating; EEG patterns associated with eating; EMG patterns associated with eating; ECG patterns associated with eating; environmental sounds associated with eating; geolocation (e.g. restaurant location) associated with eating; images of nearby food or objects associated with eating; jaw, mouth, and/or teeth motions associated with eating; time of day associated with eating; and/or smells associated with food and/or eating.

In an example, a system for nutritional monitoring and management can have a first mode with only one or more motion sensors activated when a person is not eating and second mode with one or more motion sensors and a camera activated when the person is eating. In an example, a second mode with motion sensors and a camera activated can be more intrusive with respect to the person's privacy. Accordingly, it can be advantageous to only activate the second (motion sensor and camera) mode when the person is eating. In an example, a person can actively (e.g. manually) change a system from a first mode with only motion sensors activated to a second mode with motion sensors and a camera activated when the person is going to start eating. In an example, a system can automatically change from a first mode with only motion sensors activated to a second mode with motion sensors and a camera activated when the system detects that a person is eating (or probably going to start eating). In an example, a system can automatically change from a first mode with only motion sensors activated to a second mode with motion sensors and a camera activated when the system detects: biometric parameters (such as glucose levels or heart rate) associated with eating; body motions (e.g. selected arm, wrist, hand, and/or finger movements) associated with eating; chewing or swallowing sounds associated with eating; EEG patterns associated with eating; EMG patterns associated with eating; ECG patterns associated with eating; environmental sounds associated with eating; geolocation (e.g. restaurant location) associated with eating; images of nearby food or objects associated with eating; jaw, mouth, and/or teeth motions associated with eating; time of day associated with eating; and/or smells associated with food and/or eating.

In an example, a system for nutritional monitoring and management can have a first mode with only motion sensors activated when a person is not eating and second mode with motion sensor, camera, and microphone activated when the person is eating. In an example, a second mode with motion sensor, camera, and microphone activated can be more intrusive with respect to the person's privacy. Accordingly, it can be advantageous to only activate the second (motion sensor, camera, and microphone) mode when the person is eating. In an example, a person can actively (e.g. manually) change a system from a first mode with only motion sensors activated to a second mode with motion sensor, camera, and microphone activated when the person is going to start eating. In an example, a system can automatically change from a first mode with only motion sensors activated to a second mode with motion sensor, camera, and microphone activated when the system detects that a person is eating (or probably going to start eating). In an example, a system can automatically change from a first mode with only motion sensors activated to a second mode with motion sensor, camera, and microphone activated when the system detects: biometric parameters (such as glucose levels or heart rate) associated with eating; body motions (e.g. selected arm, wrist, hand, and/or finger movements) associated with eating; chewing or swallowing sounds associated with eating; EEG patterns associated with eating; EMG patterns associated with eating; ECG patterns associated with eating; environmental sounds associated with eating; geolocation (e.g. restaurant location) associated with eating; images of nearby food or objects associated with eating; jaw, mouth, and/or teeth motions associated with eating; time of day associated with eating; and/or smells associated with food and/or eating.

In an example, a system for nutritional monitoring and management can have a first mode with only motion sensors activated when a person is not eating and second mode with motion sensor, camera, microphone, and biometric sensor activated when the person is eating. In an example, a person can actively (e.g. manually) change a system from a first mode with only motion sensors activated to a second mode with motion sensor, camera, microphone, and biometric sensor activated when the person is going to start eating. In an example, a system can automatically change from a first mode with only motion sensors activated to a second mode with motion sensor, camera, microphone, and biometric sensor activated when the system detects that a person is eating (or probably going to start eating). In an example, a system can automatically change from a first mode with only motion sensors activated to a second mode with motion sensor, camera, microphone, and biometric sensor activated when the system detects: biometric parameters (such as glucose levels or heart rate) associated with eating; body motions (e.g. selected arm, wrist, hand, and/or finger movements) associated with eating; chewing or swallowing sounds associated with eating; EEG patterns associated with eating; EMG patterns associated with eating; ECG patterns associated with eating; environmental sounds associated with eating; geolocation (e.g. restaurant location) associated with eating; images of nearby food or objects associated with eating; jaw, mouth, and/or teeth motions associated with eating; time of day associated with eating; and/or smells associated with food and/or eating.

In an example, a system for nutritional monitoring and management can analyze eating-related motion patterns to determine optimal times to perform a spectroscopic scan of food. In an example, a spectroscopic scan can be triggered at times during eating motions when a person's arm is most extended and, thus, most likely to be closest to remaining food. In an example, a spectroscopic scan can be triggered by a gesture indicating that a person is grasping food or bringing food up to their mouth. In an example, repeated spectroscopic scans of food at different times during a meal can help to analyze the composition of multiple food layers, not just the surface layer. This can provide a more accurate estimate of food composition, especially for foods with different internal layers and/or a composite (non-uniform) ingredient structure.

In an example, a system for nutritional monitoring and management can trigger and/or activate a spectroscopic sensor to take spectroscopic scans of food when a wearable motion sensor indicates that a person is eating. In an example, a system can automatically trigger spectroscopic scanning when data from a motion sensor indicates eating-related motion. In an example, a system can include a wearable device with an outward and/or forward directed spectroscopic scanner which is automatically activated when data from a motion sensor indicates eating-related motion. In an example, a system can include a wrist-worn device with an outward and/or forward directed spectroscopic scanner which is automatically activated to scan near a person's hand for food items when data from a motion sensor indicates eating-related motion. In an example, a system can include a smart watch with a spectroscopic scanner which is automatically activated to scan near a person's hand for food items when data from a motion sensor indicates eating-related motion. In an example, a system can include a smart necklace with a spectroscopic scanner which is automatically activated to scan near a person's mouth for food items when data from a motion sensor indicates eating-related motion.

In an example, a system for nutritional monitoring and management can have a plurality of sensors of different types, wherein a first subset of one or more sensors are active all the time and a second subset of the sensors are only activated when the data from the first set of sensors indicates that a person is eating (or probably will start eating soon). In an example, the first subset of sensors can include a motion sensor (e.g. accelerometer and gyroscope) and/or biometric sensor (e.g. heart rate sensor and blood glucose sensor). In an example, the second subset of sensors can include a camera and/or a microphone. In an example, a system can be triggered to activate a second subset of sensors based on one or more triggers selected from the group consisting of: arm, hand, wrist, and/or finger motions associated with eating; ECG signals associated with eating; EEG signals associated with eating; EMG signals associated with eating; geolocation associated with eating; images or written words associated with eating; room in a building associated with eating; smells or odors associated with eating; spoken words associated with eating; and time of day associated with eating.

In an example, a system for nutritional monitoring and management can comprise: a wearable motion sensor that automatically collects data concerning body motion, wherein this body motion data is used to determine when a person is eating; and a chemical composition sensor that analyzes the chemical composition of food, wherein chemical analysis is used to identify the type and quantity of food, ingredients, or nutrients that the person is eating. In an example, a system can comprise: a motion sensor that is worn by a person, wherein this motion sensor automatically and continuously collects data concerning the person's body motion, and wherein the body motion data is used to determine when the person is eating; and a chemical composition sensor, wherein this chemical composition sensor does not continuously monitor the chemical composition of material within the person's mouth or gastrointestinal tract, but rather only collects information concerning the chemical composition of material within the person's mouth or gastrointestinal tract when body motion data indicates that the person is eating.

In an example, a system for nutritional monitoring and management can include a touch-based user interface through which a person can enter their own information concerning food types and quantities. In an example, a person can touch a screen or press a button to identify a food item type by selecting a food item (e.g. food name or image) from a menu of food items. In an example, a person can touch a screen or press a button to identify a food item quantity by selecting a quantity from a menu of food quantities. In an example, a person can type information about food types and quantities using a keypad or keyboard. In an example, a system can include a gesture recognition user interface. In an example, a system can include a wearable motion sensor which tracks arm, hand, and finger motions and analyzes these motions to identify key gestures. These key gestures can be used by a person to communicate food types and quantities.

In an example, a system for nutritional monitoring and management can enable a person to provide their own (subjective) verbal description of food item types and/or quantities. For an example, if a person has a plate with fish, carrots, and tomatoes in front of them, then the person may speak into a system's microphone—"fish, one half medium size, carrots, a dozen sticks, tomatoes, one half medium size." The system can use speech recognition to translate this description into a standardized and/or digital format for comparison to a standardized database of food item types and/or quantities. In an example, translated results and/or matching information from the database can be displayed or spoken by the system for confirmation by the person. For example, the system may say—"Tilapia, 8 ounces, carrots, 12 ounces, and tomaytoes, 10 ounces. Correct?" The person may respond—"You mean tomatoes?" The system may respond—"Eh . . . tomaytoes, tomatoes." In an example, a person can follow-up with a camera to record images of food items and/or a spectroscopic sensor to scan the food items. Multivariate analysis of these multiple forms of information concerning the food can provide more accurate identification of food item types and quantities.

In an example, a system for nutritional monitoring and management can include a microphone and a speech recognition interface through which a person provides verbal input as part of an analysis of food item types and/or quantities. In an example, a system can receive and recognize a person's verbal descriptions of nearby food items types and/or quantities. In an example, a system can receive and recognize a person's verbal descriptions of food items types and/or quantities which a person selects or purchases. In an example, a system can receive and recognize a person's verbal descriptions of food items types and/or quantities which the person consumes. In an example, a system can use a microphone and speech recognition to extract information related to food selecting, ordering, purchasing, or consumption from speech overheard in a person's environment.

In an example, a system for nutritional monitoring and management can include a microphone through which a person provides verbal input to the system and/or a speaker through which the system provides verbal feedback to the person. In an example, a person can provide oral commands and/or verbal food descriptions as inputs to the system. In an example, a person can direct a virtual light pattern (e.g. a laser pointer) toward locations on nearby food items, say what they think the food items are, and say what they think are the food item quantities. In an example, a system can translate this verbal input into standardized and/or digital information using speech recognition and match this input with records in a database of food item types and quantities. In an example, a person can also record images of the food items and/or do spectroscopic scans of the food items, wherein the results of these verbal descriptions, food images, and spectroscopic scans can be linked together in multivariate analysis to more accurately identify food item types and quantities.

In an example, a system for nutritional monitoring and management can include a speech recognition user interface through which a person can enter their own information concerning food types and quantities. In an example, a person can speak a description of a food item, including the person's perception of food type and quantity. In an example, the system can use speech recognition and natural language processing to convert the person's natural language description into a standardized food type and quantity. In an example, a system may only start recording speech when a person starts it via pressing a button, touching a screen, making a specific gesture, or speaking a specific trigger/command word. For example, a person can activate audio recording by the system with a trigger/command phrase such as—"Hey, Skainet. You can stop pretending that you don't monitor every word I say."

In an example, a system for nutritional monitoring and management can provide a person with a means to provide descriptions of food item types and quantities in the form of words. In an example, a system can prompt a person to provide descriptions of food item types and quantities when food is detected nearby or when the system detects that the person has started eating. In an example, these descriptions can be spoken words (e.g. through a speech recognition interface). In an example, these descriptions can be typed words (e.g. through a keypad or keyboard). In an example, these descriptions can be words selected from a drop-down word menu on a device screen. In an example, these descriptions can be words selected from a drop-down word menu in augmented reality.

In an example, a system for nutritional monitoring and management can use single-word synonyms and/or multi-word phrase synonyms to process natural language descriptions of food items from a person. In an example a system can translate descriptions of food items between different languages. Word processing can include single-word synonyms and variations and multi-word phrase synonyms. In an example, a person can sequentially direct a projected light beam toward different food items in a multi-item meal and provide a verbal description of each food item as the light beam hits the food item. In an example, a person can touch a different food items in a meal displayed on a touch screen in a sequential manner and provide a verbal description of each food item as it is touched. In an example, a system can link food items in an image or in an augmented reality display with food item descriptions provided by a person for multivariate analysis of food items types and quantities.

In an example, word-based descriptions of food types and quantities from a person can be combined with automated food identification processes (e.g. such as image analysis and spectroscopic analysis) for multivariate analysis of food items types and quantities. In an example, word-based descriptions can be linked to food images and data from spectroscopic analysis of food. Multivariate analysis of food item types and quantities can integrate one or more of the following: word-based descriptions of food items; automated analysis of food images; spectroscopic analysis of food items; analysis of food quantity via utensil movement or bending; and arm, wrist, hand, and/or finger movements. In an example, a person can enter information about food which they are consuming via one or more modalities selected from the group consisting of: entering text via a key pad; selecting an entry from a drop-down menu displayed in their field of view (e.g. in augmented reality or on a device display screen); and speaking a description of food into a device with speech recognition functionality.

In an example, person can be given an opportunity (or be prompted) to self-report how they are feeling at times relative to (e.g. before, during, or after) food consumption (of specific types and/or quantities of foods). In an example, food consumption entries can be accompanied by geotagging (e.g. in association with particular restaurants, stores, or dining locations in a building). In an example, a person can indicate (identify or point toward) different food items using gestures which are recognized by the system. In an example, small food samples can be placed on device (or utensil) for analysis. In an example, a system project a beam (or pattern) of light which is used to aim a camera and/or spectroscopic scanner, identify selected food portions in a meal, and/or trace out food boundaries. In an example, a person can identify boundaries of a food portion (in a meal) by drawing with their finger on a touch screen; moving a projected light beam over food; and/or moving an object (e.g. cursor) in augmented reality. In an example, a person can input food-related information by forming a selected pattern of thought which is detected by a mobile EEG device. In an example, a person can input food-related information by making a gesture in proximity to a device with gesture recognition functionality. In an example, a person can input food-related information by scanning a barcode or QR code associated with food.

In an example, Bayesian analysis of food types and quantities can begin with preliminary (prior) estimates of food types and quantities based on word-based descriptions from a person and then modify (update) these estimates with the results from automated analysis. In an example, Bayesian analysis of food types and quantities can begin with preliminary (prior) estimates of food types and quantities based on automated analysis and then modify (update) these estimates based on word-based descriptions from a person. In an example, a person can be prompted to provide word-based descriptions of food items when automated analysis fails to provide estimates of food types and quantities with sufficient accuracy. In an example, a person can be prompted by a system to provide more and more information concerning food items and/or food consumption until the system is able to identify food types and estimate food quantities with a selected level of accuracy and/or certainty.

In an example, a system can include a human-to-computer interface for communication from a human to a computer. In an example, a human-to-computer interface can be based on mobile EEG monitoring and analysis of brainwaves. In an example, a human-to-computer interface can comprise scanning a bar code or QR code associated with a food item. In an example, a human-to-computer interface can comprise recognizing eating-related motions via smart clothing with motion sensors and/or bend sensors. In an example, a human-to-computer interface can comprise a virtual menu which is displayed on the screen of a handheld device or in a person's field of vision via augmented reality eyewear. In an example, a human-to-computer interface can comprise a neural interface. In an example, a human-to-computer interface can comprise a virtual keypad and/or keypad which is projected onto a surface. In an example, a human-to-computer interface can comprise a pop-up menu. In an example, a human-to-computer interface can comprise a dial or rotating bezel.

In an example, a system for nutritional monitoring and management can include a human-to-computer interface for communication from a human to a computer. In an example, a human-to-computer interface can be control buttons. In an example, a human-to-computer interface can comprise a device with gesture recognition functionality. In an example, a system can recognize gestures associated with food selection, identification, and/or consumption. In an example, a human-to-computer interface can comprise a physical or light-projected keyboard or keypad. In an example, a human-to-computer interface can comprise a computer mouse or trackball. In an example, a human-to-computer interface can comprise smart eyewear (such as augmented reality eyewear). In an example, a human-to-computer interface can enable a person to type their descriptions of food items into the system. In an example, a human-to-computer interface can comprise read what a person writes (e.g. a written dietary log) with respect to descriptions of food items consumed. In an example, a human-to-computer interface can have speech and/or voice recognition functionality.

In an example, a system for nutritional monitoring and management can include a human-to-computer interface through which a person provides food-related information. This interface can comprise one or more elements selected the group consisting of: microphone, speech recognition, and/or voice recognition interface; touch screen, touch pad, keypad, keyboard, buttons, or other touch-based interface; camera, motion recognition, gesture recognition, eye motion tracking, or other motion detection interface; interactive food-identification menu with food pictures and names; and interactive food-identification search box.

In an example, a system for nutritional monitoring and management can include a human-to-computer interface for communication from a human to a computer. In an example a human-to-computer interface can be a touch screen and/or touch pad. In an example, a human-to-computer interface can comprise an augmented reality interface on a handheld device or in smart eyewear. In an example, a human-to-computer interface can comprise eye movement and/or gaze tracking. In an example, a human-to-computer interface can comprise tracking head movement. In an example, a human-to-computer interface can comprise tracking arm, hand, wrist, and/or finger movement. In an example, a human-to-computer interface can be a graphical user interface through which a person enters information concerning food items (especially gooey food items). In an example, a human-to-computer interface can comprise gesture recognition via EMG sensors on a person's arm, hand, and/or fingers. In an example, a human-to-computer interface can comprise gesture recognition via EMG sensors on a person's arm, hand, and/or fingers. In an example, a human-to-computer interface can comprise gesture recognition via an arm band with EMG sensors. In an example, a human-to-computer interface can comprise gesture recognition via one or more wearable motion sensors. In an example, a human-to-computer interface can comprise gesture recognition via one or more wearable bend sensors or strain sensors.

In an example, a system for nutritional monitoring and management can include a device which projects a visible laser beam toward food. In an example, this visible laser beam can be different from an outward-directed light beam that is used for spectroscopic analysis. In an example, a visible laser beam can be used by a person in order to point an invisible spectroscopic beam toward a food item for compositional analysis of the food item and/or to direct a camera's focus toward the food item to record an image of the food item. In an example, a person can "point and click" by pointing a laser beam toward a food item and then activating (e.g. by touching, tapping, clicking, or pressing) a device to take a spectroscopic scan of the food, capture an image of the food, or both. In an example, a person can point a laser beam toward food and then give a verbal command to initiate a spectroscopic scan and/or image capture. In an example, spectroscopic analysis can identify food item composition and image analysis can estimate food item quantity. In an example, a visible laser beam projected toward food can also serve as a fiducial marker for calibration of food size and/or color in analysis of food images.

In an example, a person can be prompted to take a picture of food when eating is detected. In an example, a person can be prompted to take one or more actions (e.g. take a picture of food, input a description of the food, take a spectroscopic of food) when the system detects that the person is eating (or has been eating for a selected time without taking a picture or inputting description of food). In an example, a person can be guided concerning how to move a camera in a particular pattern (e.g. varying distance and angle from food) in order to create a 3D image or model of food. This guiding can be visual (e.g. via AR), auditory, or tactile. In an example, a person can be prompted to take these actions when automated analysis does not yield identification of food types and/or quantities with sufficient certainty. In an example, a person can be prompted to take one or more actions when spectroscopic or image analysis suggests lack of food homogeneity. In an example, a person can be prompted to collect additional sensor data concerning food items and/or provide additional description of food items until a system is able to identify food items and estimate food item quantities with a selected level or accuracy and/or certainty.

In an example, a system for nutritional monitoring and management can prompt a person to collect and/or provide information concerning food item types and/or quantities. In an example, a system can automatically track a first set of information concerning food item types and/or quantities (that a person eats) and prompt a person to collect and/or provide a second set of information concerning food item types and/or quantities (that the person eats). In an example, both sets of information can be jointly analyzed by the system to determine food item types and/or quantities (that a person eats). In an example, a system can prompt a person to collect and/or provide information concerning food item types and/or quantities when the system detects that the person is eating (or likely to start eating soon). In an example, a system can include a device with an eating-detection sensor worn by a person, wherein the system prompts the person to collect and/or provide information concerning food item types and/or quantities when data from the eating-detection sensor indicates that the person is eating.

In an example, a system for nutritional monitoring and management can include eating-detection sensor selected from the group consisting of: motion sensor (e.g. accelerometer, gyroscope, and/or bend sensor), microphone or some other type of sound sensor, EMG sensor or some other type of electromagnetic energy sensor, and camera. In an example, a system can prompt a person to collect and/or provide food-related information via a prompt selected from the group consisting of: a flashing light, light display, icon display, image display, or some other type of visual stimulus; a mild electrical current or some other type of electromagnetic stimulus; a phone call or some other type of telephonic stimulus; a text message or some other type of written stimulus; a tone, buzzer, alarm, note, song, computer-generated speech, prerecorded verbal message, or some other type of audio stimulus; and a vibration, moving protrusion which moves relative to a person's skin, or some other type of haptic stimulus.

In an example, a system for nutritional monitoring and management can prompt a person to collect and/or provide food information though one or more mechanisms selected from the group consisting of: using a smart utensil for food consumption; using a set of smart place-setting components (dish, plate, utensils, glass, etc) to record information about types and quantities of food; using a food scale; inserting a food probe into food; recording images (e.g. taking pictures) of food from different angles; recording a video of food from different angles; directing light energy toward (or into) food and recording the results of interaction between this energy and food; taking a spectroscopic scan of food; directing electromagnetic energy toward (or into) food and recording the results of interaction between this energy and food; and directing sound energy toward (or into) food and recording the results of interaction between this energy and food.

In an example, a system for nutritional monitoring and management can prompt a person to collect and/or provide information concerning food item types and/or quantities by performing one or more of the following actions: inserting a food probe into a food item; making a food-related gesture which is recognized by the system; moving a virtual cursor to point at a food item or outline the border of the food item; moving a projected light beam to point at a food item or outline the border of the food item; placing a fiducial marker near food to calibrate food size, orientation, or color; recording an image (e.g. take a picture) of a food item; scanning a food barcode or QR code; selecting a food item from a menu displayed on a device screen; selecting a food item from a menu displayed via augmented reality eyewear; speaking a food description into a microphone; taking a spectroscopic scan of a food item; typing a food description via a keypad or touch screen; using a smart utensil to eat; and weighing food on a scale.

In an example, a system for nutritional monitoring and management can prompt a person to collect and/or provide food-related information by recording an image (e.g. take a picture) of a food item. In an example, a system can prompt a person to collect and/or provide food-related information by weighing food on a scale. In an example, a system can prompt a person to collect and/or provide food-related information by scanning a food barcode or QR code. In an example, a system can prompt a person to collect and/or provide food-related information by moving a virtual cursor to point at a food item or outline the border of the food item. In an example, a system can prompt a person with clarifying questions concerning the types and quantities of food that person has consumed. These questions can be asked in real time, as a person eats, at a subsequent time, or periodically.

In an example, a system for nutritional monitoring and management can prompt a person to collect and/or provide food-related information by speaking a food description into a microphone. In an example, a system can prompt a person to collect and/or provide food-related information by typing a food description via a keypad or touch screen. In an example, a system can prompt a person to collect and/or provide food-related information by making a food-related gesture which is recognized by the system. In an example, a system can prompt a person to collect and/or provide food-related information by selecting a food item from a menu displayed on a device screen. In an example, a system can prompt a person to collect and/or provide food-related information by selecting a food item from a menu displayed via augmented reality eyewear.

In an example, a system for nutritional monitoring and management can prompt a person to collect and/or provide food-related information by moving a projected light beam to point at a food item or outline the border of the food item. In an example, a system can prompt a person to collect and/or provide food-related information by placing a fiducial marker near food to calibrate food size, orientation, or color. In an example, a system can prompt a person to collect and/or provide food-related information by inserting a food probe into a food item. In an example, a system can prompt a person to collect and/or provide food-related information by taking a spectroscopic scan of a food item. In an example, a system can prompt a person to collect and/or provide food-related information by using a smart utensil to eat.

In an example, a system for nutritional monitoring and management can prompt a person to collect and/or provide information concerning food item types and/or quantities when food is detected near the person. In an example, a system can prompt a person to collect and/or provide information concerning food item types and/or quantities when a person first starts to eat. In an example, a system can prompt a person to collect and/or provide information concerning food item types and/or quantities after the person has eaten for a selected period of time. In an example, a system can prompt a person to collect and/or provide information concerning food item types and/or quantities after the person has eaten for a selected period of time if the person has not already collected and/or provided this information during this period of time. In an example, a system can prompt a person to collect and/or provide information concerning food item types and/or quantities after a person has finished eating a meal.

In an example, a system for nutritional monitoring and management can prompt a person to record images of food using a camera when data from the wearable sensor indicates eating and the person does not record images of food for this eating event before eating starts. In an example, the person can be prompted to record images of food when data collected by a wearable sensor indicates eating and the person does not record images of food for this eating event before a selected length of time after eating starts. In an example, the person can be prompted to record images of food when data collected by the wearable sensor indicates eating and the person does not record images of food for this eating event before a selected quantity of eating-related actions occurs during the eating event. In an example, the person can be prompted to record images of food when data collected by the wearable sensor indicates eating and the person does not record images of food for this eating event at the end of the eating event. In an example, a system can prompt the person to use one or more sensor to collect information concerning food items multiple times during a meal.

In an example, a system for nutritional monitoring and management can prompt a person to use a smart utensil, probe, or dish when data from a wearable sensor indicates that the person is eating and the person has not started using the smart utensil, probe, or dish before a selected length of time after eating starts. In an example, a person can be prompted to use a smart utensil, probe, or dish when data from a wearable sensor indicates that the person is eating and the person does not start using the smart utensil, probe, or dish before a selected quantity of eating-related actions (e.g. bites or forkfuls) occurs. In an example, a person can be prompted to record images of food when data collected by a wearable sensor indicates eating and the person does not record images of food for this eating event before a selected quantity of eating-related actions occurs during the eating event. In an example, a person can be prompted to use a smart utensil, probe, or dish when data from the wearable sensor indicates eating and the person does not use the smart utensil, probe, or dish throughout an entire eating event. In an example, a person can collect and/or provide food-related information before, during, or after eating. In an example, collection and/or provision of food information by a person can be prompted or solicited in real time when eating is first detected. In an example, collection and/or provision of food information by a person can be prompted or solicited at the end of the day and can be associated with multiple eating events throughout the day.

In an example, a system for nutritional monitoring and management can create a sound or voice, light, vibration or tactile sensation that prompts a person to use a handheld spectroscopic food sensor when data from a wearable device indicates that the person is eating. In an example, a person can be prompted to use a spectroscopic food sensor by a prompt selected from the group consisting of: beep, buzz, tone, sequence of tones, alarm, voice, music, or other sound-based prompt; vibration, prod, sliding rotating, or pressing protrusion, contracting garment or accessory, or other tactile prompt; mild shock, neurostimulation, or other electromagnetic energy prompt; and LED, LED pattern, blinking light, flash, image display, or other light energy prompt. In an example, a system can comprise a speaker, light, actuator or other moving member, or electromagnetic energy emitter which creates such a prompt. In an example, a wearable device which is in wireless communication with a handheld spectroscopic food sensor can include a speaker, light, actuator or other moving member, or electromagnetic energy emitter which creates such a prompt.

In an example, a system for nutritional monitoring and management can project a light pattern in a sequential manner toward a series of selected locations on a meal where a person should take spectroscopic scans. In another example, a person can move a projected light pattern from one food item to another in a meal in order to separately identify each food item. In an example, a person can sequentially take spectroscopic scans from one food item to another in the same sequence in which the person moves a projected light beam from one food item to another. This can link each food item in a food image with the results of the appropriate spectroscopic scan of that food item. Using these or similar methods, each food item in an image can be linked with the results of its corresponding spectroscopic scan.

In an example, a system for nutritional monitoring and management can prompt a person to take spectroscopic scans at selected locations on a food item or across multiple food items in a meal based on the analysis of food images taken by a camera. In an example, food images can be analyzed to identify different food items in a meal. In an example, a person can be prompted to take spectroscopic scans at different locations on the mail which are associated with different food items. In an example, suggested locations for these spectroscopic scans can be communicated from a system to a person by a light pattern which is projected onto food at these different locations. In an example, the results of spectroscopic scans of food at a plurality of selected locations can be linked to different food items in a meal image. In an example, a person can take a scan at a selected location on food and then take a picture of the food with that location highlighted by a light pattern pointed toward that location.

In an example, a system for nutritional monitoring and management can use a combination of food-related information which is collected automatically from sensors and food-related information which is voluntarily provided by a person. In an example, a system can automatically collect food-related information from a combination of motion sensors, sound sensors, food images, and/or spectroscopic sensors and can also receive voluntary food-related information from a person via a microphone, touch screen, keypad, and/or gesture recognition interface. In an example, multivariate analysis of automatically-collected food information and voluntarily-provided food information can enable more accurate identification of food item types and estimation of food item quantities than either type of food information alone. In an example, a system can prompt a person to enter verbal descriptions of what they eat each time that they eat.

In an example, a system for nutritional monitoring and management can measure a person's consumption of at least one type of food, ingredient, or nutrient. In an example, a system can identify and track in an entirely automatic manner the types and quantities of foods, ingredients, or nutrients that a person consumes. Alternatively, such identification can occur in a partially-automatic manner in which there is interaction between automated and human food identification methods. In an example, identification of the types and quantities of food, ingredients, or nutrients that a person consumes can be a combination of, or interaction between, automated food identification methods and human-based food identification methods. In an example, automatic identification of food types and quantities can be based on: color and texture analysis; image segmentation; image pattern recognition; volumetric analysis based on a fiducial marker or other object of known size; and/or three-dimensional modeling based on pictures from multiple perspectives.

In an example, a system for nutritional monitoring and management can estimate the level of accuracy and/or certainty with which a system can identify food item types and estimate food item quantities based on information which is automatically collected when a person eats. In an example, a system can estimate the level of accuracy and/or certainty with which the system can identify food item types and estimate food item quantities based on information from motion sensors, food images, sound sensors, and/or spectroscopic sensors when a person eats. In example, if the level of accuracy and/or certainty is below a target level, then the system can prompt a person to provide additional food-related information. In example, if the level of accuracy and/or certainty is below a target level, then the system can prompt a person to provide additional food-related information in an iterative and interactive manner until the target level is achieved. In an example, a person can be prompted to take additional pictures of food, take additional spectroscopic scans of food, and/or provide additional verbal descriptions of food until a target level of food identification accuracy and/or certainty is achieved. In an example a target level can be higher when the risk of an error is greater, such as when a system is relied upon to avoid food items to which a person is allergic or to detect toxic substances in food items.

In an example, a system for nutritional monitoring and management can determine initial estimates of food types and quantities, convey these initial estimates to a person, and then receive information from the person which is used by the system to refine these initial estimates. In an example, a system can: (a) determine initial estimates of food item types and quantities based on data which is automatically collected by sensors when a person eats, (b) convey these initial estimates to the person; and (c) receive voluntary food-related information from the person which is used to refine these initial estimates. In an example, a system can: (a) determine preliminary estimates of food item types and quantities based on data from motion sensors, sound sensors, food images, and/or spectroscopic sensors, (b) communicate these preliminary estimates to a person through a display screen, augmented reality eyewear, and/or synthesized speech; and (c) receive additional food-related information directly from the person, wherein the system uses this additional information to refine the preliminary estimates of food item types and quantities.

In an example, a method for nutritional monitoring and management can comprise: collecting primary data using a wearable food-consumption monitor to detect when a person is eating, wherein this monitor is worn on the person, and wherein primary data collection does not require action by the person during eating apart from the act of eating; and collecting secondary data using a handheld food-identifying sensor to identify the selected types of foods, ingredients, or nutrients that the person is eating, wherein secondary data collection by the handheld food-identifying sensor requires action by the person during eating apart from the act of eating, and wherein the person is prompted to take this action when primary data indicates that the person is eating and secondary data has not already been collected.

In an example, a system for nutritional monitoring and management can comprise a wearable device which detects when a person is eating. In an example, a system can prompt a person (e.g. via vibration, voice, sound, or light) to use a mobile device to scan food and/or record images of food when the person is eating. In an example, a person can be prompted to use a device to monitor nutritional intake when a wearable device detects that they are eating. In an example, eating can be detected by a person swallowing a selected number of times in a period of time, by a pattern of chewing, and/or by a pattern of repeated hand motions. In an example, a wearable device can be selected from the group consisting of: smart watch; wrist band; necklace and/or pendant; ear bud; and eyewear.

In an example, a system for nutritional monitoring and management can comprise: (a) a wearable sensor that is worn on a person's body or clothing, wherein this wearable sensor automatically collects data that is used to detect eating without requiring action by the person in association with eating apart from the act of eating; (b) a camera, wherein this camera is used by the person to record images of food that the person eats, wherein using this camera to record images of food requires voluntary action by the person apart from the act of eating, and wherein the person is prompted to record images of food using this camera when data collected by the wearable sensor indicates eating; and (c) a data analysis component, wherein this component analyzes food images taken by the camera to estimate the types and quantities of foods, ingredients, nutrients, and/or calories that are eaten by the person.

In an example, a system for nutritional monitoring and management can comprise: (a) a wearable food-consumption monitor that is configured to be worn on a person's body or clothing, wherein this monitor automatically collects primary data that is used to detect when the person is eating; (b) a computer-to-human prompting interface which a person uses to enter secondary data concerning the person's consumption of at least one selected type of food, ingredient, or nutrient, wherein this interface selected from the group consisting of: speech or voice recognition, touch or gesture recognition, motion recognition or eye tracking, and buttons or keys, and wherein this interface prompts the person to enter secondary data in association with a specific food consumption event when the primary data indicates that the person is eating and the person has not already entered this data. In an example, primary data can be body movement data or data concerning electromagnetic signals from the person's body. In an example, secondary data can be collected by a mobile phone, smart utensil, food probe, smart necklace, smart eyewear, or a smart watch.

In an example, a system for nutritional monitoring and management can comprise: a wearable motion sensor that automatically collects data concerning a person's body motion, wherein this body motion data is used to determine when this person is eating; and a user interface that prompts the person to provide additional information concerning the selected types of foods, ingredients, or nutrients that the person is eating when the body motion data indicates that the person is eating. In an example, a method for nutritional monitoring and management can comprise: (a) having a person wear a motion sensor on a body member selected from the group consisting of wrist, hand, finger, and arm; wherein this motion sensor continually monitors body motion to provide primary data that is used to detect when a person is eating; and (b) prompting the person to collect secondary data concerning food consumption when the primary data indicates that the person is eating; wherein secondary data is selected from the group consisting of: data from the interaction between food and reflected, absorbed, or emitted light energy including pictures, chromatographic results, fluorescence results, absorption spectra, reflection spectra, infrared radiation, and ultraviolet radiation; data from the interaction between food and electromagnetic energy including electrical conductivity, electrical resistance, and magnetic interaction; data from the interaction between food and sonic energy including ultrasonic energy; data from the interaction between food and chemical receptors including reagents, enzymes, biological cells, and microorganisms; and data from the interaction between food and mass measuring devices including scales and inertial sensors.

In an example, a system for nutritional monitoring and management can include a smart watch which collects primary data concerning eating and can prompt a person to collect and/or provide secondary data for food identification when primary data indicates that the person is eating and the person has not yet collected secondary data. In an example, primary data can be body motion data and secondary data can be food images. In an example, a smart watch can be a mechanism for collecting primary data and a smart spoon can be a mechanism for collecting secondary data. In an example, collection of primary data can be automatic, not requiring any action by the person in association with eating apart from the actual act of eating, but collection of secondary data can require a specific action (e.g. triggering and aiming a camera). In an example, automatic primary data collection and non-automatic secondary data collection can combine to provide relatively high-accuracy and high-compliance food consumption measurement with relatively low privacy intrusion.

In an example, a system for nutritional monitoring and management can include a wearable device which detects changes in person's heart rate, heart rhythm, and/or heart rate variation which indicates that the person is eating. When data from a wearable device indicates that a person is eating, the system can prompt the person to record food images using a camera and/or to scan food using a spectroscopic sensor. In an example, a system can include: a wearable camera that automatically records images, wherein the images are analyzed to detect when the person is eating; and a user interface that prompts the person to provide additional information concerning the selected types of foods, ingredients, or nutrients that the person is eating when the images indicate that the person is eating. In an example, a system can include a mobile EEG monitor which detects changes in a person's electromagnetic brain activity which indicate that a person is eating. This system can prompt the person to record food images using a camera and/or scan food using the spectroscopic sensor when eating is detected.

In an example, a system for nutritional monitoring and management can prompt a person to trigger, activate, or operate secondary data collection in association with eating when analysis of primary data indicates that this person is eating. In an example, a system can prompt a person to trigger, activate, or operate a secondary data collection component in association with eating when analysis of primary data indicates that this person is eating. In an example, a system with a component that automatically collects primary data to detect when a person is eating can prompt the person to collect secondary data to identify food consumed when the person is eating. In an example, a system can prompt a person to collect and/or provide secondary data in association with eating when analysis of primary data indicates that the person is eating and the person has not yet collected secondary data. In an example, secondary data can be the results of chemical analysis of food. In an example, collection of secondary data can require that the person bring a nutrient-identifying utensil or sensor into physical contact with food. In an example, collection of secondary data can require that the person speak into a voice-recognizing device and verbally identify the food that they are eating. In an example, collection of secondary data can require that a person use a computerized menu-interface to identify the food that they are eating. In an example, a system can include a smart watch (with a motion sensor) to detect eating and a smart spoon (with a built-in chemical composition sensor), wherein a person is prompted to use the smart spoon to eat food when the smart watch detects that the person is eating.

In an example, a system for nutritional monitoring and management can prompt a person to use a smart spoon for eating and automatically record images of portions of food that are in the spoon's scoop. In an example, such automatic picture taking can be triggered by infrared reflection, some other type of optical sensor, a pressure sensor, an electromagnetic sensor, or some other type of contact sensor in the spoon scoop. In an example, a system can prompt a person to use a camera to record an image of food in the spoon's scoop. In an example, a system can prompt a person to aim a camera toward food on a plate, in a bowl, or in original packaging to record images of food before it is apportioned into portions by the spoon. In an example, food on a plate, in a bowl, or in original packaging can be easier to identify by analysis of its shape, texture, scale, and colors than food apportioned into portions.

In an example, a system for nutritional monitoring and management can prompt a person to use a mobile device to provide and/or collect food-related information when a wearable device detects that that person is eating. In an example, a system can prompt a person (e.g. by vibration, sound, or light) to use a mobile device to provide and/or collect food information when a wearable device worn that that person detects (e.g. based on eating-related body motions or sounds) that the person is eating. In an example, a system can prompt a person to use a mobile device to take spectroscopic scans of food and/or to record images of food when a wearable device detects that the person is eating.

In an example, a system for nutritional monitoring and management can track the amount of food eaten during a meal or during a period of time spanning multiple meals. In an example, a system can track calories consumed per day and cumulative calories consumed. In an example, a system can track calories consumed during a period of time and compare this to a calorie budget for that period of time. In an example, a system can track the number of bites and/or swallows during a meal and/or during a period of time. In an example, a system can track arm, wrist, and/or hand motion to help estimate the quantity of food consumed. In an example, a system can track the pitch, roll, and yaw of wrist and/or hand motion to help estimate the quantity of food consumed. In an example, a system can track the speed and/or pace of bites or sips by tracking the speed and/or pace of wrist and/or hand motions. In an example, a system can recognize arm and/or hand gestures to help estimate the quantity and/or speed of food consumption. In an example, a system can track and report historical food consumption patterns for a person.

In an example, a system for nutritional monitoring and management can include a camera whose field of vision and/or the focal length is automatically adjusted to track a moving object such as a person's hand, a person's mouth, or a food item. In an example, a system can include a camera which scans space around a person's hand or mouth in order to detect and identify food items. In an example, a system can include a wrist-worn camera which tracks the ends of a person's fingers in order to detect and identify food items. In an example, a system can monitor: the types and volumes of food items within view and/or reach of the person; changes in the volumes of these food items over time; the number of times that the person brings their hand (with food) to their mouth; the sizes or portions of food that the person brings to their mouth; and the number, frequency, speed, or magnitude of chewing, biting, or swallowing movements.

In an example, a system for nutritional monitoring and management can associate a timestamp with a food consumption event. In an example, a system can track and analyze the timing, speed, and/or pace of a person's food consumption. In an example, a system can track and analyze when a person eats meals and whether the person eats snacks between meals. In an example, a system can track and analyze how quickly a person eats meals or snacks between meals. In an example, a system can track and analyze the speed and/or pace of a person's hand-to-mouth motions, chewing motions, sipping motions, swallowing motions, and/or biting motions. In an example, a system can track and analyze the duration of a person's meals and/or between-meal snacks. In an example, a system can analyze associations between food consumption speed and food consumption amount. For example, if a person tends to be satiated with less food when the person eats more slowly, then a system can encourage a person to eat more slowly. In an example, a system can encourage a person to eat more slowly via sound cues, haptic cues, and/or visual cues. In an example, a system can encourage a person to eat more slowly by providing: visual cues (e.g. display of virtual objects) via augmented reality eyewear; sound cues (e.g. musical tones or other sounds) via an ear-worn wearable device; haptic cues (e.g. vibrations) via a smart watch or band; and/or haptic cues (e.g. vibrations) via a smart utensil.

In an example, a system can collect food-related information before and after a person eats. Differences in food-related information before vs. after eating can be analyzed to estimate the quantities of food items which a person has actually eaten. In an example, a system can collect food-related information before and after a person eats a meal, wherein differences in food-related information before vs. after eating are analyzed to estimate the quantities of food items which a person actually eats during the meal. In an example, food-related information can include food images before vs. after the person eats. In an example, differences in food size in before vs. after images can be used to estimate the quantity of food which a person has eaten. In an example, food-related information can include food weight before vs. after the person eats. In an example, a system can collect data that enables tracking the cumulative amount of foods, ingredients, and/or nutrients which a person consumes during a period of time (such as an hour, day, week, or month) or during a particular eating event.

In an example, a system can collect food-related information multiple times while a person is eating. In an example, a system can collect food-related information multiple times while a person is eating a meal. In example, a system can take spectroscopic scans of food at multiple times (and/or prompt a person to take spectroscopic scans at multiple times) during a meal. Taking multiple spectroscopic scans during a meal can collect spectroscopic information about multiple layers or structures of the interior of a food item. If a spectroscopic sensor only measures the surface of a food item which is exposed at a given time, then taking multiple scans during a meal is particularly important when the interior of a food item has a different composition than the exterior of the food item.

In an example, a system for nutritional monitoring and management can automatically record images of food items at the start of a meal and the end of the meal. Differences between images at the start and end of a meal can be used to estimate the actual quantity of food items consumed by a person. In an example, a system can automatically record images of food items at multiple times during a meal, using sequential reductions in the quantity of food items remaining to estimate the actual quantity of food items consumed by a person. In an example, a system can be triggered to automatically record images of food when eating (a meal) begins and when eating (the meal) ends, using differences in food in the before vs. after images to estimate the actual quantity of food consumed by a person. In an example, a system can prompt a person to record images of food when eating (a meal) begins and when eating (the meal) ends and use differences in food in the before vs. after images to estimate the actual quantity of food consumed by a person.

In an example, a system for nutritional monitoring and management can automatically record the weight of food on a scale at the start of a meal and at the end of the meal, using differences in weight between the before and after measurements to estimate the actual quantity of food items consumed by a person. In an example, a food scale can measure the overall weight of food items in a meal by measuring, at different times during a meal, the overall weight of a food holding item (such as a plate, bowl, cup, or tray) which holds different types and/or portions of food. In an example, a multi-part food scale can measure the weights of different food items or portions in a meal, wherein different food items or portions in the meal are located on different parts and/or segments of the multi-part scale. In an example, each part and/or segment of a multi-part food scale can individually and independently measure the weight of a type of food on that particular part and/or segment. In an example, parts and/or segments of a multi-part food scale can be separated by ridges or partitions. In an example, a system can include a food scale. In example, the weight of food can be measured before and after a meal to determine the weight of food eaten by a person. In an example, food portions can be eaten sequentially and scale measurements can be made after each portion. In an example, a scale can have multiple sub-scales, one for each segment of a meal (e.g. for each type of food).

In an example, a system for nutritional monitoring and management can analyze multiple food characteristics in order to identify food item types and quantities. In an example, these food characteristics can include the amounts of vitamins and minerals in a food item. In an example, these food characteristics can include the ingredient list on packaging of a food item. In an example, these food characteristics can include the ingredients in a recipe for a food item. In an example, these food characteristics can include the light absorption spectrum of a food item. In an example, these food characteristics can include the light reflection spectrum of a food item. In an example, these food characteristics can include the nutritional composition of a food item. In an example, these food characteristics can include the percentage or amount of dietary fiber in food item. In an example, these food characteristics can include the percentage or amount of saturated fat in food item. In an example, these food characteristics can include the percentage or amount of carbohydrates in a food item. In an example, these food characteristics can include the percentage or amount of fats in a food item. In an example, these food characteristics can include the percentage or amount of protein in a food item. In an example, these food characteristics can include the percentage or amount of sugars in a food item. In an example, these food characteristics can include the percentage or amount of trans fat in a food item.

In an example, a system for nutritional monitoring and management can estimate total calories in a food item or meal. In an example, a system can estimate types and quantities of carbohydrates, sugars, fats, salts, proteins, vitamins, and/or minerals in a food item or meal. In an example, a system can identify allergens, carcinogens, toxins, metals, chemicals, pathogens, bacteria, and/or fungi in a food item or meal. In an example, a system can identify: antioxidants, beans, beef, bread, cereal, cheese, corn, dairy, egg, fish, fruit, grain, milk, nuts, oats, pasta, pork, poultry, rice, starch, sugar, vegetables, and/or wheat. In an example, a system can estimate the freshness of beef, cheese, dairy, egg, fish, fruit, milk, nuts, pork, poultry, and/or vegetables. In an example, a system can estimate the water content of: beans, bread, cereal, corn, grain, oats, pasta, rice, and/or wheat.

In an example, a system for nutritional monitoring and management can estimate the quantities of food items and/or nutrients in those food items. In an example, a system can estimate quantities of food items or nutrients which are near a person before the person starts eating, after the person has eaten, or the difference between before and after eating. In an example, a system can estimate the quantities of food items or nutrients which a person actually consumes. In an example, a system can estimate the cumulative quantity of food items or nutrients being consumed by a person in real time (or close to real time). In an example, a system can estimate quantities of food and/or nutrients consumed in real time during a meal.

In an example, a system for nutritional monitoring and management can estimate quantities of food and/or nutrients consumed by a person by estimating changes in the volume of food near the person during a meal. In an example, a system can count the number of times that a person lifts a spoon, fork, or other food-transporting utensil up to their mouth using data from motion and/or force sensors. In an example, motion sensors can be part of a utensil. In an example, motion sensors can be part of a device worn on a person's arm, wrist, and/or finger. In an example, a device worn on a person's arm, wrist, or finger can include a proximity sensor which detects when a food utensil is near the device. Such a proximity sensor can enable indirectly tracking utensil movement via a motion sensor on a wearable device.

In an example, a system for nutritional monitoring and management can estimate quantities of food and/or nutrients consumed by a person by: estimating the amount of food per spoon or fork full; estimating the number of times a spoon or fork has been lifted up to a person's mouth; and multiplying the amount in a spoonful or a forkful times the number of lifts. In an example, the amount of food per spoonful or forkful can be estimated by data from a force sensor and/or motion sensor on a spoon or fork. In an example, the amount of food per spoonful or forkful can be estimated by (past) correlation between a decreasing amount of food near a person in images and an increasing number of times that a spoon or fork is lifted up to a person's mouth. In an example, the amount of food per spoonful or forkful can be estimated by the amount of time that a spoon or fork is held in proximity to a person's mouth during a lift. In an example, the amount of food per spoonful or forkful can be estimated by the number of times that a person chews and/or swallows per spoonful or forkful. In an example, chews and/or swallows can be monitoring using a wearable sound sensor, wearable motion sensor, wearable vibration sensor, or wearable electromagnet energy (e.g. EMG) sensor. In an example, chewing and/or swallowing can be monitoring by a device worn around a person's neck, a device worn on a person's throat or neck, an ear-worn device, or an intra-oral device.

In an example, a system for nutritional monitoring and management can estimate quantities of liquids consumed by a person by: estimating the amount of liquid per sip from a beverage container (e.g. glass, cup, mug, or bottle); estimating the number of times a beverage container has been lifted up to a person's mouth; and multiplying amount in a sip times the number of container lifts. In an example, the amount of food per sip can be estimated by data from an optical sensor (e.g. liquid level detector) in a beverage container. In an example, the amount of food per sip can be estimated by the number of times that a person swallows per sip. In an example, swallowing can be monitoring using a wearable sound sensor, wearable motion sensor, wearable vibration sensor, or wearable electromagnet energy (e.g. EMG) sensor. In an example, swallowing can be monitoring by a device worn around a person's neck, a device worn on a person's throat or neck, an ear-worn device, or an intra-oral device.

In an example, a system for nutritional monitoring and management can also analyze the packaging and/or label of a food item in order to identify food item types and estimate food item quantities. In an example, a system can also analyze a barcode or QR code of food packaging. In an example, a system can also analyze food pairings (e.g. which types of food are near a food item in a meal). In an example, a system can also analyze the configurations of borders between food items in a meal or on a dish. In an example, a system can also analyze the homogeneity of a food item. In an example, a system can also analyze the type of serving dish (e.g. plate, bowl, glass, cup, bottle, can, package, wrapper, bag, box) on which (or in which) a food item is served. In an example, a system can also analyze food shading or light intensity. In an example, a system can also analyze food shape. In an example, a system can also analyze food size.

In an example, a system for nutritional monitoring and management can also analyze where food is stored (e.g. on a shelf or in a refrigerator) as part of identification of food item types and estimation of food item quantities. In an example, a system can also analyze food temperature. In an example, a system can also analyze food texture. In an example, a system can also analyze the type of utensil (e.g. fork, spoon, knife, and/or chop sticks) which is used to eat a food item. In an example, a system can also analyze whether a food item is held by a person's hand during eating. In an example, a system can also analyze chewing or swallowing sounds during food consumption. In an example, a system can also analyze food viscosity and/or motion. In an example, a system can also analyze the geolocation of food selection, purchase, or consumption (e.g. via GPS). In an example, a system can also analyze the reflection of infrared light from food. In an example, a system can also analyze the spectral distribution of light reflection or absorption by food (e.g. spectroscopic scan data).

In an example, a system for nutritional monitoring and management can analyze the environmental context for food selection, purchase, or consumption as part of identifying food item types and estimating food item quantities. In an example, a system can also analyze food color (or color spectral distribution) in ambient light. In an example, a system can also analyze food configuration (e.g. food orientation in a meal). In an example, a system can also analyze the type of container in which food is stored. In an example, a system can also analyze the electromagnetic impedance of food. In an example, a system can also analyze the location of a food item in a meal. In an example, a system can also analyze the location of a food item on a dish (e.g. where is it located on a plate of food).

In an example, a system for nutritional monitoring and management can analyze multiple food characteristics in order to identify food items types and estimate food item quantities. In an example, a system for nutritional monitoring and management can analyze multiple food characteristics selected from the group consisting of: environmental context for food selection, purchase, or consumption; food color or color spectral distribution in ambient light; food configuration (e.g. food orientation); food container type; food electromagnetic impedance; food location in a meal; food location on a dish; food packaging and/or label; food packaging barcode or QR code; food pairings (e.g. types of food nearby in a meal); food portion border; food portion homogeneity; food serving dish type (e.g. plate, bowl, glass, cup, bottle, can, package, wrapper, bag, box); food shading; food shape; food size; food storage type (e.g. shelf, refrigerator); food temperature; food texture; type of food utensil (or person's hand) used to eat food; food viscosity and/or motion; chewing or swallowing sounds during food consumption; geolocation (e.g. GPS) of food selection, purchase, or consumption; infrared reflection pattern; spectral distribution of light reflection or absorption; spectroscopic scan data; and ultrasonic energy reflection pattern.

In an example, a system for nutritional monitoring and management can analyze multiple food characteristics into order to identify food item types and quantities. In an example, these food characteristics can include a barcode or QR code on the label or packaging of a food item. In an example, these food characteristics can include a logo or other images on the label or packaging of a food item. In an example, these food characteristics can include the name or location of a restaurant where a food item is served. In an example, these food characteristics can include the presence of allergens or pathogens in a food item. In an example, these food characteristics can include the shape of a food item. In an example, these food characteristics can include the shape of the perimeter of a food item. In an example, these food characteristics can include the three-dimensional shape of a food item. In an example, these food characteristics can include the size of a food item. In an example, these food characteristics can include the volume of a food item. In an example, these food characteristics can include text on a label or packaging of a food item. In an example, these food characteristics can include the texture of a food item.

In an example, a system for nutritional monitoring and management can analyze multiple food characteristics into order to identify food item types and quantities. In an example, these food characteristics can include a description of a food item on a restaurant menu. In an example, these food characteristics can include verbal descriptions of food items by one or more users. In an example, these food characteristics can include the color and/or spectral distribution of a food item. In an example, these food characteristics can include the distance from a camera to a food item in an image. In an example, these food characteristics can include the food items which are paired with (or otherwise accompany) a food item in a meal. In an example, these food characteristics can include the geolocation of the consumption of a food item. In an example, these food characteristics can include the geolocation of cooking and/or preparation of a food item. In an example, these food characteristics can include the geolocation of the purchase of a food item. In an example, these food characteristics can include the history of consumption of a food item by a person or persons. In an example, these food characteristics can include the temperature of a food item. In an example, these food characteristics can include the time of consumption of a food item. In an example, these food characteristics can include the type of dish or container on (or in) which a food item is served. In an example, these food characteristics can include the weight of a food item.

In an example, a system for nutritional monitoring and management can record food item images from multiple angles and/or distances to create a three-dimensional model for determining food item volumes and/or quantities. In an example, a system can estimate quantities of food items from food images by volumetric analysis of food from multiple perspectives and/or three-dimensional modeling of food. In an example, a system can record food images from multiple angles to segment a meal into different food item types, estimate the three-dimensional volume of each food item type, and control for lighting and shading differences. In an example, a system can guide a person how to record food images from different angles for volumetric analysis of food item quantities.

In an example, a system for nutritional monitoring and management can analyze images of food items to determine the types and/or quantities of foot items in an image. In an example, a system can analyze a video of food items and/or sequential still images of food items to estimate a three-dimensional food item's size, volume, and/or quantity. In an example, a system can prompt a person to move a mobile device in a selected pattern in proximity to a food item in order to record a video and/or sequential still images of the food item to estimate three-dimensional food size, volume, and/or quantity. In an example, a mobile device of a nutritional monitoring and management system can include an infrared light projector which projects infrared light toward a food item and an infrared light receiver which receives that light after it has been reflected in order to estimate the distance from the mobile device to the food item.

In an example, there can be inter-portion food variation in a meal. Inter-portion variation is variation in food characteristics between different portions (e.g. different types or items) of food in a meal and/or given location. Inter-portion variation can include differences in molecular composition, color, texture, shape, temperature, and location. Different types of food can be identified by inter-portion differences in their molecular composition, color, texture, shape, temperature, and location in a meal. To address inter-portion variation, a person can take spectroscopic scans of food items in a meal. The locations of these scans can be based on the person's evaluation of the number and locations of these different portions. Alternatively, to address inter-portion variation, a system can guide person how to take spectroscopic scans at different locations and/or of different portions of a meal based on automated analysis of food images.

In an example, there can be intra-portion food variation in a meal. Intra-portion variation is variation in food characteristics within a portion (e.g. a single type or item) of food. Intra-portion variation also include differences in molecular composition, color, texture, shape, temperature, and location. Some foods are non-homogenous. For example, there can be pieces of fruit or nuts at different locations on the outer surface of a food item. Different locations on the outer surface of a food item can have different molecular compositions, colors, textures, shapes, temperatures, or locations. To address intra-portion variation on the outer surface of food, a person can take spectroscopic scans of different locations on the surface of a food item based on the person's evaluation of different types of ingredients and/or components on that surface.

In an example, an image of a meal comprising multiple food items can be automatically segmented into different food items (e.g. portions of different types of food in a meal) using pattern analysis. In an example, different food items (or portions) in a meal can be automatically identified and segmented using one or more food characteristics selected from the group consisting of: dish or container on (or in) which a food item is served, food item borders, food item chemical composition, food item color, food item description on a menu, food item distance, food item geolocation, food item light absorption spectrum, food item light reflection spectrum, food item orientation, food item positions in a meal, food item shading, food item shape, food item size, food item temperature, food item texture, food item volume, juxtaposition of food items in a meal, and within-meal food item relationships.

In an example, a system for nutritional monitoring and management can detect unhealthy food, wherein unhealthy food is selected from the group consisting of: food that is high in simple carbohydrates; food that is high in simple sugars; food that is high in saturated or trans fat; fried food; food that is high in Low Density Lipoprotein (LDL); and food that is high in sodium. In an example, a system can identify and quantify food that is high in simple sugars. In an example, a system can identify and quantify food that is high in saturated fats. In an example, a system can identify and quantify food that is high in trans fats. In an example, a system can identify and quantify food that is high in Low Density Lipoprotein (LDL). In an example, a system can identify and quantify food that is high in sodium. In an example, a system can identify and quantify food that is high in simple carbohydrates.

In an example, a system for nutritional monitoring and management can identify and quantify one or more types of food, ingredients, and/or nutrients selected from the group consisting of: a selected food, ingredient, or nutrient that has been designated as unhealthy by a health care professional organization or by a specific health care provider for a specific person; a selected substance that has been identified as an allergen for a specific person; peanuts, shellfish, or dairy products; a selected substance that has been identified as being addictive for a specific person; alcohol; a vitamin or mineral; vitamin A, vitamin B1, thiamin, vitamin B12, cyanocobalamin, vitamin B2, riboflavin, vitamin C, ascorbic acid, vitamin D, vitamin E, calcium, copper, iodine, iron, magnesium, manganese, niacin, pantothenic acid, phosphorus, potassium, riboflavin, thiamin, and zinc; a selected type of carbohydrate, class of carbohydrates, or all carbohydrates; a selected type of sugar, class of sugars, or all sugars; simple carbohydrates, complex carbohydrates; simple sugars, complex sugars, monosaccharides, glucose, fructose, oligosaccharides, polysaccharides, starch, glycogen, disaccharides, sucrose, lactose, starch, sugar, dextrose, disaccharide, fructose, galactose, glucose, lactose, maltose, monosaccharide, processed sugars, raw sugars, and sucrose; a selected type of fat, class of fats, or all fats; fatty acids, monounsaturated fat, polyunsaturated fat, saturated fat, trans fat, and unsaturated fat; a selected type of cholesterol, a class of cholesterols, or all cholesterols; Low Density Lipoprotein (LDL), High Density Lipoprotein (HDL), Very Low Density Lipoprotein (VLDL), and triglycerides; a selected type of protein, a class of proteins, or all proteins; dairy protein, egg protein, fish protein, fruit protein, grain protein, legume protein, lipoprotein, meat protein, nut protein, poultry protein, tofu protein, vegetable protein, complete protein, incomplete protein, or other amino acids; a selected type of fiber, a class of fiber, or all fiber; dietary fiber, insoluble fiber, soluble fiber, and cellulose; a specific sodium compound, a class of sodium compounds, and all sodium compounds; salt; a selected type of meat, a class of meats, and all meats; a selected type of vegetable, a class of vegetables, and all vegetables; a selected type of fruit, a class of fruits, and all fruits; a selected type of grain, a class of grains, and all grains; high-carbohydrate food, high-sugar food, high-fat food, fried food, high-cholesterol food, high-protein food, high-fiber food, and high-sodium food.

In an example, a system for nutritional monitoring and management can identify and quantify one or more selected types of food, ingredients, and/or nutrients selected from the group consisting of: amino acid or protein (a selected type or general class), carbohydrate (a selected type or general class, such as single carbohydrates or complex carbohydrates), cholesterol (a selected type or class, such as HDL or LDL), dairy products (a selected type or general class), fat (a selected type or general class, such as unsaturated fat, saturated fat, or trans fat), fiber (a selected type or class, such as insoluble fiber or soluble fiber), mineral (a selected type), vitamin (a selected type), nuts (a selected type or general class, such as peanuts), sodium compounds (a selected type or general class), sugar (a selected type or general class, such as glucose), and water.

In an example, a system for nutritional monitoring and management can identify and quantify one or more types of food, ingredients, and/or nutrients selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In an example, a system for nutritional monitoring and management can identify one or more types of food whose consumption is prohibited or discouraged for religious, moral, and/or cultural reasons, such as pork or meat products of any kind. In an example, food can be classified into general categories such as fruits, vegetables, or meat. In an example, a system can identify one or more potential food allergens, toxins, or other substances selected from the group consisting of: ground nuts, tree nuts, dairy products, shell fish, eggs, gluten, pesticides, animal hormones, and antibiotics. In an example, a system can track the quantities of chemicals in food selected from the group consisting of carbon, hydrogen, nitrogen, oxygen, phosphorus, and sulfur.

In an example, a system for nutritional monitoring and management can collect and analyze data concerning food items in order to identify food item types and estimate food item quantities. In an example, identification of food item types and estimation of food item quantities can include estimation of ingredients in food items and/or the nutritional composition of food items. In an example, identification of food item types and estimation of food quantities can include identification of allergens and/or impurities. In an example, images of food items can be taken before and after food consumption by a person in order to estimate the amount of food actually consumed by the person. In an example, the amount of food remaining after food consumption can be subtracted from the amount of food before food consumption in order to estimate the amount of food actually consumed by a person. In an example, a system for monitoring and managing nutrition can analyze food items with respect to: dish or container on (or in) which a food item is served, food item borders, food item chemical composition, food item color, food item description on a menu, food item distance, food item geolocation, food item light absorption spectrum, food item light reflection spectrum, food item orientation, food item positions in a meal, food item shading, food item shape, food item size, food item temperature, food item texture, food item volume, juxtaposition of food items in a meal, and within-meal food item relationships.

In an example, a system for nutritional monitoring and management can classify a type or quantity of a food or nutrient as being unhealthy based on one or more factors selected from the group consisting of: the type of food or nutrient; the speed or pace of food or nutrient consumption; a person's age, gender, and/or weight; changes in a person's weight; a person's diagnosed health conditions; one or more general health status indicators; the magnitude and/or certainty of the effects of past consumption of the selected nutrient on a person's health; achievement of a person's health goals; a person's exercise patterns and/or caloric expenditure; a person's physical location; the time of day; the day of the week; occurrence of a holiday or other occasion involving special meals; input from a social network and/or behavioral support group; input from a virtual health coach; the cost of food; financial payments, constraints, and/or incentives; health insurance copay and/or health insurance premium; the amount and/or duration of a person's consumption of healthy food or nutrients; a dietary plan created for a person by a health care provider; and the severity of a food allergy.

Quantities of food, ingredients, and nutrients can be measured in terms of volume, mass, or weight. Volume measures how much space the food occupies. Mass measures how much matter the food contains. Weight measures the pull of gravity on the food. The concepts of mass and weight are related, but not identical. In an example, volume can be expressed in metric units (such as cubic millimeters, cubic centimeters, or liters) or U.S. (historically English) units (such as cubic inches, teaspoons, tablespoons, cups, pints, quarts, gallons, or fluid ounces). Mass (and often weight in colloquial use) can be expressed in metric units (such as milligrams, grams, and kilograms) or U.S. (historically English) units (ounces or pounds).

The density of specific ingredients or nutrients within food is sometimes measured in terms of the volume of specific ingredients or nutrients per total food volume or measured in terms of the mass of specific ingredients or nutrients per total food mass. In an example, nutrient density or concentration can be measured as part of an automatic food, ingredient, or nutrient identification method. In an example, nutrient density can be expressed as the average amount of a specific ingredient or nutrient per unit of food weight. In an example, nutrient density can be expressed as the average amount of a specific ingredient or nutrient per unit of food volume. In an example, food density can be estimated by interacting food with light, sound, or electromagnetic energy and measuring the results of this interaction. Such interaction can include energy absorption or reflection.

In an example, a system for nutritional monitoring and management can measure food weight, mass, volume, or density. In an example, a system can include a food scale, strain gauge, or inertial sensor. In an example, a system can measure the weight or mass of an entire meal, a portion of one type of food or food item within that meal, or a mouthful of a type of food that is being conveyed to a person's mouth. In general, a weight, mass, or volume sensor is more useful for general detection of food consumption and food amount than it is for identification of type of food, ingredients, and nutrients.

In an example, a system for nutritional monitoring and management can include a food database. In an example, a food database can have multiple levels, including super-sets of food types (e.g. meals with selected combinations of food types and quantities) and sub-sets of food types (e.g. types and quantities of ingredients, nutrients, and/or chemicals which comprise food types). In an example, a system can include a database of different types and quantities of food items. In an example, a system can include a database of different food items and characteristics associated with each food item. In an example, food item characteristics can be used to match a nearby food item with a food item in the database. In an example, a system can include a database of different food item types and quantities, including standardized nutritional composition for each listed quantity for each listed food item. In an example, a database can include standardized types and quantities of ingredients, nutrients, and/or calories for each listed quantity for each food item. In an example, a food database can link common types and quantities of food with common types and quantities of ingredients and/or nutrients. In an example, a system can be in wireless communication with a remote database which links food items with standardized quantities of ingredients and/or nutrients.

In an example, a food database can include data elements selected from the group consisting of: barcode (or QR code) associated with food item; food item (probable) color; food item (probable) health effects; food item (probable) ingredients and/or nutritional composition; food item (probable) location or position with respect to selected dishware (e.g. plate, bowl, or beverage container); food item (probable) pairings with other specific food items; food item (probable) portion size; food item (probable) shape; food item (probable) size; food item (probable) temperature; food item (probable) texture; food item (probable) use in selected meals; food item (probable) allergic effects; food item association with particular times of day, days of the week, times of the year, or holidays; food item cost; food item health rating or ranking; food item homogeneity or lack thereof; food item image (including possible multiple images in different contexts such as on a plate vs. utensil, or from different angles and distances); food item light absorption or reflection spectrum (including the results of spectroscopic analysis); food item name (including possible synonyms and different languages); food item status with respect to specific diets and/or religious observations; general health effects associated with food item; geolocations associated with food item availability; packaging, label, and/or logo associated with food item; person's past consumption quantity or patterns concerning food item; person-specific health effects associated with food item; restaurants or grocery stores associated with food item; and suggested substitutions for food item. In an example, a food database can be based on historical information concerning (food consumption by) a group of people and/or the general population. In an example, a food database can be based on historical information concerning (food consumption by) a specific person.

In an example, a system for nutritional monitoring and management can estimate types and quantities of ingredients and/or nutrients indirectly using a database than links identified food items with standardized quantities ingredients and/or nutrients. In an example, a system for nutritional monitoring and management can estimate quantities of ingredients or nutrients indirectly by: (a) collecting and/or receiving characteristics of food item types and identifying food types and estimating food item quantities; (b) linking these food item types and quantities to records in a food database which link foods with ingredients and/or nutrients; and (c) extracting estimated types and quantities of ingredients and/or nutrients from the database associated with those food item types and quantities. Alternatively, a system can estimate types and quantities of ingredients and/or nutrients directly using a chemical and/or molecular composition sensor (such as a spectroscopic sensor).

In an example, images of one or more food times can be analyzed to help identify types and quantities of food items and/or nutrients. Analysis of food images can include one or more methods selected from the group consisting of: 3D image modeling, volumetric analysis, adjusting image aspect ratio, computer vision, discriminant analysis, image color calibration and/or adjustment, image composition analysis including food pairings and juxtapositions, image compression, image deletion or editing, image filtering, image lighting intensity calibration and/or adjustment, image rectification, image resizing, image resolution calibration and/or adjustment, image rotation, image segmentation, image size calibration and/or adjustment, machine learning, multivariate analysis, and artificial neural network analysis. In an example, a user can be prompted to provide additional and/or supplemental information concerning their evaluation of food item type and quantity when the results of automated analysis do not achieve a desired level of accuracy or certainty.

In an example, a system for nutritional monitoring and management can automatically identify food item types and estimate food items quantities using one or more automated methods. In an example, a system can automatically identify food item types and estimate food items quantities using Artificial Intelligence (AI). In an example, a system can automatically identify food item types and estimate food items quantities using association rule learning. In an example, a system can automatically identify food item types and estimate food items quantities using Bayesian analysis.

In an example, a system for nutritional monitoring and management can automatically identify food item types and estimate food items quantities using clustering. In an example, a system can automatically identify food item types and estimate food items quantities using computer vision. In an example, a system can automatically identify food item types and estimate food items quantities using computer vision. In an example, a system can automatically identify food item types and estimate food items quantities using crowd sourcing. In an example, a system can automatically identify food item types and estimate food items quantities using data analytics.

In an example, a system for nutritional monitoring and management can automatically identify food item types and estimate food items quantities using decision tree analysis. In an example, a system can automatically identify food item types and estimate food items quantities using deep learning algorithms. In an example, a system can automatically identify food item types and estimate food items quantities using fuzzy logic. In an example, a system can automatically identify food item types and estimate food items quantities using inductive logic programming. In an example, a system can automatically identify food item types and estimate food items quantities using least squares estimation. In an example, a system can automatically identify food item types and estimate food items quantities using logistic discrimination. In an example, a system can automatically identify food item types and estimate food items quantities using machine learning.

In an example, a system for nutritional monitoring and management can automatically identify food item types and estimate food items quantities using machine learning. In an example, a system can automatically identify food item types and estimate food items quantities using multivariate analysis. In an example, a system can automatically identify food item types and estimate food items quantities using multivariate linear regression. In an example, a system can automatically identify food item types and estimate food items quantities using an Artificial Neural Network (ANN). In an example, a system can automatically identify food item types and estimate food items quantities using pattern recognition. In an example, a system can automatically identify food item types and estimate food items quantities using pattern recognition.

In an example, a system for nutritional monitoring and management can identify food item types and estimate food item quantities using one or more methods selected from the group consisting of: chemical analysis, Chi-squared analysis, cluster analysis, color analysis, factor analysis, probit analysis, survival analysis, texture analysis, volumetric analysis, machine learning, 3D modeling, three-dimensional modeling, image normalization, non-linear programming, face recognition, gesture recognition, logo recognition, motion recognition, pattern recognition, speech recognition, linear regression, logistic regression, Fourier Transformation, principal components analysis (PCA), linear discriminant analysis, time series analysis, Bayesian statistical analysis, inter-food boundary determination, artificial neural network (ANN), bar code or QR code recognition, linear mathematical programming, optical character recognition (OCR), sound pattern recognition, multivariate linear regression, food portion segmentation, and analysis of variance.

In an example, a system for nutritional monitoring and management can automatically identify food item types and estimate food items quantities using Principal Component Analysis (PCA). In an example, a system can automatically identify food item types and estimate food items quantities using Random Forest (RF) analysis. In an example, a system can automatically identify food item types and estimate food items quantities using a Support Vector Machine (SVM).

In an example, a system for nutritional monitoring and management can use multivariate analysis including factors selected from the group consisting of: image-related variables (e.g. food images and automated analysis of those images, food item packaging logo, food item packaging type, UPC or QR code on food packaging, type of dish or other container used to hold fold); spectroscopic variables (e.g. data from spectroscopic analysis of food, light absorption and/or reflection spectra of food items, data from spectroscopic analysis of person's body tissue, light absorption and/or reflection spectra of body tissue); motion-related variables (e.g. number of eating-related motions or gestures by a person's arm, wrist, or hand; number of times a person brings their hand up to their mouth in a specific manner; utensil movement, number of chews based on motion, number of swallows based on motion); utensil-related variables (e.g. type of dish or container used to hold food, type of utensil used to bring food from dish or container up to a person's mouth); and timing variables (e.g. day of the week; frequency of eating-related motions or gestures by a person's arm, wrist, or hand; pace with which a person brings their hand repeatedly up to their mouth during a meal; person's frequency or pace of chews during a meal or period of time; person's frequency or pace of swallows during a meal or period of time; time since person's last meal; timing of a holiday or other special occasion; time of day).

In an example, a system for nutritional monitoring and management can use multivariate analysis which including factors selected from the group consisting of: voice or sound-related variables (e.g. verbal descriptions of food items or meals; number of chews based on sound; number of swallows based on sound; sound spectrum of chews and/or swallows); person-specific biometric parameters or health-related variables (e.g. person's acute illness or chronic condition, person's age, person's blood pressure, person's body temperature, person's body weight, person's eating pace, person's fatigue level, person's gender, person's glucose level, person's heart rate, person's historical eating patterns, person's past biometric parameter changes in response to consumption of specific types or quantities of food, person's sleep level or pattern, person's socioeconomic status, and person's stress level); scale-related variables (e.g. food weight as measured by a scale integrated into a food dish or container); energy balance variables (e.g. person's amount of exercise and/or physical activity during a period of time, person's cumulative food consumption during a period of time); and environmental variables (e.g. geolocation, ambient humidity, ambient light level, ambient temperature, altitude, restaurant type or name, grocery store type or name, food source).

In an example, a method for nutritional monitoring and management can comprise: collecting primary data concerning food consumption using a wearable food-consumption monitor to detect when a person is eating; and collecting secondary data concerning food consumption using a handheld food-identifying sensor when analysis of primary data indicates that the person is eating. In an example, a method can comprise: automatically collecting primary data from an eating-detection sensor that a person wears on their body or clothing; and prompting the person to use a handheld food-identifying sensor to collect secondary data when primary data indicates that the person is eating and the person has not already collected secondary data associated with that eating event.

In an example, a system for nutritional monitoring and management can have a target level of accuracy and/or certainty with which food item types are to be identified and/or food item quantities are to be estimated. In an example, if a first set of sensors do not provide food identification and quantification with the target level of accuracy and/or certainty, then the system can activate a second set of sensors to collect additional food-related information. In an example, if automated sensors do not provide food identification and quantification with the target level of accuracy and/or certainty, then the system can prompt a person to collect and/or provide additional food-related information. In an example, additional food-related information can be collected and/or provided in an iterative manner until the target level of accuracy and/or certainty is achieved. In an example, a system can determine food item types and quantities based on a first set of data and a second set of data. If results from these two sets of data converge, then the system can stop collecting data. However, if the results from these two sets of data do not converge, then the system can collect additional data and/or prompt a person to provide additional data. In an example, a system for nutritional monitoring and management can start with the descriptions of food types and estimations of food quantities provided by a person and then refine them, in a Bayesian manner, based on the results of spectroscopic analysis and food image analysis.

In an example, a system for nutritional monitoring and management can include a food database that is used to identify food types and quantify food amounts. In an example, a food database can include average (or standardized) types and quantities of ingredients and/or nutrients associated with specific food items. In an example, average types and quantities of ingredients and/or nutrients from the database can be used to estimate consumption of ingredients and/nutrients associated with a person's consumption of a food item. In an example, estimation of specific ingredients or nutrients eaten can be done using a database that links specific foods (and quantities thereof) with specific ingredients or nutrients (and quantities thereof). In an example, a database can be customized for a specific person based on that person's past eating habits. In an example, identification of food item types and quantities for a person can be done, in whole or in part, by predicting the person's current eating patterns based on the person's historical eating patterns. In an example, a system can analyze one or more factors selected from the group consisting of: number of nearby food items; types of food items; changes in the volume of nearby food items; number of times that a person brings food up to their mouth; number of chewing movements; frequency or speed of chewing movements; and number of swallowing movements.

In an example, a system for nutritional monitoring and management can analyze food images to determine food item types and estimate food item quantities. In an example, a system can analyze food using one or more methods selected from the group consisting of: volumetric analysis, image normalization, face recognition, gesture recognition, pattern recognition, calibration of an image using a fiducial marker of known size and/or color, analyzing the chemical composition of food, analyzing food color, recognizing packaging design, inter-food boundary determination, segmentation of meal image into food items, bar code or QR code recognition, optical character recognition, food logo recognition, analyzing food shape, analyzing food size and changes in food size during eating, analyzing food texture, analyzing food volume, 3D or volumetric modeling of food, and recognizing words on food packaging.

In an example, a system for nutritional monitoring and management can record images of a person's mouth and nearby food from multiple perspectives to create a three-dimensional model of food. In an example, images of a person's mouth, a nearby food item, and the interaction between the person's mouth and food can be automatically, or semi-automatically, analyzed to estimate the types and quantities of food that the person eats. In an example, a system can automatically determine borders between different food items in a meal image, segmenting the meal into different food items before comparison with food item images in a food database. In an example, a system can compare an image of a meal (with multiple types of food) as a whole with images of meals (with multiple types of food) in a food database.

In an example, a method for nutritional monitoring and management can comprise: collecting a first set of data in an automatic and continuous manner to detect when a person is eating; collecting a second set of data to identify what selected types of foods, ingredients, or nutrients the person is eating when the first set of data indicates that the person is eating; and jointly analyzing both the first and second sets of data to estimate consumption of at least one specific food, ingredient, or nutrient by the person. In an example, a method can comprise: receiving descriptions of nearby food types and quantities from a person; receiving data from spectroscopic analysis of the food; receiving data from analysis of images of the food; and performing multivariate analysis on the descriptions from the person, spectroscopic data, and image data in order to identify types and quantities of the food (or the ingredients, nutrients, and/or chemicals therein).

In an example, a method for nutritional monitoring and management can comprise: recording images of nearby food using at least one camera which is worn on a person's body; collecting data concerning the spectrum of light that is transmitted through and/or reflected from nearby food using at least one optical sensor which is worn on the person's body; and automatically analyzing the food images to identify the types and quantities of food, ingredients, and/or nutrients. In an example, a system can combine data from a spectroscopic sensor with data from analysis of food images to determine types and quantities of food (or ingredients, nutrients, and/or chemicals therein). In an example, a system can identify types and quantities of foods, ingredients, or nutrients from images or images of food using a combination of automated food identification methods and human-based food identification methods. In an example, a system which combines both spectroscopic analysis and image analysis can provide good information on both the types and quantities of nearby food (and nutrients, chemicals, and/or possibly even microorganisms in that food).

In an example, a system for nutritional monitoring and management can include an augmented reality (AR) interface between the system and a person whose nutritional intake is being monitored and managed. In an example, an AR interface can be a computer-to-human interface through which information is conveyed from the system to a person. In an example, an AR interface can be a human-to-computer interface through which information is conveyed from a person to the system. In an example, an augmented reality (AR) interface can be incorporated into smart eyewear. In an example, AR eyewear can display food-related information visually in a person's field of view, optionally accompanied by information conveyed in auditory and/or haptic modalities. In an example, AR eyewear can receive food-related information from a person via voice, gestures, text entry, eye movement, and/or EEG signals.

In an example, a system for nutritional monitoring and management can include augmented reality (AR) eyewear which displays virtual content in a person's field of view in juxtaposition with (e.g. over or near) food items. In an example, virtual content displayed in juxtaposition with (e.g. over or near) food items can be selected from the group consisting of: name of a food item; estimated total calories and/or nutritional composition (e.g. fats, carbohydrates, proteins, etc.) of a food item; binary (e.g. healthy vs. unhealthy) or continuous (e.g. health rating) information concerning a food item; probable health effects of consuming a food item; information concerning allergens, pathogens, and/or carcinogens in a food item; estimated quantity of a food item;

cost and/or nearby location where a food item can be purchased; and review or poll results concerning a food item.

In an example, food-related information can be displayed in virtual words, graphics, or images in juxtaposition with (e.g. over or near) food items in an augmented reality display. In an example, displayed information for a specific food item in a person's field of view can be visually linked to that food item by a virtual connecting arrow or line in an augmented reality display. In an example, information concerning each of a plurality of food items in a person's field of view (e.g. in a multi-food meal) can be consistently displayed in the same direction (e.g. to the right, to the left, above, or under) relative to a food item. For example, total estimated calories for each food item in a meal can be virtually displayed under each food item in a meal in an augmented reality display. In an example, displayed information for a specific food item in a person's field of view can be visually linked to that food item by being the same color as a virtual circle, box, or outline displayed around the specific food item in an augmented reality display. For example, each food item in a meal can be outlined in a different color and information about each food item can be displayed above or below the meal, wherein the color of the information about each item matches the color of the outline around the item.

In an example, a system for nutritional monitoring and management can include augmented reality eyewear. In an example, augmented reality eyewear can display a virtual pointer at different locations (e.g. different portions or types of food) in a meal to direct where a person should place a spectroscopic sensor to take scans of the food. In an example, augmented reality eyewear can track (using gesture recognition) where a person moves a spectroscopic sensor for food scans and can link scan results from those locations with different portions or types of food which are identified by image analysis. In an example, the results of food identification and quantification from a mobile device can be displayed in a person's field of view using augmented reality eyewear. In an example, a system can include augmented reality via a mobile handheld device. In an example, the information discussed above can be display on the screen of a mobile device instead by (or in addition to) augmented reality eyewear.

In an example, a system for nutritional monitoring and management can superimpose suggested areas for spectroscopic analysis on a person's view of a meal in using augmented reality eyewear. In an example, augmented reality eyewear can display one or more virtual pointers at selected locations on a meal to guide a person as to where they should take spectroscopic cans of the meal. For example, augmented reality eyewear can display a virtual pointer on a portion of fish on a plate. The person then uses the handheld device to take a spectroscopic scan of that fish. Then, the augmented reality eyewear can move the virtual point to a portion of carrots on the plate. Then the person takes a scan of the carrots. This continues for each type of food on the plate and/or in the meal. Portion specific spectroscopic information is then combined with food quantity information from analysis of food images to get an overall estimation of types and quantities of foods, ingredients, and/or nutrients. In an example, a system can identify locations on food where a person should a the spectroscopic scanner. In an example, augmented reality eyewear can display virtual pointers on food to direct where a person should use a spectroscopic scanner.

In an example, smart eyewear which is part of a system can further comprise a gesture recognition function. In an example, information about a specific food item may be displayed in augmented reality when a person makes a specific gesture relative to (e.g. points toward) that specific food item. In an example, smart eyewear which is part of a system can further comprise an eye movement and/or gaze-tracking function. In an example, information about a particular food item may be displayed in augmented reality when a person looks at that specific food item.

In an example, food item information can be conveyed via the color or configuration of virtual objects shown in juxtaposition with (e.g. over or near) food items in a person's field of view. In an example, the color of a virtual circle or borders around a specific food item displayed in augmented reality in a person's field of view can indicate whether that food item is relatively healthy or unhealthy for the person to consume. In an example, a green circle or border around a food item can mean that the food is healthy, a yellow circle or border can mean that the food item is neutral, and a red circle or border can mean that the food item is unhealthy. In an example, a circle or border of a specific color around a specific food item can indicate that the food item contains something to which the person is allergic, a pathogen, and/or a carcinogen.

In an example, a system for nutritional monitoring and management can superimpose nutrition information on a person's view of their environment via augmented reality. In an example, virtual nutrition information can be superimposed directly over the food in question. In an example, display of negative nutritional information and/or information about the potential negative effects of unhealthy nutrients can reduce a person's consumption of an unhealthy type or quantity of food. In an example, a system can display warnings about potential negative health effects and/or allergic reactions. In an example, display of positive nutritional information and/or information on the potential positive effects of healthy nutrients can increase a person's consumption of healthy food. In an example, a system can display encouraging information about potential health benefits of selected foods or nutrients.

In an example, augmented reality eyewear can change the perceived color spectrum of selected food items in a person's field of view in order to change how appetizing or unappetizing the food appears. For example, the color spectrum of unhealthy food (or food which a person should not eat for other reasons) can be changed to make that food less appealing. For example, some people like green eggs and ham but would like not like green fries and spam. In an example, augmented reality eyewear can display an image next to a food item in a person's field of view in order to change the appeal of that food item. In an example, an unappetizing image can be displayed in juxtaposition with unhealthy food (or food which the person should not eat for other reasons) to make that food less appealing. For example, would you be interested in eating French fries next to a picture of Jabba the Hutt? How about if Jabba winked at you with each fry you ate? I didn't think so.

In an example, a system for nutritional monitoring and management can display images or other visual information in a person's field of view in order to modify the person's consumption of food. In an example, unpleasant or unappetizing images can be displayed in proximity to unhealthy food. In an example, pleasant or appetizing images can be displayed in proximity to healthy food. In an example, a system can display images or other visual information in proximity to food in the person's field of view in a manner which modifies the person's consumption of that food. In an example, a system can be part of an augmented reality system which displays virtual images and/or information in proximity to real world objects. In an example, a nutritional intake modification system can superimpose virtual images and/or information on food in a person's field of view.

In an example, a system for nutritional monitoring and management can include smart eyewear with an augmented reality interface which enables a person to provide information (from their perspective) concerning types and quantities of food items in their field of view. In an example, smart eyewear with gesture recognition capability can track the location of a person's finger as the person points to different food items in a meal. In an example, a person can sequentially point to different food items in a meal and provide verbal descriptions of each item, wherein the system associates each verbal description with the appropriate food item. In an example, the system can combine these verbal descriptions with information which the system collected automatically (e.g. via image analysis or spectroscopic analysis) in order to better determine food item types and quantities.

In an example, a system for nutritional monitoring and management can track a person's finger as the person moves their finger in the air tracing the borders between food items in a multi-food meal. Such border tracing can serve as additional input for a system to segment and analyze different food item types and quantities in a multi-food meal. In another example, a system can track a person's finger as the person moves their finger to point sequentially to different food items in a meal, which directs the system to perform sequential spectroscopic scans of those different food items in the meal. In an example, a person can move a virtual cursor in augmented reality to perform the above-mentioned user inputs for system identification of food item types and quantities. In an example, a system can track a person's eye movements and the person can shift their eye gaze and/or focal direction to perform the above-mentioned user inputs for system identification of food types and quantities. In an example, a person can provide user inputs by selecting an entry in a virtual (drop-down) menu in augmented reality.

In an example, a system for nutritional monitoring and management can include a mobile device (such as a smart phone or smart watch) with augmented reality (AR) functionality which displays food information (over a live image of food) on a device screen. In example, food information concerning one or more specific food items can be displayed in juxtaposition with those food items on the mobile device screen. In an example, virtual content which is displayed on a mobile device screen in juxtaposition with (e.g. over or near) food items can be information about food items selected from the group consisting of: name of a food item; estimated total calories and/or nutritional composition (e.g. fats, carbohydrates, proteins, etc.) of a food item; binary (e.g. healthy vs. unhealthy) or continuous (e.g. health rating) information concerning a food item; probable health effects of consuming a food item; information concerning allergens, pathogens, and/or carcinogens in a food item; estimated quantity of a food item; cost and/or nearby location to purchase a food item; and review or poll results concerning a food item. In an example, this information can be displayed in words.

In an example, food-related information can be displayed in virtual words, graphics, or images in juxtaposition with (e.g. over or near) food items on the screen of a mobile device. In an example, displayed information for a specific food item on a screen can be visually linked to that food item by a virtual connecting arrow or line in an augmented reality display. In an example, information concerning each of a plurality of food items on a screen (e.g. in a multi-food meal) can be consistently displayed in the same direction (e.g. to the right, to the left, above, or under) relative to a food item. For example, total calories for each food item in a meal can be virtually displayed under each food item in a meal in an augmented reality display. In an example, displayed information for a specific food item can be visually linked to that food item by being the same color as a virtual circle, box, or outline displayed around the specific food item in an augmented reality display. For example, each food item in a meal can be outlined in a different color and information about each food item can be displayed below the meal, wherein the color of the information about each item matches the color of the outline around the item.

In an example, food item information can be conveyed via the color or configuration of virtual objects shown in juxtaposition with (e.g. over or near) food items on a mobile device screen. In an example, the color of a virtual circle or borders around a specific food item displayed in augmented reality on a mobile device screen can indicate whether that food item is relatively healthy or unhealthy for the person to consume. In an example, a green circle or border around a food item can mean that the food is healthy, a yellow circle or border can mean that the food item is neutral, and a red circle or border can mean that the food item is unhealthy. In an example, a circle or border of a particular color around a specific food item can indicate that it contains something to which the person is allergic, a pathogen, and/or a carcinogen.

In an example, a mobile device (e.g. smart phone) with augmented reality functionality can change the perceived color spectrum of selected food items on its screen in order to change how appetizing or unappetizing the food appears. For example, the color spectrum of unhealthy food (or food which a person should not eat for other reasons) can be changed to make that food less appealing. For example, some people like green eggs and ham but would like not like green fries and spam. In an example, a mobile device (e.g. smart phone) can display an image next to a food item on the device screen in order to change the appeal of that food item. In an example, an unappetizing image can be displayed in juxtaposition with unhealthy food (or food which the person should not eat for other reasons) to make that food less appealing. For example, would you be interested in eating French fries shown next to a picture of Jabba the Hutt? How about if Jabba winked at you each time you ate a French fry? I didn't think so.

In an example, a system for nutritional monitoring and management can include a smart mobile device (e.g. smart phone) with an augmented reality interface which enables a person to provide information (from their perspective) concerning types and quantities of food items in their field of view. In an example, smart mobile device (e.g. smart phone) with gesture recognition capability can track the location of a person's finger as the person points to different food items in a meal. In an example, a person can sequentially point to different food items in a meal and provide verbal descriptions of each item, wherein the system associates these verbal descriptions with the food items. In an example, the system can combine these verbal descriptions with information which the system collected automatically (e.g. via image analysis or spectroscopic analysis) in order to better determine food item types and quantities.

In an example, a smart mobile device (e.g. a smart phone or smart wearable device) which is part of a system can further comprise a gesture recognition function. In an example, information about a specific food item may be displayed on a device screen when a person makes a specific gesture relative to (e.g. points toward) that specific food item. In an example, a system can track a person's finger as the person moves their finger in the air tracing the borders between food items in a multi-food meal. Such border tracing can serve as additional input for a system to segment and analyze different food types and quantities in a multi-food meal. In another example, a system can track a person's finger as the person moves their finger to point sequentially to different food items in a meal, which directs the system to perform sequential spectroscopic scans of those different food items in the meal. In an example, a person can move a virtual cursor in augmented reality to perform the above-mentioned user inputs for system identification of food types and quantities.

In an example, a system for nutritional monitoring and management can track the location of a person's finger on a touch screen as the person touches different food items in an image of a multi-food meal. In an example, a person can sequentially touch different food items in a meal and provide verbal descriptions of each item, wherein the system combines these verbal descriptions with automatically-collected information (e.g. via image analysis, spectroscopic analysis) for determining food types and quantities. In an example, a person can move (e.g. trace) their finger around the borders between food items in a meal on a touch screen as additional input for the system in analysis of food types and quantities. In an example, a person can touch different food items in a meal on a screen to direct sequential (spectroscopic) scans of different food items in the meal. In an example, a person can move a projected light beam to perform the above-mentioned user inputs for system identification of food types and quantities. In an example, a person can select an entry in a virtual (drop-down) menu in augmented reality.

In an example, a system for nutritional monitoring and management can provide a person with food-related information and/or feedback. In an example, a system can provide food-related information via visual, auditory, and/or haptic modalities. In an example, a system can provide food-related information via a visual, auditory, and/or haptic computer-to-human interface. In an example, a system can provide a person with information concerning identified food item types and estimated food item quantities. In an example, a system can provide information concerning the nutritional composition and/or chemical composition of food items. In an example, a system can provide information concerning food item types and quantities which are nearby and which a person may eat. In an example, a system can provide information concerning food item types and quantities which a person has already eaten. In an example, a system can provide negative feedback in association with consumption of unhealthy food and/or positive feedback in association with consumption of healthy food.

In an example, a system for nutritional monitoring and management can provide a person with information concerning which food item types and/or quantities are relatively healthy or unhealthy to eat. In an example, a system can provide a person with the likely positive and/or negative health effects of eating selected food item types and/or quantities. In an example, a system can provide information which encourages a person to eat less unhealthy food and/or to eat more healthy food. In an example, a system can provide a person with information concerning the person's cumulative food consumption during an eating event (e.g. during a meal) or during a period of time (e.g. during a day). In an example, the actual amount of food consumed by the person can be compared to a target amount (e.g. dietary goal) of food consumption for an eating event (e.g. for a meal) or for a period of time (e.g. for a day).

In various examples, a target amount of consumption can be based on one or more factors selected from the group consisting of: the selected type of selected food, ingredient, or nutrient; amount of this type recommended by a health care professional or governmental agency; specificity or breadth of the selected nutrient type; the person's age, gender, and/or weight; the person's diagnosed health conditions; the person's exercise patterns and/or caloric expenditure; the person's physical location; the person's health goals and progress thus far toward achieving them; one or more general health status indicators; magnitude and/or certainty of the effects of past consumption of the selected nutrient on the person's health; the amount and/or duration of the person's consumption of healthy food or nutrients; changes in the person's weight; time of day; day of the week; occurrence of a holiday or other occasion involving special meals; dietary plan created for the person by a health care provider; input from a social network and/or behavioral support group; input from a virtual health coach; health insurance copay and/or health insurance premium; financial payments, constraints, and/or incentives; cost of food; speed or pace of nutrient consumption; and accuracy of a sensor in detecting a selected nutrient.

In an example, a system for nutritional monitoring and management can provide information on a person's energy balance during a period of time. In an example, a system for nutritional monitoring and management can compare a person's caloric intake vs. caloric expenditure during a period of time. In an example, a system can set and monitor caloric intake goals based on a person's caloric expenditure during a period of time. In an example, a system can set and monitor caloric expenditure goals based on a person's caloric intake during a period of time. In an example, a system can set and monitor caloric intake goals and caloric expenditure goals in order for the person to achieve a body weight goal (e.g. maintaining weight, losing weight, or gaining weight).

In an example, a system for nutritional monitoring and management can provide a person with information concerning nearby food before the person starts to eat. In example, providing information before a person eats can be triggered by visual detection of nearby food (e.g. food image recognition) and/or geolocation associated with food purchasing or consumption (e.g. the person is at a restaurant). In an example, a system can provide a person with food-related information when a person starts to eat. In an example, such information during eating can be triggered by detection of eating by motion sensors, image sensors, sound sensors, biometric parameters, and/or geolocation. In an example, a system can provide a person with food-related information at multiple times (or even continuously) while the person eats. In an example, a system for can provide a person with information about consumed food after a person has eaten. In an example, a system can provide a person with information concerning the types and quantities of food that the person has eaten during a specific eating event (e.g. during a meal) or during a period of time (e.g. during a day). In an example, a system can provide a person with periodic information on the types and quantities of food that the person has eaten.

In an example, a system for nutritional monitoring and management can provide a person with information about food item types and quantities before a person chooses which food items to consume and how much of these food items to consume. In an example, a system can provide information to encourage a person to make healthier choices about which food items to consume and how much of them to consume. In an example, a system can provide information about different food choices on a menu to encourage a person to order healthier food. In an example, a system can provide information about food items in real time as a person is consuming those food items. In an example, a system can encourage a person to eat no more than a selected cumulative quantity of one or more food items. In an example, a system can encourage a person to moderate the speed and/or pace at which they are eating food items.

In an example, a system for nutritional monitoring and management can provide a person with information about their food consumption and nutritional intake at times which are not related to specific meals or eating events. In an example, a system can provide a person with information about their cumulative food consumption and nutritional intake for a selected period of time (e.g. a day) in a regular (e.g. daily) manner. In an example, a system can track a person's progress toward dietary and/or health goals over time and provide a person with feedback on their progress toward those goals.

In an example, a system can display images in a person's field of view which influence the person's food consumption. In an example, a system can include augmented reality eyewear which displays images which increase or decrease the appeal of selected types of nearby food. In an example, a system can include augmented reality eyewear which displays appetite-reducing images next to unhealthy foods and/or appetite-enhancing images next to healthy foods. In an example, looking at gummi worms can be tempting to a candy lover, but a super-imposed image of actual worms might have the opposite effect. In an example, looking at a mug of beer might be appealing, but a super-imposed image of a person (perhaps even an augmented image of that person) with a beer gut might have the opposite effect.

In an example, a system for nutritional monitoring and management can display food-related information visually. In an example, a system can provide visual information concerning food items types and quantities. In an example, a system can display food-related information on the screen of a handheld mobile device. In an example, a system can display food-related information superimposed next to nearby food via augmented reality on the screen of a handheld mobile device. In an example, a system can display food-related information in a person's field of view via augmented reality eyewear. In an example, a system can display food-related information via text, graphics, colors, visual patterns, icons, and/or images. In an example, different graphics, colors, visual patterns, icons, and/or images can be associated with different food types and/or quantities. In an example, different graphics, colors, visual patterns, icons, and/or images can be associated with healthy vs. unhealthy food types and/or quantities. In an example, a system can visually display the results of image analysis and/or spectroscopic analysis of food items.

In an example, a system for nutritional monitoring and management can provide a person with visual food-related information and/or feedback through device lights; images, objects, or text on the screen of a handheld device; images, objects, or text from a light projector; and/or images, objects, or text displayed in a person's field of view via augmented reality eyewear. In an example, system can communicate food information to a person in graphic form. In an example, a system can include one or more lights (e.g. LEDs) whose colors and/or light patterns convey information concerning food item types and quantities. In an example, selected light colors and/or patterns can indicate high concentrations of selected types of ingredients, nutrients, and/or chemicals. In an example, selected light colors and/or patterns can indicate whether food items are high in protein, carbohydrates, or fats. In an example, a system can display different colors and/or patterns for different food items in a meal.

In an example, a system for nutritional monitoring and management can passively provide information to a person whose nutritional intake is being monitored and managed. In an example, a system can provide food information to a person in a visual mode. In an example, visual information concerning food and/or nutritional intake can be provided via the screen of a mobile or wearable device. In an example, visual information concerning food and/or nutritional intake can be provided via a display on augmented reality eyewear. In an example, visual information concerning food and/or nutritional intake can be provided via light beams projected from a mobile device or smart eyewear. In an example, visual information can comprise displayed text, graphics, images, virtual objects, or video content. In an example, different colors or light patterns can be used to convey attributes of food such as the nutrient composition of the food and/or whether the food is relatively healthy or unhealthy. In an example, particular color patterns, light patterns, light blinks, or light motions can convey food information to a person. In an example, visual information can be selected or modified based on tracking a person's gaze. In an example, if a person ignores (e.g. does not look at) visual information, then a system may provide auditory or haptic feedback.

In an example, a system for nutritional monitoring and management can provide visual feedback concerning a person's food consumption via the display screen of a mobile or wearable device (such as a smart phone or smart watch). In an example, a system can display selected light patterns, colors, blinks, motions, shapes, and/or intensity levels to signal information about specific types of food and/or a person's consumption of that food. In an example, a system can display selected light patterns, colors, blinks, motions, shapes, and/or intensity levels to indicate how healthy or unhealthy nearby food items are. In an example, visual feedback concerning food consumption and its implications for a person can be provided before a person eats (in order to influence the person's eating decisions before a meal), while a person is eating (in order to influence the person's eating decisions during a meal), or after a person has eaten. In an example, recommended choices with respect to types or portions of food items can be displayed in a visual mode. In an example, the mode (e.g. visual, sound, or haptic) through which feedback is provided from a system to a person can be automatically changed based on environmental cues (e.g. ambient light level, ambient sound level, or geolocation).

In an example, a system for nutritional monitoring and management can provide a person with auditory food-related information. In an example, a system can include a device with a speaker which emits sounds. In an example, a system can convey auditory food-related information via: a tone or note; a ring tone or song; an alarm or buzzer; computer-synthesize speech; a pre-recorded vocal message (by the person or a significant other person); or another type of sound. In an example, a system can convey food-related information to a person via sounds emitted from a smart watch or band, from smart eyewear, from smart earwear, or from a handheld mobile device. In an example, nutritional composition information can be communicated by computer-synthesized speech from a smart watch or band, from smart eyewear, from smart earwear, or from a handheld mobile device. In an example, a system can modify a person's eating behavior by shouting—"If you don't eat yer meat, you can't have any pudding."

In an example, a system for nutritional monitoring and management can provide food information to a person in an auditory mode (e.g. via sound). In an example, auditory feedback can be provided through speakers in smart eyewear, a mobile device (such as a smart phone), a smart watch, or some other mobile or wearable device. In an example, sounds, tones, buzzers, alarms, songs, music, synthesized speech, and/or prerecorded speech can be used to convey attributes of food such as the nutritional composition of the food and/or whether the food is relatively healthy or unhealthy. In an example, a system can emit selected sounds at selected time intervals in order change a person's eating pace. In an example, a system can change the speed and/or pace of a person's arm or hand motions during eating by entrainment with sound beats, pulses, tones, or notes. In an example, a system can emit selected sounds in order to change a person's consumption of selected types or quantities of food. In an example, sound frequency or volume can increase as a person approaches or exceeds a target amount of food consumption (e.g. during a meal or period of time). In an example, a device can play "Highway to Hell" when a person looks at very unhealthy food or play "Oops . . . I Did It Again" if the person actually eats that food.

In an example, a system for nutritional monitoring and management can provide a person with food-related information or consumption-modifying stimuli through a haptic and/or tactile mechanism. In an example, a haptic and/or tactile mechanism for conveying food-related information or consumption-modifying stimuli can be selected from the group consisting of: electromagnetic stimulation; electromagnetic actuator; haptic array; haptic interface; piezoelectric actuator; pressurized compartment; rotating element; and vibrating element. In an example, different haptic and/or tactile patterns can be associated with different food item types and/or quantities. In an example, different haptic and/or tactile patterns can be associated with healthy vs. unhealthy food types and/or quantities. In an example, haptic and/or tactile stimuli can be delivered when a person is evaluating eating alternatives. In an example, haptic and/or tactile stimuli can be delivered while a person is eating. In an example, haptic and/or tactile stimuli can be delivered after a person has eaten.

In an example, a system for nutritional monitoring and management can provide food information to a person in a haptic mode. In an example, different vibrations, pressures, device movements across skin, and/or protrusion arrays can be used to convey attributes of food such as the nutritional composition of the food and/or whether the food is relatively healthy or unhealthy. In an example, a system can provide haptic feedback (such as vibration, tactile sensation, kinetic sensation, thermal feedback, mild electromagnetic energy delivery) to person concerning the person's food consumption choices and/or the nutritional composition of food items. In an example, a system can provide selected haptic feedback (e.g. vibrations) at selected time intervals in order change a person's eating pace. In an example, a system can provide selected haptic feedback (e.g. vibrations) in order to change a person's consumption of selected types or quantities of food. In an example, haptic feedback frequency or intensity can increase as a person approaches or exceeds a target amount of food consumption (e.g. during a meal or period of time).

In an example, a system for nutritional monitoring and management can have a display screen which shows the results of a spectroscopic scan of food via text, graphic objects, icons, colors, or patterns. In an example, different graphics, objects, icons, and/or colors on a display screen can indicate high concentrations of different types of ingredients, nutrients, and/or chemicals for particular food items and/or at particular locations in a meal. In an example, different graphics, objects, icons, and/or colors on a display screen can indicate whether a particular food item is high in protein, carbohydrates, or fats. In an example, a system can display different graphics, objects, icons, and/or colors for different food items in a meal and/or alternative food items. In an example, a system can include a smart phone, wherein the results of spectroscopic analysis of food are shown on the phone's screen.

In an example, a system for nutritional monitoring and management can provide a person with information concerning the type, total calories, nutritional composition, chemical composition, and/or quantity of nearby food. In an example, a system can display estimated quantity of a food item and/or the estimated total calories of that food item. In an example, a system can display the nutritional composition of food items (e.g. based on image analysis and spectroscopic analysis) in a person's field of view via augmented reality or on the screen of a mobile device. In an example, different colors can be associated with different types of nutrients (e.g. carbohydrates, sugars, fats, and proteins). In an example, a system can display visual cues concerning whether food is relatively healthy or unhealthy for a person to eat. In an example, a system can identify whether a food item contains a specific ingredient, such as an ingredient to which a person is allergic or intolerant.

In an example, a system for nutritional monitoring and management can measure the speed, pace, or rate at which a person eats and encourage the person to eat slower if the speed, pace, or rate is too fast. In an example, feedback from the system to the person can be light-based, such as a blinking light. In an example, feedback can be sound-based, such as a tone, note, alarm, buzzer, song, or computer-generated voice. In an example, feedback can be haptic or tactile, such as a vibration. In an example, visual, auditory, or haptic feedback concerning a person's eating pace can be delivered by a wrist-worn device such as a smart watch. In an example, visual, auditory, or haptic feedback concerning a person's eating pace can be delivered by a smart food utensil.

In an example, a system for nutritional monitoring and management can provide information to a person concerning how fast they are eating and/or prompt the person to slow down if they are eating too fast. In an example, a system can track how fast a person is eating by tracking: the speed of eating-related arm and wrist movements (e.g. tracked by a motion sensor, an EMG sensor, a camera), the speed of food utensil movements (e.g. tracked by a motion sensor on a utensil or image analysis), the speed of chewing or swallowing (tracked by a motion sensor, a vibration sensor, a microphone, or an EMG sensor), or the speed of changes in food weight on a food scale during a meal. In an example, a system can comprise a visual, auditory, of haptic signal when a person eats too fast. In an example, a visual signal can comprise the appearance of a virtual object in a person's field of view in augmented reality. In an example, a haptic signal can comprise vibration of a food utensil which a person is using to eat food. In an example, a haptic signal can comprise vibration of a smart watch worn by a person. In an example, specific colors, visual patterns, light blinks, light motions, or visual icons can be associated with particular types of nutrients. In an example, specific sound patterns and/or songs can be associated with particular types of nutrients.

In an example, a system for nutritional monitoring and management can track the cumulative amount of food eaten by a person during an eating event (e.g. during a meal) or during a period of time (e.g. during a day) and provide feedback to the person based on comparison of actual food consumption to a target amount of food consumption. In an example, a system can provide negative feedback if a person approaches and/or exceeds a target amount of food consumption for an eating event or a period of time. In an example, a device and system can sound an alarm or provide other real-time feedback to a person if the cumulative amount consumed (in total or of a selected type of food, ingredient, or nutrient) exceeds an allowable amount (in total or of a selected type of food, ingredient, or nutrient).

In an example, a system for nutritional monitoring and management can provide information to a person concerning the cumulative quantity of food (or of a particular nutrient) which the person has consumed during a meal or during a period of time. In an example, quantity of food consumed can be compared with a dietary goal or budget for a meal or a period of time. In an example, a system can provide an alert, alarm, or warning when a person is approaching or exceeding a dietary goal or budget for quantity of food (or a particular nutrient) during a meal or during a period of time. In an example, a goal or budget for a quantity of food (or a particular nutrient) can be based at least in part on a person's dietary goals, energy balance goals, body weight goals, and/or energy expenditure during a period of time. In an example, a system can provide recommendations concerning goals for a person's nutritional intake, exercise level, and the relationship between them. In an example, the recommend amount of calories that a system recommends for a person to consume during a period of time can depend on the amount of calories that the person has expended during a period of time. In an example, a person's caloric expenditure can be monitored by a schlep tracker. For example, if a person schleps groceries home from the store and schleps books to class, then their recommended caloric intake increases; but if they are a foyler, then their recommended caloric intake decreases. In an example, a system can track whether a person is consuming too little of a selected food or nutrient. For example, a system can remind a person to drink more water to avoid dehydration if the person has consumed too little water during a period of time. In an example, the amount of water which a person should drink can be determined in part by their activities and environmental factors.

In an example, a system for nutritional monitoring and management can provide a person with dietary recommendations and coaching. In an example, recommendations and coaching can be in real-time as a person is making food consumption decisions or can be with respect to planning future meals. In an example, a system can provide lists of generally healthy vs. unhealthy foods, meals, recipes, and/or restaurants. In an example, a system can provide information about the nutritional composition of particular foods, meals, recipes, and/or (meals at selected) restaurants. In an example, a system can provide health rankings or reviews of foods, meals, recipes, and/or restaurants. In an example, dietary recommendations and coaching by a system can be at least partially based on results reported in scientific and medical literature. In an example, dietary recommendations and coaching by a system can be at least partially based on previously-identified correlations between consumption of particular types and quantities of food items by a person and subsequent changes in that person's biometric parameters and/or health status.

In an example, a system for nutritional monitoring and management can recommend less consumption of foods or meals which are identified as unhealthy for a specific person or as generally unhealthy for people. For example, a system can recommend more consumption of foods or meals which are identified as healthy for a specific person or as generally healthy for people. In an example, a system can recommend (nearby) stores where healthy foods can be bought and/or (nearby) restaurants where healthy meals can be consumed. In an example, a system can provide shopping lists to help a person purchase healthy foods. In an example, a system can automatically order healthy foods for delivery to a person's home. In an example, a system can plan healthy meals for a person. In an example, a system can recommend healthy foods which can be substituted for unhealthy foods in a recipe or in a meal. In an example, a system can recommend restaurants which tend to serve healthy food as substitutes for a restaurant which tends to serve unhealthy food. In an example, a system can recommend amounts of (particular types of) food to be consumed in a given meal or during a period of time. In an example, a system can recommend that a person eat a particularly healthy food item on a periodic (e.g. daily) basis. For example, each day a system can say—"It's Hummus Time!" On the other hand, if a person is looking at unhealthy food, then the system can say—"U Can't Touch This!"

In an example, a system for nutritional monitoring and management can include an electromagnetic actuator, piezoelectric actuator, inflatable member, and/or pneumatic member which exerts pressure on a person's body in response to consumption of an unhealthy type and/or quantity of food. In an example a system can include an article of smart clothing or clothing accessory with an actuator, inflatable member, and/or pneumatic member which exerts pressure on a person's body in response to consumption of an unhealthy type and/or quantity of food. In an example, this clothing or accessory can be a shirt or pair of pants. In an example, this clothing or accessory can be a belt.

In an example, a system for nutritional monitoring and management can provide a person with one or more stimuli related to food consumption, wherein these stimuli are selected from the group consisting of: auditory stimulus (such as a voice message, alarm, buzzer, ring tone, or song); computer-generated speech; mild external electric charge or neural stimulation; periodic stimulus at a selected time of the day or week; phantom taste or smell; phone call; prerecorded audio or video message by the person from an earlier time; television-based messages; and tactile, vibratory, or pressure-based stimulus. In an example, a system can provide negative stimuli in association with consumption of unhealthy types and quantities of food and/or provide positive stimuli in association with consumption of healthy types and quantities of food.

In an example, a system for nutritional monitoring and management can provide a person with stimuli to modify the person's eating behavior. In an example, a system can provide a person with visual, auditory, and/or haptic stimuli to modify the person's eating behavior. In an example, a system can provide negative stimuli which encourage a person to eat less unhealthy food and/or positive stimuli which encourage a person to eat more healthy food. In an example, a system can provide stimuli to encourage a person to avoid eating an unhealthy amount of food. In an example, a system can provide a negative stimulus associated with unhealthy food which is nearby and a person may eat. In an example, a system can provide a negative stimulus associated with unhealthy food which a person is eating or has just eaten. In an example, a system can provide a positive stimulus associated with healthy food which is nearby and a person may eat. In an example, a system can provide a positive stimulus associated with healthy food which a person is eating or has just eaten.

In an example, a system for nutritional monitoring and management can provide visual, auditory, haptic, or taste stimuli which actively discourage consumption of unhealthy food types or quantities. In an example, a system can provide visual, auditory, haptic, or taste stimuli which actively encourage consumption of healthy food types or quantities. In an example, a behavior-affecting stimulus can be provided before food consumption in order to influence a person's decision whether or not to consume a selected type or quantity of food. In an example, a behavior-affecting stimulus can be provided after food consumption in order to positively or negatively reinforce a person's consumption of a selected type or quantity of food. In an example, a system can provide a visual, auditory, haptic, or taste stimulus which makes unhealthy food less appealing to a person and/or makes healthy food more appealing to the person. In an example, the modality (e.g. visual, auditory, or haptic) of a behavior-affecting stimulus can be selected for a particular setting based analysis of environmental cues. For example, a more discreet stimulus modality can be selected in a public/social eating situation than in a home/individual eating situation. In an example, the modality (e.g. visual, auditory, or haptic) of a behavior-affecting stimulus can be selected for a particular person or in that particular setting based on past success of that modality in affecting the behavior of that particular person or in that particular setting.

In an example, a system for nutritional monitoring and management can display an appetite-influencing image in juxtaposition to a nearby food item in a person's field of view via augmented reality eyewear. In an example, a system can display an appetite-influencing image in juxtaposition to a nearby food item via the screen of a mobile device with augmented reality functionality. In an example, a system can display an unappetizing image in juxtaposition to unhealthy food and/or an appetizing image in juxtaposition to healthy food. In an example, a system can provide a person with real-time (or close to real-time) feedback on pending or recent food consumption choices. In an example, a system can display a person's historical nutritional intake data in graphic form, highlighting trends and implications. In an example, a system can provide a person with information about their progress toward a dietary goal. In an example, a system can connect a person's progress toward a dietary goal with a support group or social network. In an example, a system can connect a person's progress toward a dietary goal with a dietician or other healthcare professional.

In an example, a person can request that a system share information concerning the person's food consumption with friends, social networks, social media, healthcare professionals in order to receive feedback from those people to improve the person's food consumption choices and health.

In an example, a system can provide a person with benchmark information by which to evaluate their food consumption and/or nutritional intake. In an example, a system can provide a person with reviews and/or ratings of selected meals, recipes, and/or food items. In an example, a system can provide a person with personalized dietary coaching and advice.

In an example, a system for nutritional monitoring and management can monitor, analyze, and provide feedback concerning a person's food consumption and/or nutritional intake. In an example, a system can provide a person with graphs showing historical trends with respect to their eating patterns and food consumption. In an example, a system can provide a person with personalized dietary recommendations and coaching based on automated analysis of the person's food consumption, changes in the person's biometric parameters, or the interaction thereof. In an example, a system can remind a person to take insulin before eating and/or recommend insulin dosage quantities based on types and/or quantities of food consumed.

In an example, a system for nutritional monitoring and management can help to prevent adverse diet-related conditions and diseases (such as diabetes). In an example, a system can help to treat and/or cure adverse diet-related conditions and diseases (such as diabetes). In an example, a system can provide therapy to treat adverse diet-related conditions and diseases (such as diabetes). In an example, a system can analyze types and quantities of food consumed by a person and provide recommended insulin doses for the person. In an example, recommended insulin doses can be at least partly based on identified associations between consumption of specific types and quantities of food in the past and subsequent changes in blood glucose levels following that food consumption. In an example, a system can be part of a closed-loop glucose monitoring and insulin delivery system. In an example, a system can be a closed-loop glucose monitoring and insulin delivery system. In an example, insulin can be delivered automatically by a closed-loop insulin therapy system.

In an example, a system for nutritional monitoring and management can include an implanted or wearable drug delivery device. In an example, a system can include an implanted or wearable device which dispenses a drug which modifies a person's appetite, food digestion, and/or food metabolism. In an example, a system can include an implanted or wearable insulin pump. In an example, a system can allow normal absorption of nutrients from a healthy type of food in a person's gastrointestinal tract, but can reduce absorption of nutrients from an unhealthy type of food by releasing an absorption-affecting substance. In an example, a system can include an implanted device which reduces absorption of nutrients from unhealthy types and/or quantities of food.

In an example, biometric information can be used to estimate blood glucose levels, but there is a lag between when food is consumed and when nutrients from this food enter a person's blood stream. In an example, a system such as is described in this disclosure can be combined with a wearable biometric device to form a system for predicting and estimating blood glucose levels. This system can use information on current blood glucose levels and also information on food that a person is consuming which can be helpful in predicting changes in glucose levels. In an example, a device to monitor nutritional intake can be wirelessly linked with a wearable device for non-invasive blood glucose monitoring as part of a system for estimating and/or predicting blood glucose levels. In an example data from the mobile device concerning the types and quantities of food that a person is eating can be used in a multivariate analysis, in combination with biometric information from a wearable device, to estimate and/or predict blood glucose levels more accurately than is possible with either food consumption monitoring or wearable biometric monitoring alone.

In an example, a system for nutritional monitoring and management can monitor and help to manage a person's food consumption and eating habits. In an example, a system can monitor and help to manage a person's food consumption triggers. In an example, a system can monitor a person's food consumption and provide the person with feedback to help the person manage their food consumption. In an example, a system can help a person to overcome food triggers and/or food addictions. In an example, food can include beverages as well as solid foods. In an example, a system can monitor a person's alcohol consumption and help the person to manage their alcohol consumption.

In an example, a system for nutritional monitoring and management can prompt a person to provide user input concerning identification of (nearby) food item types and/or quantities. In an example, this user input can be incorporated into multivariate analysis for determination of food item types and quantities. In an example, a system can prompt a person to enter user input (e.g. descriptions of food types and quantities) if the system detects that the person has begun eating (e.g. through motion sensors, image analysis, or other automated inputs) without providing such input.

In an example, user input from a person can be combined with automatically collected information (e.g. automatically collected images and spectroscopic analysis) concerning food item types and quantities for multivariate estimation of food item types and quantities. In an example, if analysis of automatically collected information is insufficient to determine food types and quantities with sufficient accuracy or certainty, then the system can prompt a person to enter user input (e.g. descriptions of food types and quantities) as well. In an example, a system can use Bayesian statistical methods to update analysis of food types and quantities with information from multiple (automated and manual) sources, sensors, and modalities until a desired level of measurement accuracy or certainty is obtained.

In an example, a system for nutritional monitoring and management can allow normal sensory perception of healthy food, but modifies the taste and/or smell of unhealthy food. In an example, a system can release a taste and/or smell modifying substance into a person's oral cavity and/or nasal passages. In an example, a system can allow normal sensory perception of a healthy quantity of food, but can modify the taste and/or smell of an unhealthy quantity of food by releasing a taste and/or smell modifying substance into a person's oral cavity and/or nasal passages. In an example, a system can release a substance with a strong flavor into a person's oral cavity when the person consumes an unhealthy type and/or quantity of food. In an example, a system can release a substance with a strong smell into a person's nasal passages when the person consumes an unhealthy type and/or quantity of food.

In an example, a system for nutritional monitoring and management can cause a person to experience an unpleasant virtual taste and/or smell when the person consumes an unhealthy type or quantity of food. In an example, a phantom taste or smell can be triggered by delivering electromagnetic energy to afferent nerves which innervate a person's tongue and/or nasal passages. In an example, a system can cause temporary dysgeusia when a person consumes an unhealthy type or quantity of food. In an example, a system can cause a person to experience reduced taste and/or smell when the person consumes an unhealthy type or quantity of food by delivering electromagnetic energy to afferent nerves which innervate a person's tongue and/or nose.

In an example, a system for nutritional monitoring and management can send a communication or message to a person who is wearing a device. In an example, a system can send nutritional information concerning food that a person is near, food that the person is purchasing, food that the person is ordering, and/or food that the person is eating. This nutritional information can include food ingredients, nutrients, and/or calories. In an example, a system can send information concerning the likely health effects of consuming food that a person is near, food that the person is purchasing, food that the person is ordering, and/or food that the person has already starting consuming. In an example, a system can communicate food information in text form. In an example, a communication can recommend a healthier substitute for unhealthy food which a person is considering purchasing, ordering, and/or consuming.

In an example, a system for nutritional monitoring and management can send a communication to a person other than the person who is wearing a device. In an example, this other person can provide encouragement and support for the person wearing the device to eat less unhealthy food and/or to eat more healthy food. In an example, this other person can be a friend, support group member, family member, or a health care provider. In an example, this device could send a text to Kevin Bacon, or someone who knows him, or someone who knows someone who knows him, or someone who knows someone who knows someone who knows him. In an example, a system can connect with a social network and/or an internet-based support group. In an example, a system can engage a person's friends to encourage the person to reduce consumption of unhealthy types and/or quantities of food (and increase consumption of healthy food) in order to achieve personal health goals. In an example, a system can encourage a person to compete with people in a peer group with respect to achievement of health goals. In an example, a system can function as a virtual dietary health coach.

In an example, a system for nutritional monitoring and management can include a battery or other power source. In an example, a system can include a power transducer which generates electrical energy from body heat or motion. In an example, a system can comprise a power management unit which regulates the amount of power used the system based on whether or not the person is eating. In an example, a system can comprise a power management unit which regulates the amount of power used the system based on whether or not the person is sleeping. In an example, a system can be set in low-power mode when a person is not eating or is sleeping. In an example, this system can comprise a touch screen and/or display. In an example, this system can comprise a keypad or keyboard. In an example, this system can comprise a camera and microphone.

In an example, a system for nutritional monitoring and management can comprise one or more devices selected from the group consisting of: augmented reality device, bioimpedance monitor, blood pressure monitor, body temperature sensor, camera, chewing-sound sensor, continuous glucose monitor, ECG monitor, ear bud or pod, electromagnetic energy sensor, EMG sensor, GPS receiver, heart rate monitor, intra-oral sensor, microphone, mobile device, mobile EEG device, motion sensor (e.g. accelerometer and gyroscope); pacemaker, smart clothing, smart eyewear, smart necklace, smart ring, smart watch, spectroscopic sensor, and sweat analysis device.

In an example, a system for nutritional monitoring and management can comprise a data processing unit, memory, wireless data transmitter, and wireless data receiver. In an example, analysis of food types and quantities by a system can be done by a local data processor which is in a handheld or wearable device. In an example, a handheld or wearable device can transmit data to a remote data processor, wherein analysis of food types and quantities is done. In an example, data can be transmitted from a handheld or wearable device to a remote data processor via the internet. In an example, this system can comprise a first data processing unit (e.g. in a wearable or handheld mobile device), a data transmitter, and a second data processing unit in a remote location (e.g. in electromagnetic communication with the mobile device via the data transmitter). In an example, the second data processing unit can be in the cloud.

In an example, a system for nutritional monitoring and management can include a handheld device and a wearable device which are in wireless electromagnetic communication with each other. In an example, a system can include a local (e.g. handheld or wearable) device which is in wireless electromagnetic communication with a remote (e.g. cloud-based) data processor. In an example, different devices and/or processors in a system can exchange information via wireless electromagnetic communication, including sensor data, analysis results, notifications, text messages, and voice messages.

In an example, a system for nutritional monitoring and management can include augmented reality eyewear or other smart eyewear. In an example, a system can include buttons or a keypad. In an example, a system can include one or more electromagnet energy sensors selected from the group consisting of: EEG sensor, EMG sensor, and other electromagnetic sensor. In an example, a system can include one or more energy related components selected from the group consisting of: battery or other power source, power transducer, and thermal energy transducer. In an example, a system can include one or more light energy components selected from the group consisting of: display screen, graphic display, handheld spectroscopy sensor, laser pointer, LCD display, light emitter, light projector, light receiver, optical diffuser, optical sensor, spectroscopic sensor, and touch screen.

In an example, a system for nutritional monitoring and management can include one or more sensor components selected from the group consisting of: chemical sensor, gesture recognition component, GPS component, and motion sensor (e.g. accelerometer and gyroscope). In an example, a system can include one or more sound-related components selected from the group consisting of: microphone, speaker, and speech recognition component. In an example, a system can include one or more wearable and/or handheld devices selected from the group consisting of: ear bud, fitness band, mobile EEG device, smart finger ring, smart necklace, smart phone, smart watch, and wrist band. In an example, a system for nutritional monitoring and management can include one or more data-related components selected from the group consisting of: data analysis component, food database, local data processor, memory, remote data processor, wireless data receiver, and wireless data transmitter.

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; and (c) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a fiducial component which displays objects in images of food items which help to calibrate the distance, size, shape, color, and/or brightness of the food items; wherein the fiducial component is selected from the group consisting of: an object with (markings of) known size, shape, and/or colors which is placed near the food items; a light emitter (e.g. low-power laser) which projects a light pattern with known size, shape, and/or colors on or near the food items; and a mobile device with a screen which is placed near the food items and displays an image on the screen with known size, shape, and/or colors; and (d) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a fiducial component which displays objects in images of food items which help to calibrate the distance, size, shape, color, and/or brightness of the food items; wherein the fiducial component is selected from the group consisting of: an object with (markings of) known size, shape, and/or colors which is placed near the food items; a light emitter (e.g. low-power laser) which projects a light pattern with known size, shape, and/or colors on or near the food items; and a mobile device with a screen which is placed near the food items and displays an image on the screen with known size, shape, and/or colors; (d) a wearable biometric sensor which collects biometric data concerning a person whose nutritional intake is being monitored, wherein the biometric sensor is selected from the group consisting of: motion sensor (e.g. accelerometer, gyroscope, and/or compass), electromagnetic energy sensor (e.g. impedance sensor, EMG sensor, EKG sensor), spectroscopic sensor (e.g. spectrometer) and/or photoplethysmographic sensor, sound sensor (e.g. microphone, chew sensor, swallow sensor), and chemical sensor (e.g. sweat sensor, saliva sensor); wherein data from the biometric sensor is used for one or more functions selected from the group consisting of: recognizing when the person is eating in order to automatically activate the system to take an action (e.g. recording images or monitoring sounds) to help identify food item types and/or estimate food item quantities; recognizing when the person is eating in order to automatically prompt the person to take an action (e.g. recording images or entering food descriptions) to help identify food item types and/or estimate food item quantities; and identifying relationships between consumption of selected food item types and/or food item quantities by the person and subsequent changes in the person's biometric parameters (e.g. glucose level, blood pressure, lactic acid level, or oxygen level); and wherein the biometric sensor is part of a device selected from the group consisting of: smart watch or other wrist-worn device, smart finger ring, smart armband, smart eyewear, smart earwear, smart necklace or pendant, smart button, smart belt, smart garment, adhesive sensor patch, mobile EEG device, and continuous glucose monitor; and (e) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a fiducial component which displays objects in images of food items which help to calibrate the distance, size, shape, color, and/or brightness of the food items; wherein the fiducial component is selected from the group consisting of: an object with (markings of) known size, shape, and/or colors which is placed near the food items; a light emitter (e.g. low-power laser) which projects a light pattern with known size, shape, and/or colors on or near the food items; and a mobile device with a screen which is placed near the food items and displays an image on the screen with known size, shape, and/or colors; (d) a wearable biometric sensor which collects biometric data concerning a person whose nutritional intake is being monitored, wherein the biometric sensor is selected from the group consisting of: motion sensor (e.g. accelerometer, gyroscope, and/or compass), electromagnetic energy sensor (e.g. impedance sensor, EMG sensor, EKG sensor), spectroscopic sensor (e.g. spectrometer) and/or photoplethysmographic sensor, sound sensor (e.g. microphone, chew sensor, swallow sensor), and chemical sensor (e.g. sweat sensor, saliva sensor); wherein data from the biometric sensor is used for one or more functions selected from the group consisting of: recognizing when the person is eating in order to automatically activate the system to take an action (e.g. recording images or monitoring sounds) to help identify food item types and/or estimate food item quantities; recognizing when the person is eating in order to automatically prompt the person to take an action (e.g. recording images or entering food descriptions) to help identify food item types and/or estimate food item quantities; and identifying relationships between consumption of selected food item types and/or food item quantities by the person and subsequent changes in the person's biometric parameters (e.g. glucose level, blood pressure, lactic acid level, or oxygen level); and wherein the biometric sensor is part of a device selected from the group consisting of: smart watch or other wrist-worn device, smart finger ring, smart armband, smart eyewear, smart earwear, smart necklace or pendant, smart button, smart belt, smart garment, adhesive sensor patch, mobile EEG device, and continuous glucose monitor; (e) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; and (f) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a fiducial component which displays objects in images of food items which help to calibrate the distance, size, shape, color, and/or brightness of the food items; wherein the fiducial component is selected from the group consisting of: an object with (markings of) known size, shape, and/or colors which is placed near the food items; a light emitter (e.g. low-power laser) which projects a light pattern with known size, shape, and/or colors on or near the food items; and a mobile device with a screen which is placed near the food items and displays an image on the screen with known size, shape, and/or colors; (d) a wearable biometric sensor which collects biometric data concerning a person whose nutritional intake is being monitored, wherein the biometric sensor is selected from the group consisting of: motion sensor (e.g. accelerometer, gyroscope, and/or compass), electromagnetic energy sensor (e.g. impedance sensor, EMG sensor, EKG sensor), spectroscopic sensor (e.g. spectrometer) and/or photoplethysmographic sensor, sound sensor (e.g. microphone, chew sensor, swallow sensor), and chemical sensor (e.g. sweat sensor, saliva sensor); wherein data from the biometric sensor is used for one or more functions selected from the group consisting of: recognizing when the person is eating in order to automatically activate the system to take an action (e.g. recording images or monitoring sounds) to help identify food item types and/or estimate food item quantities; recognizing when the person is eating in order to automatically prompt the person to take an action (e.g. recording images or entering food descriptions) to help identify food item types and/or estimate food item quantities; and identifying relationships between consumption of selected food item types and/or food item quantities by the person and subsequent changes in the person's biometric parameters (e.g. glucose level, blood pressure, lactic acid level, or oxygen level); and wherein the biometric sensor is part of a device selected from the group consisting of: smart watch or other wrist-worn device, smart finger ring, smart armband, smart eyewear, smart earwear, smart necklace or pendant, smart button, smart belt, smart garment, adhesive sensor patch, mobile EEG device, and continuous glucose monitor; (e) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; (f) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); and (g) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a fiducial component which displays objects in images of food items which help to calibrate the distance, size, shape, color, and/or brightness of the food items; wherein the fiducial component is selected from the group consisting of: an object with (markings of) known size, shape, and/or colors which is placed near the food items; a light emitter (e.g. low-power laser) which projects a light pattern with known size, shape, and/or colors on or near the food items; and a mobile device with a screen which is placed near the food items and displays an image on the screen with known size, shape, and/or colors; (d) a wearable biometric sensor which collects biometric data concerning a person whose nutritional intake is being monitored, wherein the biometric sensor is selected from the group consisting of: motion sensor (e.g. accelerometer, gyroscope, and/or compass), electromagnetic energy sensor (e.g. impedance sensor, EMG sensor, EKG sensor), spectroscopic sensor (e.g. spectrometer) and/or photoplethysmographic sensor, sound sensor (e.g. microphone, chew sensor, swallow sensor), and chemical sensor (e.g. sweat sensor, saliva sensor); wherein data from the biometric sensor is used for one or more functions selected from the group consisting of: recognizing when the person is eating in order to automatically activate the system to take an action (e.g. recording images or monitoring sounds) to help identify food item types and/or estimate food item quantities; recognizing when the person is eating in order to automatically prompt the person to take an action (e.g. recording images or entering food descriptions) to help identify food item types and/or estimate food item quantities; and identifying relationships between consumption of selected food item types and/or food item quantities by the person and subsequent changes in the person's biometric parameters (e.g. glucose level, blood pressure, lactic acid level, or oxygen level); and wherein the biometric sensor is part of a device selected from the group consisting of: smart watch or other wrist-worn device, smart finger ring, smart armband, smart eyewear, smart earwear, smart necklace or pendant, smart button, smart belt, smart garment, adhesive sensor patch, mobile EEG device, and continuous glucose monitor; (e) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; (f) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); (g) an active stimulus mechanism which automatically responds to food consumption by the person, wherein the active stimulus mechanism automatically modifies a person's physiological processes (e.g. by delivering a therapeutic agent, such as insulin, into the person's body; by delivering a therapeutic pattern of electromagnetic energy to a selected portion of the person's body, such as the vagus nerve; or by delivering a taste-modifying substance into a person's mouth); and (h) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a wearable biometric sensor which collects biometric data concerning a person whose nutritional intake is being monitored, wherein the biometric sensor is selected from the group consisting of: motion sensor (e.g. accelerometer, gyroscope, and/or compass), electromagnetic energy sensor (e.g. impedance sensor, EMG sensor, EKG sensor), spectroscopic sensor (e.g. spectrometer) and/or photoplethysmographic sensor, sound sensor (e.g. microphone, chew sensor, swallow sensor), and chemical sensor (e.g. sweat sensor, saliva sensor); wherein data from the biometric sensor is used for one or more functions selected from the group consisting of: recognizing when the person is eating in order to automatically activate the system to take an action (e.g. recording images or monitoring sounds) to help identify food item types and/or estimate food item quantities; recognizing when the person is eating in order to automatically prompt the person to take an action (e.g. recording images or entering food descriptions) to help identify food item types and/or estimate food item quantities; and identifying relationships between consumption of selected food item types and/or food item quantities by the person and subsequent changes in the person's biometric parameters (e.g. glucose level, blood pressure, lactic acid level, or oxygen level); and wherein the biometric sensor is part of a device selected from the group consisting of: smart watch or other wrist-worn device, smart finger ring, smart armband, smart eyewear, smart earwear, smart necklace or pendant, smart button, smart belt, smart garment, adhesive sensor patch, mobile EEG device, and continuous glucose monitor; (d) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; (e) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); (f) an active stimulus mechanism which automatically responds to food consumption by the person, wherein the active stimulus mechanism automatically modifies a person's physiological processes (e.g. by delivering a therapeutic agent, such as insulin, into the person's body; by delivering a therapeutic pattern of electromagnetic energy to a selected portion of the person's body, such as the vagus nerve; or by delivering a taste-modifying substance into a person's mouth); and (g) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a wearable biometric sensor which collects biometric data concerning a person whose nutritional intake is being monitored, wherein the biometric sensor is selected from the group consisting of: motion sensor (e.g. accelerometer, gyroscope, and/or compass), electromagnetic energy sensor (e.g. impedance sensor, EMG sensor, EKG sensor), spectroscopic sensor (e.g. spectrometer) and/or photoplethysmographic sensor, sound sensor (e.g. microphone, chew sensor, swallow sensor), and chemical sensor (e.g. sweat sensor, saliva sensor); wherein data from the biometric sensor is used for one or more functions selected from the group consisting of: recognizing when the person is eating in order to automatically activate the system to take an action (e.g. recording images or monitoring sounds) to help identify food item types and/or estimate food item quantities; recognizing when the person is eating in order to automatically prompt the person to take an action (e.g. recording images or entering food descriptions) to help identify food item types and/or estimate food item quantities; and identifying relationships between consumption of selected food item types and/or food item quantities by the person and subsequent changes in the person's biometric parameters (e.g. glucose level, blood pressure, lactic acid level, or oxygen level); and wherein the biometric sensor is part of a device selected from the group consisting of: smart watch or other wrist-worn device, smart finger ring, smart armband, smart eyewear, smart earwear, smart necklace or pendant, smart button, smart belt, smart garment, adhesive sensor patch, mobile EEG device, and continuous glucose monitor; (d) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; (e) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); and (f) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a wearable biometric sensor which collects biometric data concerning a person whose nutritional intake is being monitored, wherein the biometric sensor is selected from the group consisting of: motion sensor (e.g. accelerometer, gyroscope, and/or compass), electromagnetic energy sensor (e.g. impedance sensor, EMG sensor, EKG sensor), spectroscopic sensor (e.g. spectrometer) and/or photoplethysmographic sensor, sound sensor (e.g. microphone, chew sensor, swallow sensor), and chemical sensor (e.g. sweat sensor, saliva sensor); wherein data from the biometric sensor is used for one or more functions selected from the group consisting of: recognizing when the person is eating in order to automatically activate the system to take an action (e.g. recording images or monitoring sounds) to help identify food item types and/or estimate food item quantities; recognizing when the person is eating in order to automatically prompt the person to take an action (e.g. recording images or entering food descriptions) to help identify food item types and/or estimate food item quantities; and identifying relationships between consumption of selected food item types and/or food item quantities by the person and subsequent changes in the person's biometric parameters (e.g. glucose level, blood pressure, lactic acid level, or oxygen level); and wherein the biometric sensor is part of a device selected from the group consisting of: smart watch or other wrist-worn device, smart finger ring, smart armband, smart eyewear, smart earwear, smart necklace or pendant, smart button, smart belt, smart garment, adhesive sensor patch, mobile EEG device, and continuous glucose monitor; (d) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; and (e) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a wearable biometric sensor which collects biometric data concerning a person whose nutritional intake is being monitored, wherein the biometric sensor is selected from the group consisting of: motion sensor (e.g. accelerometer, gyroscope, and/or compass), electromagnetic energy sensor (e.g. impedance sensor, EMG sensor, EKG sensor), spectroscopic sensor (e.g. spectrometer) and/or photoplethysmographic sensor, sound sensor (e.g. microphone, chew sensor, swallow sensor), and chemical sensor (e.g. sweat sensor, saliva sensor); wherein data from the biometric sensor is used for one or more functions selected from the group consisting of: recognizing when the person is eating in order to automatically activate the system to take an action (e.g. recording images or monitoring sounds) to help identify food item types and/or estimate food item quantities; recognizing when the person is eating in order to automatically prompt the person to take an action (e.g. recording images or entering food descriptions) to help identify food item types and/or estimate food item quantities; and identifying relationships between consumption of selected food item types and/or food item quantities by the person and subsequent changes in the person's biometric parameters (e.g. glucose level, blood pressure, lactic acid level, or oxygen level); and wherein the biometric sensor is part of a device selected from the group consisting of: smart watch or other wrist-worn device, smart finger ring, smart armband, smart eyewear, smart earwear, smart necklace or pendant, smart button, smart belt, smart garment, adhesive sensor patch, mobile EEG device, and continuous glucose monitor; and (d) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a fiducial component which displays objects in images of food items which help to calibrate the distance, size, shape, color, and/or brightness of the food items; wherein the fiducial component is selected from the group consisting of: an object with (markings of) known size, shape, and/or colors which is placed near the food items; a light emitter (e.g. low-power laser) which projects a light pattern with known size, shape, and/or colors on or near the food items; and a mobile device with a screen which is placed near the food items and displays an image on the screen with known size, shape, and/or colors; (d) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; (e) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); (f) an active stimulus mechanism which automatically responds to food consumption by the person, wherein the active stimulus mechanism automatically modifies a person's physiological processes (e.g. by delivering a therapeutic agent, such as insulin, into the person's body; by delivering a therapeutic pattern of electromagnetic energy to a selected portion of the person's body, such as the vagus nerve; or by delivering a taste-modifying substance into a person's mouth); and (g) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a fiducial component which displays objects in images of food items which help to calibrate the distance, size, shape, color, and/or brightness of the food items; wherein the fiducial component is selected from the group consisting of: an object with (markings of) known size, shape, and/or colors which is placed near the food items; a light emitter (e.g. low-power laser) which projects a light pattern with known size, shape, and/or colors on or near the food items; and a mobile device with a screen which is placed near the food items and displays an image on the screen with known size, shape, and/or colors; (d) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; (e) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); and (f) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a fiducial component which displays objects in images of food items which help to calibrate the distance, size, shape, color, and/or brightness of the food items; wherein the fiducial component is selected from the group consisting of: an object with (markings of) known size, shape, and/or colors which is placed near the food items; a light emitter (e.g. low-power laser) which projects a light pattern with known size, shape, and/or colors on or near the food items; and a mobile device with a screen which is placed near the food items and displays an image on the screen with known size, shape, and/or colors; (d) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; and (e) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a fiducial component which displays objects in images of food items which help to calibrate the distance, size, shape, color, and/or brightness of the food items; wherein the fiducial component is selected from the group consisting of: an object with (markings of) known size, shape, and/or colors which is placed near the food items; a light emitter (e.g. low-power laser) which projects a light pattern with known size, shape, and/or colors on or near the food items; and a mobile device with a screen which is placed near the food items and displays an image on the screen with known size, shape, and/or colors; (d) a wearable biometric sensor which collects biometric data concerning a person whose nutritional intake is being monitored, wherein the biometric sensor is selected from the group consisting of: motion sensor (e.g. accelerometer, gyroscope, and/or compass), electromagnetic energy sensor (e.g. impedance sensor, EMG sensor, EKG sensor), spectroscopic sensor (e.g. spectrometer) and/or photoplethysmographic sensor, sound sensor (e.g. microphone, chew sensor, swallow sensor), and chemical sensor (e.g. sweat sensor, saliva sensor); wherein data from the biometric sensor is used for one or more functions selected from the group consisting of: recognizing when the person is eating in order to automatically activate the system to take an action (e.g. recording images or monitoring sounds) to help identify food item types and/or estimate food item quantities; recognizing when the person is eating in order to automatically prompt the person to take an action (e.g. recording images or entering food descriptions) to help identify food item types and/or estimate food item quantities; and identifying relationships between consumption of selected food item types and/or food item quantities by the person and subsequent changes in the person's biometric parameters (e.g. glucose level, blood pressure, lactic acid level, or oxygen level); and wherein the biometric sensor is part of a device selected from the group consisting of: smart watch or other wrist-worn device, smart finger ring, smart armband, smart eyewear, smart earwear, smart necklace or pendant, smart button, smart belt, smart garment, adhesive sensor patch, mobile EEG device, and continuous glucose monitor; (e) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); (f) an active stimulus mechanism which automatically responds to food consumption by the person, wherein the active stimulus mechanism automatically modifies a person's physiological processes (e.g. by delivering a therapeutic agent, such as insulin, into the person's body; by delivering a therapeutic pattern of electromagnetic energy to a selected portion of the person's body, such as the vagus nerve; or by delivering a taste-modifying substance into a person's mouth); and (g) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a fiducial component which displays objects in images of food items which help to calibrate the distance, size, shape, color, and/or brightness of the food items; wherein the fiducial component is selected from the group consisting of: an object with (markings of) known size, shape, and/or colors which is placed near the food items; a light emitter (e.g. low-power laser) which projects a light pattern with known size, shape, and/or colors on or near the food items; and a mobile device with a screen which is placed near the food items and displays an image on the screen with known size, shape, and/or colors; (d) a wearable biometric sensor which collects biometric data concerning a person whose nutritional intake is being monitored, wherein the biometric sensor is selected from the group consisting of: motion sensor (e.g. accelerometer, gyroscope, and/or compass), electromagnetic energy sensor (e.g. impedance sensor, EMG sensor, EKG sensor), spectroscopic sensor (e.g. spectrometer) and/or photoplethysmographic sensor, sound sensor (e.g. microphone, chew sensor, swallow sensor), and chemical sensor (e.g. sweat sensor, saliva sensor); wherein data from the biometric sensor is used for one or more functions selected from the group consisting of: recognizing when the person is eating in order to automatically activate the system to take an action (e.g. recording images or monitoring sounds) to help identify food item types and/or estimate food item quantities; recognizing when the person is eating in order to automatically prompt the person to take an action (e.g. recording images or entering food descriptions) to help identify food item types and/or estimate food item quantities; and identifying relationships between consumption of selected food item types and/or food item quantities by the person and subsequent changes in the person's biometric parameters (e.g. glucose level, blood pressure, lactic acid level, or oxygen level); and wherein the biometric sensor is part of a device selected from the group consisting of: smart watch or other wrist-worn device, smart finger ring, smart armband, smart eyewear, smart earwear, smart necklace or pendant, smart button, smart belt, smart garment, adhesive sensor patch, mobile EEG device, and continuous glucose monitor; (e) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); and (f) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; (d) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); (e) an active stimulus mechanism which automatically responds to food consumption by the person, wherein the active stimulus mechanism automatically modifies a person's physiological processes (e.g. by delivering a therapeutic agent, such as insulin, into the person's body; by delivering a therapeutic pattern of electromagnetic energy to a selected portion of the person's body, such as the vagus nerve; or by delivering a taste-modifying substance into a person's mouth); and (f) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; (d) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); and (e) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a smart utensil, dish, plate, or beverage holder which collects data concerning food item quantities consumed by a person; wherein the smart utensil, dish, plate, or beverage holder collects data by one or more means selected from the group consisting of: measuring the number of forkfuls, spoonfuls, bites and/or sips taken by a person based on motion (e.g. upward and tilting motion) of a smart utensil or beverage holder; estimating the weight of forkfuls, spoonfuls, bites and/or sips taken by a person based on motion and/or force exerted by food on a smart utensil or beverage holder; estimating the cumulative quantity of food items consumed by a person (e.g. during a particular meal) by measuring changes in the weight of food on a disk or plate; and using chemical analysis to help to identify the type and/or composition of food in contact with the smart utensil, dish, plate, or beverage holder; and (d) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); (d) an active stimulus mechanism which automatically responds to food consumption by the person, wherein the active stimulus mechanism automatically modifies a person's physiological processes (e.g. by delivering a therapeutic agent, such as insulin, into the person's body; by delivering a therapeutic pattern of electromagnetic energy to a selected portion of the person's body, such as the vagus nerve; or by delivering a taste-modifying substance into a person's mouth); and (e) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: (a) a camera which records images of food items, wherein the images are analyzed to help identify food item types and/or estimate food item quantities, wherein food includes beverages as well as solid food, and wherein the camera is part of a device selected from the group consisting of: smart phone, smart watch or other wrist-worn device, smart finger ring, smart eyewear, electronic tablet, smart earwear, smart necklace or pendant, smart button, and dedicated handheld food identification device; (b) a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; wherein changes in the spectral distribution of the light caused by interaction with food items are used to help identify food item types and/or compositions; and wherein the spectroscopic sensor is part of a device selected from the group consisting of: smart phone, smart watch or other wrist-worn device, smart finger ring, smart eyewear, electronic tablet, smart earwear, smart necklace or pendant, smart button, and dedicated handheld food identification device; (c) a passive feedback mechanism which provides passive feedback to a person concerning the type, quantity, nutritional content, and/or health implications of food items; wherein this passive feedback is selected from the group consisting of: visual feedback (e.g. text, graphics, or images displayed on a screen or in augmented reality); sound feedback (e.g. sound, song, or voice); and haptic feedback (e.g. vibration, pressure, or delivery of electromagnetic energy); and (d) one or more other components selected from the group consisting of: data processor; data transmitter; data receiver; battery; GPS module (e.g. identifying the location of food acquisition, preparation, or consumption); clock (e.g. identifying the time of day of food consumption); calendar (e.g. identifying day of the week, holidays, or special events); voice recognition interface (e.g. to recognize voice-based food descriptions); touch-screen interface (e.g. to recognize touch-based menu-driven or text-based food descriptions); gesture recognition interface (e.g. to recognize gesture-based menu-driven food descriptions); and EEG interface (e.g. to recognize selected EEG patterns).

In an example, a system for nutritional monitoring and management can comprise: a camera which records images of food items, wherein the images are analyzed to help identify food item types and/or estimate food item quantities, and wherein food includes beverages as well as solid food; a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; and wherein changes in the spectral distribution of the light caused by interaction with food items are used to help identify food item types and/or compositions; and one or more other components selected from the group consisting of: data processor; data transmitter; data receiver; battery; GPS module; clock; calendar; voice recognition interface; touch-screen interface; gesture recognition interface; and EEG interface.

In an example, the camera can be part of a smart phone. In an example, the camera can be part of a smart watch or other wrist-worn device. In an example, the camera can be part of a smart finger ring. In an example, the camera can be part of augmented reality eyewear or other smart eyewear. In an example, the camera can be part of a smart necklace or pendant. In an example, the camera can be part of a dedicated handheld food identification device. In an example, the spectroscopic sensor can be part of a smart watch or other wrist-worn device. In an example, the spectroscopic sensor can be part of a dedicated handheld food identification device.

In an example, a system for nutritional monitoring and management can comprise: a camera which records images of food items, wherein the images are analyzed to help identify food item types and/or estimate food item quantities, and wherein food includes beverages as well as solid food; a spectroscopic sensor which collects spectral data concerning light reflected from or absorbed by food items; wherein the spectral data is used to help identify food item types and/or compositions; wherein the spectroscopic sensor further comprises a light emitter which emits light toward food items and a light receiver which receives the light after it has been reflected by or passed through the food items; and wherein changes in the spectral distribution of the light caused by interaction with food items are used to help identify food item types and/or compositions; a fiducial component which displays objects in images of food items which help to calibrate the distance, size, shape, color, and/or brightness of the food items; and one or more other components selected from the group consisting of: data processor; data transmitter; data receiver; battery; GPS module; clock; calendar; voice recognition interface; touch-screen interface; gesture recognition interface; and EEG interface.

In an example, the camera can be part of a smart phone. In an example, the camera can be part of a smart watch or other wrist-worn device. In an example, the camera can be part of a smart finger ring. In an example, the camera can be part of augmented reality eyewear or other smart eyewear. In an example, the camera can be part of a smart necklace or pendant. In an example, the camera can be part of a dedicated handheld food identification device. In an example, the spectroscopic sensor can be part of a smart watch or other wrist-worn device. In an example, the spectroscopic sensor can be part of a dedicated handheld food identification device. In an example, the fiducial component can be a light emitter which projects a light pattern with known size, shape, and/or colors on or near the food items. In an example, the fiducial component can be a mobile device with a screen which is placed near the food items and displays an image on the screen with known size, shape, and/or colors.

In an example, a system for nutritional monitoring and management can comprise: a handheld device; a camera in the handheld device which captures images of a meal with multiple types of food; wherein meal images are analyzed to identify different types of food in the meal based on variation and boundaries in food shapes, sizes, colors, and textures; and a spectroscopic sensor in the handheld device which emits light beams toward food and receives the light beams after the light beams have been reflected from (or passed through) the food; wherein a person is prompted by a virtual pointer in augmented reality to direct light beams toward different locations on the meal which are associated with different types of food identified by analysis of the meal images; wherein food images and changes in the spectra of the light beams caused by reflection from (or passage through) different types of food are analyzed together (in a multivariate manner) in order to identify food type, food composition (e.g. nutritional composition), and/or food quantity for each type of food in the meal.

In another example, a system for nutritional monitoring and management can comprise: a handheld device; a camera in the handheld device which captures images of food; a spectroscopic sensor in the handheld device which emits light beams toward the food and receives the light beams after the light beams have been reflected from (or passed through) the food; wherein the visible portion of the spectrum of light beams emitted from the spectroscopic sensor creates a visible light pattern on (or near) the food and wherein the size, shape, and/or keystone distortion of this visible light pattern is used as a fiducial marker to estimate food size, distance, and/or orientation relative to the device; and wherein changes in the spectra of light beams caused by reflection from (or passage through) the food and food images captured by the camera are analyzed to identify food type, composition (e.g. nutritional composition), and/or quantity.

In an example, a system for nutritional monitoring and management can comprise: a handheld device; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition, and/or quantity; and wherein one or more eating-related objects (e.g. bowl, chopsticks, cup, fork, glass, knife, mug, napkin, placemat, plate, or spoon) are identified in food images to help estimate food size. Alternatively, a system can comprise: a handheld device; a camera in the handheld device which captures images of food at a first time and at a second time; a spectroscopic sensor in the handheld device which emits light beams toward food and receives the light beams after the light beams have been reflected from (or passed through) food at the first time and at the second time; and a motion sensor which tracks hand-to-mouth motions, chewing motions, and/or swallowing motions; wherein food images captured by the camera, changes in the spectra of the light beams caused by reflection from (or passage through) food, and hand-to-mouth motions, chewing motions, or swallowing motions are analyzed together (e.g. in multivariate analysis) to identify the type, composition (e.g. nutritional composition), and/or quantity of food eaten by the person holding or wearing the device.

In an example, a system for nutritional monitoring and management can comprise: a handheld device; a camera in the handheld device which captures images of food, wherein the food images are automatically analyzed to identify food type and/or measure food quantity; and a spectroscopic sensor in the handheld device which emits light beams toward food and receives the light beams after the light beams have been reflected from (or passed through) food, wherein changes in the spectra of the light beams caused by reflection from (or passage through) food are analyzed to identify food type and/or composition; and where the device prompts a person with a sound, vibration, or light to use the camera and/or the spectroscopic sensor at multiple times while the person is eating a meal in order to measure changes in the amount of food remaining (and infer how much food the person has actually consumed) and to measure the composition of different layers (or parts) of the food. Alternatively, a system can comprise: a handheld device; a spectroscopic sensor in the handheld device which emits light beams toward food and receives the light beams after the light beams have been reflected from (or passed through) the food; a camera in the handheld device which captures images of the food; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity. In an example, the spectroscopic sensor can comprise a light emitter which emits light beams toward food and a light receiver which receives the light beams after the light beams have been reflected from (or passed through) the food.

In an example, a system for nutritional monitoring and management can comprise: a handheld device; a spectroscopic sensor in the handheld device which emits light beams toward food and receives the light beams after the light beams have been reflected from (or passed through) food; a camera in the handheld device which captures images of the food; a first laser which projects a first coherent light beam toward the food; and a second laser which projects a second coherent light beam toward the food; wherein the first and second light beams form a projected light pattern on (or near) the food which serves as a fiducial marker to help estimate food size, distance, and/or orientation; and wherein changes in the spectra of light beams caused by reflection from (or passage through) the food and food images captured by the camera are analyzed to identify food type, composition, and/or quantity. In another example, a system can comprise: a handheld device; a spectroscopic sensor in the handheld device which emits light beams toward food and receives the light beams after the light beams have been reflected from (or passed through) food; a camera in the handheld device which captures images of the food; and a laser which projects an arcuate (e.g. circular, elliptical, or egg-shaped) pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity.

In an example, a system for nutritional monitoring and management can comprise: a handheld device; a spectroscopic sensor in the handheld device which emits light beams toward food and receives the light beams after the light beams have been reflected from (or passed through) food; a camera in the handheld device which captures images of the food; and a laser which projects an quadrilateral grid of light on (or near) the food, wherein the grid serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity. Alternatively, a system can comprise: a handheld device; a spectroscopic sensor in the handheld device which emits light beams toward food and receives the light beams after the light beams have been reflected from (or passed through) food; a camera in the handheld device which captures images of the food; and a light pattern projector which projects a polygonal light pattern onto the food and/or a surface near the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition, and/or quantity.

In an example, a system for nutritional monitoring and management can comprise: a handheld device; a spectroscopic sensor in the handheld device which emits light beams toward food and receives the light beams after the light beams have been reflected from (or passed through) food; a camera in the handheld device which captures images of the food; and a scanning (e.g. moving) laser which projects an arcuate (e.g. circular, elliptical, or egg-shaped) pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity. Alternatively, a system can comprise: a handheld device; a spectroscopic sensor in the handheld device which emits light beams toward food and receives the light beams after the light beams have been reflected from (or passed through) food; a camera in the handheld device which captures images of the food; and one or more lasers which project a pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity.

In an example, a system for nutritional monitoring and management can comprise: a handheld device; a spectroscopic sensor in the handheld device which emits light beams toward food and receives the light beams after the light beams have been reflected from (or passed through) the food; a camera in the handheld device which captures images of the food; wherein the food images and changes in the spectra of the light beams caused by reflection from (or passage through) the food are analyzed together (in a multivariate manner) in order to identify the food's type and/or measure the food's composition; wherein the food images are analyzed to measure food quantity; and a motion sensor; wherein the handheld device is waived over the food so that the spectroscopic sensor reflects beams from the food at multiple locations and the camera creates images of the food from multiple perspectives. In another example, a system can comprise: a handheld device; a spectroscopic sensor in the handheld device which emits light beams toward food and receives the light beams after the light beams have been reflected from the food; a camera in the handheld device which captures images of the food; wherein the food images and changes in the spectra of the light beams caused by reflection from the food are analyzed together (in a multivariate manner) in order to identify the food's type and/or measure the food's composition; wherein the food images are analyzed to measure food quantity; a range finder (e.g. an infrared range finder) which measures the distance from the handheld device to the food; and wherein the spectroscopic sensor is automatically triggered at a selected distance from the food to direct and receive reflected light beams.

In an example, a system for nutritional monitoring and management can comprise: a handheld device; a spectroscopic sensor in the handheld device which emits light beams toward food and receives the light beams after the light beams have been reflected from (or passed through) the food; a camera in the handheld device which captures images of the food; wherein the food images and changes in the spectra of the light beams caused by reflection from (or passage through) the food are analyzed together using multivariate statistical methods in order to identify the food's type and/or measure the food's composition; and wherein the food images are analyzed to measure food quantity. Alternatively, a system can comprise: a handheld device; a camera in the handheld device which captures images of food, wherein the food images are automatically analyzed to identify food type and/or measure food quantity; and a spectroscopic sensor in the handheld device which emits light beams toward food and receives the light beams after the light beams have been reflected from (or passed through) food, wherein changes in the spectra of the light beams caused by reflection from (or passage through) food are analyzed to identify food type and/or composition; a wearable device; a sound sensor in the wearable device which tracks chewing or swallowing sounds; wherein the device prompts a person with a sound, vibration, or light to use the camera and/or the spectroscopic sensor based on chewing or swallowing sounds.

A system can be embodied in: a handheld device; a camera in the handheld device which captures images of a meal with multiple types of food; wherein meal images are analyzed to identify different types of food in the meal based on variation and boundaries in food shapes, sizes, colors, and textures; and a spectroscopic sensor in the handheld device which emits light beams toward food and receives the light beams after the light beams have been reflected from (or passed through) the food; wherein a person is prompted by a projected light pointer to direct light beams toward different locations on the meal which are associated with different types of food based on analysis of the meal images; wherein food images and changes in the spectra of the light beams caused by reflection from (or passage through) different types of food are analyzed together (in a multivariate manner) in order to identify, for each type of food in the meal, food type, food composition, and/or food quantity. Alternatively, a system can comprise: a handheld device; a camera in the handheld device which captures images of food; a spectroscopic sensor in the handheld device which emits light beams toward food and receives the light beams after the light beams have been reflected from (or passed through) food; wherein the camera and spectroscopic sensor are both directed toward a first food in a meal at a first point in time; wherein the camera and spectroscopic sensor are both directed toward a second food in a meal at a second point in time; wherein food images captured by the camera and changes in the spectra of the light beams caused by reflection from (or passage through) food are analyzed to identify the compositions and quantities of the first and second foods.

In an example, a system for nutritional monitoring and management can comprise: a handheld device; a camera in the handheld device which captures images of food; a spectroscopic sensor in the handheld device which emits light beams toward the food and receives the light beams after the light beams have been reflected from (or passed through) the food; wherein a light pattern formed by the projection of light beams from the spectroscopic sensor on (or near) the food is used as a fiducial marker to estimate food size, distance, and/or orientation relative to the device; and wherein changes in the spectra of light beams caused by reflection from (or passage through) the food and food images captured by the camera are analyzed to identify food type, composition (e.g. nutritional composition), and/or quantity. In another example, a system can comprise: a handheld device; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein one or more eating-related objects (e.g. bowl, chopsticks, cup, fork, glass, knife, mug, napkin, placemat, plate, or spoon) are identified in food images to estimate food distance.

In an example, a system for nutritional monitoring and management can comprise: a handheld device; a camera in the handheld device which captures images of food at a first time and at a second time; a spectroscopic sensor in the handheld device which emits light beams toward food and receives the light beams after the light beams have been reflected from (or passed through) food at the first time and at the second time; and a motion sensor which tracks hand-to-mouth motions, chewing motions, and/or swallowing motions; wherein data from the camera, the spectroscopic sensor, and the motion sensor are analyzed together (e.g. in multivariate analysis) to identify the type, composition, and/or quantity of food eaten by the person holding or wearing the device. Alternatively, a system can comprise: a handheld device; a camera in the handheld device which captures images of food, wherein the food images are automatically analyzed to identify food type and/or measure food quantity; and a spectroscopic sensor in the handheld device which emits light beams toward food and receives the light beams after the light beams have been reflected from (or passed through) food, wherein changes in the spectra of the light beams caused by reflection from (or passage through) food are analyzed to identify food type and/or composition; and where the device prompts a person to use the camera and/or the spectroscopic sensor at regular intervals while the person is eating a meal in order to measure changes in the amount of food remaining (and infer how much food the person has actually consumed) and to measure the composition of different layers (or parts) of the food.

In an example, a system for nutritional monitoring and management can comprise: a handheld device; a camera in the handheld device which captures images of food, wherein the food images are automatically analyzed to identify food type and/or measure food quantity; and a spectroscopic sensor in the handheld device which emits light beams toward food and receives the light beams after the light beams have been reflected from (or passed through) food, wherein changes in the spectra of the light beams caused by reflection from (or passage through) food are analyzed to identify food type and/or composition; a wearable motion sensor which tracks hand-to-mouth or chewing motions; and where the device prompts a person with a sound, vibration, or light to use the camera and/or the spectroscopic sensor at multiple times based on the number or timing of hand-to-mouth or chewing motions in order to measure changes in the amount of food remaining (and infer how much food the person has actually consumed) and to measure the composition of different layers (or parts) of the food. Alternatively, a system can comprise: a handheld device; a motion sensor in the handheld device; a spectroscopic sensor in the handheld device which is triggered to emit light beams toward food and receives the light beams after the light beams have been reflected from (or passed through) the food from multiple selected locations in three-dimensional space based in part on data from the motion sensor; a camera in the handheld device which is triggered to capture images of the food from multiple selected locations in three-dimensional space based in part on data from the motion sensor; wherein the food images and changes in the spectra of the light beams caused by reflection from (or passage through) the food are analyzed together (in a multivariate manner) in order to identify the food's type and/or the food's composition; and wherein food images from different perspectives are used to model the food in three dimensions in order to measure food quantity.

In an example, a system for nutritional monitoring and management can comprise: a handheld device; a spectroscopic sensor in the handheld device which emits light beams toward food and receives the light beams after the light beams have been reflected from (or passed through) food; a camera in the handheld device which captures images of the food; a first laser which projects a first coherent light beam toward the food; a second laser which projects a second coherent light beam toward the food; wherein the distance between the locations of incidence of the first and second light beams on (or near) the food is used to estimate food size, distance, and/or orientation relative to the device; and wherein changes in the spectra of light beams caused by reflection from (or passage through) the food and food images captured by the camera are analyzed to identify food type, composition, and/or quantity.

In another example, a system for nutritional monitoring and management can comprise: a handheld device; a spectroscopic sensor in the handheld device which emits light beams toward food and receives the light beams after the light beams have been reflected from (or passed through) food; a camera in the handheld device which captures images of the food; and a laser which projects an array of nested rings of light (or near) the food, wherein the array serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity.

In an example, a system for nutritional monitoring and management can comprise: a handheld device; a spectroscopic sensor in the handheld device which emits light beams toward food and receives the light beams after the light beams have been reflected from (or passed through) food; a camera in the handheld device which captures images of the food; and a laser which projects an quadrilateral grid of light on (or near) the food, wherein the size and/or keystone distortion of the (quadrilateral elements in the) grid serves as a fiducial marker to help estimate food size, distance, and/or orientation; and wherein changes in the spectra of light beams caused by reflection from (or passage through) the food and food images captured by the camera are analyzed to identify food type, composition, and/or quantity. Alternatively, a system can comprise: a handheld device; a spectroscopic sensor in the handheld device which emits light beams toward food and receives the light beams after the light beams have been reflected from (or passed through) food; a camera in the handheld device which captures images of the food; and a light pattern projector which projects an arcuate (e.g. circular or keystone-distorted circular) light pattern onto the food and/or a surface near the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity.

In an example, a system for nutritional monitoring and management can comprise: a handheld device; a spectroscopic sensor in the handheld device which emits light beams toward food and receives the light beams after the light beams have been reflected from (or passed through) food; a camera in the handheld device which captures images of the food; and a scanning (e.g. moving) laser which projects an matrix (e.g. dot matrix or linear grid) pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity. Alternatively, a system can comprise: a handheld device; a spectroscopic sensor in the handheld device which emits light beams toward food and receives the light beams after the light beams have been reflected from (or passed through) the food, wherein changes in the spectra of the light beams caused by reflection from (or passage through) the food are analyzed in order to identify the food's type and/or measure the food's composition; a camera in the handheld device which captures images of the food, wherein the food images are analyzed to measure food quantity.

A system can be embodied in: a handheld device; a spectroscopic sensor in the handheld device which emits light beams toward food and receives the light beams after the light beams have been reflected from the food; a camera in the handheld device which captures images of the food; wherein the food images and changes in the spectra of the light beams caused by reflection from the food are analyzed together (in a multivariate manner) in order to identify the food's type and/or measure the food's composition; wherein the food images are analyzed to measure food quantity; a range finder (e.g. an infrared range finder) which measures the distance from the handheld device to the food; and wherein the camera is automatically triggered at a selected distance from the food to capture images of the food. In another example, a system can comprise: a handheld device; a spectroscopic sensor in the handheld device which emits light beams toward food and receives the light beams after the light beams have been reflected from (or passed through) the food; two cameras in the handheld device which create stereoscopic images of the food; wherein the shape, size, color, tone, brightness, and/or texture of food in the food images and changes in the spectra of the light beams caused by reflection from (or passage through) the food are analyzed together (in a multivariate manner) in order to identify the food's type and/or the food's composition; and wherein the stereoscopic food images are analyzed in order to measure food quantity.

In an example, a system for nutritional monitoring and management can comprise: a handheld device; a camera in the handheld device which captures images of food; a spectroscopic sensor in the handheld device which emits light beams toward food and receives the light beams after the light beams have been reflected from (or passed through) food; wherein the person directs the camera and the spectroscopic sensor toward a first food in a meal at a first point in time; wherein the person directs the camera and the spectroscopic sensor toward a second food in a meal at a second point in time; wherein food images captured by the camera and changes in the spectra of the light beams caused by reflection from (or passage through) food are analyzed to identify the compositions and quantities of the first and second foods. Alternatively, a system can comprise: a handheld device; a camera in the handheld device which captures images of food; a spectroscopic sensor in the handheld device which emits light beams toward food and receives the light beams after the light beams have been reflected from (or passed through) food; and a motion sensor which tracks hand-to-mouth motions, chewing motions, and/or swallowing motions; wherein data from the camera, the spectroscopic sensor, and the motion sensor are analyzed together (e.g. in multivariate analysis) to identify the type, composition (e.g. nutritional composition), and/or quantity of food eaten by the person holding or wearing the device.

In an example, a system for nutritional monitoring and management can comprise: a handheld device; a camera in the handheld device which captures images of food; a spectroscopic sensor in the handheld device which emits light beams toward the food and receives the light beams after the light beams have been reflected from (or passed through) the food; wherein light beams emitted from the spectroscopic sensor create a projected light pattern on (or near) the food and wherein the size, shape, and/or keystone distortion of this projected light pattern is used to estimate food size, distance, and/or orientation relative to the device; and wherein changes in the spectra of light beams caused by reflection from (or passage through) the food and food images captured by the camera are analyzed to identify food type, composition, and/or quantity. Alternatively, a system can comprise: a handheld device; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein one or more eating-related objects (e.g. bowl, chopsticks, cup, fork, glass, knife, mug, napkin, placemat, plate, or spoon) are used to help estimate food size.

In an example, a system for nutritional monitoring and management can comprise: a handheld device; a camera in the handheld device which captures images of food at a first time and at a second time; and a spectroscopic sensor in the handheld device which emits light beams toward food and receives the light beams after the light beams have been reflected from (or passed through) food at the first time and at the second time; wherein food images captured by the camera and changes in the spectra of the light beams caused by reflection from (or passage through) food are analyzed together (e.g. in multivariate analysis) to identify the type, composition (e.g. nutritional composition), and/or quantity of food eaten by the person holding or wearing the device. In another example, a system can comprise: a handheld device; a camera in the handheld device which captures images of food, wherein the food images are automatically analyzed to identify food type and/or measure food quantity; and a spectroscopic sensor in the handheld device which emits light beams toward food and receives the light beams after the light beams have been reflected from (or passed through) food, wherein changes in the spectra of the light beams caused by reflection from (or passage through) food are analyzed to identify food type and/or composition; a wearable motion sensor which tracks hand-to-mouth or chewing motions; and where the device prompts a person with a sound, vibration, or light to use the camera and/or the spectroscopic sensor based on hand-to-mouth or chewing motions.

In an example, a system for nutritional monitoring and management can comprise: a handheld device; a motion sensor in the handheld device; a spectroscopic sensor in the handheld device which is triggered to emit light beams toward food and receives the light beams after the light beams have been reflected from (or passed through) the food from multiple selected locations in three-dimensional space based in part on data from the motion sensor; a camera in the handheld device which is triggered to capture images of the food from multiple selected locations in three-dimensional space based in part on data from the motion sensor; wherein the food images and changes in the spectra of the light beams caused by reflection from (or passage through) the food are analyzed together (in a multivariate manner) in order to identify the food's type and/or the food's composition; and wherein food images from different perspectives are used to measure food quantity. Alternatively, a system can comprise: a handheld device; a range finder (e.g. a range finder (e.g. an infrared range finder)) in the handheld device which measures the distance from the handheld device to food; a motion sensor (e.g. an accelerometer and a gyroscope) in the handheld device; a spectroscopic sensor in the handheld device which is triggered to emit light beams toward food and receives the light beams after the light beams have been reflected from (or passed through) the food from multiple selected locations in three-dimensional space based in part on data from the range finder and the motion sensor; a camera in the handheld device which is triggered to capture images of the food from multiple selected locations in three-dimensional space based in part on data from the range finder and the motion sensor; wherein the food images and changes in the spectra of the light beams caused by reflection from (or passage through) the food are analyzed together (in a multivariate manner) in order to identify the food's type and/or the food's composition; and wherein food images are used to measure food quantity.

In an example, a system for nutritional monitoring and management can comprise: a handheld device; a spectroscopic sensor in the handheld device which emits light beams toward food and receives the light beams after the light beams have been reflected from (or passed through) the food; a camera in the handheld device which captures images of the food from different perspectives and angles as the handheld device is moved; wherein the shape, size, color, tone, brightness, and/or texture of food in the food images and changes in the spectra of the light beams caused by reflection from (or passage through) the food are analyzed together (in a multivariate manner) in order to identify the food's type and/or the food's composition; and wherein food images from different perspectives and angles are used to model the food in three dimensions in order to measure food quantity. Alternatively, a system can comprise: a handheld device; a spectroscopic sensor in the handheld device which emits light beams toward food and receives the light beams after the light beams have been reflected from (or passed through) food; a camera in the handheld device which captures images of the food; a first laser which projects a first coherent light beam toward the food; a second laser which projects a second coherent light beam toward the food; a third laser which projects a third coherent light beam toward the food; wherein the distances and angles between the locations of incidence of the first, second, and third light beams on (or near) the food are used to estimate food size, distance, and/or orientation; and wherein changes in the spectra of light beams caused by reflection from (or passage through) the food and food images captured by the camera are analyzed to identify food type, composition, and/or quantity.

In an example, a system for nutritional monitoring and management can comprise: a handheld device; a spectroscopic sensor in the handheld device which emits light beams toward food and receives the light beams after the light beams have been reflected from (or passed through) food; a camera in the handheld device which captures images of the food; and a laser which projects an array of nested rings of light (or near) the food, wherein the size and distortion of rings in the array is used to help estimate food size, distance, and/or orientation; and wherein changes in the spectra of light beams caused by reflection from (or passage through) the food and food images captured by the camera are analyzed to identify food type, composition (e.g. nutritional composition), and/or quantity. In another example, a system can comprise: a handheld device; a spectroscopic sensor in the handheld device which emits light beams toward food and receives the light beams after the light beams have been reflected from (or passed through) food; a camera in the handheld device which captures images of the food; and a light pattern projector which projects a pattern of light on (or near) the food; and wherein changes in the spectra of light beams caused by reflection from (or passage through) the food and food images captured by the camera are analyzed to identify food type, composition (e.g. nutritional composition), and/or quantity.

In an example, a system for nutritional monitoring and management can comprise: a handheld device; a spectroscopic sensor in the handheld device which emits light beams toward food and receives the light beams after the light beams have been reflected from (or passed through) food; a camera in the handheld device which captures images of the food; and a scanning (e.g. moving) laser which projects a pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition, and/or quantity. Alternatively, a system can comprise: a handheld device; a spectroscopic sensor in the handheld device which emits light beams toward food and receives the light beams after the light beams have been reflected from (or passed through) food; a camera in the handheld device which captures images of the food; and a scanning laser which projects an arcuate (e.g. circular) light pattern toward the food; wherein the shape, size, and/or keystone distortion of the projected light pattern on (or near) the food is used to estimate food size, distance, and/or orientation relative to the device; and wherein changes in the spectra of light beams caused by reflection from (or passage through) the food and food images captured by the camera are analyzed to identify food type, composition (e.g. nutritional composition), and/or quantity.

A system can be embodied in: a handheld device; a spectroscopic sensor in the handheld device which emits light beams toward food and receives the light beams after the light beams have been reflected from (or passed through) the food; a camera in the handheld device which captures images of the food; wherein the field of view of the camera overlaps the projection path of light beams from the spectroscopic sensor; area wherein the food images and changes in the spectra of the light beams caused by reflection from (or passage through) the food are analyzed together (in a multivariate manner) in order to identify the food's type and/or measure the food's composition; and wherein the food images are analyzed to measure food quantity. Alternatively, a system can comprise: a handheld device; a spectroscopic sensor in the handheld device which emits light beams toward food and receives the light beams after the light beams have been reflected from the food; a camera in the handheld device which captures images of the food; wherein the food images and changes in the spectra of the light beams caused by reflection from the food are analyzed together (in a multivariate manner) in order to identify the food's type and/or measure the food's composition; wherein the food images are analyzed to measure food quantity; a range finder which measures the distance from the handheld device to the food; and wherein the spectroscopic sensor and/or the camera is automatically triggered at a selected distance from the food.

In an example, a system for nutritional monitoring and management can comprise: a handheld device; a spectroscopic sensor in the handheld device which emits light beams toward food and receives the light beams after the light beams have been reflected from (or passed through) the food; two cameras in the handheld device which create stereoscopic images of the food; wherein the food images and changes in the spectra of the light beams caused by reflection from (or passed through) the food are analyzed together (in a multivariate manner) in order to identify the food's type and/or the food's composition; and wherein the stereoscopic food images are analyzed in order to measure food quantity.

In another example, a system for nutritional monitoring and management can comprise: a handheld device; a spectroscopic sensor in the handheld device, wherein the spectroscopic sensor further comprises a light emitter which emits light beams toward food and a light receiver which receives the light beams after the light beams have been reflected from (or passed through) the food; a camera in the handheld device which captures images of the food; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity.

In an example, a system for nutritional monitoring and management can comprise: a handheld device; a camera in the handheld device which captures images of a meal with multiple types of food; wherein meal images are analyzed to identify different types of food in the meal based on variation and boundaries in food shapes, sizes, colors, and textures; and a spectroscopic sensor in the handheld device which emits light beams toward food and receives the light beams after the light beams have been reflected from (or passed through) the food; wherein a person is prompted (e.g. via sound, vibration, or light) to direct light beams toward different locations on the meal which are associated with different types of food based on analysis of the meal images; wherein food images and changes in the spectra of the light beams caused by reflection from (or passage through) different types of food are analyzed together (in a multivariate manner) in order to identify, for each type of food in the meal, food type, food composition (e.g. nutritional composition), and/or food quantity. Alternatively, a system can comprise: a handheld device; a camera in the handheld device which captures images of food; a spectroscopic sensor in the handheld device which emits light beams toward food and receives the light beams after the light beams have been reflected from (or passed through) food; a laser pointer; wherein the person uses the laser pointer to direct the camera and the spectroscopic sensor toward a first food in a meal at a first point in time; wherein the person uses the laser pointer to direct the camera and the spectroscopic sensor toward a second food in a meal at a second point in time; wherein food images captured by the camera and changes in the spectra of the light beams caused by reflection from (or passage through) food are analyzed to identify the compositions and quantities of the first and second foods.

In an example, a system for nutritional monitoring and management can comprise: a handheld device; a camera in the handheld device which captures images of food; a spectroscopic sensor in the handheld device which emits light beams toward the food and receives the light beams after the light beams have been reflected from (or passed through) the food; wherein part of the spectrum of light beams emitted from the spectroscopic sensor create a light pattern on (or near) the food which is used as a fiducial marker to estimate food size, distance, and/or orientation relative to the device; and wherein changes in the spectra of light beams caused by reflection from (or passage through) the food and food images captured by the camera are analyzed to identify food type, composition, and/or quantity. Alternatively, a system can comprise: a handheld device; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein one or more eating-related objects (e.g. bowl, chopsticks, cup, fork, glass, knife, mug, napkin, placemat, plate, or spoon) are identified in food images to help estimate food size, distance, and/or orientation.

In an example, a system for nutritional monitoring and management can comprise: a handheld device; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein one or more eating-related objects (e.g. bowl, chopsticks, cup, fork, glass, knife, mug, napkin, placemat, plate, or spoon) are used to estimate food distance. In another example, a system can comprise: a handheld device; a camera in the handheld device which captures images of food at a first time and at a second time, wherein the first time is before a person eats the food and the second time is after the person has finished eating some or all of the food; a spectroscopic sensor in the handheld device which emits light beams toward food and receives the light beams after the light beams have been reflected from (or passed through) food at the first time and at the second time; wherein food images captured by the camera and changes in the spectra of the light beams caused by reflection from (or passage through) food are analyzed together (e.g. in multivariate analysis) to identify the type, composition, and/or quantity of food eaten by the person holding or wearing the device.

A system can be embodied in: a handheld device; a spectroscopic sensor in the handheld device which emits light beams toward food and receives the light beams after the light beams have been reflected from (or passed through) the food; a camera in the handheld device which captures images of the food from different perspectives and angles as the handheld device is moved; wherein the food images and changes in the spectra of the light beams caused by reflection from (or passage through) the food are analyzed together (in a multivariate manner) in order to identify the food's type and/or the food's composition; and wherein food images from different perspectives and angles are used to model the food in three dimensions in order to measure food quantity. Alternatively, a system can comprise: a handheld device; a spectroscopic sensor in the handheld device which emits light beams toward food and receives the light beams after the light beams have been reflected from (or passed through) food; a camera in the handheld device which captures images of the food; and a laser which projects a target (e.g. cross-hairs) light pattern onto the food and/or a surface near the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity.

In an example, a system for nutritional monitoring and management can comprise: a handheld device; a spectroscopic sensor in the handheld device which emits light beams toward food and receives the light beams after the light beams have been reflected from (or passed through) food; a camera in the handheld device which captures images of the food; and a laser which projects an matrix (e.g. dot matrix or linear grid) pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity. Alternatively, a system can comprise: a handheld device; a spectroscopic sensor in the handheld device which emits light beams toward food and receives the light beams after the light beams have been reflected from (or passed through) food; a camera in the handheld device which captures images of the food; and a light pattern projector which projects a pattern of light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity.

A system can be embodied in: a handheld device; a spectroscopic sensor in the handheld device which emits light beams toward food and receives the light beams after the light beams have been reflected from (or passed through) food; a camera in the handheld device which captures images of the food; and a scanning (e.g. moving) laser which projects a polygonal light pattern onto the food and/or a surface near the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity. In another example, a system can comprise: a handheld device; a spectroscopic sensor in the handheld device which emits light beams toward food and receives the light beams after the light beams have been reflected from (or passed through) food; a camera in the handheld device which captures images of the food; and a scanning laser which projects an arcuate (e.g. circular) light pattern toward the food; wherein size of the projected light pattern on (or near) the food is used to estimate food distance; wherein keystone distortion of the projected light pattern on (or near) the food is used to estimate the orientation of the food relative to the device; and wherein changes in the spectra of light beams caused by reflection from (or passage through) the food and food images captured by the camera are analyzed to identify food type, composition, and/or quantity.

In an example, a system for nutritional monitoring and management can comprise: a handheld device; a spectroscopic sensor in the handheld device which emits light beams toward food and receives the light beams after the light beams have been reflected from (or passed through) the food; a camera in the handheld device which captures images of the food; a motion sensor; wherein the handheld device is waived over the food so that the spectroscopic sensor reflects beams from the food at multiple locations and the camera creates images of the food from multiple perspectives; wherein changes in the spectra of the light beams caused by reflection from (or passage through) the food, the food images, and movement of the handheld device are analyzed together (in a multivariate manner) in order to identify food type, measure food composition (e.g. nutritional composition), and/or measure food quantity. Alternatively, a system can comprise: a handheld device; a spectroscopic sensor in the handheld device which emits light beams toward food and receives the light beams after the light beams have been reflected from (or passed through) the food; a camera in the handheld device which captures images of the food; wherein the food images and changes in the spectra of the light beams caused by reflection from (or passage through) the food are analyzed together using a neural network in order to identify the food's type and/or measure the food's composition; and wherein the food images are analyzed to measure food quantity.

In an example, a system for nutritional monitoring and management can comprise: a handheld device; a spectroscopic sensor in the handheld device which emits light beams toward food and receives the light beams after the light beams have been reflected from (or passed through) the food; a camera in the handheld device which captures images of the food; wherein the field of view of the camera encompasses the entire projection path of light beams from the spectroscopic sensor; area wherein the food images and changes in the spectra of the light beams caused by reflection from (or passage through) the food are analyzed together (in a multivariate manner) in order to identify the food's type and/or measure the food's composition; and wherein the food images are analyzed to measure food quantity. Alternatively, a system can comprise: a handheld device; a spectroscopic sensor in the handheld device which emits light beams toward food and receives the light beams after the light beams have been reflected from the food; a camera in the handheld device which captures images of the food; wherein the food images and changes in the spectra of the light beams caused by reflection from the food are analyzed together (in a multivariate manner) in order to identify the food's type and/or measure the food's composition; wherein the food images are analyzed to measure food quantity; a range finder which measures the distance from the handheld device to the food; and wherein the spectroscopic sensor and camera are both automatically triggered at the same selected distance from the food.

In an example, a system for nutritional monitoring and management can comprise: a handheld device; a spectroscopic sensor in the handheld device which emits light beams toward food and receives the light beams after the light beams have been reflected from (or passed through) the food; a camera in the handheld device which captures images of the food; wherein the shape, size, color, tone, brightness, and/or texture of food in the food images and the changes in the spectra of the light beams caused by reflection from (or passage through) the food are analyzed together (in a multivariate manner) in order to identify the food's type and/or measure the food's composition; and wherein the food images are analyzed to measure food quantity. In another example, a system can comprise: a handheld device; a camera in the handheld device which captures images of food, wherein the food images are automatically analyzed to identify food type and/or measure food quantity; and a spectroscopic sensor in the handheld device which emits light beams toward food and receives the light beams after the light beams have been reflected from (or passed through) food, wherein changes in the spectra of the light beams caused by reflection from (or passage through) food are analyzed to identify food type and/or composition; a wearable device; a sound sensor in the wearable device which tracks chewing or swallowing sounds; wherein the device prompts a person with a sound, vibration, or light to use the camera and/or the spectroscopic sensor based on the number or timing of chewing or swallowing sounds in order to measure changes in the amount of food remaining (and infer how much food the person has actually consumed) and to measure the composition of different layers (or parts) of the food.

In an example, a system for nutritional monitoring and management can comprise: a handheld device which is held by a person; a camera in the handheld device which captures images of food; a spectroscopic sensor in the handheld device which emits light beams toward food and receives the light beams after the light beams have been reflected from (or passed through) food; a necklace which is worn by the person; and a sound sensor in the necklace which tracks chewing or swallowing sounds; wherein data from the camera, the spectroscopic sensor, and the sound sensor are analyzed together (e.g. in multivariate analysis) to identify the type, composition (e.g. nutritional composition), and/or quantity of food eaten by the person holding or wearing the device. Alternatively, a system can comprise: a handheld device which is held by a person; a camera in the wearable device which captures images of food; a spectroscopic sensor in the wearable device which emits light beams toward food and receives the light beams after the light beams have been reflected from (or passed through) food; a wearable device which is worn by the person; and a motion sensor in the wearable device which tracks hand-to-mouth motions, chewing motions, and/or swallowing motions; wherein data from the camera, the spectroscopic sensor, and the motion sensor are analyzed together (e.g. in multivariate analysis) to identify the type, composition, and/or quantity of food eaten by the person holding or wearing the device.

In an example, a system for nutritional monitoring and management can comprise: a handheld device which is waived back and forth several times over a multi-food meal; a spectroscopic sensor in the handheld device which emits light beams toward the meal and receives the light beams after the light beams have been reflected from (or passed through) a plurality of locations on the meal as the device is waived back and forth; a camera in the handheld device which captures images of a plurality of locations on the meal as the device is waived back and forth; and a motion sensor; wherein data from the spectroscopic sensor, the camera, and the motion sensor are analyzed together (in a multivariate manner) in order to identify the types, compositions, and/or quantities of foods in the multi-food meal. In another example, a system can comprise: a handheld device which is waived back and forth several times over a multi-food meal; a spectroscopic sensor in the handheld device which emits light beams toward the meal and receives the light beams after the light beams have been reflected from (or passed through) a plurality of locations on the meal as the device is waived back and forth; a camera in the handheld device which captures images of a plurality of locations on the meal as the device is waived back and forth; and a motion sensor; wherein data from the spectroscopic sensor, the camera, and the motion sensor are analyzed to segment the meal into different food portions; and wherein data from the spectroscopic sensor, the camera, and the motion sensor are analyzed to identify the types, compositions, and/or quantities of foods in the different food portions.

A system can be embodied in: a handheld device which is waived back and forth several times over a multi-food meal; a spectroscopic sensor in the handheld device which emits light beams toward the meal and receives the light beams after the light beams have been reflected from (or passed through) a plurality of locations on the meal as the device is waived back and forth; a camera in the handheld device which captures images of a plurality of locations on the meal as the device is waived back and forth; and a motion sensor; wherein variations in food color, tone, brightness, texture, shape, and molecular composition as the device is waived back and forth are analyzed to segment the meal into different food portions; and wherein data from the spectroscopic sensor, the camera, and the motion sensor are analyzed to identify the types, compositions, and/or quantities of foods in the different food portions. Alternatively, a system can comprise: a handheld device which is waived back and forth several times over a multi-food meal; a spectroscopic sensor in the handheld device which emits light beams toward the meal and receives the light beams after the light beams have been reflected from (or passed through) the meal as the device is being waived back and forth; a camera in the handheld device which captures images of the meal as the device is being waived back and forth; and a motion sensor; wherein data from the spectroscopic sensor, the camera, and the motion sensor are analyzed together (in a multivariate manner) in order to identify the types, compositions, and/or quantities of foods in the multi-food meal.

In an example, a system for nutritional monitoring and management can comprise: a handheld device which is waived back and forth several times over food; a spectroscopic sensor in the handheld device which emits light beams toward food and receives the light beams after the light beams have been reflected from (or passed through) the food as the device is being waived back and forth; a camera in the handheld device which captures images of the food as the device is being waived back and forth; and a motion sensor; wherein data from the spectroscopic sensor, the camera, and the motion sensor are analyzed together (in a multivariate manner) in order to identify the food type, composition, and/or quantity. In another example, a system can comprise: a handheld device which is waived in an arc segment of a circle over nearby food; a spectroscopic sensor in the handheld device which emits light beams toward food and receives the light beams after the light beams have been reflected from (or passed through) the food; a camera in the handheld device which captures images of the food; and a motion sensor; wherein data from the spectroscopic sensor, the camera, and the motion sensor are analyzed together (in a multivariate manner) in order to identify the food type, composition (e.g. nutritional composition), and/or quantity.

In an example, a system for nutritional monitoring and management can comprise: a handheld device which is waived over a meal in an arc which is wider than the width of the meal; a spectroscopic sensor in the handheld device which emits light beams toward food and receives the light beams after the light beams have been reflected from (or passed through) the food; a camera in the handheld device which captures images of the food; and a motion sensor; wherein data from the spectroscopic sensor, the camera, and the motion sensor are analyzed together (in a multivariate manner) in order to identify the food type, composition, and/or quantity. Alternatively, a system can comprise: a handheld device which is waived over a meal with multiple types of food; a spectroscopic sensor in the handheld device which emits light beams toward food and receives the light beams after the light beams have been reflected from (or passed through) the food; a camera in the handheld device which captures images of the food in a field of view which overlaps the projection path of light beams from the spectroscopic sensor; and a motion sensor; wherein the handheld device guides a person concerning how to waive or otherwise move the handheld device over the meal with multiple types of food; and wherein data from the spectroscopic sensor, the camera, and the motion sensor are analyzed together (in a multivariate manner) in order to identify the food type, composition (e.g. nutritional composition), and/or quantity.

In an example, a system for nutritional monitoring and management can comprise: a handheld device which is waived over a meal with multiple types of food; a spectroscopic sensor in the handheld device which emits light beams toward food and receives the light beams after the light beams have been reflected from (or passed through) the food; a camera in the handheld device which captures images of the food in a field of view which overlaps the projection path of light beams from the spectroscopic sensor; and a motion sensor; wherein the handheld device projects a light pointer to guide a person concerning how to waive the handheld device over the meal with multiple types of food; and wherein data from the spectroscopic sensor, the camera, and the motion sensor are analyzed together (in a multivariate manner) in order to identify the food type, composition, and/or quantity. Alternatively, a system can comprise: a handheld device which is waived over a meal with multiple types of food; a spectroscopic sensor in the handheld device which emits light beams toward food and receives the light beams after the light beams have been reflected from (or passed through) the food; a camera in the handheld device which captures images of the food in a field of view which overlaps the projection path of light beams from the spectroscopic sensor; and a motion sensor; wherein the handheld device has a screen which displays a virtual pointer in augmented reality to guide a person concerning how to waive or otherwise move the handheld device over the meal with multiple types of food; and wherein data from the spectroscopic sensor, the camera, and the motion sensor are analyzed together (in a multivariate manner) in order to identify the food type, composition (e.g. nutritional composition), and/or quantity.

A system can be embodied in: a handheld device which is waived over a multi-food meal; a spectroscopic sensor in the handheld device which emits light beams toward the meal and receives the light beams after the light beams have been reflected from (or passed through) the meal; and a camera in the handheld device which captures images of the food in a field of view which overlaps the projection path of light beams from the spectroscopic sensor; wherein data from the spectroscopic sensor and the camera are analyzed together (in a multivariate manner) in order to identify the type, composition (e.g. nutritional composition), and/or quantity of each type of food in the meal.

In another example, a system for nutritional monitoring and management can comprise: a handheld device which is waived over a plate of food in an arc which is wider than the plate; a spectroscopic sensor in the handheld device which emits light beams toward food and receives the light beams after the light beams have been reflected from (or passed through) the food; a camera in the handheld device which captures images of the food; and a motion sensor; wherein data from the spectroscopic sensor, the camera, and the motion sensor are analyzed together (in a multivariate manner) in order to identify the food type, composition (e.g. nutritional composition), and/or quantity.

In an example, a system for nutritional monitoring and management can comprise: a handheld device which is waived over a plate of food in an zigzag pattern which is wider than the plate; a spectroscopic sensor in the handheld device which emits light beams toward food and receives the light beams after the light beams have been reflected from (or passed through) the food; a camera in the handheld device which captures images of the food; and a motion sensor; wherein data from the spectroscopic sensor, the camera, and the motion sensor are analyzed together (in a multivariate manner) in order to identify the food type, composition, and/or quantity. Alternatively, a system can comprise: a handheld device which is waived over food; a spectroscopic sensor in the handheld device which emits light beams toward food and receives the light beams after the light beams have been reflected from (or passed through)

the food; a camera in the handheld device which captures images of the food in a field of view which overlaps the projection path of light beams from the spectroscopic sensor; and a motion sensor; wherein the handheld device guides a person concerning how and/or where to waive the handheld device over food; and wherein data from the spectroscopic sensor, the camera, and the motion sensor are analyzed together (in a multivariate manner) in order to identify the food type, composition (e.g. nutritional composition), and/or quantity.

A system can be embodied in: a handheld device which is waived over nearby food; a spectroscopic sensor in the handheld device which emits light beams toward food and receives the light beams after the light beams have been reflected from (or passed through) the food; a camera in the handheld device which captures images of the food; and a motion sensor; wherein data from the spectroscopic sensor, the camera, and the motion sensor are analyzed together (in a multivariate manner) in order to identify the food type, composition (e.g. nutritional composition), and/or quantity. Alternatively, a system can comprise: a handheld device which is waived over nearby food; a spectroscopic sensor in the handheld device which emits light beams toward food and receives the light beams after the light beams have been reflected from (or passed through) the food; and a camera in the handheld device which captures images of the food in a field of view which overlaps the projection path of light beams from the spectroscopic sensor; wherein data from the spectroscopic sensor and the camera are analyzed together (in a multivariate manner) in order to identify the food type, composition (e.g. nutritional composition), and/or quantity.

In an example, a system for nutritional monitoring and management can comprise: a handheld device which is waived over nearby food; a spectroscopic sensor in the handheld device which emits light beams toward food and receives the light beams after the light beams have been reflected from (or passed through) the food; a camera in the handheld device which captures images of the food in a field of view which overlaps the projection path of light beams from the spectroscopic sensor; and a motion sensor; wherein data from the spectroscopic sensor, the camera, and the motion sensor are analyzed together (in a multivariate manner) in order to identify the food type, composition, and/or quantity. In another example, a system can comprise: a handheld device with a longitudinal axis and cross-sectional asymmetry, wherein a proximal portion of the device has a larger cross-section than a distal portion of the device; a spectroscopic sensor in the handheld device which emits light beams from the distal end of the handheld device toward food and receives the light beams after the light beams have been reflected from (or passed through) the food; a camera in the handheld device which captures images of the food from the distal end of the device; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity.

In an example, a system for nutritional monitoring and management can comprise: a handheld device with a proximal side which is configured to face toward a person's head when the device is held and a distal surface which is configured to face away from the person's head when the device is held; a spectroscopic sensor in the handheld device which emits light beams from the distal side of the device toward food and receives the light beams after the light beams have been reflected from (or passed through) the food; a camera in the handheld device which captures images of the food from the distal side of the device; wherein the food images and changes in the spectra of the light beams caused by reflection from (or passage through) the food are analyzed together (in a multivariate manner) in order to identify the food's type and/or measure the food's composition; wherein the food images are analyzed to measure food quantity; and a display screen on the proximal side of the device, wherein the display screen shows augmented reality food images including a virtual pointer, virtual cross hairs, or other virtual guide marks to guide the user concerning where to position the device when using the spectroscopic sensor and/or the camera. Alternatively, a system can comprise: a handheld device with a proximal side which is configured to face toward a person's head when the device is held and a distal surface which is configured to face away from the person's head when the device is held; a spectroscopic sensor in the handheld device which emits light beams from the distal side of the device toward food and receives the light beams after the light beams have been reflected from (or passed through) the food; a camera in the handheld device which captures images of the food from the distal side of the device; wherein the food images and changes in the spectra of the light beams caused by reflection from (or passage through) the food are analyzed together (in a multivariate manner) in order to identify the food's type and/or measure the food's composition; wherein the food images are analyzed to measure food quantity; and a display screen on the proximal side of the device, wherein the display screen shows augmented reality food images including a virtual pointer which sequentially points at different types of food in the multi-food meal to guide the user where and when to position the device for a spectroscopic scan of each type of food in the multi-food meal.

In an example, a system for nutritional monitoring and management can comprise: a handheld device with a proximal surface which is configured to be closer to a person's head when the device is held and a distal surface which is configured to be farther from the person's head when the device is held; a spectroscopic sensor in the handheld device which emits light beams from the distal surface of the device toward food and receives the light beams after the light beams have been reflected from (or passed through) the food; a camera in the handheld device which captures images of the food from the distal surface of the device; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity. In another example, a system can comprise: a handheld device with a proximal surface which is configured to be closer to a person's head when the device is held and a distal surface which is configured to be farther from the person's head when the device is held; a spectroscopic sensor with an aperture on the distal surface of the handheld device which emits light beams toward food and receives the light beams after the light beams have been reflected from (or passed through) the food; a first camera which captures images of the food; wherein the aperture of the first camera is located to one side of the aperture of the spectroscopic sensor; a second camera which captures images of the food; wherein the aperture of the second camera is located to a second side of (e.g. on the opposite side of) the aperture of the spectroscopic sensor; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity.

A system can be embodied in: a handheld device with a proximal surface which is configured to be closer to a person's head when the device is held and a distal surface which is configured to be farther from the person's head when the device is held; a spectroscopic sensor with an aperture on the distal surface of the handheld device which emits light beams toward food and receives the light beams after the light beams have been reflected from (or passed through) the food; a camera with an aperture on the distal surface of the handheld device which captures images of the food; wherein the aperture of the spectroscopic sensor is the co-located with, co-axial with, and/or the same as the aperture of the camera; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity. Alternatively, a system can comprise: a handheld device with a proximal surface which is configured to be closer to a person's head when the device is held and a distal surface which is configured to be farther from the person's head when the device is held; a spectroscopic sensor with an aperture on the distal surface of the handheld device which emits light beams toward food and receives the light beams after the light beams have been reflected from (or passed through) the food; a camera with an aperture on the distal surface of the handheld device which captures images of the food; wherein the aperture of the spectroscopic sensor is between 5 mm and 100 mm away from the aperture of the camera; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity.

In an example, a system for nutritional monitoring and management can comprise: a handheld device with a proximal surface which is configured to be closer to a person's head when the device is held and a distal surface which is configured to be farther from the person's head when the device is held; a spectroscopic sensor on the distal surface in the handheld device which emits light beams toward food and receives the light beams after the light beams have been reflected from (or passed through) the food; a camera on the distal surface of the handheld device which captures images of the food; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity. Alternatively, a system can comprise: a handheld device with a proximal surface which is configured to be closer to a person's head when the device is held and a distal surface which is configured to be farther from the person's head when the device is held; a spectroscopic sensor with an aperture on the distal surface of the handheld device which emits light beams toward food and receives the light beams after the light beams have been reflected from (or passed through) the food; a camera with an aperture on the distal surface of the handheld device which captures images of the food; wherein the aperture of the spectroscopic sensor is between 1 mm and 10 mm away from the aperture of the camera; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity.

In an example, a system for nutritional monitoring and management can comprise: a handheld device worn by a person; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein the camera and/or the spectroscopic sensor is automatically triggered when the device detects that the person is eating. Alternatively, a system can comprise: a handheld device worn by a person; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein the camera and/or the spectroscopic sensor is automatically triggered when the device detects that the person is eating based on movement of the person's jaw, such as bending of the jaw joint.

In an example, a system for nutritional monitoring and management can comprise: a handheld device worn by a person; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein the camera and/or the spectroscopic sensor is automatically triggered when the device detects that the person is eating based on GPS or other location-based indications that a person is in an eating establishment (such as a restaurant) or food source location (such as a kitchen).

In another example, a system for nutritional monitoring and management can comprise: a handheld device worn by a person; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition, and/or quantity; and wherein the camera and/or the spectroscopic sensor is automatically triggered when the device detects that the person is eating based on acceleration, inclination, twisting, or rolling of the person's hand, wrist, or arm.

A system can be embodied in: a handheld device worn by a person; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition, and/or quantity; and wherein the camera and/or the spectroscopic sensor is automatically triggered when the device detects that the person is eating based on smells suggesting food that are detected by an artificial olfactory sensor. Alternatively, a system can comprise: a handheld device worn by a person; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein the camera and/or the spectroscopic sensor is automatically triggered when the device detects that the person is eating based on acceleration or inclination of the person's lower arm or upper arm.

In an example, a system for nutritional monitoring and management can comprise: a handheld device worn by a person; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein the camera and/or the spectroscopic sensor is automatically triggered when the device detects that the person is eating based on detection of chewing, swallowing, or other eating sounds by one or more microphones. In another example, a system can comprise: a handheld device worn by a person; a camera in the handheld device which captures images of food; and a spectroscopic sensor in the handheld device which emits light beams toward food and receives the light beams after the light beams have been reflected from (or passed through) food; and an eating detector selected from the group consisting of—accelerometer, inclinometer, motion sensor, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor; wherein food images captured by the camera and changes in the spectra of the light beams caused by reflection from (or passage through) food are analyzed to identify food type, composition, and/or quantity; and wherein the camera and/or the spectroscopic sensor is automatically triggered when the eating detector detects that the person is eating.

In an example, a system for nutritional monitoring and management can comprise: a handheld device worn by a person; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein the camera and/or the spectroscopic sensor is automatically triggered when the device detects that the person is eating based on bending of the person's shoulder, elbow, wrist, or finger joints. Alternatively, a system can comprise: a handheld device worn by a person; a camera in the handheld device which captures images of food; and a spectroscopic sensor in the handheld device which emits light beams toward food and receives the light beams after the light beams have been reflected from (or passed through) food; wherein food images captured by the camera and changes in the spectra of the light beams caused by reflection from (or passage through) food are analyzed to identify food type, composition, and/or quantity; and wherein the camera and/or the spectroscopic sensor is automatically triggered when the device detects that the person is eating based on electromagnetic waves from the person's stomach, heart, brain, or other organs.

In an example, a system for nutritional monitoring and management can comprise: a handheld food probe; a camera in the probe which captures images of food; and a spectroscopic sensor in the probe which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity. Alternatively, a system can comprise: a handheld food probe which is inserted into food; and a spectroscopic sensor which is part of (and/or in optical communication with) the food probe; wherein a first set of light beams from the spectroscopic sensor are reflected by (or pass through) a first interior portion of the food at a first time and changes in the spectra of the first set of light beams caused by reflection from (or passage through) the first interior portion of the food are analyzed to identify the composition of the first interior portion of the food; and wherein a second set of light beams from the spectroscopic sensor are reflected by (or pass through) a second interior portion of the food at a second time and changes in the spectra of the second set of light beams caused by reflection from (or passage through) the second interior portion of the food are analyzed to identify the composition of the second interior portion of the food.

In an example, a system for nutritional monitoring and management can comprise: a handheld food probe which is inserted into food; and a spectroscopic sensor which is part of (and/or in optical communication with) the food probe; wherein a first set of light beams from the spectroscopic sensor are reflected by (or pass through) a first interior portion of the food and changes in the spectra of the first set of light beams caused by reflection from (or passage through) the first interior portion of the food are analyzed to identify the composition of the first interior portion of the food; and wherein a second set of light beams from the spectroscopic sensor are reflected by (or pass through) a second interior portion of the food and changes in the spectra of the second set of light beams caused by reflection from (or passage through) the second interior portion of the food are analyzed to identify the composition of the second interior portion of the food, and wherein the second interior portion of the food is closer to the centroid of the food than the first interior portion of the food. Alternatively, a system can comprise: a handheld food probe which is inserted into food;

and a spectroscopic sensor with one or more moving optical components which is part of (and/or in optical communication with) the food probe; wherein a first set of light beams from the spectroscopic sensor are reflected by (or pass through) a first interior portion of the food at a first time and changes in the spectra of the first set of light beams caused by reflection from (or passage through) the first interior portion of the food are analyzed to identify the composition of the first interior portion of the food; and wherein a second set of light beams from the spectroscopic sensor are reflected by (or pass through) a second interior portion of the food at a second time and changes in the spectra of the second set of light beams caused by reflection from (or passage through) the second interior portion of the food are analyzed to identify the composition of the second interior portion of the food, and wherein the second interior portion of the food is at least 5 mm away from the first interior portion of the food.

In an example, a system for nutritional monitoring and management can comprise: a handheld food probe which is inserted into food; a light beam emitter which emits light beams toward the food from within the handheld food probe; a light beam receiver which receives the emitted light beams after they have been reflected from (or passed through) the food; and a moving mirror and/or lens which changes the location inside the food from which the light beams are reflected. In another example, a system can comprise: a handheld food probe which is inserted into food; and a spectroscopic sensor which is part of (and/or in optical communication with) the food probe; wherein a first set of light beams from the spectroscopic sensor are reflected by (or pass through) a first interior portion of the food at a first time and changes in the spectra of the first set of light beams caused by reflection from (or passage through) the first interior portion of the food are analyzed to identify the composition of the first interior portion of the food; and wherein a second set of light beams from the spectroscopic sensor are reflected by (or pass through) a second interior portion of the food at a second time and changes in the spectra of the second set of light beams caused by reflection from (or passage through) the second interior portion of the food are analyzed to identify the composition of the second interior portion of the food, and wherein the second interior portion of the food is closer to the centroid of the food than the first interior portion of the food.

In an example, a system for nutritional monitoring and management can comprise: a handheld food probe which is inserted into food; and a spectroscopic sensor which is part of (and/or in optical communication with) the food probe; wherein a first set of light beams from the spectroscopic sensor are reflected by (or pass through) a first interior portion of the food and changes in the spectra of the first set of light beams caused by reflection from (or passage through) the first interior portion of the food are analyzed to identify the composition of the first interior portion of the food; and wherein a second set of light beams from the spectroscopic sensor are reflected by (or pass through) a second interior portion of the food and changes in the spectra of the second set of light beams caused by reflection from (or passage through) the second interior portion of the food are analyzed to identify the composition of the second interior portion of the food, and wherein the second interior portion of the food is at least 5 mm away from the first interior portion of the food. Alternatively, a system can comprise: a handheld food probe which is inserted into food; and a spectroscopic sensor which is part of (and/or in optical communication with) the food probe; wherein a first set of light beams from the spectroscopic sensor are reflected by (or pass through) a first interior portion of the food at a first time and changes in the spectra of the first set of light beams caused by reflection from (or passage through) the first interior portion of the food are analyzed to identify the composition of the first interior portion of the food; and wherein a second set of light beams from the spectroscopic sensor are reflected by (or pass through) a second interior portion of the food at a second time and changes in the spectra of the second set of light beams caused by reflection from (or passage through) the second interior portion of the food are analyzed to identify the composition of the second interior portion of the food, and wherein the second interior portion of the food is at least 5 mm away from the first interior portion of the food.

In an example, a system for nutritional monitoring and management can comprise: a handheld food probe which is inserted into food; and a spectroscopic sensor with one or more moving optical components which is part of (and/or in optical communication with) the food probe; wherein a first set of light beams from the spectroscopic sensor are reflected by (or pass through) a first interior portion of the food at a first time and changes in the spectra of the first set of light beams caused by reflection from (or passage through) the first interior portion of the food are analyzed to identify the composition of the first interior portion of the food; and wherein a second set of light beams from the spectroscopic sensor are reflected by (or pass through) a second interior portion of the food at a second time and changes in the spectra of the second set of light beams caused by reflection from (or passage through) the second interior portion of the food are analyzed to identify the composition of the second interior portion of the food. In another example, a system can comprise: a handheld food probe which is inserted into food; and a spectroscopic sensor which is part of (and/or in optical communication with) the food probe; wherein a first set of light beams from the spectroscopic sensor are reflected by (or pass through) a first interior portion of the food and changes in the spectra of the first set of light beams caused by reflection from (or passage through) the first interior portion of the food are analyzed to identify the composition of the first interior portion of the food; and wherein a second set of light beams from the spectroscopic sensor are reflected by (or pass through) a second interior portion of the food and changes in the spectra of the second set of light beams caused by reflection from (or passage through) the second interior portion of the food are analyzed to identify the composition of the second interior portion of the food.

In an example, a system for nutritional monitoring and management can comprise: a handheld food probe which is inserted into food; and a spectroscopic sensor with one or more moving optical components which is part of (and/or in optical communication with) the food probe; wherein a first set of light beams from the spectroscopic sensor are reflected by (or pass through) a first interior portion of the food at a first time and changes in the spectra of the first set of light beams caused by reflection from (or passage through) the first interior portion of the food are analyzed to identify the composition of the first interior portion of the food; and wherein a second set of light beams from the spectroscopic sensor are reflected by (or pass through) a second interior portion of the food at a second time and changes in the spectra of the second set of light beams caused by reflection from (or passage through) the second interior portion of the food are analyzed to identify the composition of the second interior portion of the food, and wherein the second interior portion of the food is closer to the centroid of the food than the first interior portion of the food. Alternatively, a system can comprise: a handheld food scanner; a camera in the scanner which captures images of food; and a spectroscopic sensor in the scanner which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity.

In an example, a system for nutritional monitoring and management can comprise: a handheld or wearable device; a camera in the device which captures images of a multi-food meal; a laser pointer which is sequentially pointed toward different types of food in the multi-food meal; a spectroscopic sensor in the device is sequentially pointed toward different types of food in the multi-food meal, wherein the spectroscopic sensor emits light beams toward a type of food and receives the light beams after the light beams have been reflected from (or passed through) the type of food; wherein food images captured by the camera and changes in the spectra of the light beams caused by reflection from (or passage through) food are analyzed to identify food type, composition (e.g. nutritional composition), and/or quantity for each type of food in the multi-food meal. Alternatively, a system can comprise: a handheld or wearable device; a camera in the device which sequentially captures an image of each type of food in a multi-food meal; a spectroscopic sensor in the device which sequentially emits light beams toward each type of food in the multi-food meal and receives the light beams after the light beams have been reflected from (or passed through) the type of food; and a laser pointer in the device which guides the person concerning where to position the device so that camera captures an image of each type of food in the multi-food meal and/or the spectroscopic sensor sequentially emits light beams toward each type of food in the multi-food meal; wherein food images captured by the camera and changes in the spectra of the light beams caused by reflection from (or passage through) food are analyzed to identify food type, composition, and/or quantity for each type of food in the multi-food meal.

In an example, a system for nutritional monitoring and management can comprise: a handheld or wearable device; a camera in the handheld or wearable device which captures images of food; a spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and one or more other components selected from the group consisting of—accelerometer, altimeter, ambient light sensor, electromagnetic energy sensor, filter, GPS module, gyroscope, lens array, magnetometer, MEMS, microphone, parabolic reflector, temperature sensor, and vibrator.

In another example, a system for nutritional monitoring and management can comprise: a handheld or wearable device; a camera in the handheld or wearable device which captures images of a meal with different types of food; an infrared thermal sensor which measures the temperature of the different types of food; wherein different types of food in the meal are differentiated based on their shapes, sizes, colors, tones, brightness levels, textures, and/or temperatures; a spectroscopic sensor in the handheld or wearable device which emits light beams toward each of the different types of food and receives the light beams after the light beams have been reflected from (or passed through) each of the different types of food; wherein data from the camera, the spectroscopic sensor, and the infrared thermal sensor are analyzed together in order to identify types, compositions, and/or quantities of each of the different types of food in the meal.

In an example, a system for nutritional monitoring and management can comprise: a handheld or wearable device; a camera in the handheld or wearable device which captures images of food; and a holographic spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity. Alternatively, a system can comprise: a handheld or wearable device; a camera in the handheld or wearable device which captures images of food; and a spectroscopic sensor in the handheld or wearable device which emits light beams toward food and receives the light beams after the light beams have been reflected from (or passed through) food, wherein the spectroscopic sensor emits light beams with scanning variation in frequencies and/or wavelength; wherein food images captured by the camera and changes in the spectra of the light beams caused by reflection from (or passage through) food are analyzed to identify food type, composition (e.g. nutritional composition), and/or quantity.

In an example, a system for nutritional monitoring and management can comprise: a handheld or wearable device; a camera in the handheld or wearable device which captures images of food; and a spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify chemicals and/or microbes in the food. Alternatively, a system can comprise: a handheld or wearable device; a camera in the handheld or wearable device which captures images of food; and an infrared spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition, and/or quantity.

In an example, a system for nutritional monitoring and management can comprise: a handheld or wearable device; a camera in the device which captures images of a multi-food meal; a laser pointer which is sequentially pointed toward different portions of food in the multi-food meal; a spectroscopic sensor in the device is sequentially pointed toward different portions of food in the meal, wherein the spectroscopic sensor emits light beams toward a portion of food and receives the light beams after the light beams have been reflected from (or passed through) the portion of food; wherein food images captured by the camera and changes in the spectra of the light beams caused by reflection from (or passage through) food are analyzed to identify food type, composition, and/or quantity for each portion of food in the multi-food meal. In another example, a system can comprise: a handheld or wearable device; a camera in the device which captures images of food; a spectroscopic sensor in the device which emits light beams toward food and receives the light beams after the light beams have been reflected from (or passed through) food; and a laser pointer in the device which guides the person concerning where to position the device so that camera captures images of the food and/or the spectroscopic sensor emits light beams toward the food; wherein food images captured by the camera and changes in the spectra of the light beams caused by reflection from (or passage through) food are analyzed to identify food type, composition (e.g. nutritional composition), and/or quantity.

A system can be embodied in: a handheld or wearable device; a camera in the handheld or wearable device which captures images of food; a light emitter in the handheld or wearable device which emits light beams toward food; a light receiver in the handheld or wearable device which receives the light beams after the light beams have been reflected from (or passed through) food; and an optical filter selected from the group consisting of acousto-optic filter, Bragg filter, cascaded filter, dielectric thin-film filter, Fabry-Perot filter, hybrid filter, optical absorption filter, and optical interference filter; wherein food images captured by the camera and changes in the spectra of the light beams caused by reflection from (or passage through) food are analyzed to identify food type, composition, and/or quantity. Alternatively, a system can comprise: a handheld or wearable device; a camera in the handheld or wearable device which captures images of food; a light emitter which emits light beams toward food; and a light receiver which receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity.

In an example, a system for nutritional monitoring and management can comprise: a handheld or wearable device; a camera in the handheld or wearable device which captures images of a meal with different types of food; an infrared thermal sensor which measures the temperature of the different types of food; wherein different types of food in the meal are differentiated based on their shapes, sizes, colors, tones, brightness levels, textures, and/or temperatures; and a spectroscopic sensor in the handheld or wearable device; wherein the device prompts the person to direct the spectroscopic sensor toward a central location on each of the different types of food; wherein the spectroscopic sensor emits light beams toward each of the different types of food and receives the light beams after the light beams have been reflected from (or passed through) each of the different types of food; wherein data from the camera, the spectroscopic sensor, and the infrared thermal sensor are analyzed together in order to identify types, compositions, and/or quantities of each of the different types of food in the meal. In another example, a system can comprise: a handheld or wearable device; a camera in the handheld or wearable device which captures images of food; and a Fabry-Perot spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity.

In an example, a system for nutritional monitoring and management can comprise: a handheld or wearable device; a camera in the handheld or wearable device which captures images of food; and a near-infrared spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity. Alternatively, a system can comprise: a handheld or wearable device; a camera in the handheld or wearable device which captures images of food; and a spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and a cover or lid which automatically closes to prevent the camera and/or the spectroscopic sensor from coming into direct contact with viscous food.

In an example, a system for nutritional monitoring and management can comprise: a handheld or wearable device; a camera in the handheld or wearable device which captures images of food; and a spectroscopic sensor in the handheld or wearable device which emits light beams toward food and receives the light beams after the light beams have been reflected from (or passed through) food, wherein the spectroscopic sensor comprises a plurality of light emitters which emit light beams n different wavelength ranges; wherein food images captured by the camera and changes in the spectra of the light beams caused by reflection from (or passage through) food are analyzed to identify food type, composition, and/or quantity. Alternatively, a system can comprise: a handheld or wearable device; a camera in the handheld or wearable device which captures images of different foods in a multi-food meal; and a spectroscopic sensor in the handheld or wearable device which emits light beams toward the different foods in the multi-food meal and receives the light beams after the light beams have been reflected from (or passed through) the different foods; wherein differences in food size, color, tone, brightness, texture, and/or shape among different foods in the food images captured by the camera and changes in the spectra of the light beams caused by reflection from (or passage through) food are analyzed to identify the food type, composition (e.g. nutritional composition), and/or quantity for each of the different foods in the multi-food meal.

In an example, a system for nutritional monitoring and management can comprise: a handheld or wearable device; a camera in the handheld or wearable device which captures images of food, wherein the food images are automatically analyzed to identify food type and/or measure food quantity; and a spectroscopic sensor in the handheld or wearable device which emits light beams toward food and receives the light beams after the light beams have been reflected from (or passed through) food, wherein changes in the spectra of the light beams caused by reflection from (or passage through) food are analyzed to identify food type and/or composition; and where the device prompts a person to use the camera and/or the spectroscopic sensor at multiple times while the person is eating a meal in order to measure changes in the amount of food remaining (and infer how much food the person has actually consumed) and to measure the composition of different layers (or parts) of the food. Alternatively, a system can comprise: a handheld or wearable device; a camera in the device which captures images of a multi-food meal; a spectroscopic sensor in the device which emits light beams toward food and receives the light beams after the light beams have been reflected from (or passed through) food; and a laser pointer in the device which guides the person concerning where to position the device so that camera captures images of each type of food in the multi-food meal and/or the spectroscopic sensor emits light beams toward each type of food in the multi-food meal; wherein food images captured by the camera and changes in the spectra of the light beams caused by reflection from (or passage through) food are analyzed to identify food type, composition, and/or quantity for each type of food in the multi-food meal.

In an example, a system for nutritional monitoring and management can comprise: a handheld or wearable device; a camera in the handheld or wearable device which captures images of food; a light emitter which emits light beams toward food; wherein the light emitter is selected from the group consisting of—light emitting diode (LED), organic light emitting diode (OLED), quantum dot light emitting diode (QLED), dye laser, filament lamp, fluorescent lamp, gas laser, halogen lamp, incandescent lamp, low pressure sodium lamp, super luminescent diode, tunable laser, and vertical cavity surface emitting laser (VCSEL); and a light receiver which receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity. In another example, a system can comprise: a handheld or wearable device; a camera in the handheld or wearable device which captures images of food; a spectroscopic sensor in the handheld or wearable device which emits light beams toward food and receives the light beams after the light beams have been reflected from (or passed through) food; an infrared thermal sensor; wherein data from the camera, the spectroscopic sensor, and the infrared thermal sensor are analyzed together in order to identify food type, composition (e.g. nutritional composition), and/or quantity.

In an example, a system for nutritional monitoring and management can comprise: a handheld or wearable device; a camera in the handheld or wearable device which captures images of a meal with different types of food; an infrared thermal sensor which measures the temperature of the different types of food; wherein different types of food in the meal are differentiated based on their shapes, sizes, colors, tones, brightness levels, textures, and/or temperatures; and a spectroscopic sensor in the handheld or wearable device; wherein the device guides the person using a projected light pointer concerning where to orient the spectroscopic sensor toward a central location on each of the different types of food; wherein the spectroscopic sensor emits light beams toward each of the different types of food and receives the light beams after the light beams have been reflected from (or passed through) each of the different types of food; wherein data from the camera, the spectroscopic sensor, and the infrared thermal sensor are analyzed together in order to identify types, compositions, and/or quantities of each of the different types of food in the meal. Alternatively, a system can comprise: a handheld or wearable device; a camera in the handheld or wearable device which captures images of food; and a prism spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity.

In an example, a system for nutritional monitoring and management can comprise: a handheld or wearable device; a camera in the handheld or wearable device which captures images of food; and a spectroscopic sensor in the handheld or wearable device which emits light beams toward food and receives the light beams after the light beams have been reflected from (or passed through) food, wherein the spectroscopic sensor emits light beams at different frequencies at different times; wherein food images captured by the camera and changes in the spectra of the light beams caused by reflection from (or passage through) food are analyzed to identify food type, composition, and/or quantity. Alternatively, a system can comprise: a handheld or wearable device; a camera in the handheld or wearable device which captures images of different foods in a multi-food meal; and a spectroscopic sensor in the handheld or wearable device which emits light beams toward the different foods in the multi-food meal and receives the light beams after the light beams have been reflected from (or passed through) the different foods; wherein multivariate differences in food size, color, tone, brightness, texture, and shape among different foods in the food images captured by the camera and changes in the spectra of the light beams caused by reflection from (or passage through) food are analyzed to identify the food type, composition, and/or quantity for each of the different foods in the multi-food meal.

In an example, a system for nutritional monitoring and management can comprise: a handheld or wearable device; a camera in the handheld or wearable device which captures images of food; and a spectroscopic sensor in the handheld or wearable device with frequency-based modulation which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity.

In another example, a system for nutritional monitoring and management can comprise: a handheld or wearable device; a camera in the handheld or wearable device which captures images of food; and a UV-VIS spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity.

In an example, a system for nutritional monitoring and management can comprise: a handheld or wearable device; a camera in the device which captures images of food; a laser pointer which is directed toward the food; a spectroscopic sensor in the device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity. Alternatively, a system can comprise: a handheld or wearable device; a camera in the handheld or wearable device which captures images of food; a light emitter which emits light beams toward food; and a light receiver which receives the light beams after the light beams have been reflected from (or passed through) food, wherein the light receiver is selected from the group consisting of—avalanche photo-diode (APD) array, charge-coupled device (CCD), complementary metal-oxide semiconductor (CMOS), focal plane array (FPA), and photo-diode array (PDA); and wherein food images captured by the camera and changes in the spectra of the light beams caused by reflection from (or passage through) food are analyzed to identify food type, composition, and/or quantity.

In an example, a system for nutritional monitoring and management can comprise: a handheld or wearable device; a camera in the handheld or wearable device which captures images of a meal with different types of food; a spectroscopic sensor in the handheld or wearable device which emits light beams toward the different types of food and receives the light beams after the light beams have been reflected from (or passed through) the different types of food; an infrared thermal sensor which measures the temperature of the different types of food; wherein data from the camera, the spectroscopic sensor, and the infrared thermal sensor are analyzed together in order to identify types, compositions, and/or quantities of the different types of food in the meal. Alternatively, a system can comprise: a handheld or wearable device; a camera in the handheld or wearable device which captures images of a meal with different types of food; an infrared thermal sensor which measures the temperature of the different types of food; wherein different types of food in the meal are differentiated based on their shapes, sizes, colors, tones, brightness levels, textures, and/or temperatures; and a spectroscopic sensor in the handheld or wearable device; wherein the device guides the person using a virtual augmented reality pointer concerning where to orient the spectroscopic sensor toward a central location on each of the different types of food; wherein the spectroscopic sensor emits light beams toward each of the different types of food and receives the light beams after the light beams have been reflected from (or passed through) each of the different types of food; wherein data from the camera, the spectroscopic sensor, and the infrared thermal sensor are analyzed together in order to identify types, compositions, and/or quantities of each of the different types of food in the meal.

In an example, a system for nutritional monitoring and management can comprise: a handheld or wearable device; a camera in the handheld or wearable device which captures images of food; and a grating spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition, and/or quantity. In another example, a system can comprise: a handheld or wearable device; a camera in the handheld or wearable device which captures images of food; and a Raman spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity.

In an example, a system for nutritional monitoring and management can comprise: a handheld or wearable device; a camera in the handheld or wearable device which captures images of food; and a spectroscopic sensor in the handheld or wearable device which emits light beams toward food and receives the light beams after the light beams have been reflected from (or passed through) food, wherein the spectroscopic sensor emits a sequence of light beams at different frequencies; wherein food images captured by the camera and changes in the spectra of the light beams caused by reflection from (or passage through) food are analyzed to identify food type, composition, and/or quantity. Alternatively, a system can comprise: a handheld or wearable device; a camera in the handheld or wearable device which captures images of food; and a spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity.

In an example, a system for nutritional monitoring and management can comprise: a handheld or wearable device; a camera in the handheld or wearable device which captures images of food; and a spectroscopic sensor in the handheld or wearable device which emits light beams toward food and receives the light beams after the light beams have been reflected from (or passed through) food; wherein food images captured by the camera and data concerning changes in the spectra of the light beams caused by reflection from (or passage through) food are analyzed in order to identify food type, composition (e.g. nutritional composition), and/or quantity using multivariate statistical analysis to obtain more accurate results than are possible by analysis of either food images alone or spectroscopic data alone. In another example, a system can comprise: a handheld or wearable device; an auto-focusing camera in the handheld or wearable device which captures images of food; and a spectroscopic sensor in the handheld or wearable device which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity.

In an example, a system for nutritional monitoring and management can comprise: a handheld phone; a camera in the handheld phone which captures images of food at a first time and at a second time, wherein the first time is before a person eats the food and the second time is after the person has finished eating some or all of the food; a spectroscopic sensor in the handheld phone which emits light beams toward food and receives the light beams after the light beams have been reflected from (or passed through) food at the first time and at the second time; wherein food images captured by the camera and changes in the spectra of the light beams caused by reflection from (or passage through) food are analyzed together (e.g. in multivariate analysis) to identify the type, composition, and/or quantity of food eaten by the person holding or wearing the device. In another example, a system can comprise: a handheld phone; a camera in the phone which captures images of food; a spectroscopic sensor in the phone which emits light beams toward the food and receives the light beams after the light beams have been reflected from (or passed through) the food; wherein a light pattern formed by the projection of light beams from the spectroscopic sensor on (or near) the food is used as a fiducial marker to estimate food size, distance, and/or orientation relative to the phone; and wherein changes in the spectra of light beams caused by reflection from (or passage through) the food and food images captured by the camera are analyzed to identify food type, composition, and/or quantity.

In an example, a system for nutritional monitoring and management can comprise: a handheld phone; a camera in the phone which captures images of food; and a spectroscopic sensor in the phone which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein one or more eating-related objects (e.g. bowl, chopsticks, cup, fork, glass, knife, mug, napkin, placemat, plate, or spoon) are identified in food images to estimate food distance. Alternatively, a system can comprise: a handheld phone; a spectroscopic sensor in the phone which emits light beams toward food and receives the light beams after the light beams have been reflected from (or passed through) the food; a camera in the phone which captures images of the food; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity.

A system can be embodied in: a handheld phone; a spectroscopic sensor in the phone which emits light beams toward food and receives the light beams after the light beams have been reflected from (or passed through) food; a camera in the phone which captures images of the food; a first laser which projects a first coherent light beam toward the food; a second laser which projects a second coherent light beam toward the food; wherein the distance between the locations of incidence of the first and second light beams on (or near) the food is used to estimate food size, distance, and/or orientation relative to the phone; and wherein changes in the spectra of light beams caused by reflection from (or passage through) the food and food images captured by the camera are analyzed to identify food type, composition (e.g. nutritional composition), and/or quantity. Alternatively, a system can comprise: a handheld phone; a spectroscopic sensor in the phone which emits light beams toward food and receives the light beams after the light beams have been reflected from (or passed through) food; a camera in the phone which captures images of the food; and a laser which projects an array of nested rings of light (or near) the food, wherein the array serves as a fiducial marker to help estimate food size, distance, and/or orientation; and wherein changes in the spectra of light beams caused by reflection from (or passage through) the food and food images captured by the camera are analyzed to identify food type, composition, and/or quantity.

In an example, a system for nutritional monitoring and management can comprise: a handheld phone; a spectroscopic sensor in the phone which emits light beams toward food and receives the light beams after the light beams have been reflected from (or passed through) food; a camera in the phone which captures images of the food; and a laser which projects an quadrilateral grid of light on (or near) the food, wherein the size and/or keystone distortion of the (quadrilateral elements in the) grid serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity. Alternatively, a system can comprise: a handheld phone; a spectroscopic sensor in the phone which emits light beams toward food and receives the light beams after the light beams have been reflected from (or passed through) food; a camera in the phone which captures images of the food; and a light pattern projector which projects an arcuate (e.g. circular or keystone-distorted circular) light pattern onto the food and/or a surface near the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition, and/or quantity.

In an example, a system for nutritional monitoring and management can comprise: a handheld phone; a spectroscopic sensor in the phone which emits light beams toward food and receives the light beams after the light beams have been reflected from (or passed through) food; a camera in the phone which captures images of the food; and a scanning (e.g. moving) laser which projects an matrix (e.g. dot matrix or linear grid) pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity. In another example, a system can comprise: a handheld phone; a spectroscopic sensor in the phone which emits light beams toward food and receives the light beams after the light beams have been reflected from (or passed through) the food; a camera in the phone which captures images of the food from different perspectives and angles as the phone is moved; wherein the shape, size, color, tone, brightness, and/or texture of food in the food images and changes in the spectra of the light beams caused by reflection from (or passage through) the food are analyzed together (in a multivariate manner) in order to identify the food's type and/or the food's composition; and wherein food images from different perspectives and angles are used to model the food in three dimensions in order to measure food quantity.

In an example, a system for nutritional monitoring and management can comprise: a handheld phone; a spectroscopic sensor in the phone, wherein the spectroscopic sensor further comprises a light emitter which emits light beams toward food and a light receiver which receives the light beams after the light beams have been reflected from (or passed through) the food; a camera in the phone which captures images of the food; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity. Alternatively, a system can comprise: a handheld phone; a spectroscopic sensor with an aperture on the distal surface of the phone which emits light beams toward food and receives the light beams after the light beams have been reflected from (or passed through) the food; a first camera which captures images of the food; wherein the aperture of the first camera is located to one side of the aperture of the spectroscopic sensor; a second camera which captures images of the food; wherein the aperture of the second camera is located to a second side of (e.g. on the opposite side of) the aperture of the spectroscopic sensor; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity.

In an example, a system for nutritional monitoring and management can comprise: a handheld phone; a camera in the phone which captures images of a multi-food meal; a spectroscopic sensor in the phone which emits light beams toward food and receives the light beams after the light beams have been reflected from (or passed through) food; and a laser pointer in the phone which guides the person concerning where to position the phone so that camera captures images of each type of food in the multi-food meal and/or the spectroscopic sensor emits light beams toward each type of food in the multi-food meal; wherein food images captured by the camera and changes in the spectra of the light beams caused by reflection from (or passage through) food are analyzed to identify food type, composition, and/or quantity for each type of food in the multi-food meal.

In another example, a system for nutritional monitoring and management can comprise: a handheld phone; a camera in the phone which captures images of food; a spectroscopic sensor in the phone which emits light beams toward food and receives the light beams after the light beams have been reflected from (or passed through) food; wherein the camera and spectroscopic sensor are both directed toward a first food in a meal at a first point in time; wherein the camera and spectroscopic sensor are both directed toward a second food in a meal at a second point in time; wherein food images captured by the camera and changes in the spectra of the light beams caused by reflection from (or passage through) food are analyzed to identify the compositions and quantities of the first and second foods.

In an example, a system for nutritional monitoring and management can comprise: a handheld phone; a camera in the phone which captures images of food; a spectroscopic sensor in the phone which emits light beams toward the food and receives the light beams after the light beams have been reflected from (or passed through) the food; wherein light beams emitted from the spectroscopic sensor create a projected light pattern on (or near) the food and wherein the size, shape, and/or keystone distortion of this projected light pattern is used to estimate food size, distance, and/or orientation relative to the phone; and wherein changes in the spectra of light beams caused by reflection from (or passage through) the food and food images captured by the camera are analyzed to identify food type, composition (e.g. nutritional composition), and/or quantity. Alternatively, a system can comprise: a handheld phone; a camera in the phone which captures images of food; and a spectroscopic sensor in the phone which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein one or more eating-related objects (e.g. bowl, chopsticks, cup, fork, glass, knife, mug, napkin, placemat, plate, or spoon) are used to help estimate food size.

In an example, a system for nutritional monitoring and management can comprise: a handheld phone; a spectroscopic sensor in the phone which emits light beams toward food and receives the light beams after the light beams have been reflected from (or passed through) food; a camera in the phone which captures images of the food; a first laser which projects a first coherent light beam toward the food; a second laser which projects a second coherent light beam toward the food; a third laser which projects a third coherent light beam toward the food; wherein the distances and angles between the locations of incidence of the first, second, and third light beams on (or near) the food are used to estimate food size, distance, and/or orientation; and wherein changes in the spectra of light beams caused by reflection from (or passage through) the food and food images captured by the camera are analyzed to identify food type, composition (e.g. nutritional composition), and/or quantity. In another example, a system can comprise: a handheld phone; a spectroscopic sensor in the phone which emits light beams toward food and receives the light beams after the light beams have been reflected from (or passed through) food; a camera in the phone which captures images of the food; and a laser which projects an array of nested rings of light (or near) the food, wherein the size and distortion of rings in the array is used to help estimate food size, distance, and/or orientation; and wherein changes in the spectra of light beams caused by reflection from (or passage through) the food and food images captured by the camera are analyzed to identify food type, composition (e.g. nutritional composition), and/or quantity.

In an example, a system for nutritional monitoring and management can comprise: a handheld phone; a spectroscopic sensor in the phone which emits light beams toward food and receives the light beams after the light beams have been reflected from (or passed through) food; a camera in the phone which captures images of the food; and a light pattern projector which projects a pattern of light on (or near) the food; and wherein changes in the spectra of light beams caused by reflection from (or passage through) the food and food images captured by the camera are analyzed to identify food type, composition, and/or quantity. Alternatively, a system can comprise: a handheld phone; a spectroscopic sensor in the phone which emits light beams toward food and receives the light beams after the light beams have been reflected from (or passed through) food; a camera in the phone which captures images of the food; and a scanning (e.g. moving) laser which projects a pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity.

In an example, a system for nutritional monitoring and management can comprise: a handheld phone; a spectroscopic sensor in the phone which emits light beams toward food and receives the light beams after the light beams have been reflected from (or passed through) food; a camera in the phone which captures images of the food; and a scanning laser which projects an arcuate (e.g. circular) light pattern toward the food; wherein the shape, size, and/or keystone distortion of the projected light pattern on (or near) the food is used to estimate food size, distance, and/or orientation relative to the phone; and wherein changes in the spectra of light beams caused by reflection from (or passage through) the food and food images captured by the camera are analyzed to identify food type, composition, and/or quantity. Alternatively, a system can comprise: a handheld phone; a spectroscopic sensor in the phone which emits light beams toward food and receives the light beams after the light beams have been reflected from (or passed through) the food; a camera in the phone which captures images of the food from different perspectives and angles as the phone is moved; wherein the food images and changes in the spectra of the light beams caused by reflection from (or passage through) the food are analyzed together (in a multivariate manner) in order to identify the food's type and/or the food's composition; and wherein food images from different perspectives and angles are used to model the food in three dimensions in order to measure food quantity.

In an example, a system for nutritional monitoring and management can comprise: a handheld phone; a spectroscopic sensor on the distal surface in the phone which emits light beams toward food and receives the light beams after the light beams have been reflected from (or passed through) the food; a camera on the distal surface of the phone which captures images of the food; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity. Alternatively, a system can comprise: a handheld phone; a spectroscopic sensor with an aperture on the distal surface of the phone which emits light beams toward food and receives the light beams after the light beams have been reflected from (or passed through) the food; a camera with an aperture on the distal surface of the phone which captures images of the food; wherein the aperture of the spectroscopic sensor is the co-located with, co-axial with, and/or the same as the aperture of the camera; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity.

In an example, a system for nutritional monitoring and management can comprise: a handheld phone; a camera in the phone which captures images of food; a laser pointer which is directed toward the food; a spectroscopic sensor in the phone which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity.

In another example, a system for nutritional monitoring and management can comprise: a handheld phone; a camera in the phone which captures images of food; a spectroscopic sensor in the phone which emits light beams toward food and receives the light beams after the light beams have been reflected from (or passed through) food; wherein the person directs the camera and the spectroscopic sensor toward a first food in a meal at a first point in time; wherein the person directs the camera and the spectroscopic sensor toward a second food in a meal at a second point in time; wherein food images captured by the camera and changes in the spectra of the light beams caused by reflection from (or passage through) food are analyzed to identify the compositions and quantities of the first and second foods.

A system can be embodied in: a handheld phone; a camera in the phone which captures images of food; a spectroscopic sensor in the phone which emits light beams toward the food and receives the light beams after the light beams have been reflected from (or passed through) the food; wherein part of the spectrum of light beams emitted from the spectroscopic sensor create a light pattern on (or near) the food which is used as a fiducial marker to estimate food size, distance, and/or orientation relative to the phone; and wherein changes in the spectra of light beams caused by reflection from (or passage through) the food and food images captured by the camera are analyzed to identify food type, composition, and/or quantity. Alternatively, a system can comprise: a handheld phone; a camera in the phone which captures images of food; and a spectroscopic sensor in the phone which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein one or more eating-related objects (e.g. bowl, chopsticks, cup, fork, glass, knife, mug, napkin, placemat, plate, or spoon) are identified in food images to help estimate food size, distance, and/or orientation.

In an example, a system for nutritional monitoring and management can comprise: a handheld phone; a camera in the phone which captures images of food; and a spectroscopic sensor in the phone which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein one or more eating-related objects (e.g. bowl, chopsticks, cup, fork, glass, knife, mug, napkin, placemat, plate, or spoon) are used to estimate food distance. In another example, a system can comprise: a handheld phone; a spectroscopic sensor in the phone which emits light beams from the distal surface of the device toward food and receives the light beams after the light beams have been reflected from (or passed through) the food; a camera in the phone which captures images of the food from the distal surface of the device; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity.

A system can be embodied in: a handheld phone; a spectroscopic sensor in the phone which emits light beams toward food and receives the light beams after the light beams have been reflected from (or passed through) food; a camera in the phone which captures images of the food; and a laser which projects a target (e.g. cross-hairs) light pattern onto the food and/or a surface near the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity. Alternatively, a system can comprise: a handheld phone; a spectroscopic sensor in the phone which emits light beams toward food and receives the light beams after the light beams have been reflected from (or passed through) food; a camera in the phone which captures images of the food; and a laser which projects an matrix (e.g. dot matrix or linear grid) pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition, and/or quantity.

In an example, a system for nutritional monitoring and management can comprise: a handheld phone; a spectroscopic sensor in the phone which emits light beams toward food and receives the light beams after the light beams have been reflected from (or passed through) food; a camera in the phone which captures images of the food; and a light pattern projector which projects a pattern of light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition, and/or quantity. Alternatively, a system can comprise: a handheld phone; a spectroscopic sensor in the phone which emits light beams toward food and receives the light beams after the light beams have been reflected from (or passed through) food; a camera in the phone which captures images of the food; and a scanning (e.g. moving) laser which projects a polygonal light pattern onto the food and/or a surface near the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity.

In an example, a system for nutritional monitoring and management can comprise: a handheld phone; a spectroscopic sensor in the phone which emits light beams toward food and receives the light beams after the light beams have been reflected from (or passed through) food; a camera in the phone which captures images of the food; and a scanning laser which projects an arcuate (e.g. circular) light pattern toward the food; wherein size of the projected light pattern on (or near) the food is used to estimate food distance; wherein keystone distortion of the projected light pattern on (or near) the food is used to estimate the orientation of the food relative to the phone; and wherein changes in the spectra of light beams caused by reflection from (or passage through) the food and food images captured by the camera are analyzed to identify food type, composition (e.g. nutritional composition), and/or quantity. In another example, a system can comprise: a handheld phone; a spectroscopic sensor with an aperture on the distal surface of the phone which emits light beams toward food and receives the light beams after the light beams have been reflected from (or passed through) the food; a camera with an aperture on the distal surface of the phone which captures images of the food; wherein the aperture of the spectroscopic sensor is between 5 mm and 100 mm away from the aperture of the camera; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity.

In an example, a system for nutritional monitoring and management can comprise: a handheld phone; a camera in the phone which captures images of a multi-food meal; a laser pointer which is sequentially pointed toward different types of food in the multi-food meal; a spectroscopic sensor in the phone is sequentially pointed toward different types of food in the meal, wherein the spectroscopic sensor emits light beams toward a type of food and receives the light beams after the light beams have been reflected from (or passed through) the type of food; wherein food images captured by the camera and changes in the spectra of the light beams caused by reflection from (or passage through) food are analyzed to identify food type, composition, and/or quantity for each type of food in the multi-food meal. Alternatively, a system can comprise: a handheld phone; a camera in the phone which sequentially captures an image of each type of food in a multi-food meal; a spectroscopic sensor in the phone which sequentially emits light beams toward each type of food in the multi-food meal and receives the light beams after the light beams have been reflected from (or passed through) the type of food; and a laser pointer in the phone which guides the person concerning where to position the phone so that camera captures an image of each type of food in the multi-food meal and/or the spectroscopic sensor sequentially emits light beams toward each type of food in the multi-food meal; wherein food images captured by the camera and changes in the spectra of the light beams caused by reflection from (or passage through) food are analyzed to identify food type, composition, and/or quantity for each type of food in the multi-food meal.

In an example, a system for nutritional monitoring and management can comprise: a handheld phone; a camera in the handheld phone which captures images of food at a first time and at a second time; and a spectroscopic sensor in the handheld phone which emits light beams toward food and receives the light beams after the light beams have been reflected from (or passed through) food at the first time and at the second time; wherein food images captured by the camera and changes in the spectra of the light beams caused by reflection from (or passage through) food are analyzed together (e.g. in multivariate analysis) to identify the type, composition (e.g. nutritional composition), and/or quantity of food eaten by the person holding or wearing the device. In another example, a system can comprise: a handheld phone; a camera in the phone which captures images of food; a spectroscopic sensor in the phone which emits light beams toward food and receives the light beams after the light beams have been reflected from (or passed through) food; a laser pointer; wherein the person uses the laser pointer to direct the camera and the spectroscopic sensor toward a first food in a meal at a first point in time; wherein the person uses the laser pointer to direct the camera and the spectroscopic sensor toward a second food in a meal at a second point in time; wherein food images captured by the camera and changes in the spectra of the light beams caused by reflection from (or passage through) food are analyzed to identify the compositions and quantities of the first and second foods.

A system can be embodied in: a handheld phone; a camera in the phone which captures images of food; a spectroscopic sensor in the phone which emits light beams toward the food and receives the light beams after the light beams have been reflected from (or passed through) the food; wherein the visible portion of the spectrum of light beams emitted from the spectroscopic sensor creates a visible light pattern on (or near) the food and wherein the size, shape, and/or keystone distortion of this visible light pattern is used as a fiducial marker to estimate food size, distance, and/or orientation relative to the phone; and wherein changes in the spectra of light beams caused by reflection from (or passage through) the food and food images captured by the camera are analyzed to identify food type, composition (e.g. nutritional composition), and/or quantity. Alternatively, a system can comprise: a handheld phone; a camera in the phone which captures images of food; and a spectroscopic sensor in the phone which emits light beams toward food and receives the light beams after the light beams have been reflected from (or passed through) food; wherein food images captured by the camera and changes in the spectra of the light beams caused by reflection from (or passage through) food are analyzed to identify food type, composition (e.g. nutritional composition), and/or quantity; and wherein one or more eating-related objects (e.g. bowl, chopsticks, cup, fork, glass, knife, mug, napkin, placemat, plate, or spoon) are identified in food images to help estimate food size.

In an example, a system for nutritional monitoring and management can comprise: a handheld phone; a spectroscopic sensor in the phone which emits light beams toward food and receives the light beams after the light beams have been reflected from (or passed through) food; a camera in the phone which captures images of the food; a first laser which projects a first coherent light beam toward the food; and a second laser which projects a second coherent light beam toward the food; wherein the first and second light beams form a projected light pattern on (or near) the food which serves as a fiducial marker to help estimate food size, distance, and/or orientation; and wherein changes in the spectra of light beams caused by reflection from (or passage through) the food and food images captured by the camera are analyzed to identify food type, composition, and/or quantity. Alternatively, a system can comprise: a handheld phone; a spectroscopic sensor in the phone which emits light beams toward food and receives the light beams after the light beams have been reflected from (or passed through) food; a camera in the phone which captures images of the food; and a laser which projects an arcuate (e.g. circular, elliptical, or egg-shaped) pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition, and/or quantity.

A system can be embodied in: a handheld phone; a spectroscopic sensor in the phone which emits light beams toward food and receives the light beams after the light beams have been reflected from (or passed through) food; a camera in the phone which captures images of the food; and a laser which projects an quadrilateral grid of light on (or near) the food, wherein the grid serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity. Alternatively, a system can comprise: a handheld phone; a spectroscopic sensor in the phone which emits light beams toward food and receives the light beams after the light beams have been reflected from (or passed through) food; a camera in the phone which captures images of the food; and a light pattern projector which projects a polygonal light pattern onto the food and/or a surface near the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition, and/or quantity.

In an example, a system for nutritional monitoring and management can comprise: a handheld phone; a spectroscopic sensor in the phone which emits light beams toward food and receives the light beams after the light beams have been reflected from (or passed through) food; a camera in the phone which captures images of the food; and a scanning (e.g. moving) laser which projects an arcuate (e.g. circular, elliptical, or egg-shaped) pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition (e.g. nutritional composition), and/or quantity.

In another example, a system for nutritional monitoring and management can comprise: a handheld phone; a spectroscopic sensor in the phone which emits light beams toward food and receives the light beams after the light beams have been reflected from (or passed through) food; a camera in the phone which captures images of the food; and one or more lasers which project a pattern of coherent light on (or near) the food, wherein the light pattern serves as a fiducial marker to help estimate food size, distance, and/or orientation; and wherein changes in the spectra of light beams caused by reflection from (or passage through) the food and food images captured by the camera are analyzed to identify food type, composition, and/or quantity.

A system can be embodied in: a handheld phone; a spectroscopic sensor with an aperture on the distal surface of the phone which emits light beams toward food and receives the light beams after the light beams have been reflected from (or passed through) the food; a camera with an aperture on the distal surface of the phone which captures images of the food; wherein the aperture of the spectroscopic sensor is between 1 mm and 10 mm away from the aperture of the camera; wherein the food images and changes in the spectra of the light beams caused by reflection from (or passage through) the food are analyzed together (in a multivariate manner) in order to identify the food's type and/or measure the food's composition; and wherein the food images are analyzed to measure food quantity. Alternatively, a system can comprise: a handheld phone; a camera in the phone which captures images of a multi-food meal; a laser pointer which is sequentially pointed toward different portions of food in the multi-food meal; a spectroscopic sensor in the phone is sequentially pointed toward different portions of food in the meal, wherein the spectroscopic sensor emits light beams toward a portion of food and receives the light beams after the light beams have been reflected from (or passed through) the portion of food; wherein food images captured by the camera and changes in the spectra of the light beams caused by reflection from (or passage through) food are analyzed to identify food type, composition (e.g. nutritional composition), and/or quantity for each portion of food in the multi-food meal.

In an example, a system for nutritional monitoring and management can comprise: a handheld phone; a camera in the phone which captures images of food; a spectroscopic sensor in the phone which emits light beams toward food and receives the light beams after the light beams have been reflected from (or passed through) food; and a laser pointer in the phone which guides the person concerning where to position the phone so that camera captures images of the food and/or the spectroscopic sensor emits light beams toward the food; wherein food images captured by the camera and changes in the spectra of the light beams caused by reflection from (or passage through) food are analyzed to identify food type, composition (e.g. nutritional composition), and/or quantity. In another example, a system can comprise: a handheld phone which is held by a person; a camera in the handheld device which captures images of food; a spectroscopic sensor in the handheld device which emits light beams toward food and receives the light beams after the light beams have been reflected from (or passed through) food; a wrist-worn device which is worn by the person; and a motion sensor in the wrist-worn device which tracks hand-to-mouth or chewing motions; wherein data from the camera, the spectroscopic sensor, and the motion sensor are analyzed together (e.g. in multivariate analysis) to identify the type, composition (e.g. nutritional composition), and/or quantity of food eaten by the person holding or wearing the device.

In an example, a system for nutritional monitoring and management can comprise: a handheld phone which is held by a person; a camera in the handheld device which captures images of food; a spectroscopic sensor in the handheld device which emits light beams toward food and receives the light beams after the light beams have been reflected from (or passed through) food; a smart watch which is worn by the person; and a motion sensor in the smart watch which tracks hand-to-mouth or chewing motions; wherein data from the camera, the spectroscopic sensor, and the motion sensor are analyzed together (e.g. in multivariate analysis) to identify the type, composition, and/or quantity of food eaten by the person holding or wearing the device. Alternatively, a system can comprise: a handheld phone which is held by a person; a camera in the handheld device which captures images of food; a spectroscopic sensor in the handheld device which emits light beams toward food and receives the light beams after the light beams have been reflected from (or passed through) food; a neck-worn device which is worn by the person; and a motion sensor in the neck-worn device which tracks chewing or swallowing motions; wherein data from the camera, the spectroscopic sensor, and the motion sensor are analyzed together (e.g. in multivariate analysis) to identify the type, composition (e.g. nutritional composition), and/or quantity of food eaten by the person holding or wearing the device.

In an example, a system for nutritional monitoring and management can comprise: a handheld phone which is held by a person; a camera in the handheld device which captures images of food; a spectroscopic sensor in the handheld device which emits light beams toward food and receives the light beams after the light beams have been reflected from (or passed through) food; a wearable device which is worn by the person; and a motion sensor in the handheld device which tracks hand-to-mouth motions, chewing motions, and/or swallowing motions; wherein data from the camera, the spectroscopic sensor, and the motion sensor are analyzed together (e.g. in multivariate analysis) to identify the type, composition, and/or quantity of food eaten by the person holding or wearing the device. Alternatively, a system can comprise: a handheld phone which is held by a person; a camera in the handheld device which captures images of food; a spectroscopic sensor in the handheld device which emits light beams toward food and receives the light beams after the light beams have been reflected from (or passed through) food; a neck-worn device which is worn by the person; and a sound sensor in the neck-worn device which tracks chewing or swallowing sounds; wherein data from the camera, the spectroscopic sensor, and the sound sensor are analyzed together (e.g. in multivariate analysis) to identify the type, composition (e.g. nutritional composition), and/or quantity of food eaten by the person holding or wearing the device.

In an example, a system for nutritional monitoring and management can comprise: a handheld phone which is waived back and forth several times over a multi-food meal; a spectroscopic sensor in the handheld phone which emits light beams toward the meal and receives the light beams after the light beams have been reflected from (or passed through) a plurality of locations on the meal as the device is waived back and forth; a camera in the handheld phone which captures images of a plurality of locations on the meal as the device is waived back and forth; and a motion sensor; wherein data from the spectroscopic sensor, the camera, and the motion sensor are analyzed together (in a multivariate manner) in order to identify the types, compositions, and/or quantities of foods in the multi-food meal. Alternatively, a system can comprise: a handheld phone which is waived back and forth several times over a multi-food meal; a spectroscopic sensor in the handheld phone which emits light beams toward the meal and receives the light beams after the light beams have been reflected from (or passed through) a plurality of locations on the meal as the device is waived back and forth; a camera in the handheld phone which captures images of a plurality of locations on the meal as the device is waived back and forth; and a motion sensor; wherein data from the spectroscopic sensor, the camera, and the motion sensor are analyzed to segment the meal into different food portions; and wherein data from the spectroscopic sensor, the camera, and the motion sensor are analyzed to identify the types, compositions, and/or quantities of foods in the different food portions.

A system can be embodied in: a handheld phone which is waived back and forth several times over a multi-food meal; a spectroscopic sensor in the handheld phone which emits light beams toward the meal and receives the light beams after the light beams have been reflected from (or passed through) a plurality of locations on the meal as the device is waived back and forth; a camera in the handheld phone which captures images of a plurality of locations on the meal as the device is waived back and forth; and a motion sensor; wherein variations in food color, tone, brightness, texture, shape, and molecular composition as the device is waived back and forth are analyzed to segment the meal into different food portions; and wherein data from the spectroscopic sensor, the camera, and the motion sensor are analyzed to identify the types, compositions, and/or quantities of foods in the different food portions. In another example, a system can comprise: a handheld phone which is waived back and forth several times over a multi-food meal; a spectroscopic sensor in the handheld phone which emits light beams toward the meal and receives the light beams after the light beams have been reflected from (or passed through) the meal as the device is being waived back and forth; a camera in the handheld phone which captures images of the meal as the device is being waived back and forth; and a motion sensor; wherein data from the spectroscopic sensor, the camera, and the motion sensor are analyzed together (in a multivariate manner) in order to identify the types, compositions, and/or quantities of foods in the multi-food meal.

In an example, a system for nutritional monitoring and management can comprise: a handheld phone which is waived back and forth several times over food; a spectroscopic sensor in the handheld phone which emits light beams toward food and receives the light beams after the light beams have been reflected from (or passed through) the food as the device is being waived back and forth; a camera in the handheld phone which captures images of the food as the device is being waived back and forth; and a motion sensor; wherein data from the spectroscopic sensor, the camera, and the motion sensor are analyzed together (in a multivariate manner) in order to identify the food type, composition, and/or quantity. Alternatively, a system can comprise: a handheld phone which is waived in an arc segment of a circle over nearby food; a spectroscopic sensor in the handheld phone which emits light beams toward food and receives the light beams after the light beams have been reflected from (or passed through) the food; a camera in the handheld phone which captures images of the food; and a motion sensor; wherein data from the spectroscopic sensor, the camera, and the motion sensor are analyzed together (in a multivariate manner) in order to identify the food type, composition (e.g. nutritional composition), and/or quantity.

A system for nutritional monitoring and management can be embodied in: a handheld phone which is waived over a meal in an arc which is wider than the width of the meal; a spectroscopic sensor in the handheld phone which emits light beams toward food and receives the light beams after the light beams have been reflected from (or passed through) the food; a camera in the handheld phone which captures images of the food; and a motion sensor; wherein data from the spectroscopic sensor, the camera, and the motion sensor are analyzed together (in a multivariate manner) in order to identify the food type, composition (e.g. nutritional composition), and/or quantity. In another example, a system can comprise: a handheld phone which is waived over a meal with multiple types of food; a spectroscopic sensor in the handheld phone which emits light beams toward food and receives the light beams after the light beams have been reflected from (or passed through) the food; a camera in the handheld phone which captures images of the food in a field of view which overlaps the projection path of light beams from the spectroscopic sensor; and a motion sensor; wherein the handheld phone guides a person concerning how to waive or otherwise move the handheld phone over the meal with multiple types of food; and wherein data from the spectroscopic sensor, the camera, and the motion sensor are analyzed together (in a multivariate manner) in order to identify the food type, composition (e.g. nutritional composition), and/or quantity.

I claim:
1. A device for nutritional monitoring and management comprising:
   a watch or other wrist-worn device which is configured to be worn by a person;
   a camera on the watch or other wrist-worn device which records images of food items, wherein the images are analyzed to identify food item types and/or estimate food item quantities, wherein the food items include beverages as well as solid food, and wherein the camera is configured to be on an anterior side of the person's wrist;
   a spectroscopic sensor on the watch or other wrist-worn device which collects spectral data concerning light reflected from or absorbed by the food items; wherein the spectral data is used to identify food item types and/or compositions; wherein the spectroscopic sensor further comprises a light emitter which emits light toward the food items and a light receiver which receives the light after it has been reflected by or passed through the food items; and wherein changes in the spectral distribution of the light caused by interaction with the food items are used to identify the food item types and/or compositions; and wherein the spectroscopic sensor is configured to be on the anterior side of the person's wrist;
   a cover or lid on the spectroscopic sensor, wherein the cover or lid is configured to automatically open or close based on distance to food;
   a data processor configured to analyze the images of food items recorded by the camera and the changes in the spectral distribution of the light detected by the spectroscopic sensor;
   one or more other components on the watch or other wrist-worn device selected from the group consisting of: data transmitter; data receiver; battery; GPS module; clock; calendar; voice recognition interface; touch-screen interface; and gesture recognition interface.

* * * * *